United States Patent
Quibell

(10) Patent No.: US 7,425,562 B2
(45) Date of Patent: Sep. 16, 2008

(54) INHIBITORS OF CRUZIPAIN AND OTHER CYSTEINE PROTEASES

(75) Inventor: Martin Quibell, Cambridge (GB)

(73) Assignee: Amura Therapeutics Ltd., Babraham (GB)

(*) Notice: Subject to any disclaimer, the term of this patent is extended or adjusted under 35 U.S.C. 154(b) by 525 days.

(21) Appl. No.: 10/466,384

(22) PCT Filed: Jan. 17, 2002

(86) PCT No.: PCT/GB02/00184

§ 371 (c)(1),
(2), (4) Date: Jan. 8, 2004

(87) PCT Pub. No.: WO02/057270

PCT Pub. Date: Jul. 25, 2002

(65) Prior Publication Data

US 2004/0138250 A1    Jul. 15, 2004

Related U.S. Application Data

(60) Provisional application No. 60/275,359, filed on Mar. 13, 2001.

(30) Foreign Application Priority Data

Jan. 17, 2001 (GB) .................. 0101179.0

(51) Int. Cl.
*A61K 31/44* (2006.01)
*A61K 31/40* (2006.01)
*C07D 471/02* (2006.01)
*C07D 487/04* (2006.01)

(52) U.S. Cl. ............ 514/300; 514/301; 514/302; 514/412; 546/113; 546/114; 546/115; 548/453

(58) Field of Classification Search ............... 514/300, 514/301, 302, 412; 546/113, 114, 115, 453
See application file for complete search history.

(56) References Cited

U.S. PATENT DOCUMENTS 3,652,574 A    3/1972    Garmaise .................. 260/296

FOREIGN PATENT DOCUMENTS

| WO | 98/05336 | 2/1998 |
|---|---|---|
| WO | 98/08802 | 3/1998 |
| WO | 98/28268 | 7/1998 |
| WO | 98/50533 | 11/1998 |
| WO | 99/53039 | 10/1999 |
| WO | 00/29408 | 5/2000 |
| WO | 02/40462 | 5/2000 |
| WO | 00/69855 | 11/2000 |
| WO | 02/051983 | 7/2002 |

OTHER PUBLICATIONS

Fenwick, et al., "Diastereoselective Synthesis, Activity and Chiral Stability of Cyclic Alkoxyketone Inhibitors of Cathepsin K," *Bioorganic & Medicinal Chemistry Letters*, vol. 11, pp. 199-202 (2001).

Marquis, et al., "Conformationally Constrained 1, 3-Diamino Ketones: A Series of Potent Inhibitors of the Cysteine Protease Cathepsin K," *J. Med. Chem.*, vol. 41, pp. 3563-3567 (1998).

*Primary Examiner*—James O. Wilson
*Assistant Examiner*—Ebenezer Sackey
(74) *Attorney, Agent, or Firm*—Edwards Angell Palmer & Dodge LLP; Ralph A. Loren, Esq.; Mark D. Russett, Esq.

(57) ABSTRACT

Compounds of general formula (I) or general formula (II)

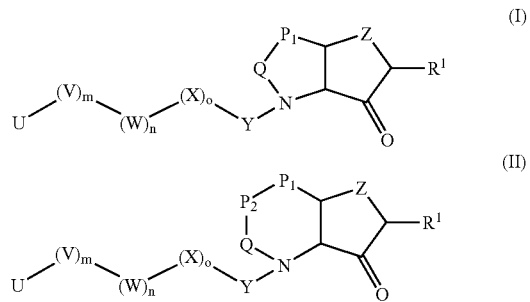

wherein $R^1$, $P_1$, $P_2$, Q, Y, $(X)_o$, $(W)_n$, $(V)_m$, Z and U are as defined in the specification, are inhibitors of cruzipain and other cysteine protease inhibitors and are useful as therapeutic agents, for example in Chagas' disease, or for validating therapeutic target compounds.

29 Claims, No Drawings

INHIBITORS OF CRUZIPAIN AND OTHER CYSTEINE PROTEASES

This invention relates to compounds which are inhibitors of the protease cruzipain, a gene product of the *Trypanosoma cruzi* parasite. In particular, the invention provides compounds that are useful for the therapeutic treatment of *Trypanosoma cruzi* infection, to the use of these compounds, and to pharmaceutical compositions comprising them. Furthermore, this invention relates to compounds which are inhibitors across a broad range of cysteine proteases, to the use of these compounds, and to pharmaceutical compositions comprising them. Such compounds are useful for the therapeutic treatment of diseases in which participation of a cysteine protease is implicated.

The trypanosomal family of parasites have a substantial worldwide impact on human and animal healthcare (McKerrow, J. H., et al, *Ann. Rev. Microbiol.* 47, 821-853, 1993). One parasite of this family, *Trypanosoma cruzi*, is the causative agent of Chagas' disease, which affects in excess of twenty million people annually in Latin and South America, is the leading cause of heart disease in these regions and results in more than 45,000 deaths per annum (Centers for Disease Control and prevention website). In addition, with the increase in migration of the infected population from rural to urban sites and movements from South and Central America into North America, the infection is spreading via blood transfusions, and at birth. The present treatments of choice for *Trypanosoma cruzi* infection, nifurtimox and benznidazole (an NADH fumarate reductase inhibitor, Turrens, J F, et al, *Mol Biochem Parasitol.,* 82(1), 125-9, 1996) are at best moderately successful, achieving ~60% cure during the acute phase of infection (see Docampo, R. *Curr. Pharm. Design,* 7, 1157-1164, 2001 for a general discussion) whilst not being prescribed at all during the chronic phase where cardiomyopathy associated heart failure often occurs (Kirchhoff, L. V. *New Engl. J. Med* 329, 639-644, 1993). Additionally, these two drugs have serious adverse toxic effects, requiring close medical supervision during treatment, and have been shown to induce chromosomal damage in chagastic infants (Gorla, N. B. et al, *Mutat. Res.* 206, 217-220, 1988). Therefore, a strong medical need exists for new effective drugs for the chemotherapeutic treatment of *Trypanosoma cruzi* infection. Classically, the identification of enzymes found to be crucial for the establishment or propagation of an infectious disease has been instrumental in the development of successful drugs such as antivirals (e.g. HIV aspartyl protease inhibitors) and anti-bacterials (e.g. β-lactam antibiotics). The search for a similar Achilles heel in parasitic infections has examined numerous enzymes (e.g. parasitic dihydrofolate reductase, see Chowdhury, S. F. et al, *J. Med. Chem.,* 42(21), 4300-4312, 1999; trypanothione reductase, see Li, Z. et al, *Bioorg. Med. Chem. Lett.,* 11(2), 251-254, 2001; parasitic glyceraldehydes-3-phosphate dehydrogenase, see Aranov, A. M. et al, *J. Med. Chem.,* 41(24), 4790-4799, 1998). A particularly promising area of research has identified the role of cysteine proteases, encoded by the parasite, that play a pivotal role during the life cycle of the parasite (McKerrow, J. H., et al, *Bioorg. Med. Chem.,* 7, 639-644, 1999). Proteases form a substantial group of biological molecules which to date constitute approximately 2% of all the gene products identified following analysis of several genome sequencing programmes (e.g. see Southan, C. *J. Pept. Sci,* 6, 453-458, 2000). Proteases have evolved to participate in an enormous range of biological processes, mediating their effect by cleavage of peptide amide bonds within the myriad of proteins found in nature. This hydrolytic action is performed by initially recognising, then binding to, particular three-dimensional electronic surfaces displayed by a protein, which aligns the bond for cleavage precisely within the protease catalytic site. Catalytic hydrolysis then commences through nucleophilic attack of the amide bond to be cleaved either via an amino acid side-chain of the protease itself, or through the action of a water molecule that is bound to and activated by the protease. Proteases in which the attacking nucleophile is the thiol side-chain of a Cys residue are known as cysteine proteases. The general classification of 'cysteine protease' contains many members found across a wide range of organisms from viruses, bacteria, protozoa, plants and fungi to mammals.

Biological investigation of *Trypanosoma cruzi* infection has highlighted a number of specific enzymes that are crucial for the progression of the parasite's life cycle. One such enzyme, cruzipain, a cathepsin L-like cysteine protease, is a clear therapeutic target for the treatment of Chagas' disease ((a) Cazzulo, J. J. et al, *Curr. Pharm. Des.* 7, 1143-1156, 2001; (b) Caffrey, C. R. et al, *Curr. Drug Targets,* 1, 155-162, 2000). Although the precise biological role of cruzipain within the parasite's life cycle remains unclear, elevated cruzipain messenger RNA levels in the epimastigote developmental stage indicate a role in the nutritional degradation of host-molecules in lysosomal-like vesicles (Engel, J. C. et al, *J. Cell. Sci,* 111, 597-606, 1998). The validation of cruzipain as a viable therapeutic target has been achieved with increasing levels of complexity. Addition of a general cysteine protease inhibitor, Z-Phe-Ala-FMK to *Trypanosoma cruzi*-infected mammalian cell cultures blocked replication and differentiation of the parasite, thus arresting the parasite life cycle (Harth, G., et al, *Mol. Biochem. Parasitol.* 58, 17-24, 1993). Administration of a vinyl sulphone-based inhibitor in a *Trypanosoma cruzi*-infected murine animal model not only rescued the mice from lethal infections, but also produced a complete recovery (Engel, J. C. et al, *J. Exp. Med,* 188(4), 725-734, 1998). Numerous other in vivo studies have confirmed that infections with alternative parasites such as *Leishmania major* (Selzer, P. M. et al, *Proc. Nat'l. Acad. Sci. U.S.A.,* 96, 11015-11022, 1999), *Schistosoma mansoni* and *Plasmodium falciparium* (Olson, J. E. et al, *Bioorg. Med. Chem.,* 7, 633-638, 1999) can be halted or cured by treatment with cysteine protease inhibitors.

A variety of synthetic approaches have been described towards the design of cruzipain inhibitors. However, although providing a biological 'proof-of-principle' for the treatment of *Trypanosoma cruzi* infection, current inhibitors exhibit a number of biochemical and physical properties that may preclude their clinical development. (e.g. see (a) Brinen, L. S. et al, *Structure,* 8, 831-840, 2000, peptidomimetic vinyl sulphones, possible adverse mammalian cell toxicity (see McKerrow, J. H. and Engel, J. unpublished results cited in Scheidt, K. A. et al, *Bioorg. Med. Chem,* 6, 2477-2494, 1998); (b) Du, X. et al, *Chem. Biol.,* 7, 733-742, 2000, aryl ureas, generally with low µM activity, and high ClogP values, thus poor aqueous solubility and probably low oral bioavailability; (c) Roush, W. R. et al, *Tetrahedron,* 56, 9747-9762, 2000, peptidyl epoxysuccinates, irreversible inhibitors, with potent activity verses house-keeping mammalian proteases such as cathepsin B; (d) Li, R. et al, *Bioorg. Med. Chem.* 4-(9), 1421-1427, 1996, bisarylacylhydrazides and chalcones, polyhydroxylated aromatics; (e) U.S. Pat. No. 6,143,931, WO 9846559, non-peptide α-ketoamides). Of the many different approaches to enzyme inhibition to date, only the cruzipain protease inhibitors have proven effective in curing disease-related animal models of *Trypanosoma cruzi* infection. Therefore, a clear medical need exists to progress these 'proof-of-principle' findings towards clinical candidates, suitable for human use, through the discovery of more efficacious cruzipain inhibitors that have a desirable combination of potency, selectivity, low toxicity and optimised pharmacokinetic parameters.

Cruzipain and indeed many other crucial parasitic proteases belong to the papain-like CA C1 family and have close structural mammalian homologues. Cysteine proteases are classified into 'clans' based upon a similarity in the three-dimensional structure or a conserved arrangement of catalytic residues within the protease primary sequence. Additionally, 'clans' are further classified into 'families' in which each protease shares a statistically significant relationship with other members when comparing the portions of amino acid sequence which constitute the parts responsible for the protease activity (see Barrett, A. J et al, in 'Handbook of Proteolytic Enzymes', Eds. Barrett, A. J., Rawlings, N. D., and Woessner, J. F. Publ. Academic Press, 1998, for a thorough discussion). To date, cysteine proteases have been classified into five clans, CA, CB, CC, CD and CE (Barrett, A. J. et al, 1998). A protease from the tropical papaya fruit 'papain' forms the foundation of clan CA, which currently contains over 80 distinct and complete entries in various sequence databases, with many more expected from the current genome sequencing efforts. Proteases of clan CA/family C1 have been implicated in a multitude of disease processes e.g. human proteases such as cathepsin K (osteoporosis), cathepsin S (autoimmune disorders), cathepsin L (metastases) or parasitic proteases such as falcipain (malaria parasite *Plasmodium falciparum*), cruzipain (*Trypanosoma cruzi* infection). Recently a bacterial protease, staphylopain (*S. aureus* infection) has also been tentatively assigned to clan CA. X-ray crystallographic structures are available for a range of the above mentioned proteases in complex with a range of inhibitors e.g. papain (PDB entries, 1pad, 1pe6, 1pip, 1pop, 4-pad, 5pad, 6pad, 1ppp, 1the, 1csb, 1huc), cathepsin K (1au0, 1au2, 1au3, 1au4, 1atk, 1mem, 1bgo, 1ayw, 1ayu), cathepsin L (1cs8), cathepsin S (currently on-hold, but published McGrath, M. E. et al, *Protein Science,* 7, 1294-1302, 1998), cruzain (a recombinant form of cruzipain see Eakin, A. E. et al, 268(9), 6115-6118, 1993) (1ewp, 1aim, 2aim, 1F29, 1F2A, 1F2B, 1F2C), staphylopain (1cv8). Each of the structures displays a similar overall active-site topology, as would be expected by their 'clan' and 'family' classification and such structural similarity exemplifies one aspect of the difficulties involved in discovering a selective inhibitor of cruzipain suitable for human use. However, subtle differences in terms of the depth and intricate shape of the active site groove of each CA C1 protease are evident, which may be exploited for selective inhibitor design. Additionally, many of the current substrate-based inhibitor complexes of CA C1 family proteases show a series of conserved hydrogen bonds between the inhibitor and the protease backbone, which contribute significantly to inhibitor potency. Primarily a bidentate hydrogen-bond is observed between the protease Gly66 (C═O)/inhibitor N—H and the protease Gly66(NH)/inhibitor (C═O), where the inhibitor (C═O) and (NH) are provided by an amino acid residue NHCHRCO that constitutes the S2 sub-site binding element within the inhibitor (see Berger, A. and Schecter, I. *Philos. Trans. R. Soc. Lond.* [Biol.], 257, 249-264, 1970 for a description of protease binding site nomenclature). A further hydrogen-bond between the protease main-chain (C═O) of asparagine or aspartic acid (158 to 163, residue number varies between proteases) and an inhibitor (N—H) is often observed, where the inhibitor (N—H) is provided by the S1 sub-site binding element within the inhibitor. Thus, the motif X—NHCHR CO—NH—Y is widely observed amongst the prior art substrate-based inhibitors of CA C1 proteases.

In the prior art, the development of cysteine protease inhibitors for human use has recently been an area of intense activity. Considering the CA C1 family members, particular emphasis has been placed upon the development of inhibitors of human cathepsins, primarily cathepsin K (osteoporosis), cathepsin S (autoimmune disorders) and cathepsin L (metastases), through the use of peptide and peptidomimetic nitriles (e.g. see WO-A-0109910, WO-A-0051998, WO-A-0119816, WO-A-9924460, WO-A-0049008, WO-A-0048992, WO-A-0049007, WO-A-0130772, WO-A-0055125, WO-A-0055126, WO-A-0119808, WO-A-0149288, WO-A-0147886), linear and cyclic peptide and peptidomimetic ketones (e.g. see Veber, D. F. and Thompson, S. K, *Curr. Opin. Drug Discovery Dev.,* 3(4), 362-369, 2000, WO-A-0170232, WO-A-0178734, WO-A-0009653, WO-A-0069855, WO-A-0029408, WO-A-0134153 to WO-A-0134160, WO-A-0029408, WO-A-9964399, WO-A-9805336, WO-A-9850533), ketoheterocycles (e.g. see WO-A-0055144, WO-A-0055124) and monobactams (e.g. see WO-A-0059881, WO-A-9948911, WO-A-0109169). The prior art describes potent in vitro inhibitors, but also highlights the many difficulties in developing a human therapeutic. For example, WO-A-9850533 and WO-A-0029408 describe compounds that may be referred to as cyclic ketones and are inhibitors of cysteine proteases with a particular reference towards papain family proteases and as a most preferred embodiment, cathepsin K. WO-A-9850533 describes compounds subsequently detailed in the literature as potent inhibitors of cathepsin K with good oral bioavailability (Witherington, J., 'Tetrahydrofurans as Selective Cathepsin K inhibitors', RSC meeting, Burlington House, London, 1999). The compounds of WO-A-9850533 were reported to bind to cathepsin K through the formation of a reversible covalent bond between the tetrahydrofuran carbonyl and the active site catalytic cysteine residue (Witherington, J., 1999). Additionally, the same cyclic ketone compounds are described in WO-A-9953039 as part of a wide-ranging description of inhibitors of cysteine proteases associated with parasitic diseases, with particular reference to the treatment of malaria by inhibition of falcipain. However, subsequent literature describes the cyclic ketone compounds of WO-A-9850533 to be unsuitable for further development or for full pharmacokinetic evaluation due to a physiochemical property of the inhibitors, the poor chiral stability of the α-aminoketone chiral centre (Marquis, R. W. et al, J. Med. Chem., 44-(5), 725-736, 2001). WO-A-0069855 describes compounds that may also be referred to as cyclic ketones with particular reference towards inhibition of cathepsin S. The compounds of WO-A-0069855 are considered to be an advance on compounds of WO-A-9850533 due to the presence of the β-substituent on the cyclic ketone ring system that provides chiral stability to the α-carbon of the cyclic ketone ring system. However, the compounds of WO-A-0069855 and indeed those of WO-A-9850533 describe a requirement for the presence of the potential hydrogen-bonding motif X-NHCHRCO—NH—Y that is widely observed amongst the prior art substrate-based inhibitors of CA C1 proteases.

It has now been discovered that certain compounds, defined by general formulae (I) and (II), are potent and selective cruzipain protease inhibitors which are useful in the treatment of *Trypanosoma cruzi* infection. Other compounds defined by general formulae (I) and (II) are protease inhibitors across a broad range of CA C1 cysteine proteases and compounds useful in the treatment of diseases caused by cysteine proteases. Compounds described by general formulae (I) and (II) do not contain the X—<u>NHCHRCO</u>—NH—Y motif that is widely observed amongst the prior art substrate-based inhibitors of CA C1 proteases, yet surprisingly compounds defined by general formulae (I) and (II) retain good potency. The present invention provides substituted tetrahydrofuro[3,2-b]pyrrol-3-one, tetrahydrothieno[3,2-b]pyrrol-3-one, hexahydropyrrolo[3,2-b]pyrrol-3-one, hexahydrocyclopenta[b]pyrrol-6-one, tetrahydrofuro[3,2-c]pyrazol-6-one, tetrahydrothieno[3,2-c]pyrazol-6-one, hexahydropyrrolo[3,2-c]pyrazol-6-one, hexahydrocyclopentapyrazol-6-one, hexahydrofuro[3,2-b]pyridin-3-one, hexahydrothieno[3,2-b]pyridin-3-one, octahydropyrrolo[3,2-b]pyridin-3-one, octahydrocyclopenta[b]pyridin-7-one, hexahydrofuro[3,2-c]pyridazin-7-one, hexahydrothieno[3,2-c]pyridazin-7-one, octahydropyrrolo[3,2-c]pyridazin-7-one or octahydrocyclopenta[c]pyridazin-7-one bicyclic compounds defined by general formulae (I) and (II).

Accordingly, the first aspect of the invention provides a compound according to general formula (I) or general formula (II):—

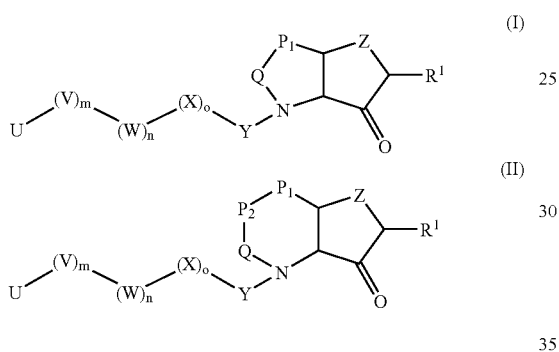

wherein: $R^1 = C_{0-7}$-alkyl (when C=0, $R^1$ is simply hydrogen), $C_{3-6}$-cycloalkyl or Ar—$C_{0-7}$-alkyl (when C=0, $R^1$ is simply an aromatic moiety Ar);

Z=O, S, $CR^2R^3$ or $NR^4$, where $R^4$ is chosen from $C_{0-7}$-alkyl, $C_{3-6}$-cycloalkyl or Ar—$C_{0-7}$-alkyl;

$P^1 = CR^5R^6$, $P^2 = CR^7R^8$,

Q=$CR^9R^{10}$ or $NR^{11}$, where $R^{11}$ is chosen from $C_{0-7}$-alkyl, $C_{3-6}$-cycloalkyl or Ar—$C_{0-7}$-alkyl;

Each of $R^2$, $R^3$, $R^5$, $R^6$, $R^7$, $R^8$, $R^9$ and $R^{10}$ is independently chosen from $C_{0-7}$-alkyl, $C_{3-6}$-cycloalkyl, Ar—$C_{0-7}$-alkyl, O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N($C_{0-7}$-alkyl)$_2$, N($C_{3-6}$-cycloalkyl)$_2$ or N(Ar—$C_{0-7}$-alkyl)$_2$;

Y=$CR^{12}R^{13}$—CO, where $R^{12}$, $R^{13}$ are chosen from $C_{0-7}$-alkyl, $C_{3-6}$-cycloalkyl or Ar—$C_{0-7}$-alkyl;

$(X)_o = CR^{14}R^{15}$, where $R^{14}$ and $R^{15}$ are independently chosen from $C_{0-7}$ alkyl, $C_{3-6}$-cycloalkyl and Ar—$C_{0-7}$-alkyl and o is a number from zero to three;

$(W)_n$=O, S, C(O), S(O) or S(O)$_2$ or $NR^{16}$, where $R^{16}$ is chosen from $C_{0-7}$-alkyl, $C_{3-6}$-cycloalkyl and Ar—$C_{0-7}$-alkyl and n is zero or one;

$(V)_m$=C(O), C(S), S(O), S(O)$_2$, S(O)$_2$NH, OC(O), NHC(O), NHS(O), NHS(O)$_2$, OC(O)NH, C(O)NH or $CR^{17}R^{18}$, where $R^{17}$ and $R^{18}$ are independently chosen from $C_{0-7}$-alkyl, $C_{3-6}$-cycloalkyl, Ar—$C_{0-7}$-alkyl and m is a number from zero to three, provided that when m is greater than one, $(V)_m$ contains a maximum of one carbonyl or sulphonyl group;

U=a stable 5- to 7-membered monocyclic or a stable 8- to 11-membered bicyclic ring which is either saturated or unsaturated and which includes zero to four heteroatoms (as detailed below):

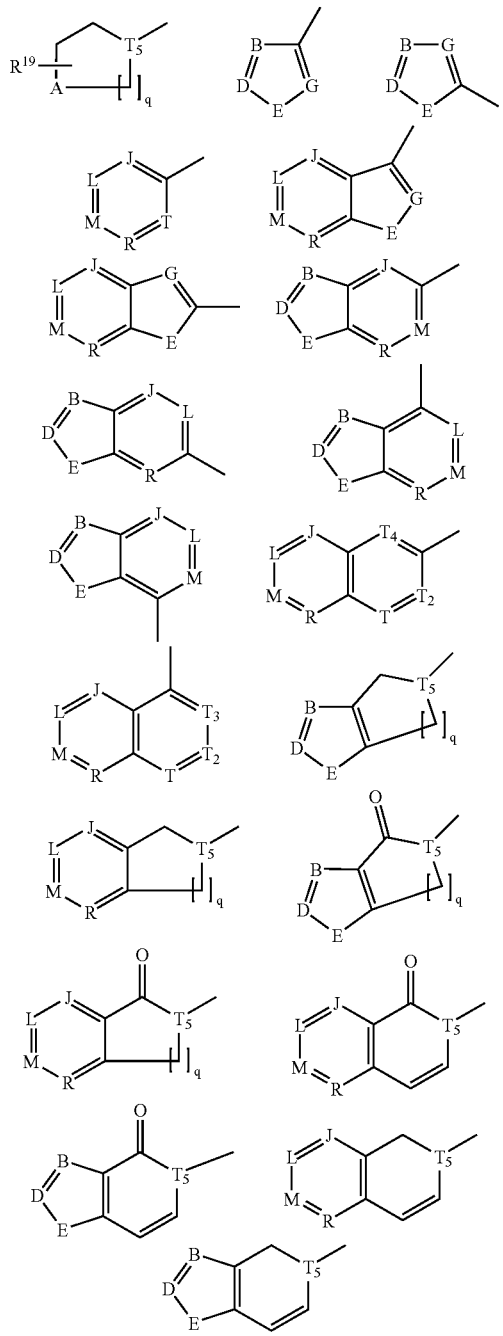

wherein $R^{19}$ is:

$C_{0-7}$-alkyl, $C_{3-6}$-cycloalkyl, Ar—$C_{0-7}$-alkyl, O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$CO_{0-7}$-alkyl, N($C_{0-7}$-alkyl)$_2$, N($C_{3-6}$-cycloalkyl)$_2$ or N(Ar—$C_{0-7}$-alkyl)$_2$; or, when part of a $CHR^{19}$ or $CR^{19}$ group, $R^{19}$ may be halogen;

A is chosen from:
    $CH_2$, $CHR^{19}$, O, S and $NR^{20}$;
        where $R^{19}$ is as defined above; and $R^{20}$ is chosen from:
            $C_{0-7}$-alkylyl, $C_{3-6}$-cycloalkyl and Ar—$C_{0-7}$-alkyl;
B, D and G are independently chosen from:
    $CR^{19}$, where $R^{19}$ is as defined above, or N;
E is chosen from:
    $CH_2$, $CHR^{19}$, O, S and $NR^{20}$, where $R^{19}$ and $R^{20}$ are defined as above;
J, L, M, R, T, $T_2$, $T_3$ and $T_4$ are independently chosen from:
    $CR^{19}$ and N, where $R^{19}$ is as defined above;
$T_5$ is chosen from:
    CH or N;
q is a number from one to three, thereby defining a 5-, 6- or 7-membered ring.

B, D, G, J, L, M, R, T, $T_2$, $T_3$ and $T_4$ may additionally represent an N-oxide (N→O).

The present invention includes all salts, hydrates, solvates, complexes and prodrugs of the compounds of this invention. The term "compound" is intended to include all such salts, hydrates, solvates, complexes and prodrugs, unless the context requires otherwise.

Appropriate pharmaceutically and veterinarily acceptable salts of the compounds of general formulae (I) and (II) include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Salts which are not pharmaceutically or veterinarily acceptable may still be valuable as intermediates.

Prodrugs are any covalently bonded compounds which release the active parent drug according to general formulae (I) or (II) in vivo. A prodrug may for example constitute an acetal or hemiacetal derivative of the exocyclic ketone functionality present in the tetrahydrofuro[3,2-b]pyrrol-3-one, tetrahydrothieno[3,2-b]pyrrol-3-one, hexahydropyrrolo[3,2-b]pyrrol-3-one, hexahydrocyclopenta[b]pyrrol-6-one, tetrahydrofuro[3,2-c]pyrazol-6-one, tetrahydrothieno[3,2-c]pyrazol-6-one, hexahydropyrrolo[3,2-c]pyrazol-6-one, hexahydrocyclopentapyrazol-6-one, hexahydrofuro[3,2-b]pyridin-3-one, hexahydrothieno[3,2-b]pyridin-3-one, octahydropyrrolo[3,2-b]pyridin-3-one, octahydrocyclopenta[b]pyridin-7-one, hexahydrofuro[3,2-c]pyridazin-7-one, hexahydrothieno[3,2-c]pyridazin-7-one, octahydropyrrolo[3,2-c]pyridazin-7-one or octahydrocyclopenta[c]pyridazin-7-one scaffold. If a chiral centre or another form of isomeric centre is present in a compound of the present invention, all forms of such isomer or isomers, including enantiomers and diastereoisomers, are intended to be covered herein. Compounds of the invention containing a chiral centre may be used as a racemic mixture, an enantiomerically enriched mixture, or the racemic mixture may be separated using well-known techniques and an individual enantiomer may be used alone.

'Halogen' as applied herein is meant to include F, Cl, Br, I;

'Heteroatom' as applied herein is meant to include O, S and N;

'$C_{0-7}$-alkyl' as applied herein is meant to include stable straight and branched chain aliphatic carbon chains containing zero (i.e. simply hydrogen) to seven carbon atoms such as methyl, ethyl, n-propyl, isopropyl, n-butyl, isobutyl, t-butyl, pentyl, isopentyl, hexyl, heptyl and any simple isomers thereof. Additionally, any $C_{0-7}$-alkyl may optionally be substituted at any point by one, two or three halogen atoms (as defined above) for example to give a trifluoromethyl substituent. Furthermore, $C_{0-7}$-alkyl may contain one or more heteroatoms (as defined above) for example to give ethers, thioethers, sulphones, sulphonamides, substituted amines, amidines, guanidines, carboxylic acids, carboxamides. If the heteroatom is located at a chain terminus then it is appropriately substituted with one or two hydrogen atoms. A heteroatom or halogen is only present when $C_{0-7}$-alkyl contains a minimum of one carbon atom.

'$C_{3-6}$-cycloalkyl' as applied herein is meant to include any variation of '$C_{0-7}$-alkyl' which additionally contains a carbocyclic ring such as cyclopropyl, cyclobutyl, cyclopentyl, cyclohexyl. The carbocyclic ring may optionally be substituted with one or more halogens (as defined above) or heteroatoms (as defined above) for example to give a tetrahydrofuran, pyrrolidine, piperidine, piperazine or morpholine substituent.

'Ar—$C_{0-7}$-alkyl' as applied herein is meant to include any variation of $C_{0-7}$-alkyl which additionally contains an aromatic ring moiety 'Ar'. The aromatic ring moiety Ar can be a stable 5 or 6-membered monocyclic or a stable 9 or 10 membered bicyclic ring which is unsaturated, as defined previously for U in general formulae (I) and (II). The aromatic ring moiety Ar may be substituted by $R^{19}$ (as defined above for U in general formulae (I) and (II)). When C=0 in the substituent Ar—$C_{0-7}$-alkyl, the substituent is simply the aromatic ring moiety Ar.

Other expressions containing terms such as alkyl and cycloalkyl are intended to be construed according to the definitions above. For example "$C_{1-4}$ alkyl" is the same as $C_{0-7}$-alkyl except that it contains from one to four carbon atoms.

If different structural isomers are present, and/or one or more chiral centres are present, all isomeric forms are intended to be covered. Enantiomers are characterised by the absolute configuration of their chiral centres and described by the R- and S-sequencing rules of Calm, Ingold and Prelog. Such conventions are well known in the art (e.g. see 'Advanced Organic Chemistry', 3rd edition, ed. March, J., John Wiley and Sons, New York, 1985).

Preferred compounds of general formulae (I) and (II) include, but are not limited to, those in which, independently or in combination:
Z is O, S, NH or $CH_2$;
$P^1$ and $P^2$ are $CH_2$; and
Q is $CH_2$ or NH.

Also, preferred compounds of general formulae (I) and (II) include, but are not limited to, those in which, independently or in combination
Z is $NR^4$, where $R^4$ is a Ar—$C_{1-4}$-alkyl or a substituted carbonyl or sulphonyl group;
$P^1$ and $P^2$ are $CH_2$; and
Q is $CH_2$ or NH.

Thus, examples of preferred compounds include those containing a bicyclic moiety chosen from tetrahydrofuro[3,2-b]pyrrol-3-one, tetrahydrothieno[3,2-b]pyrrol-3-one, hexahydropyrrolo[3,2-b]pyrrol-3-one, hexahydrocyclopenta[b]pyrrol-6-one, tetrahydrofuro[3,2-c]pyrazol-6-one, tetrahydro-thieno[3,2-c]pyrazol-6-one, hexahydropyrrolo[3,2-c]pyrazol-6-one, hexahydro-cyclo-pentapyrazol-6-one, hexahydrofuro[3,2-b]pyridin-3-one, hexahydrothieno[3,2-b]pyridin-3-one, octahydropyrrolo[3,2-b]pyridin-3-one, octahydrocyclopenta[b]pyridin-7-one, hexahydrofuro[3,2-c]pyridazin-7-one, hexahydrothieno[3,2-c]pyridazin-7-one, octahydropyrrolo[3,2-c]pyridazin-7-one or octahydrocyclopenta[c]pyridazin-7-one as shown below.

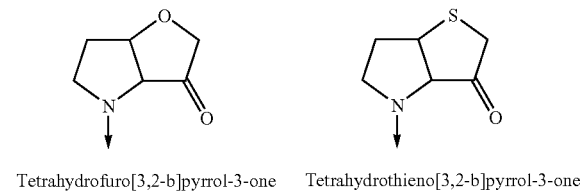

Tetrahydrofuro[3,2-b]pyrrol-3-one   Tetrahydrothieno[3,2-b]pyrrol-3-one

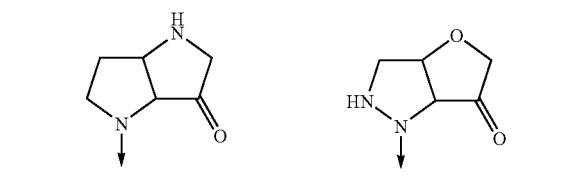

Hexahydropyrrolo[3,2-b]pyrrol-3-one   Tetrahydrofuro[3,2-c]pyrazol-6-one

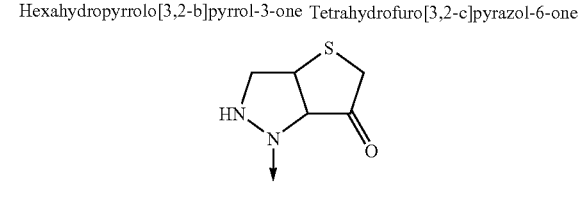

Tetrahydrothieno[3,2-c]pyrazol-6-one

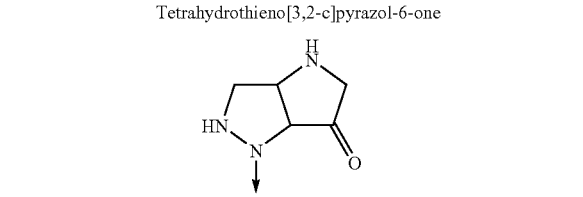

Hexahydropynolo[3,2-c]pyrazol-6-one

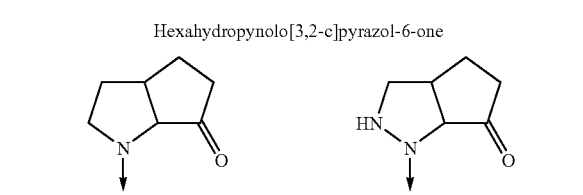

Hexahydrocyclopenta[b]pyrrol-6-one   Hexahydrocyclopentapyrazol-6-one

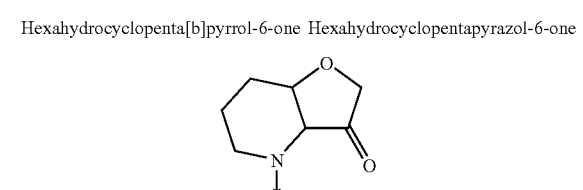

Hexahydrofuro[3,2-b]pyridin-3-one

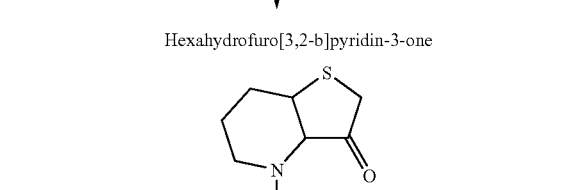

Hexahydrothieno[3,2-b]pyridin-3-one

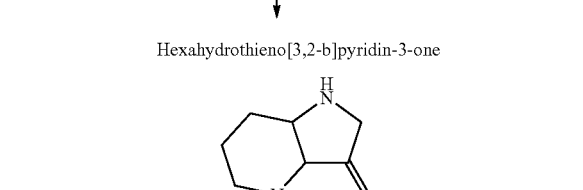

Octahydropyrrolo[3,2-b]pyridin-3-one

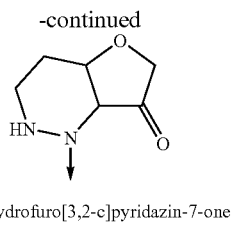

Hexahydrofuro[3,2-c]pyridazin-7-one

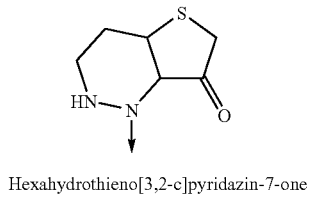

Hexahydrothieno[3,2-c]pyridazin-7-one

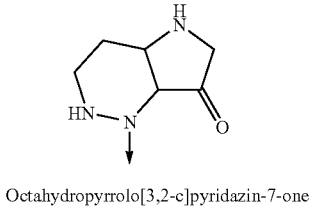

Octahydropyrrolo[3,2-c]pyridazin-7-one

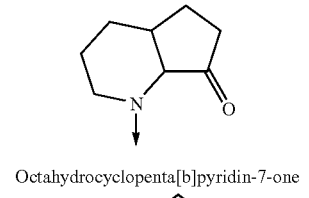

Octahydrocyclopenta[b]pyridin-7-one

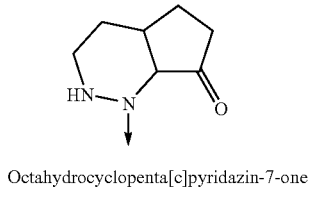

Octahydrocyclopenta[c]pyridazin-7-one

In compounds of general formulae (I) and (II), it is preferred that $R^1$ comprises $C_{0-7}$-alkyl or Ar—$C_{0-7}$-alkyl. Thus, for example, preferred $R^1$ moieties include hydrogen, or a straight or branched alkyl chain, or a straight or branched heteroalkyl chain, or an optionally substituted arylalkyl chain, or an optionally substituted arylheteroalkyl chain.

It is particularly preferred that $R^1$ is hydrogen or $C_{1-4}$ alkyl or Ar—$C_{1-4}$-alkyl and examples of such $R^1$ substituents include, but are not limited to:

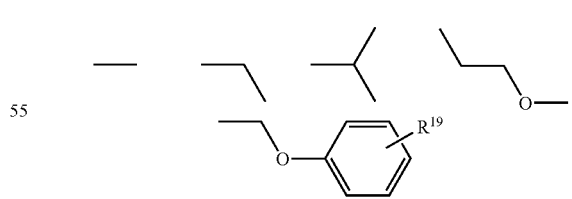

where $R^{19}$ is defined above.

In preferred compounds of general formulae (I) and (II), Y is $CHR^{13}CO$ where $R^{13}$ is selected from $C_{0-7}$-alkyl or Ar—$C_{0-7}$-alkyl, for example hydrogen, a straight or branched alkyl chain, a straight or branched heteroalkyl chain, an optionally substituted arylalkyl chain or an optionally substituted arylheteroalkyl chain. Additionally, in preferred compounds of general formulae (I) and (II), $R^{13}$ is selected from $C_{3-6}$-cycloalkyl, for example cyclohexylmethyl.

Examples of preferred Y substituents include the following:

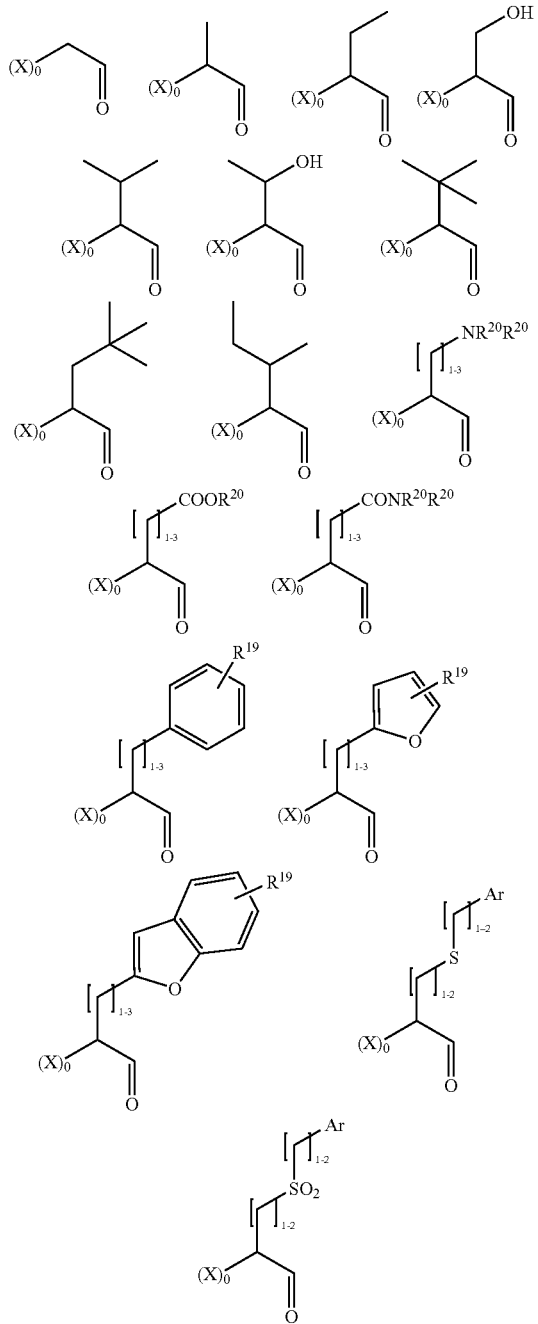

wherein $R^{19}$, $R^{20}$ and Ar are as defined above.

More preferred $R^{13}$ groups include $C_{1-4}$-alkyl, which may be substituted with OH, $NR^{20}R^{20}$, $COOR^{20}$, or $CONR^{20}$ or cycloalkylmethyl or Ar—$C_{1-4}$-alkyl, where the aryl group may be substituted with $R^{19}$; wherein each $R^{19}$ and $R^{20}$ is independently as defined above.

Even more preferred $R^{13}$ groups comprise Ar—$CH_2$—, where the aromatic ring is an optionally substituted phenyl or monocyclic heterocycle. Additionally, even more preferred $R^{13}$ groups comprise simple branched alkyl groups such as isobutyl or straight heteroalkyl chains such as benzylsulfanylmethyl or benzylsulphonylmethyl.

Furthermore, even more preferred $R^{13}$ groups comprise cyclohexylmethyl. Examples of even more preferred Y substituents comprise the following,

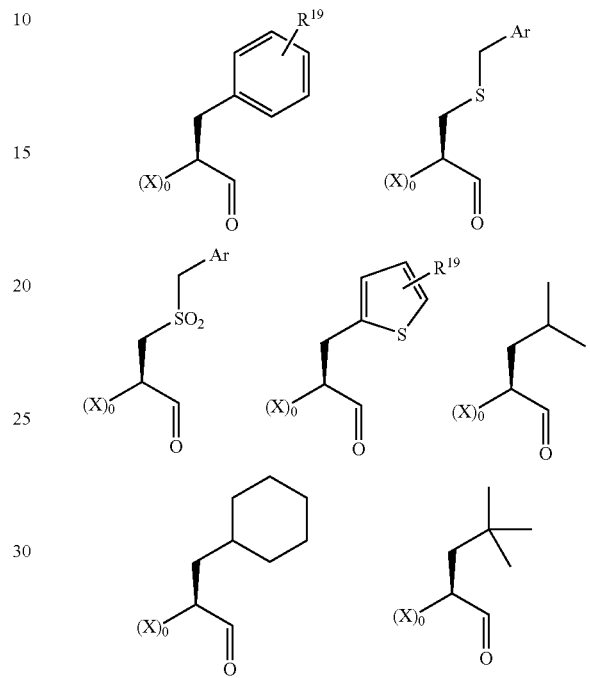

wherein $R^{19}$ and Ar are as defined previously

It is preferred that in the group $(X)_o$, each of $R^{14}$ and $R^{15}$ is selected from $C_{0-7}$-alkyl or Ar—$C_{0-7}$-alkyl, for example hydrogen, a straight or branched alkyl chain, a straight or branched heteroalkyl chain, an optionally substituted arylalkyl chain or an optionally substituted arylheteroalkyl chain.

More preferred $(X)_o$ groups comprise $R^{14}$ chosen from hydrogen; $R^{15}$ is $C_{1-4}$-alkyl, which may be substituted with OH, $NR^{20}R^{20}$, $COOR^{20}$, or $CONR^{20}$; or Ar—$C_{1-4}$-alkyl, where the aryl group may be substituted with $R^{19}$, wherein each $R^{19}$ and $R^{20}$ is independently as defined above.

Examples of preferred $(X)_o$ groups include the following:

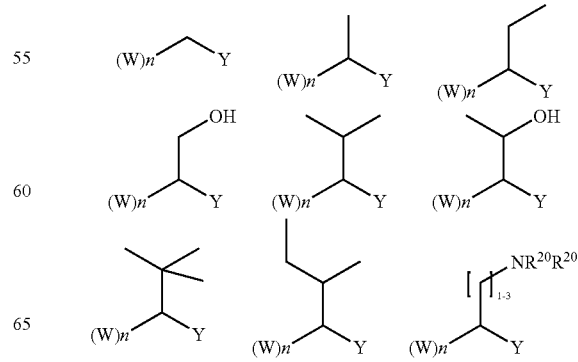

-continued

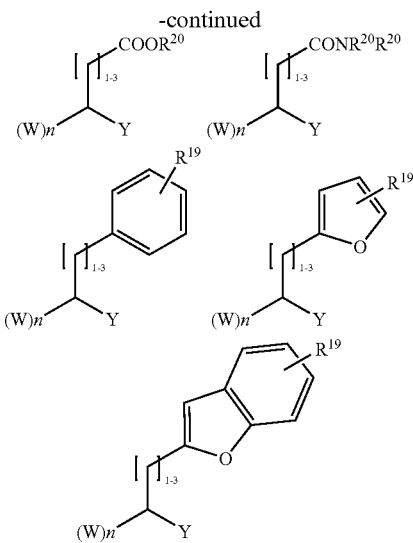

wherein $R^{19}$ and $R^{20}$ are as defined previously.

Even more preferred compounds of general formulae (I) and (II), comprise $(X)_o$ groups that are simple alkyl groups such as methylene and where o=0 or 1.

In the group $(W)_n$, W is preferably O, S, $SO_2$, S(O), C(O) or $NR^{16}$, where $R^{16}$ is $C_{0-4}$-alkyl; and n is 0 or 1.

More preferred compounds of general formulae (I) and (II), comprise $(W)_n$ groups defined as O, S, $SO_2$, C(O) and NH where n=0 or 1.

Yet even more preferred compounds of general formulae (I) and (II), comprise $(W)_n$ groups defined as NH where n=1.

In the group $(V)_m$:

V is preferably C(O), C(O)NH or $CHR^{18}$, where $R^{18}$ is $C_{0-4}$-alkyl; and m is 0 or 1.

Preferred V and W substituent combinations encompassed by general formulae (I) and (II) include, but are not limited to:

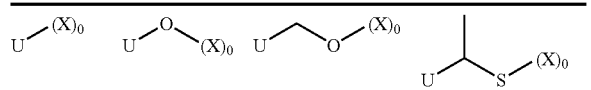

| 'n' = 0 | 'n' = 1 | 'n' = 1 | 'n' = 1 |
| 'm' = 0 | 'W' = O | 'W' = O | 'W' = S |
|  | 'm' = 0 | 'V' = C(O) | 'W' = $NR^{16}$ |
|  |  | 'm' = 1 | 'm' = 1 |

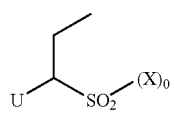 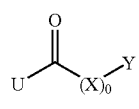

| 'n' = 1 | 'n' = 0 |
| 'W' = $SO_2$ | 'V' = C(O) |
| 'V' = $CH(CH_2CH_3)$ | 'm' = 1 |
| 'm' = 1 |  |

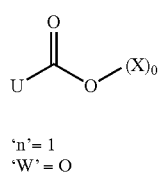

| 'n'= 1 | $(X)_o > 0$ |
| 'W' = O | 'n' = 1 |

| 'V' = C(O) | 'W' = $NR^{16}$ |
| 'm' = 1 | $R^{16}$ = H |
|  | 'V' = C(O) |
|  | 'm' = 1 |

Additionally, a preferred V and W substituent combination encompassed by general formulae (I) and (II) includes, but is not limited to:

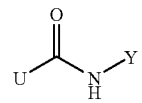

$(X)_0$ = '-'
n = 1
'W' = $NR^{16}$, $R^{16}$ = 'H'
'V' = C(O)
m = 1

More preferred V, W and X substituent combinations encompassed by general formulae (I) and (II) comprise, but are not limited to

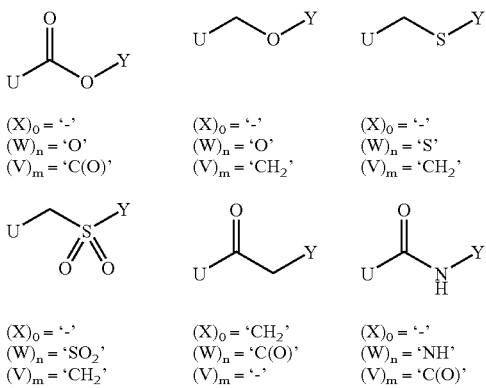

| $(X)_0$ = '-' | $(X)_0$ = '-' | $(X)_0$ = '-' |
| $(W)_n$ = 'O' | $(W)_n$ = 'O' | $(W)_n$ = 'S' |
| $(V)_m$ = 'C(O)' | $(V)_m$ = '$CH_2$' | $(V)_m$ = '$CH_2$' |

| $(X)_0$ = '-' | $(X)_0$ = '$CH_2$' | $(X)_0$ = '-' |
| $(W)_n$ = '$SO_2$' | $(W)_n$ = 'C(O)' | $(W)_n$ = 'NH' |
| $(V)_m$ = '$CH_2$' | $(V)_m$ = '-' | $(V)_m$ = 'C(O)' |

In preferred compounds of general formulae (I) and (II), U comprises an optionally substituted 5- or 6-membered saturated or unsaturated heterocycle or Ar group or an optionally substituted saturated or unsaturated 9- or 10-membered heterocycle or Ar group. Examples of such preferred U rings include the following:

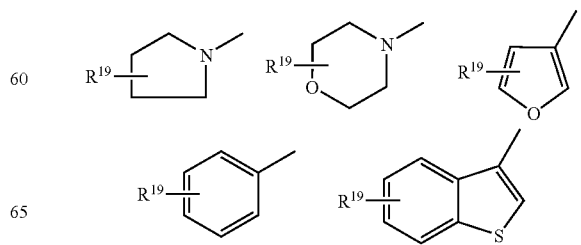

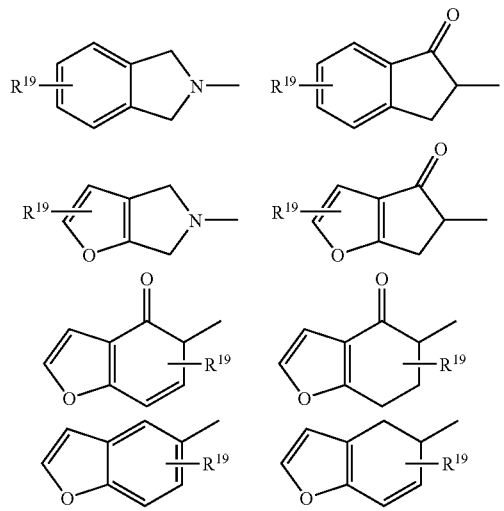

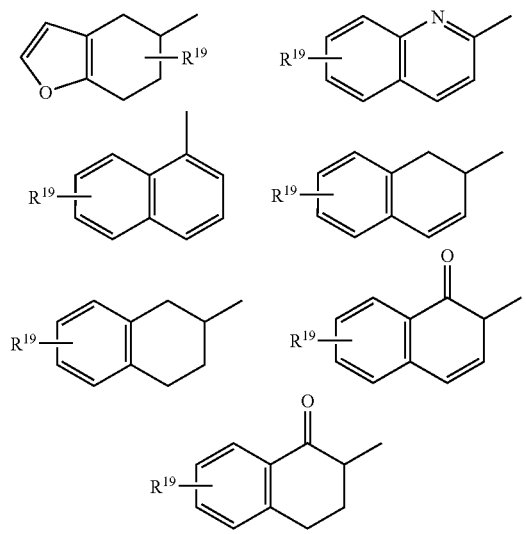

and also the following

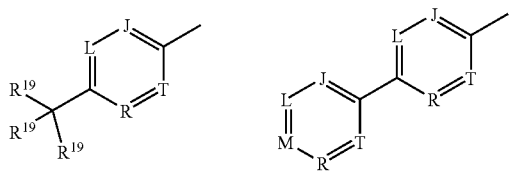

wherein $R^{19}$ is as defined previously.

More preferred compounds of general formulae (I) and (II), contain a U group comprising of a bulky alkyl or aryl group at the para position of an aryl Ar. Also, more preferred compounds contain a meta or para-biaryl Ar—Ar, where Ar is as previously defined. Additionally, more preferred compounds contain a 6,6 or 6,5 or 5,6-fused aromatic ring. Examples of more preferred U groups are

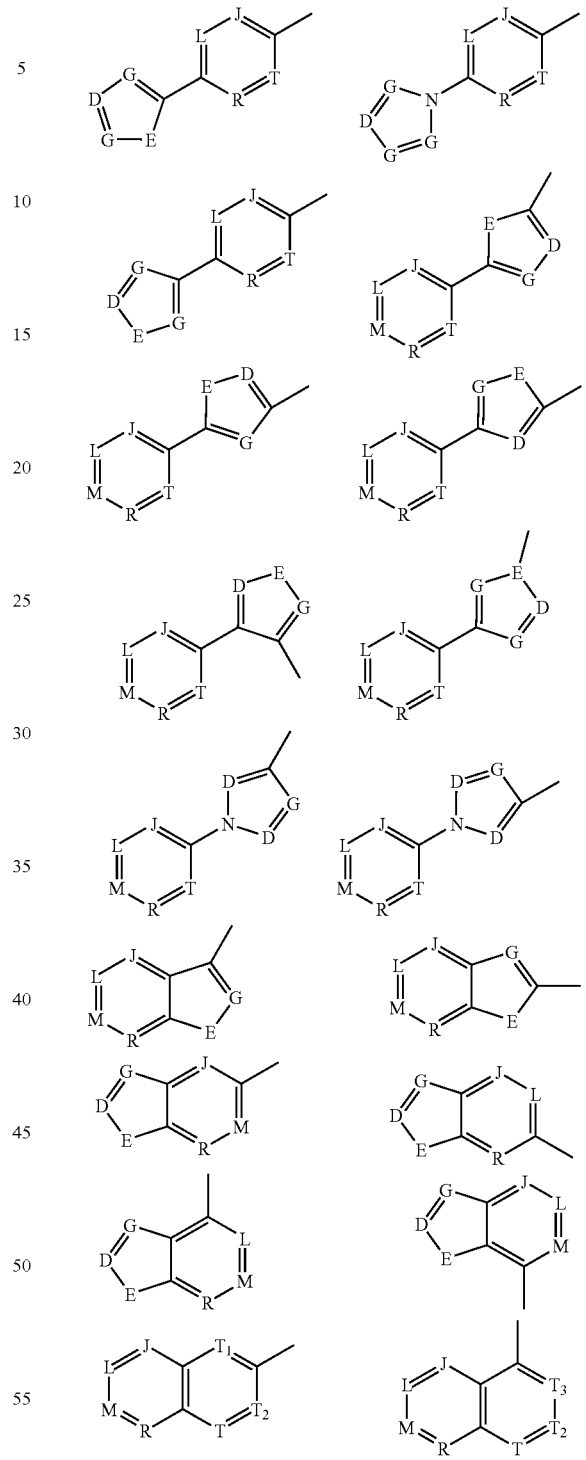

wherein $R^{19}$, D, E, G. J. L, M, R, T, $T_2$, $T_3$ and $T_4$ are as defined previously.

Even more preferred compounds of general formulae (I) and (II), particularly for inhibition of cruzipain, contain a U group comprising a 6-membered Ar ring containing a bulky alkyl or aryl group at the para position, where Ar is as previously defined

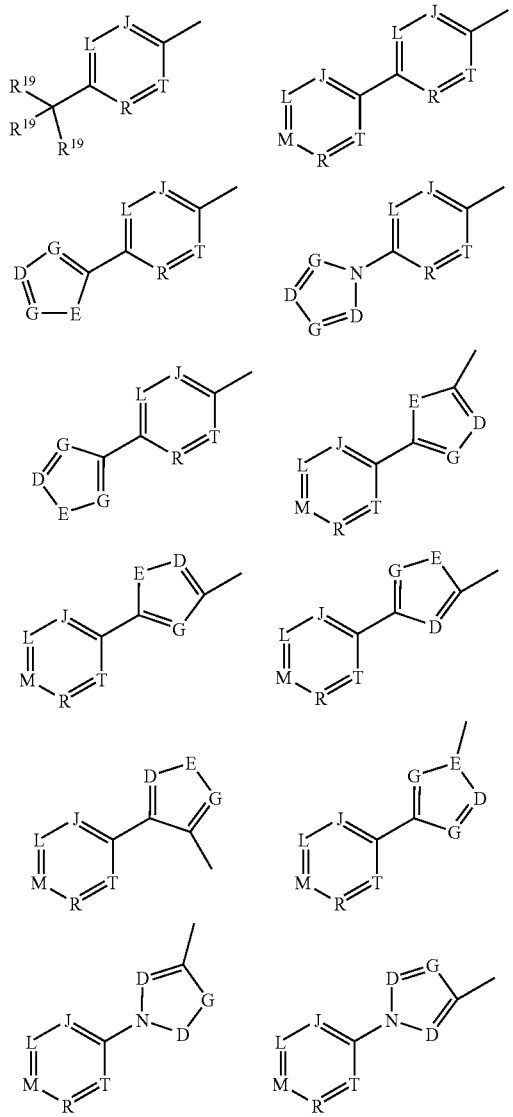

wherein $R^{19}$, D, E, G. J, L, M, R and T are as defined previously

Yet even more preferred compounds of general formulae (I) and (II), contain a U group comprising but are not limited to the following,

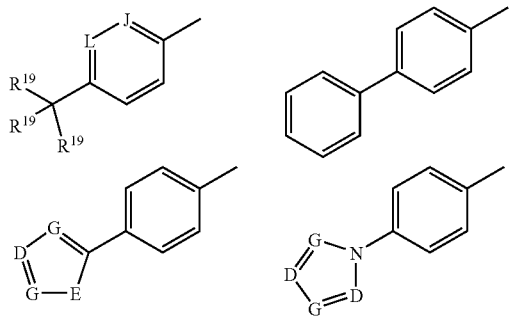

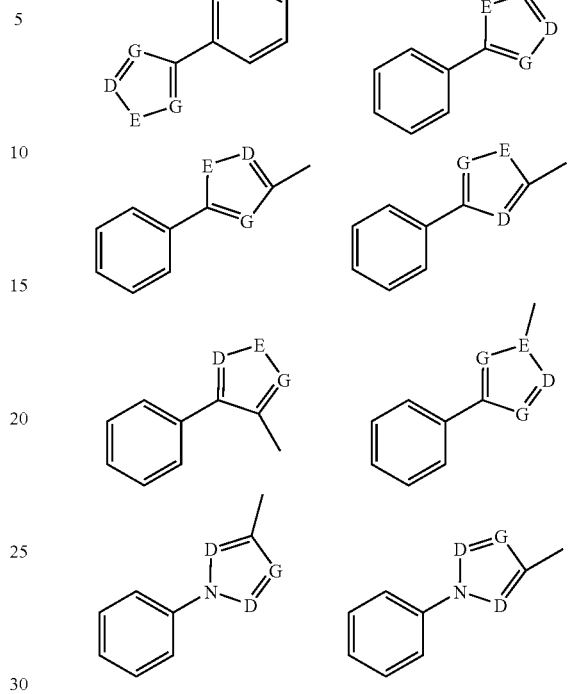

wherein $R^{19}$, D, E, G, J and L are as defined previously.

Abbreviations and symbols commonly used in the peptide and chemical arts are used herein to describe compounds of the present invention, following the general guidelines presented by the IUPAC-IUB Joint Commission on Biochemical Nomenclature as described in *Eur. J. Biochem.*, 158, 9-, 1984. Compounds of formulae (I) and (II) and the intermediates and starting materials used in their preparation are named in accordance with the IUPAC rules of nomenclature in which the characteristic groups have decreasing priority for citation as the principle group. An example compound of formula (I), compound (1) in which $R^1$ is H, $P_1$ is methylene, Q is methylene, Z is oxygen, Y is 4-methylpentyl, $(X)_o$ is zero, $(W)_n$ is oxygen, $(V)_m$ is methylene and U is phenyl is thus named:

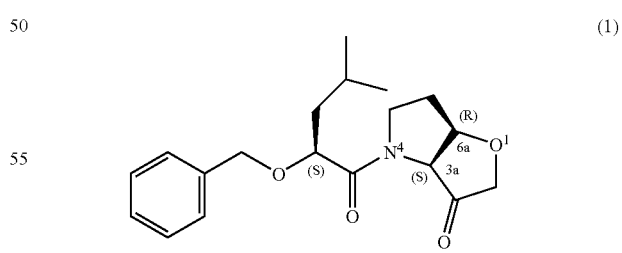

(3aS,6aR) 4-(2S-Benzyloxy methylpentanoyl)tetrahydrofuro[3,2-b]pyrrol-3-one

A second example compound of formula (I), compound (2) in which $R^1$ is H, $P_1$ is methylene, Q is methylene, Z is sulphur, Y is 4-methylpentyl, $(X)_o$ is zero, $(W)_n$ is oxygen, $(V)_m$ is methylene and U is phenyl is thus named:

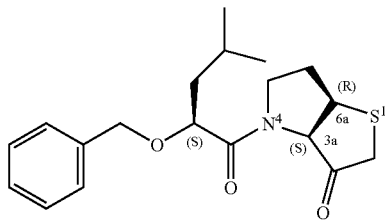

(3aR,6aR) 4-(2S-Benzyloxy-4-methylpentanoyl)tetrahydrothieno[3,2-b]pyrrol-3-one

A third example compound of formula (I), compound (3) in $R^1$ is H, $P_1$ is methylene, Q is methylene, Z is methylene, Y is 4-methylpentyl, $(X)_o$ is zero, $(W)_n$ is oxygen, $(V)_m$ is methylene and U is phenyl is thus named:

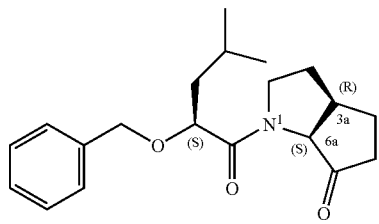

(3aR,6aS) 1-(2S-Benzyloxy-4-methylpentanoyl)hexahydrocyclopenta[b]pyrrol-6-one

A fourth example compound of formula (I), compound (4) in $R^1$ is H, $P_1$ is methylene, Q is methylene, Z is NH, Y is 4-methylpentyl, $(X)_o$ is zero, $(W)_n$ is oxygen, $(V)_m$ is methylene and U is phenyl is thus named:

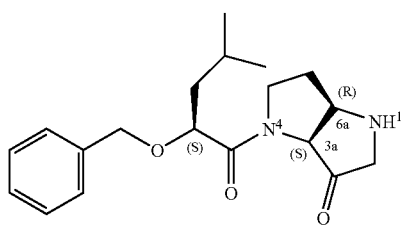

(3aS,6aR) 1-(2S-Benzyloxy-4-methylpentanoyl)hexahydropyrrolo[3,2-b]pyrrol-3-one

A fifth example compound of formula (I), compound (5) in which $R^1$ is H, $P_1$ is methylene, Q is NH, Z is oxygen, Y is 4-methylpentyl, $(X)_o$ is zero, $(W)_n$ is oxygen, $(V)_m$ is methylene and U is phenyl is thus named:

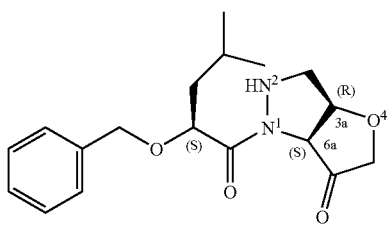

(3aR,6aS) 4-(2S-Benzyloxy-4-methylpentanoyl)tetrahydrofuro[3,2-c]pyrazol-6-one

A sixth example compound of formula (I), compound (6) in which $R^1$ is H, $P_1$ is methylene, Q is NH, Z is sulphur, Y is 4-methylpentyl, $(X)_o$ is zero, $(W)_n$ is oxygen, $(V)_m$ is methylene and U is phenyl is thus named:

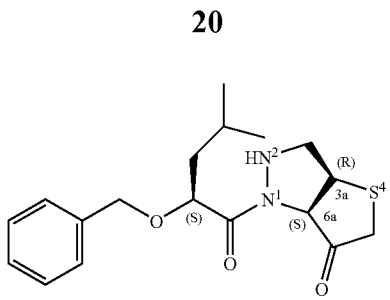

(3aR,6aR) 4-(2S-Benzyloxy-4-methylpentanoyl)tetrahydrothieno[3,2-c]pyrazol-6-one A seventh example compound of formula (I), compound (7) in $R^1$ is H, $P_1$ is methylene, Q is NH, Z is methylene, Y is 4-methylpentyl, $(X)_o$ is zero, $(W)_n$ is oxygen, $(V)_m$ is methylene and U is phenyl is thus named:

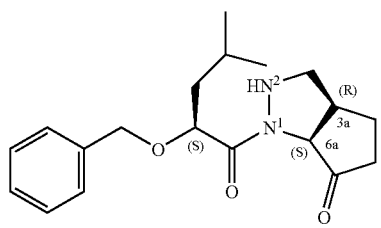

(3aR,6aS) 1-(2S-Benzyloxy-4-methylpentanoyl)hexahydrocyclopentapyrazol-6-one

An eighth example compound of formula (I), compound (8) in $R^1$ is H, $P_1$ is methylene, Q is NH, Z is NH, Y is 4-methylpentyl, $(X)_o$ is zero, $(W)_n$ is oxygen, $(V)_m$ is methylene and U is phenyl is thus named:

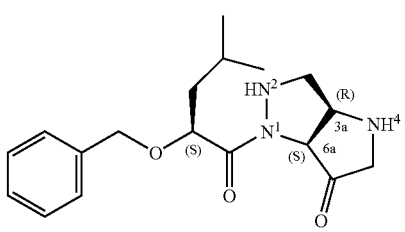

(3aR,6aS) 1-(2S-Benzyloxy-4-methylpentanoyl)hexahydropyrrolo[3,2-c]pyrazol-6-one An example compound of formula (II), compound (9) in which $R^1$ is H, $P_1$ is methylene, $P_2$ is methylene, Q is methylene, Z is oxygen, Y is 4-methylpentyl, $(X)_o$ is zero, $(W)_n$ is oxygen, $(V)_m$ is methylene and U is phenyl is thus named:

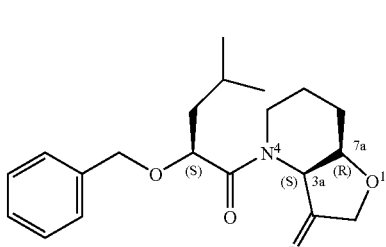

(3aS,7aR) 4-(2S-Benzyloxy-4-methylpentanoyl)hexahydrofuro[3,2-b]pyridin-3-one

A second example compound of formula (II), compound (10) in which $R^1$ is H, $P_1$ is methylene, $P_2$ is methylene, Q is methylene, Z is sulphur, Y is 4-methylpentyl, $(X)_o$ is zero, $(W)_n$ is oxygen, $(V)_m$ is methylene and U is phenyl is thus named:

(10)

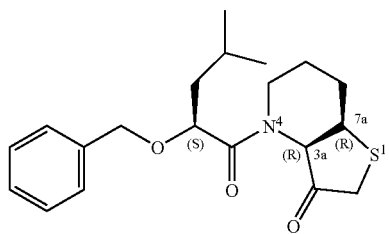

(3aR,7aR) 4-(2S-Benzyloxy-4-methylpentanoyl)hexahydrothieno[3,2-b]pyridin-3-one

A third example compound of formula (II), compound (11) in which $R^1$ is H, $P_1$ is methylene, $P_2$ is methylene, Q is methylene, Z is methylene, Y is 4-methylpentyl, $(X)_o$ is zero, $(W)_n$ is oxygen, $(V)_m$ is methylene and U is phenyl is thus named:

(11)

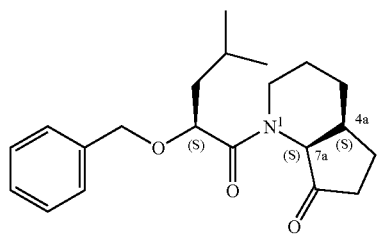

(4-aS, 7 as) 1-(2S-Benzyloxy-4-methylpentanoyl)octahydrocyclopenta[b]pyridin-7-one A fourth example compound of formula (II), compound (12) in which $R^1$ is H, $P_1$ is methylene, $P_2$ is methylene, Q is methylene, Z is NH, Y is 4-methylpentyl, $(X)_o$ is zero, $(W)_n$ is oxygen, $(V)_m$ is methylene and U is phenyl is thus named:

(12)

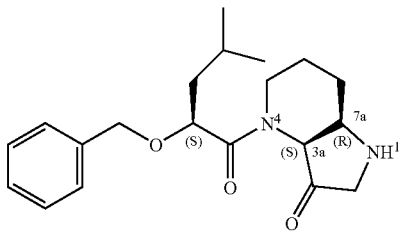

(3aS,7aR) 4-(2S-Benzyloxy-4-methylpentanoyl)octahydropyrrolo[3,2-b]pyridin-3-one A fifth example compound of formula (II), compound (13) in which $R^1$ is H, $P_1$ is methylene, $P_2$ is methylene, Q is NH, Z is oxygen, Y is 4-methylpentyl, $(X)_o$ is zero, $(W)_n$ is oxygen, $(V)_m$ is methylene and U is phenyl is thus named:

(13)

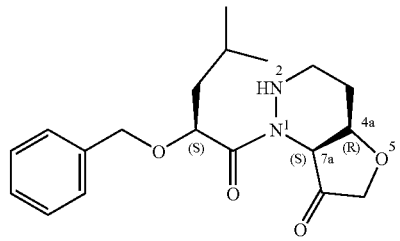

(4-aR,7aS) 4-(2S-Benzyloxy-4-methylpentanoyl)hexahydrofuro[3,2-c]pyridazin-7-one A sixth example compound of formula (II), compound (14) in which $R^1$ is H, $P_1$ is methylene, $P_2$ is methylene, Q is NH, Z is sulphur, Y is 4-methylpentyl, $(X)_o$ is zero, $(W)_n$ is oxygen, $(V)_m$ is methylene and U is phenyl is thus named:

(14)

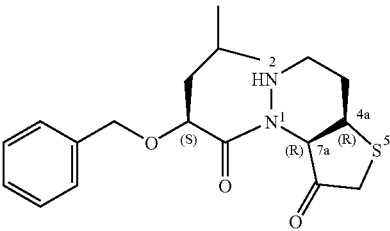

(4-aR,7aR) 4-(2S-Benzyloxy-4-methylpentanoyl)hexahydrofuro[3,2-c]pyridazin-7-one A seventh example compound of formula (II), compound (15) in which $R^1$ is H, $P_1$ is methylene, $P_2$ is methylene, Q is NH, Z is methylene, Y is 4-methylpentyl, $(X)_o$ is zero, $(W)_n$ is oxygen, $(V)_m$ is methylene and U is phenyl is thus named:

(15)

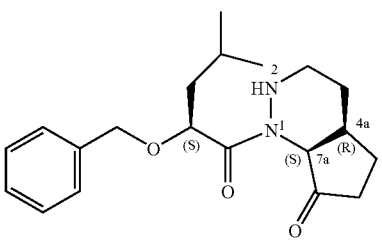

(4-aR,7aS) 4-(2S-Benzyloxy-4-methylpentanoyl)octahydrocyclopenta[c]pyridazin-7-one An eighth example compound of formula (II), compound (16) in which $R^1$ is H, $P_1$ is methylene, $P_2$ is methylene, Q is NH, Z is NH, Y is 4-methylpentyl, $(X)_o$ is zero, $(W)_n$ is oxygen, $(V)_m$ is methylene and U is phenyl is thus named:

(16)

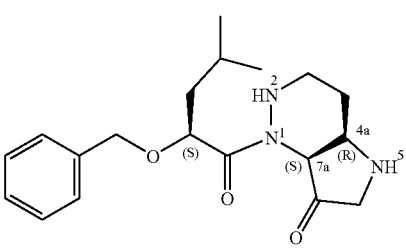

(4-aR,7aS) 4-(2S-Benzyloxy-4-methylpentanoyl)octahydropyrrolo[3,2-c]pyridazin-7-one Compounds of the invention include, but are not limited to, the following examples that are the (3aS,6aR) isomer of general formula (II), where Z='O' and $R^1$='H', and also include the equivalent analogues included in the fill definition of Z and $R^1$ N-[1-(4-Hydroxybenzyl)-2-oxo-2-(3-oxo-hexahydrofuro[3,2-b]pyrrol-4-yl)ethyl]benzamide 4-tert-Butyl-N-[1-(4-hydroxybenyl)-2-oxo-2-(3-oxo-hexahydrofuro[3,2-b]pyrrol-4-yl)ethyl]benzamide N-[1-(4-Hydroxybenzyl)-2-oxo-2-(3-oxo-hexahydrofuro[3,2-b]pyrrol-4-yl)ethyl]-4-trifluoromethoxybenzamide 4-Dimethylamino-N-[1-(4-hydroxybenzyl)-2-oxo-2-(3-oxo-hexahydrofuro[3,2-b]pyrrol-4-yl)ethyl]benzamide N-[1-(4-Hydroxybenzyl)-2-oxo-2-(3-oxo-hexahydrofuro[3,2-b]pyrrol-4-yl)ethyl]-4-isopropylbenzamide 4-Difluoromethoxy-N-[1-(4-hydroxybenzyl)-2-oxo-2-(3-oxo-hexahydrofuro[3,2-b]pyrrol-4-yl)ethyl]benzamide N-[1-(4-Hydroxybenzyl)-2-oxo-2-(3-oxo-hexahydrofuro[3,2-b]pyrrol-4-yl)ethyl]-4-trifluoromethylbenzamide 4-Bromo-N-[1-(4-hydroxybenzyl)-2-oxo-2-(3-oxo-hexahydrofuro[3,2-b]pyrrol-4-yl)ethyl]benzamide 3-Bromo-N-[1-(4-hydroxybenzyl)-2-oxo-2-(3-oxo-hexahydrofuro[3,2-b]pyrrol-4-yl)ethyl]benzamide N-[1-(4-Hydroxybenzyl)-2-oxo-2-(3-oxo-hexahydrofuro[3,2-b]pyrrol-4-yl)ethyl]-4-vinylbenzamide Naphthalene-2-carboxylic acid [1-(4-hydroxybenzyl)-2-oxo-2-(3-oxo-hexahydrofuro[3,2-b]pyrrol-4-yl)ethyl]amide Naphthalene-1-carboxylic acid [1-(4-hydroxybenzyl)-2-oxo-2-(3-oxo-hexahydrofuro[3,2-b]pyrrol-4-yl)ethyl]amide Quinoline-6-carboxylic acid [1-(4-hydroxybenzyl)-2-oxo-2-(3-oxo-hexahydrofuro[3,2-b]pyrrol-4-yl)ethyl]amide Benzo[b]thiophene-2-carboxylic acid [1-(4-hydroxybenzyl)-2-oxo-2-(3-oxo-hexa hydrofuro[3,2-b]pyrrol-4-yl)ethyl]amide Benzo[b]thiophene-3-carboxylic acid [1-(4-hydroxybenzyl)-2-oxo-2-(3-oxo-hexa hydrofuro[3,2-b]pyrrol-yl)ethyl]amide Benzothiazole-5-carboxylic acid [1-(4-hydroxybenzyl)-2-oxo-2-(3-oxo-hexahydrofuro[3,2-b]pyn-ol-4-yl)ethyl]amide Biphenyl-4-carboxylic acid [1-(4-hydroxybenzyl)-2-oxo-2-(3-oxo-hexahydrofuro[3,2-b]pyrrol-4-yl)ethyl]amide N-[1-(4-Hydroxybenzyl)-2-oxo-2-(3-oxo-hexahydrofuro[3,2-b]pyrrol-4-yl)ethyl]-4-phenoxybenzamide N-[1-(4-Hydroxybenzyl)-2-oxo-2-(3-oxo-hexahydrofuro[3,2-b]pyrrol-4-yl)ethyl]-3-phenoxybenzamide N-[1-(4-Hydroxybenzyl)-2-oxo-2-(3-oxo-hexahydrofuro[3,2-b]pyrrol-4-yl)ethyl]-4-imidazol-1-ylbenzamide N-[1-(4-Hydroxybenzyl)-2-oxo-2-(3-oxo-hexahydrofuro[3,2-b]pyrrol-4-yl)ethyl]-4-thiophen-2-ylbenzamide N-[1-(4-Hydroxybenzyl)-2-oxo-2-(3-oxo-hexahydrofuro[3,2-b]pyrrol-4-yl)ethyl]-4-oxazol-5-ylbenzamide N-[1-(4-Hydroxybenzyl)-2-oxo-2-(3-oxo-hexahydrofuro[3,2-b]pyrrol-4-yl)ethyl]-4-[1,2,3]thiadiazol-5-ylbenzamide N-[1-(4-Hydroxybenzyl)-2-oxo-2-(3-oxo-hexahydrofuro[3,2-b]pyrrol-4-yl)ethyl]-4-pyrazol-1-ylbenzamide N-[1-(4-Hydroxybenzyl)-2-oxo-2-(3-oxo-hexahydrofuro[3,2-b]pyrrol-4-yl)ethyl]-5-thiophen-2-ylnicotinamide N-[1-(4-Hydroxybenzyl)-2-oxo-2-(3-oxo-hexahydrofuro[3,2-b]pyrrol-4-yl)ethyl]-6-phenylnicotinamide 2-Phenylthiazole-4-carboxylic acid [1-(4-hydroxybenzyl)-2-oxo-2-(3-oxo-hexa hydrofuro[3,2-b]pyrrol-4-yl)ethyl]amide 2-Pyridin-3-ylthiazole-4-carboxylic acid [1-(4-hydroxybenzyl)-2-oxo-2-(3-oxo-hexa hydrofuro[3,2-b]pyrrol-4-yl)ethyl]amide 5-Phenylthiophene-2-carboxylic acid [1-(4-hydroxybenzyl)-2-oxo-2-(3-oxo-hexa hydrofuro[3,2-b]pyrrol-4-yl)ethyl]amide 5-Pyridin-3-ylthiophene-2-carboxylic acid [1-(4-hydroxybenzyl)-2-oxo-2-(3-oxo-hexahydrofuro[3,2-b]pyrrol-4-yl)ethyl]amide 2-Methyl-5-phenylfuran-3-carboxylic acid [1-(4-hydroxybenzyl)-2-oxo-2-(3-oxo-hexahydrofuro[3,2-b]pyrrol-4-yl)ethyl]amide 4-Phenylthiophene-2-carboxylic acid [1-(4-hydroxybenzyl)-2-oxo-2-(3-oxo-hexa hydrofuro[3,2-b]pyrrol-4-yl)ethyl]amide 4-Pyridin-3-ylthiophene-2-carboxylic acid [1-(4-hydroxybenzyl)-2-oxo-2-(3-oxo-hexahydrofuro[3,2-b]pyrrol-4-yl)ethyl]amide 2-Thiophen-2-ylthiazole-4-carboxylic acid [1-(4-hydroxybenzyl)-2-oxo-2-(3-oxo-hexahydrofuro[3,2-b]pyrrol-4-yl)ethyl]amide 2-Methyl-5-(pyrrolidine-1-sulfonyl)furan-3-carboxylic acid [1-(4-hydroxybenzyl)-2-oxo-2-(3-oxo-hexahydrofuro[3,2-b]pyrrol-4-yl)ethyl]amide 3-Phenylpyrrole-1-carboxylic acid [1-(4-hydroxybenzyl)-2-oxo-2-(3-oxo-hexahydro furo[3,2-b]pyrrol-4-yl)ethyl]amide N-[3-Methyl-1-(3-oxo-hexahydrofuro[3,2-b]pyrrole-4-carbonyl)butyl]benzamide 4-tert-Butyl-N-[3-methyl-1-(3-oxo-hexahydrofuro[3,2-b]pyrrole-4-carbonyl)butyl]benzamide N-[3-Methyl-1-(3-oxo-hexahydrofuro[3,2-b]pyrrole-4-carbonyl)butyl]-4-trifluoro methoxybenzamide 4-Dimethylamino-N-[3-methyl-1-(3-oxo-hexahydrofuro[3,2-b]pyrrole-4-carbonyl) butyl]benzamide 4-Isopropyl-N-[3-methyl-1-(3-oxo-hexahydrofuro[3,2-b]pyrrole-4-carbonyl)butyl]benzamide 4-Difluoromethoxy-N-[3-methyl-1-(3-oxo-hexahydrofuro[3,2-b]pyrrol-4-carbonyl) butyl]benzamide N-[3-Methyl-1-(3-oxo-hexahydrofuro[3,2-b]pyrrole-4-carbonyl)butyl]-4-trifiuoro methyl]benzamide 4-Bromo-N-[3-methyl-1-(3-oxo-hexahydrofuro[3,2-b]pyrrole-4-carbonyl)butyl]benzamide 3-Bromo-N-[3-methyl-1-(3-oxo-hexahydrofuro[3,2-b]pyrrole-4-carbonyl)butyl]benzamide N-[3-Methyl-1-(3-oxo-hexahydrofuro[3,2-b]pyrrole-4-carbonyl)butyl]-4-vinyl benzamide Naphthalene-2-carboxylic acid [3-methyl-1-(3-oxo-hexahydrofuro[3,2-b]pyrrole-4-carbonyl)butyl]amide Naphthalene-1-carboxylic acid [3-methyl-1-(3-oxo-hexahydrofuro[3,2-b]pyrrole-4-carbonyl)butyl]amide Quinoline-6-carboxylic acid [3-methyl-1-(3-oxo-hexahydrofuro[3,2-b]pyrrole-4-carbonyl)butyl]amide Benzo[b]thiophene-2-carboxylic acid [3-methyl-1-(3-oxo-hexahydrofuro[3,2-b]pyrrole-4-carbonyl)butyl]amide Benzo[b]thiophene-3-carboxylic acid [3-methyl-1-(3-oxo-hexahydrofuro[3,2-b]pyrrole-4-carbonyl)butyl]amide Benzothiazole-5-carboxylic acid [3-methyl-1-(3-oxo-hexahydrofuro[3,2-b]pyrrole-4-carbonyl)butyl]amide Biphenyl-4-carboxylic acid [3-methyl-1-(3-oxo-hexahydrofuro[3,2-b]pyrrole-4-carbonyl)butyl]amide N-[3-Methyl-1-(3-oxo-hexahydrofuro[3,2-b]pyrrole-4-carbonyl)butyl]-4-phenoxy benzamide N-[3-Methyl-1-(3-oxo-hexahydrofuro[3,2-b]pyrrol-carbonyl)butyl]-3-phenoxy benzamide 4-Imidazol-1-yl-N-[3-methyl-1-(3-oxo-hexahydrofuro[3,2-b]pyrrole-4-carbonyl)butyl]benzamide N-[3-Methyl-1-(3-oxo-hexahydrofuro[3,2-b]pyrrole-4-carbonyl)butyl]-4-thiophen-2-ylbenzamide N-[3-Methyl-1-(3-oxo-hexahydrofuro[3,2-b]pyrrole 4-carbonyl)butyl]-4-oxazol-5-ylbenzamide N-[3-Methyl-1-(3-oxo-hexahydrofuro[3,2-b]pyrrole-4-carbonyl)butyl]-4-[1,2,3]thiadiazol-4-ylbenzamide N-[3-Methyl-1-(3-oxo-hexahydrofuro[3,2-b]pyrrole-4-carbonyl)butyl]-4-pyrazol-1-ylbenzamide N-[3-Methyl-1-(3-oxo-hexahydrofuro[3,2-b]pyrrole-4-carbonyl)butyl]-5-thiophen-2-ylnicotinamide N-[3-Methyl-1-(3-oxo-hexahydrofuro[3,2-b]pyrrole-4-carbonyl)butyl]-6-phenyl nicotinamide 2-Phenylthiazole-4-carboxylic acid [3-methyl-1-(3-oxo-hexahydrofuro[3,2-b]pyrrole-4-carbonyl)butyl]amide 2-Pyridin-3-ylthiazole-4-carboxylic acid [3-methyl-1-(3-oxo-hexahydrofuro[3,2-b]pyrrole-4-carbonyl)butyl]amide
5-Phenylthiophene-2-carboxylic acid [3-methyl-1-(3-oxo-hexahydrofuro[3,2-b]pyrrole-4-carbonyl)butyl]amide
5-Pyridin-3-ylthiophene-2-carboxylic acid [3-methyl-1-(3-oxo-hexahydrofuro[3,2-b]pyrrole-4-carbonyl)butyl]amide
2-Methyl-5-phenylfuran-3-carboxylic acid [3-methyl-1-(3-oxo-hexahydrofuro[3,2-b]pyrrole-4-carbonyl)butyl]amide
4-Phenylthiophene-2-carboxylic acid [3-methyl-1-(3-oxo-hexahydrofuro[3,2-b]pyrrole-4-carbonyl)butyl]amide
4-Pyridin-3-ylthiophene-2-carboxylic acid [3-methyl-1-(3-oxo-hexahydrofuro[3,2-b]pyrrole-4-carbonyl)butyl]amide
2-Thiophen-2-ylthiazole-4-carboxylic acid [3-methyl-1-(3-oxo-hexahydrofuro[3,2-b]pyrrole-4-carbonyl)butyl]amide
2-Methyl-5-(pyrrolidine-1-sulfonyl)furan-3-carboxylic acid [3-methyl-1-(3-oxo-hexahydrofuro[3,2-b]pyrrole-4-carbonyl)butyl]amide
3-Phenylpyrrole-1-carboxylic acid [3-methyl-1-(3-oxo-hexahydrofuro[3,2-b]pyrrole-4-carbonyl)butyl]amide
N-[1-(3-Hydroxybenzyl)-2-oxo-2-(3-oxo-hexahydrofuro[3,2-b]pyrrol-4-yl)ethyl]benzamide
4-tert-Butyl-N-[1-(3-hydroxybenzyl)-2-oxo-2-(3-oxo-hexahydrofuro[3,2-b]pyrrol-4-yl)ethyl]benzamide
N-[1-(3-Hydroxybenzyl)-2-oxo-2-(3-oxo-hexahydrofuro[3,2-b]pyrrol-4-yl)ethyl]-4-trifluoromethoxybenzamide
4-Dimethylamino-N-[1-(3-hydroxybenzyl)-2-oxo-2-(3-oxo-hexahydrofuro[3,2-b]pyrrol-4-yl)ethyl]benzamide
N-[1-(3-Hydroxybenzyl)-2-oxo-2-(3-oxo-hexahydrofuro[3,2-b]pyrrol-4-yl)ethyl]-4-isopropylbenzamide
4-Difluoromethoxy-N-[1-(3-hydroxybenzyl)-2-oxo-2-(3-oxo-hexahydrofuro[3,2-b]pyrrol-4-yl)ethyl]benzamide
N-[1-(3-Hydroxybenzyl)-2-oxo-2-(3-oxo-hexahydrofuro[3,2-b]pyrrol-4-yl)ethyl]-4-trifluoromethylbenzamide
4-Bromo-N-[1-(3-hydroxybenzyl)-2-oxo-2-(3-oxo-hexahydrofuro[3,2-b]pyrrol-4-yl)ethyl]benzamide
3-Bromo-N-[1-(3-hydroxybenzyl)-2-oxo-2-(3-oxo-hexahydrofuro[3,2-b]pyrrol-4-yl)ethyl]benzamide
N-[1-(3-Hydroxybenzyl)-2-oxo-2-(3-oxo-hexahydrofuro[3,2-b]pyrrol-4-yl)ethyl]-4-vinylbenzamide
Naphthalene-2-carboxylic acid [1-(3-hydroxybenzyl)-2-oxo-2-(3-oxo-hexahydrofuro[3,2-b]pyrrol-4-yl)ethyl]amide
Naphthalene-1-carboxylic acid [1-(3-hydroxybenzyl)-2-oxo-2-(3-oxo-hexahydrofuro[3,2-b]pyrrol-4-yl)ethyl]amide
Quinoline-6-carboxylic acid [1-(3-hydroxybenzyl)-2-oxo-2-(3-oxo-hexahydrofuro[3,2-b]pyrrol-4-yl)ethyl]amide
Benzo[b]thiophene-2-carboxylic acid [1-(3-hydroxybenzyl)-2-oxo-2-(3-oxo-hexa hydrofuro[3,2-b]pyrrol-4-yl)ethyl]amide
Benzo[b]thiophene-3-carboxylic acid [1-(3-hydroxybenzyl)-2-oxo-2-(3-oxo-hexa hydrofuro[3,2-b]pyrrol-4-yl)ethyl]amide
Benzothiazole-5-carboxylic acid [1-(3-hydroxybenzyl)-2-oxo-2-(3-oxo-hexahydro furo[3,2-b]pyrrol-4-yl)ethyl]amide
Biphenyl-4-carboxylic acid [1-(3-hydroxybenzyl)-2-oxo-2-(3-oxo-hexahydrofuro[3,2-b]pyrrol-4-yl)ethyl]amide
N-[1-(3-Hydroxybenzyl)-2-oxo-2-(3-oxo-hexahydrofuro[3,2-b]pyrrol-4-yl)ethyl]-4-phenoxybenzamide
N-[1-(3-Hydroxybenzyl)-2-oxo-2-(3-oxo-hexahydrofuro[3,2-b]pyrrol-4-yl)ethyl]-3-phenoxybenzamide
N-[1-(3-Hydroxybenzyl)-2-oxo-2-(3-oxo-hexahydrofuro[3,2-b]pyrrol-4-yl)ethyl]-4-imidazol-1-ylbenzamide
N-[1-(3-Hydroxybenzyl)-2-oxo-2-(3-oxo-hexahydrofuro[3,2-b]pyrrol-4-yl)ethyl]-4-thiophen-2-ylbenzamide
N-[1-(3-Hydroxybenzyl)-2-oxo-2-(3-oxo-hexahydrofuro[3,2-b]pyrrol-4-yl)ethyl]-4-oxazol-5-ylbenzamide
N-[1-(3-Hydroxybenzyl)-2-oxo-2-(3-oxo-hexahydrofuro[3,2-b]pyrrol-4-yl)ethyl]-4-[1,2,3]thiadiazol-5-ylbenzamide
N-[1-(3-Hydroxybenzyl)-2-oxo-2-(3-oxo-hexahydrofuro[3,2-b]pyrrol-4-yl)ethyl]-4-pyrazol-1-ylbenzamide
N-[1-(3-Hydroxybenzyl)-2-oxo-2-(3-oxo-hexahydrofuro[3,2-b]pyrrol-4-yl)ethyl]-5-thiophen-2-ylnicotinamide
N-[1-(3-Hydroxybenzyl)-2-oxo-2-(3-oxo-hexahydrofuro[3,2-b]pyrrol-4-yl)ethyl]-6-phenylnicotinamide
2-Phenylthiazole-4-carboxylic acid [1-(3-hydroxybenzyl)-2-oxo-2-(3-oxo-hexa hydrofuro[3,2-b]pyrrol-4-yl)ethyl]amide
2-Pyridin-3-ylthiazole-4-carboxylic acid [1-(3-hydroxybenzyl)-2-oxo-2-(3-oxo-hexa hydrofuro[3,2-b]pyrrol-4-yl)ethyl]amide
5-Phenylthiophene-2-carboxylic acid [1-(3-hydroxybenzyl)-2-oxo-2-(3-oxo-hexa hydrofuro[3,2-b]pyrrol-4-yl)ethyl]amide
5-Pyridin-3-ylthiophene-2-carboxylic acid [1-(3-hydroxybenzyl)-2-oxo-2-(3-oxo-hexahydrofuro[3,2-b]pyrrol-4-yl)ethyl]amide
2-Methyl-5-phenylfuran-3-carboxylic acid [1-(3-hydroxybenzyl)-2-oxo-2-(3-oxo-hexahydrofuro[3,2-b]pyrrol-4-yl)ethyl]amide
4-Phenylthiophene-2-carboxylic acid [1-(3-hydroxybenzyl)-2-oxo-2-(3-oxo-hexa hydrofuro[3,2-b]pyrrol-4-yl)ethyl]amide
4-Pyridin-3-ylthiophene-2-carboxylic acid [1-(3-hydroxybenzyl)-2-oxo-2-(3-oxo-hexahydrofuro[3,2-b]pyrrol-4-yl)ethyl]amide
2-Thiophen-2-ylthiazole-4-carboxylic acid [1-(3-hydroxybenzyl)-2-oxo-2-(3-oxo-hexahydrofuro[3,2-b]pyrrol-4-yl)ethyl]amide
2-Methyl-5-(pyrrolidine-1-sulfonyl)furan-3-carboxylic acid [1-(3-hydroxybenzyl)-2-oxo-2-3-oxo-hexahydrofuro[3,2-b]pyrrol-4-yl)ethyl]amide
3-Phenylpyrrole-1-carboxylic acid [1-(3-hydroxybenzyl)-2-oxo-2-(3-oxo-hexahydro furo[3,2-b]pyrrol-4-yl)ethyl]amide
N-[2-Oxo-2-(3-oxo-hexahydrofuro[3,2-b]pyrrol-4-yl)-1-pyridin-4-ylmethylethyl]benzamide
4-tert-Butyl-N-[2-oxo-2-(3-oxo-hexahydrofuro[3,2-b]pyrrol-4-yl)-1-pyridin-4-ylmethylethyl]benzamide
N-[2-Oxo-2-(3-oxo-hexahydrofuro[3,2-b]pyrrol-4-yl)-1-pyridin-4-ylmethylethyl]-4-trifluoromethoxybenzamide
4-Dimethylamino-N-[2-oxo-2-(3-oxo-hexahydrofuro[3,2-b]pyrrol-4-yl)-1-pyridin-4-ylmethylethyl]benzamide
N-[2-Oxo-2-(3-oxo-hexahydrofuro[3,2-b]pyrrol-4-yl)-1-pyridin-4-ylmethylethyl]-4-isopropylbenzamide
4-Difluoromethoxy-N-[2-oxo-2-(3-oxo-hexahydrofuro[3,2-b]pyrrol-4-yl)-1-pyridin-4-ylmethylethyl]benzamide
N-[2-Oxo-2-(3-oxo-hexahydrofuro[3,2-b]pyrrol-4-yl)-1-pyridin-4-ylmethylethyl]-4-trifluoromethylbenzamide
4-Bromo-N-[2-oxo-2-(3-oxo-hexahydrofuro[3,2-b]pyrrol-4-yl)-1-pyridin-4-ylmethylethyl]benzamide
3-Bromo-N-[2-oxo-2-(3-oxo-hexahydrofuro[3,2-b]pyrrol-4-yl)-1-pyridin-4-yl methylethyl]benzamide
N-[2-Oxo-2-(3-oxo-hexahydrofuro[3,2-b]pyrrol-4-yl)-1-pyridin-4-ylmethylethyl]-4-vinylbenzamide
Naphthalene-2-carboxylic acid [2-oxo-2-(3-oxo-hexahydrofuro[3,2-b]pyrrol-4-yl)-1-pyridin-4-ylmethylethyl]amide Naphthalene-1-carboxylic acid [2-oxo-2-(3-oxo-hexahydrofuro[3,2-b]pyrrol-4-yl)-1-pyridin-4-ylmethylethyl]amide Quinoline-6-carboxylic acid [2-oxo-2-(3-oxo-hexahydrofuro[3,2-b]pyrrol-4-yl)-1-pyridin-4-ylmethylethyl]amide Benzo[b]thiophene-2-carboxylic acid [2-oxo-2-(3-oxo-hexahydrofuro[3,2-b]pyrrol-4-yl)-1-pyridin-4-ylmethylethyl]amide Benzo[b]thiophene-3-carboxylic acid [2-oxo-2-(3-oxo-hexahydrofuro[3,2-b]pyrrol-4-yl)-1-pyridin-4-ylmethylethyl]amide Benzothiazole-5-carboxylic acid [2-oxo-2-(3-oxo-hexahydrofuro[3,2-b]pyrrol-4-yl)-1-pyridin-4-ylmethylethyl]amide Biphenyl-4-carboxylic acid [2-oxo-2-(3-oxo-hexahydrofuro[3,2-b]pyrrol-4-yl)-1-pyridin-4-ylmethylethyl]amide N-[2-Oxo-2-(3-oxo-hexahydrofuro[3,2-b]pyrrol-4-yl)-1-pyridin-4-ylmethylethyl]-4-phenoxybenzamide N-[2-Oxo-2-(3-oxo-hexahydrofuro[3,2-b]pyrrol-4-yl)-1-pyridin-4-ylmethylethyl]-3-phenoxybenzamide N-[2-Oxo-2-(3-oxo-hexahydrofuro[3,2-b]pyrrol-4-yl)-1-pyridin-4-ylmethylethyl]-4-imidazol-1-ylbenzamide N-[2-Oxo-2-(3-oxo-hexahydrofuro[3,2-b]pyrrol-4-yl)-1-pyridin-4-ylmethylethyl]-4-thiophen-2-ylbenzamide N-[2-Oxo-2-(3-oxo-hexahydrofuro[3,2-b]pyrrol-4-yl)-1-pyridin-4-ylmethylethyl]-4 oxazol-5-ylbenzamide N-[2-Oxo-2-(3-oxo-hexahydrofuro[3,2-b]pyrrol-4-yl)-1-pyridin-4-ylmethylethyl]-4 [1,2,3]thiadiazol-5-ylbenzamide N-[2-Oxo-2-(3-oxo-hexahydrofuro[3,2-b]pyrrol-4-yl)-1-pyridin-4-ylmethylethyl]-4-pyrazol-1-ylbenzamide N-[2-Oxo-2-(3-oxo-hexahydrofuro[3,2-b]pyrrol-4-yl)-1-pyridin-4-ylmethylethyl]-5-thiophen-2-ylnicotinamide N-[2-Oxo-2-(3-oxo-hexahydrofuro[3,2-b]pyrrol-4-yl)-1-pyridin-4-ylmethylethyl]-6-phenylnicotinamide 2-Phenylthiazole-4-carboxylic acid [2-oxo-2-(3-oxo-hexahydrofuro[3,2-b]pyrrol-4-yl)-1-pyridin 4-ylmethylethyl]amide 2-Pyridin-3-ylthiazole-4-carboxylic acid [2-oxo-2-(3-oxo-hexahydrofuro[3,2-b]pyrrol-4-yl)-1-pyridin-4-ylmethylethyl]amide 5-Phenylthiophene-2-carboxylic acid [2-oxo-2-(3-oxo-hexahydrofuro[3,2-b]pyrrol-4-yl)-1-pyridin-4-ylmethylethyl]amide 5-Pyridin-3-ylthiophene-2-carboxylic acid [2-oxo-2-(3-oxo-hexahydrofuro[3,2-b]pyrrol-4-yl)-1-pyridin-4-ylmethylethyl]amide 2-Methyl-5-phenylfuran-3-carboxylic acid [2-oxo-2-(3-oxo-hexahydrofuro[3,2-b]pyrrol-4-yl)-pyridin-4-ylmethylethyl]amide 4-Phenylthiophene-2-carboxylic acid [2-oxo-2-(3-oxo-hexahydrofuro[3,2-b]pyrrol-4-yl)-1-pyridin-4-ylmethylethyl]amide 4-Pyridin-3-ylthiophene-2-carboxylic acid [2-oxo-2-(3-oxo-hexahydrofuro[3,2-b]pyrrol-4-yl)-1-pyridin-4-ylmethylethyl]amide 2-Thiophen-2-ylthiazole-4-carboxylic acid [2-oxo-2-(3-oxo-hexahydrofuro[3,2-b]pyrrol-4-yl)-1-pyridin-4-ylmethylethyl]amide 2-Methyl-5-(pyrrolidine-1-sulfonyl)furan-3-carboxylic acid [2-oxo-2-(3-oxo-hexa hydrofuro[3,2-b]pyrrol-4-yl)-1-pyridin-4-ylmethylethyl]amide 3-Phenylpyrrole-1-carboxylic acid [2-oxo-2-(3-oxo-hexahydrofuro[3,2-b]pyrrol-4-yl)-1-pyridin-4-ylmethylethyl]amide N-[2-Oxo-2-(3-oxo-hexahydrofuro[3,2-b]pyrrol-4-yl)-1-pyridin-3-ylmethylethyl]benzamide 4-tert-Butyl-N-[2-oxo-2-(3-oxo-hexahydrofuro[3,2-b]pyrrol-4-yl)-1-pyridin-3-ylmethylethyl]benzamide N-[2-Oxo-2-(3-oxo-hexahydrofuro[3,2-b]pyrrol-4-yl)-1-pyridin-3-ylmethylethyl]-4-trifluoromethoxybenzamide 4-Dimethylamino-N-[2-oxo-2-(3-oxo-hexahydrofuro[3,2-b]pyrrol-4-yl)-1-pyridin-3-ylmethylethyl]benzamide N-[2-Oxo-2-(3-oxo-hexahydrofuro[3,2-b]pyrrol-4-yl)-1-pyridin-3-ylmethylethyl]-4-isopropylbenzamide 4-Difluoromethoxy-N-[2-oxo-2-(3-oxo-hexahydrofuro[3,2-b]pyrrol-4-yl)-1-pyridin-3-ylmethylethyl]benzamide N-[2-Oxo-2-(3-oxo-hexahydrofuro[3,2-b]pyrrol-4-yl)-1-pyridin-3-ylmethylethyl]-4-trifluoromethylbenzamide 4-Bromo-N-[2-oxo-2-(3-oxo-hexahydrofuro[3,2-b]pyrrol-4-yl)-1-pyridin-3-ylmethylethyl]benzamide 3-Bromo-N-[2-oxo-2-(3-oxo-hexahydrofuro[3,2-b]pyrrol-4-yl)-1-pyridin-3-ylmethylethyl]benzamide N-[2-Oxo-2-(3-oxo-hexahydrofuro[3,2-b]pyrrol-4-yl)-1-pyridin-3-ylmethylethyl]-4-vinylbenzamide Naphthalene-2-carboxylic acid [2-oxo-2-(3-oxo-hexahydrofuro[3,2-b]pyrrol-4-yl)-1-pyridin-3-ylmethylethyl]amide Naphthalene-1-carboxylic acid [2-oxo-2-(3-oxo-hexahydrofuro[3,2-b]pyrrol-4-yl)-1-pyridin-3-ylmethylethyl]amide Quinoline-6-carboxylic acid [2-oxo-2-(3-oxo-hexahydrofuro[3,2-b]pyrrol-4-yl)-1-pyridin-3-ylmethylethyl]amide Benzo[b]thiophene-2-carboxylic acid [2-oxo-2-(3-oxo-hexahydrofuro[3,2-b]pyrrol-4-yl)-1-pyridin-3-ylmethylethyl]amide Benzo[b]thiophene-3-carboxylic acid [2-oxo-2-(3-oxo-hexahydrofuro[3,2-b]pyrrol-4-yl)-1-pyridin-3-ylmethylethyl]amide Benzothiazole-5-carboxylic acid [2-oxo-2-(3-oxo-hexahydrofuro[3,2-b]pyrrol-4-yl)-1-pyridin-3-ylmethylethyl]amide Biphenyl-4-carboxylic acid [2-oxo-2-3-oxo-hexahydrofuro[3,2-b]pyrrol-4-yl)-1-pyridin-3-ylmethylethyl]amide N-[2-Oxo-2-(3-oxo-hexahydrofuro[3,2-b]pyrrol-4-yl)-1-pyridin-3-ylmethylethyl]-4-phenoxybenzamide N-[2-Oxo-2-(3-oxo-hexahydrofuro[3,2-b]pyrrol-4-yl)-1-pyridin-3-ylmethylethyl]-3-phenoxybenzamide N-[2-Oxo-2-(3-oxo-hexahydrofuro[3,2-b]pyrrol-4-yl)-1-pyridin-3-ylmethylethyl]-4-imidazol-1-ylbenzamide N-[2-Oxo-2-(3-oxo-hexahydrofuro[3,2-b]pyrrol-4-yl)-1-pyridin-3-ylmethylethyl]-4-thiophen-2-ylbenzamide N-[2-Oxo-2-(3-oxo-hexahydrofuro[3,2-b]pyrrol-4-yl)-1-pyridin-3-ylmethylethyl]-4-oxazol-5-ylbenzamide N-[2-Oxo-2-(3-oxo-hexahydrofuro[3,2-b]pyrrol-4-yl)-1-pyridin-3-ylmethylethyl]-4-[1,2,3]thiadiazol-5-ylbenzamide N-[2-Oxo-2-(3-oxo-hexahydrofuro[3,2-b]pyrrol-4-yl)-1-pyridin-3-ylmethylethyl]-4-pyrazol-1-ylbenzamide N-[2-Oxo-2-(3-oxo-hexahydrofuro[3,2-b]pyrrol-4-yl)-1-pyridin-3-ylmethylethyl]-5-thiophen-2-ylnicotinamide N-[2-Oxo-2-(3-oxo-hexahydrofuro[3,2-b]pyrrol-4-yl)-1-pyridin-3-ylmethylethyl]-6-phenylnicotinamide 2-Phenylthiazole-4-carboxylic acid [2-oxo-2-(3-oxo-hexahydrofuro[3,2-b]pyrrol-4-yl)-1-pyridin-3-ylmethylethyl]amide 2-Pyridin-3-ylthiazole-4-carboxylic acid [2-oxo-2-(3-oxo-hexahydrofuro[3,2-b]pyrrol-4-yl)-1-pyridin-3-ylmethylethyl]amide 5-Phenylthiophene-2-carboxylic acid [2-oxo-2-(3-oxo-hexahydrofuro[3,2-b]pyrrol-4-yl)-1-pyridin-3-ylmethylethyl]amide 5-Pyridin-3-ylthiophene-2-carboxylic acid [2-oxo-2-(3-oxo-hexahydrofuro[3,2-b]pyrrol-4-yl)-1-pyridin-3-ylmethylethyl]amide 2-Methyl-5-phenylfuran-3-carboxylic acid [2-oxo-2-(3-oxo-hexahydrofuro[3,2-b]pyrrol-4-yl)-1-pyridin-3-ylmethylethyl]amide 4-Phenylthiophene-2-carboxylic acid [2-oxo-2-(3-oxo-hexahydrofuro[3,2-b]pyrrol-4-yl)-1-pyridin-3-ylmethylethyl]amide 4-Pyridin-3-ylthiophene-2-carboxylic acid [2-oxo-2-(3-oxo-hexahydrofuro[3,2-b]pyrrol-4-yl)-1-pyridin-3-ylmethylethyl]amide 2-Thiophen-2-ylthiazole-4-carboxylic acid [2-oxo-2-(3-oxo-hexahydrofuro[3,2-b]pyrrol-4-yl)-1-pyridin-3-ylmethylethyl]amide 2-Methyl-5-(pyrrolidine-1-sulfonyl)furan-3-carboxylic acid [2-oxo-2-(3-oxo-hexa hydrofuro[3,2-b]pyrrol-4-yl)-1-pyridin-3-ylmethylethyl]amide 3-Phenylpyrrole-1-carboxylic acid [2-oxo-2-(3-oxo-hexahydrofuro[3,2-b]pyrrol-4-yl)-1-pyridin-3-ylmethylethyl]amide N-[1-(4-Bromobenzyl)-2-oxo-2-(3-oxo-hexahydrofuro[3,2-b]pyrrol-4-yl)ethyl]benzamide 4-tert-Butyl-N-[1-(4-bromobenzyl)-2-oxo-2-(3-oxo-hexahydrofuro[3,2-b]pyrrol-4-yl)ethyl]benzamide N-[1-(4-Bromobenzyl)-2-oxo-2-(3-oxo-hexahydrofuro[3,2-b]pyrrol-4-yl)ethyl]4 trifluoromethoxybenzamide 4-Dimethylamino-N-[1-(4-bromobenzyl)-2-oxo-2-(3-oxo-hexahydrofuro[3,2-b]pyrrol-4-yl)ethyl]benzamide N-[1-(4-Bromobenzyl)-2-oxo-2-(3-oxo-hexahydrofuro[3,2-b]pyrrol-4-yl)ethyl]-4-isopropylbenzamide 4-Difluoromethoxy-N-[1-(4-bromobenzyl)-2-oxo-2-(3-oxo-hexahydrofuro[3,2-b]pyrrol-4-yl)ethyl]benzamide N-[1-(4-Bromobenzyl)-2-oxo-2-(3-oxo-hexahydrofuro[3,2-b]pyrrol-4-yl)ethyl]-4-trifluoromethylbenzamide 4-Bromo-N-[1-(4-bromobenzyl)-2-oxo-2-(3-oxo-hexahydrofuro[3,2-b]pyrrol-4-yl)ethyl]benzamide 3-Bromo-N-[1-(4-bromobenzyl)-2-oxo-2-(3-oxo-hexahydrofuro[3,2-b]pyrrol-4-yl)ethyl]benzamide N-[1-(4-Bromobenzyl)-2-oxo-2-(3-oxo-hexahydrofuro[3,2-b]pyrrol-4-yl)ethyl]-4vinylbenzamide Naphthalene-2-carboxylic acid [1-(4-bromobenzyl)-2-oxo-2-(3-oxo-hexahydrofuro[3,2-b]pyrrol-4-yl)ethyl]amide Naphthalene-1-carboxylic acid [1-(4-bromobenzyl)-2-oxo-2-(3-oxo-hexahydrofuro[3,2-b]pyrrol-4-yl)ethyl]amide Quinoline-6-carboxylic acid [1-(4-bromobenzyl)-2-oxo-2-(3-oxo-hexahydrofuro[3,2-b]pyrrol-4-yl)ethyl]amide Benzo[b]thiophene-2-carboxylic acid [1-(4-bromobenzyl)-2-oxo-2-(3-oxo-hexa hydrofuro[3,2-b]pyrrol-4-yl)ethyl]amide Benzo[b]thiophene-3-carboxylic acid [1-(4-bromobenzyl)-2-oxo-2-(3-oxo-hexa hydrofuro[3,2-b]pyrrol-4-yl)ethyl]amide Benzothiazole-5-carboxylic acid [1-(4-bromobenzyl)-2-oxo-2-(3-oxo-hexahydro furo[3,2-b]pyrrol-4-yl)ethyl]amide Biphenyl-4-carboxylic acid [1-(4-bromobenzyl)-2-oxo-2-(3-oxo-hexahydrofuro[3,2-b]pyrrol-4-yl)ethyl]amide N-[1-(4 Bromobenzyl)-2-oxo-2-(3-oxo-hexahydrofuro[3,2-b]pyrrol-4-yl)ethyl]-4-phenoxybenzamide N-[1-(4-Bromobenzyl)-2-oxo-2-(3-oxo-hexahydrofuro[3,2-b]pyrrol-4-yl)ethyl]-3-phenoxybenzamide N-[1-(4-Bromobenzyl)-2-oxo-2-(3-oxo-hexahydrofuro[3,2-b]pyrrol-4-yl)ethyl]-4-imidazol-1-ylbenzamide N-[1-(4-Bromobenzyl)-2-oxo-2-(3-oxo-hexahydrofuro[3,2-b]pyrrol-4-yl)ethyl]-4-thiophen-2-ylbenzamide N-[1-(4-Bromobenzyl)-2-oxo-2-(3-oxo-hexahydrofuro[3,2-b]pyrrol-4-yl)ethyl]-4-oxazol-5-ylbenzamide N-[1-(4-Bromobenzyl)-2-oxo-2-(3-oxo-hexahydrofuro[3,2-b]pyrrol-4-yl)ethyl]-4-[1,2,3]thiadiazol-5-ylbenzamide N-[1-(4-Bromobenzyl)-2-oxo-2-(3-oxo-hexahydrofuro[3,2-b]pyrrol-4-yl)ethyl]-4-pyrazol-1-ylbenzamide N-[1-(4-Bromobenzyl)-2-oxo-2-(3-oxo-hexahydrofuro[3,2-b]pyrrol-4-yl)ethyl]-5-thiophen-2-ylnicotinamide N-[1-(4-Bromobenzyl)-2-oxo-2-(3-oxo-hexahydrofuro[3,2-b]pyrrol-4-yl)ethyl]-6-phenylnicotinamide 2-Phenylthiazole-4-carboxylic acid [1-(4-bromobenzyl)-2-oxo-2-(3-oxo-hexa hydrofuro[3,2-b]pyrrol-4-yl)ethyl]amide 2-Pyridin-3-ylthiazole-4-carboxylic acid [1-(4-bromobenzyl)-2-oxo-2-(3-oxo-hexa hydrofuro[3,2-b]pyrrol-4-yl)ethyl]amide 5-Phenylthiophene-2-carboxylic acid [1-(4-bromobenzyl)-2-oxo-2-(3-oxo-hexa hydrofuro[3,2-b]pyrrol-4-yl)ethyl]amide 5-Pyridin-3-ylthiophene-2-carboxylic acid [1-(4-bromobenzyl)-2-oxo-2-(3-oxo-hexahydrofuro[3,2-b]pyrrol-4-yl)ethyl]amide 2-Methyl-5-phenylfuran-3-carboxylic acid [1-(4-bromobenzyl)-2-oxo-2-(3-oxo-hexahydrofuro[3,2-b]pyrrol-4-yl)ethyl]amide 4-Phenylthiophene-2-carboxylic acid [1-(4-bromobenzyl)-2-oxo-2-(3-oxo-hexa hydrofuro[3,2-b]pyrrol-4-yl)ethyl]amide 4-Pyridin-3-ylthiophene-2-carboxylic acid [1-(4-bromobenzyl)-2-oxo-2-(3-oxo-hexahydrofuro[3,2-b]pyrrol-4-yl)ethyl]amide 2-Thiophen-2-ylthiazole-4-carboxylic acid [1-(4-bromobenzyl)-2-oxo-2-(3-oxo-hexahydrofuro[3,2-b]pyrrol-4-yl)ethyl]amide 2-Methyl-5-(pyrrolidine-1-sulfonyl)furan-3-carboxylic acid [1-(4-bromobenzyl)-2-oxo-2-(3-oxo-hexahydrofuro[3,2-b]pyrrol-4-yl)ethyl]amide 3-Phenylpyrrole-1-carboxylic acid [1-(4-bromobenzyl)-2-oxo-2-(3-oxo-hexahydro furo[3,2-b]pyrrol-4-yl)ethyl]amide N-[1-(4-Fluorobenzyl)-2-oxo-2-(3-oxo-hexahydrofuro[3,2-b]pyrrol-4-yl)ethyl]benzamide 4-tert-Butyl-N-[1-(4-fluorobenzyl)-2-oxo-2-(3-oxo-hexahydrofuro[3,2-b]pyrrol-4-yl)ethyl]benzamide N-[1-(4-Fluorobenzyl)-2-oxo-2-(3-oxo-hexahydrofuro[3,2-b]pyrrol-yl)ethyl]-4-trifluoromethoxybenzamide 4-Dimethylamino-N-[1-(4-fluorobenzyl)-2-oxo-2-(3-oxo-hexahydrofuro[3,2-b]pyrrol-4-yl)ethyl]benzamide N-[1-(4-Fluorobenzyl)-2-oxo-2-(3-oxo-hexahydrofuro[3,2-b]pyrrol-4-yl)ethyl]-4-isopropylbenzamide 4-Difluoromethoxy-N-[1-(4-fluorobenzyl)-2-oxo-2-(3-oxo-hexahydrofuro[3,2-b]pyrrol-4-yl)ethyl]benzamide N-[1-(4-Fluorobenzyl)-2-oxo-2-3-oxo-hexahydrofuro[3,2-b]pyrrol-4-yl)ethyl]-4-trifluoromethylbenzamide 4-Bromo-N-[1-(4-fluorobenzyl)-2-oxo-2-(3-oxo-hexahydrofuro[3,2-b]pyrrol-4-yl)ethyl]benzamide 3-Bromo-N-[1-(4-fluorobenzyl)-2-oxo-2-(3-oxo-hexahydrofuro[3,2-b]pyrrol-4-yl)ethyl]benzamide N-[1-(4-Fluorobenzyl)-2-oxo-2-(3-oxo-hexahydrofuro[3,2-b]pyrrol-4-yl)ethyl]-vinylbenzamide Naphthalene-2-carboxylic acid [1-(4-fluorobenzyl)-2-oxo-2-(3-oxo-hexahydrofuro[3,2-b]pyrrol-4-yl)ethyl]amide Naphthalene-1-carboxylic acid [1-(4-fluorobenzyl)-2-oxo-2-(3-oxo-hexahydrofuro[3,2-b]pyrrol-4-yl)ethyl]amide Quinoline-6-carboxylic acid [1-(4-fluorobenzyl)-2-oxo-2-(3-oxo-hexahydrofuro[3,2-b]pyrrol-4-yl)ethyl]amide Benzo[b]thiophene-2-carboxylic acid [1-(4-fluorobenzyl)-2-oxo-2-(3-oxo-hexa hydrofuro[3,2-b]pyrrol-4-yl)ethyl]amide Benzo[b]thiophene-3-carboxylic acid [1-(4-fluorobenzyl)-2-oxo-2-(3-oxo-hexa hydrofuro[3,2-b]pyrrol-4-yl)ethyl]amide Benzothiazole-5-carboxylic acid [1-(4-fluorobenzyl)-2-oxo-2-(3-oxo-hexahydro furo[3,2-b]pyrrol-4-yl)ethyl]amide
Biphenyl-4-carboxylic acid [1-(4-fluorobenzyl)-2-oxo-2-(3-oxo-hexahydrofuro[3,2-b]pyrrol-4-yl)ethyl]amide
N-[1-(4-Fluorobenzyl)-2-oxo-2-(3-oxo-hexahydrofuro[3,2-b]pyrrol-4-yl)ethyl]-4-phenoxybenzamide
N-[1-(4-Fluorobenzyl)-2-oxo-2-(3-oxo-hexahydrofuro[3,2-b]pyrrol-4-yl)ethyl]-3-phenoxybenzamide
N-[1-(4-Fluorobenzyl)-2-oxo-2-(3-oxo-hexahydro r[3,2-b]pyrrol-4-yl)ethyl]-4-imidazol-1-ylbenzamide
N-[1-(4-Fluorobenzyl)-2-oxo-2-(3-oxo-hexahydrofuro[3,2-b]pyrrol-4-yl)ethyl]-4-thiophen-2-ylbenzamide
N-(1-(4-Fluorobenzyl)-2-oxo-2-(3-oxo-hexahydrofuro[3,2-b]pyrrol-4-yl)ethyl]-4oxazol-5-ylbenzamide
N-[1-(4-Fluorobenzyl)-2-oxo-2-(3-oxo-hexahydrofuro[3,2-b]pyrrol-4-yl)ethyl]-4 [1,2,3]thiadiazol-5-ylbenzamide
N-[1-(4-Fluorobenzyl)-2-oxo-2-(3-oxo-hexahydrofuro[3,2-b]pyrrol-4-yl)ethyl]-4-pyrazol-1-ylbenzamide
N-[1-(4-Fluorobenzyl)-2-oxo-2-(3-oxo-hexahydrofuro[3,2-b]pyrrol yl)ethyl]-5-thiophen-2-ylnicotinamide
N-[1-(4-Fluorobenzyl)-2-oxo-2-(3-oxo-hexahydrofuro[3,2-b]pyrrol yl)ethyl]-6-phenylnicotinamide
2-Phenylthiazole-4-carboxylic acid [1-(4-fluorobenzyl)-2-oxo-2-(3-oxo-hexa hydrofuro[3,2-b]pyrrol-4-yl)ethyl]amide
2-Pyridin-3-ylthiazole-4-carboxylic acid [1-(4-fluorobenzyl)-2-oxo-2-(3-oxo-hexa hydrofuro[3,2-b]pyrrol-4-yl)ethyl]amide
5-Phenylthiophene-2-carboxylic acid [1-(4-fluorobenzyl)-2-oxo-2-(3-oxo-hexa hydrofuro[3,2-b]pyrrol-4-yl)ethyl]amide
5-Pyridin-3-ylthiophene-2-carboxylic acid [1-(4-fluorobenzyl)-2-oxo-2-(3-oxo-hexahydrofuro[3,2-b]pyrrol-4-yl)ethyl]amide
2-Methyl-5-phenylfuran-3-carboxylic acid [1-(4-fluorobenzyl)-2-oxo-2-(3-oxo-hexahydrofuro[3,2-b]pyrrol-4-yl)ethyl]amide
4-Phenylthiophene-2-carboxylic acid 11-(4-fluorobenzyl)-2-oxo-2-(3-oxo-hexa hydrofuro[3,2-b]pyrrol-4-yl)ethyl]amide
4-Pyridin-3-ylthiophene-2-carboxylic acid [1-(4-fluorobenzyl)-2-oxo-2-(3-oxo-hexahydrofuro[3,2-b]pyrrol-4-yl)ethyl]amide
2-Thiophen-2-ylthiazole-4-carboxylic acid [1-(4-fluorobenzyl)-2-oxo-2-(3-oxo-hexahydrofuro[3,2-b]pyrrol-4-yl)ethyl]amide
2-Methyl-5-(pyrrolidine-1-sulfonyl)furan-3-carboxylic acid [1-(4-fluorobenzyl)-2-oxo-2-(3-oxo-hexahydrofuro[3,2-b]pyrrol-4-yl)ethyl]amide
3-Phenylpyrrole-1-carboxylic acid [1-(4-fluorobenzyl)-2-oxo-2-(3-oxo-hexahydro furo[3,2-b]pyrrol-4-yl)ethyl]amide
N-[1-(4-Chlorobenzyl)-2-oxo-2-(3-oxo-hexahydrofuro[3,2-b]pyrrol-4-yl)ethyl]benzamide
4-tert-Butyl-N-[1-(4-chlorobenzyl)-2-oxo-2-(3-oxo-hexahydrofuro[3,2-b]pyrrol-4-yl)ethyl]benzamide
N-[1-(4-Chlorobenzyl)-2-oxo-2-3-oxo-hexahydrofuro[3,2-b]pyrrol-4-yl)ethyl]-4-trifluoromethoxybenzamide
4-Dimethylamino-N-[1-(4-chlorobenzyl)-2-oxo-2-(3-oxo-hexahydrofuro[3,2-b]pyrrol-4-yl)ethyl]benzamide
N-[1-(4-Chlorobenzyl)-2-oxo-2-(3-oxo-hexahydrofuro[3,2-b]pyrrol-4-yl)ethyl]-4-isopropylbenzamide
4-Difluoromethoxy-N-[1-(4-chlorobenzyl)-2-oxo-2-(3-oxo-hexahydrofuro[3,2-b]pyrrol-4-yl)ethyl]benzamide
N-[1-(4-Chlorobenzyl)-2-oxo-2-(3-oxo-hexahydrofuro[3,2-b]pyrrol-4-yl)ethyl]-4-trifluoromethylbenzamide
4-Bromo-N-[1-(4-chlorobenzyl)-2-oxo-2-(3-oxo-hexahydrofuro[3,2-b]pyrrol-4-yl)ethyl]benzamide
3-Bromo-N-[1-(4-chlorobenzyl)-2-oxo-2-(3-oxo-hexahydrofuro[3,2-b]pyrrol-4-yl)ethyl]benzamide
N-[1-(4-Chlorobenzyl)-2-oxo-2-(3-oxo-hexahydrofuro[3,2-b]pyrrol-4-yl)ethyl]-4-vinylbenzamide
Naphthalene-2-carboxylic acid [1-(4-chlorobenzyl)-2-oxo-2-(3-oxo-hexahydrofuro[3,2-b]pyrrol-4-yl)ethyl]amide
Naphthalene-1-carboxylic acid [1-(4-chlorobenzyl)-2-oxo-2-(3-oxo-hexahydrofuro[3,2-b]pyrrol-4-yl)ethyl]amide
Quinoline-6-carboxylic acid [1-(4-chlorobenzyl)-2-oxo-2-(3-oxo-hexahydrofuro[3,2-b]pyrrol-4-yl)ethyl]amide
Benzo[b]thiophene-2-carboxylic acid [1-(4-chlorobenzyl)-2-oxo-2-(3-oxo-hexa hydrofuro[3,2-b]pyrrol-4-yl)ethyl]amide
Benzo[b]thiophene-3-carboxylic acid [1-(4-chlorobenzyl)-2-oxo-2-(3-oxo-hexa hydrofuro[3,2-b]pyrrol-4-yl)ethyl]amide
Benzothiazole-5-carboxylic acid [1-(4-chlorobenzyl)-2-oxo-2-(3-oxo-hexahydro furo[3,2-b]pyrrol-4-yl)ethyl]amide
Biphenyl-4-carboxylic acid [1-(4-chlorobenzyl)-2-oxo-2-(3-oxo-hexahydrofuro[3,2-b]pyrrol-4-yl)ethyl]amide
N-[1-(4-Chlorobenzyl)-2-oxo-2-(3-oxo-hexahydrofuro[3,2-b]pyrrol-4-yl)ethyl]-4-phenoxybenzamide
N-[1-(4-Chlorobenzyl)-2-oxo-2-3-oxo-hexahydrofuro[3,2-b]pyrrol-4-yl)ethyl]-3-phenoxybenzamide
N-[1-(4-Chlorobenzyl)-2-oxo-2-(3-oxo-hexahydrofuro[3,2-b]pyrrol-4-yl)ethyl]-4-imidazol-1-ylbenzamide
N-[1-(4-Chlorobenzyl)-2-oxo-2-(3-oxo-hexahydrofuro[3,2-b]pyrrol-4-yl)ethyl]-4-thiophen-2-ylbenzamide
N-[1-(4-Chlorobenzyl)-2-oxo-2-(3-oxo-hexahydrofuro[3,2-b]pyrrol-4-yl)ethyl]-4-oxazol-5-ylbenzamide
N-[1-(4-Chlorobenzyl)-2-oxo-2-(3-oxo-hexahydrofuro[3,2-b]pyrrol-4-yl)ethyl]-4-[1,2,3]thiadiazol-5-ylbenzamide
N-[1-(4-Chlorobenzyl)-2-oxo-2-(3-oxo-hexahydrofuro[3,2-b]pyrrol-4-yl)ethyl]-4-pyrazol-1-ylbenzamide
N-[1-(4-Chlorobenzyl)-2-oxo-2-(3-oxo-hexahydrofuro[3,2-b]pyrrol-4-yl)ethyl]-5-thiophen-2-ylnicotinamide
N-[1-(4-Chlorobenzyl)-2-oxo-2-(3-oxo-hexahydrofuro[3,2-b]pyrrol-4-yl)ethyl]-6-phenylnicotinamide
2-Phenylthiazole-4-carboxylic acid [1-(4-chlorobenzyl)-2-oxo-2-(3-oxo-hexa hydrofuro[3,2-b]pyrrol-4-yl)ethyl]amide
2-Pyridin-3-ylthiazole-4-carboxylic acid [1-(4-chlorobenzyl)-2-oxo-2-(3-oxo-hexa hydrofuro[3,2-b]pyrrol-4-yl)ethyl]amide
5-Phenylthiophene-2-carboxylic acid [1-(4-chlorobenzyl)-2-oxo-2-(3-oxo-hexa hydrofuro[3,2-b]pyrrol-4-yl)ethyl]amide
5-Pyridin-3-ylthiophene-2-carboxylic acid [1-(4-chlorobenzyl)-2-oxo-2-(3-oxo-hexahydrofuro[3,2-b]pyrrol-4-yl)ethyl]amide
2-Methyl-5-phenylfuran-3-carboxylic acid [1-(4-chlorobenzyl)-2-oxo-2-(3-oxo-hexahydrofuro[3,2-b]pyrrol-4-yl)ethyl]amide
4-Phenylthiophene-2-carboxylic acid [1-(4-chlorobenzyl)-2-oxo-2-(3-oxo-hexa hydrofuro[3,2-b]pyrrol-4-yl)ethyl]amide
4-Pyridin-3-ylthiophene-2-carboxylic acid [1-(4-chlorobenzyl)-2-oxo-2-(3-oxo-hexahydrofuro[3,2-b]pyrrol-4-yl)ethyl]amide
2-Thiophen-2-ylthiazole-4-carboxylic acid [1-(4-chlorobenzyl)-2-oxo-2-(3-oxo-hexahydrofuro[3,2-b]pyrrol-4-yl)ethyl]amide
2-Methyl-5-(pyrrolidine-1-sulfonyl)furan-3-carboxylic acid [1-(4-chlorobenzyl)-2-oxo-2-(3-oxo-hexahydrofuro[3,2-b]pyrrol-4-yl)ethyl]amide 3-Phenylpyrrole-1-carboxylic acid [1-(4-chlorobenzyl)-2-oxo-2-(3-oxo-hexahydrofuro[3,2-b]pyrrol-4-yl)ethyl]amide
N-[1-(3,4-Dichlorobenzyl)-2-oxo-2-(3-oxo-hexahydrofuro[3,2-b]pyrrol-4-yl)ethyl]benzamide
4-tert-Butyl-N-[1-(3,4-dichlorobenzyl)-2-oxo-2-(3-oxo-hexahydrofuro[3,2-b]pyrrol-4-yl)ethyl]benzamide
N-[1-(3,4-Dichlorobenzyl)-2-oxo-2-(3-oxo-hexahydrofuro[3,2-b]pyrrol-4-yl)ethyl]-4-trifluoromethoxybenzamide
4-Dimethylamino-N-[1-(3,4-chlorobenzyl)-2-oxo-2-(3-oxo-hexahydrofuro[3,2-b]pyrrol-4-yl)ethyl]benzamide
N-[1-(3,4-Dichlorobenzyl)-2-oxo-2-(3-oxo-hexahydrofuro[3,2-b]pyrrol-4-yl)ethyl]-4-isopropylbenzamide
4-Difluoromethoxy-N-[1-(3,4-dichlorobenzyl)-2-oxo-2-(3-oxo-hexahydrofuro[3,2-b]pyrrol-4-yl)ethyl]benzamide
N-[1-(3,4-Dichlorobenzyl)-2-oxo-2-(3-oxo-hexahydrofuro[3,2-b]pyrrol-4-yl)ethyl]-4-trifluoromethylbenzamide
4-Bromo-N-[1-(3,4-dichlorobenzyl)-2-oxo-2-(3-oxo-hexahydrofuro[3,2-b]pyrrol-4-yl)ethyl]benzamide
3-Bromo-N-[1-(3,4-dichlorobenzyl)-2-oxo-2-(3-oxo-hexahydrofuro[3,2-b]pyrrol-4-yl)ethyl]benzamide
N-[1-(3,4-Dichlorobenzyl)-2-oxo-2-(3-oxo-hexahydrofuro[3,2-b]pyrrol-4-yl)ethyl]-4-vinylbenzamide
Naphthalene-2-carboxylic acid [1-(3,5-dichlorobenzyl)-2-oxo-2-(3-oxo-hexahydrofuro[3,2-b]pyrrol-4-yl)ethyl]amide
Naphthalene-1-carboxylic acid [1-(3,4-dichlorobenzyl)-2-oxo-2-(3-oxo-hexahydrofuro[3,2-b]pyrrol-4-yl)ethyl]amide
Quinoline-6-carboxylic acid [1-(3,4-dichlorobenzyl)-2-oxo-2-(3-oxo-hexahydrofuro[3,2-b]pyrrol-4-yl)ethyl]amide
Benzo[b]thiophene-2-carboxylic acid [1-(3,4-dichlorobenzyl)-2-oxo-2-(3-oxo-hexa hydrofuro[3,2-b]pyrrol-4-yl)ethyl]amide
Benzo[b]thiophene-3-carboxylic acid [1-(3,4-dichlorobenzyl)-2-oxo-2-(3-oxo-hexa hydrofuro[3,2-b]pyrrol-4-yl)ethyl]amide
Benzothiazole-5-carboxylic acid [1-(3,4-dichlorobenzyl)-2-oxo-2-(3-oxo-hexahydro furo[3,2-b]pyrrol-4-yl)ethyl]amide
Biphenyl-4-carboxylic acid [1-(3,4-dichlorobenzyl)-2-oxo-2-(3-oxo-hexahydrofuro[3,2-b]pyrrol-4-yl)ethyl]amide
N-[1-(3,4-Dichlorobenzyl)-2-oxo-2-(3-oxo-hexahydrofuro[3,2-b]pyrrol-4-yl)ethyl]-4-phenoxybenzamide
N-[1-(3,4-Dichlorobenzyl)-2-oxo-2-(3-oxo-hexahydrofuro[3,2-b]pyrrol-4-yl)ethyl]-3-phenoxybenzamide
N-[1-(3,4-Dichlorobenzyl)-2-oxo-2-(3-oxo-hexahydrofuro[3,2-b]pyrrol-4-yl)ethyl]-4-imidazol-1-ylbenzamide
N-[1-(3,4-Dichlorobenzyl)-2-oxo-2-(3-oxo-hexahydrofuro[3,2-b]pyrrol-4-yl)ethyl]-4-thiophen-2-ylbenzamide
N-[1-(3,4-Dichlorobenzyl)-2-oxo-2-(3-oxo-hexahydrofuro[3,2-b]pyrrol-4-yl)ethyl]-4-oxazol-5-ylbenzamide
N-[1-(3,4-Dichlorobenzyl)-2-oxo-2-(3-oxo-hexahydrofuro[3,2-b]pyrrol-4-yl)ethyl]-4-[1,2,3]thiadiazol-5-ylbenzamide
N-[1-(3,4-Dichlorobenzyl)-2-oxo-2-(3-oxo-hexahydrofuro[3,2-b]pyrrol-4-yl)ethyl]-4-pyrazol-1-ylbenzamide
N-[1-(3,4-Dichlorobenzyl)-2-oxo-2-(3-oxo-hexahydrofuro[3,2-b]pyrrol-4-yl)ethyl]-5-thiophen-2-ylnicotinamide
N-[1-(3,4-Dichlorobenzyl)-2-oxo-2-(3-oxo-hexahydrofuro[3,2-b]pyrrol-4-yl)ethyl]-6-phenylnicotinamide
2-Phenylthiazole-4-carboxylic acid [1-(3,4-dichlorobenzyl)-2-oxo-2-(3-oxo-hexa hydrofuro[3,2-b]pyrrol-4-yl)ethyl]amide
2-Pyridin-3-ylthiazole-4-carboxylic acid [1-(3,4-dichlorobenzyl)-2-oxo-2-(3-oxo-hexa hydrofuro[3,2-b]pyrrol-4-yl)ethyl]amide
5-Phenylthiophene-2-carboxylic acid [1-(3,4-dichlorobenzyl)-2-oxo-2-(3-oxo-hexa hydrofuro[3,2-b]pyrrol-4-yl)ethyl]amide
5-Pyridin-3-ylthiophene-2-carboxylic acid [1-(3,4-dichlorobenzyl)-2-oxo-2-(3-oxo-hexahydrofuro[3,2-b]pyrrol-4-yl)ethyl]amide
2-Methyl-5-phenylfuran-3-carboxylic acid [1-(3,4-dichlorobenzyl)-2-oxo-2-(3-oxo-hexahydrofuro[3,2-b]pyrrol-4-yl)ethyl]amide
4-Phenylthiophene-2-carboxylic acid [1-(3,4-dichlorobenzyl)-2-oxo-2-(3-oxo-hexa hydrofuro[3,2-b]pyrrol-4-yl)ethyl]amide
4-Pyridin-3-ylthiophene-2-carboxylic acid [1-(3,4-dichlorobenzyl)-2-oxo-2-(3-oxo-hexahydrofuro[3,2-b]pyrrol-4-yl)ethyl]amide
2-Thiophen-2-ylthiazole-4-carboxylic acid [1-(3,4-dichlorobenzyl)-2-oxo-2-(3-oxo-hexahydrofuro[3,2-b]pyrrol-4-yl)ethyl]amide
2-Methyl-5-(pyrrolidine-1-sulfonyl)furan-3-carboxylic acid [1-(3,4-dichlorobenzyl)-2-oxo-2-(3-oxo-hexahydrofuro[3,2-b]pyrrol-4-yl)ethyl]amide
3-Phenylpyrrole-1-carboxylic acid [1-(3,4-dichlorobenzyl)-2-oxo-2-(3-oxo-hexahydrofuro[3,2-b]pyrrol-4-yl)ethyl]amide
N-[2-Oxo-2-(3-oxo-hexahydrofuro[3,2-b]pyrrol-4-yl)-1-thiophen-2-ylmethylethyl]benzamide
4-tert-Butyl-N-[2-oxo-2-(3-oxo-hexahydrofuro[3,2-b]pyrrol-4-yl)-1-thiophen-2-ylmethylethyl]benzamide
N-[2-Oxo-2-(3-oxo-hexahydrofuro[3,2-b]pyrrol-4-yl)-1-thiophen-2-ylmethylethyl]-4-trifluoromethoxybenzamide
4-Dimethylamino-N-[2-oxo-2-(3-oxo-hexahydrofuro[3,2-b]pyrrol-4-yl)-1-thiophen-2-ylmethylethyl]benzamide
N-[2-Oxo-2-(3-oxo-hexahydrofuro[3,2-b]pyrrol-4-yl)-1-thiophen-2-ylmethylethyl]-4-isopropylbenzamide
4-Difluoromethoxy-N-[2-oxo-2-(3-oxo-hexahydrofuro[3,2-b]pyrrol-4-yl)-1-thiophen-2-ylmethylethyl]benzamide
N-[2-Oxo-2-(3-oxo-hexahydrofuro[3,2-b]pyrrol-4-yl)-1-thiophen-2-ylmethylethyl]-4-trifluoromethylbenzamide
4-Bromo-N-[2-oxo-2-(3-oxo-hexahydrofuro[3,2-b]pyrrol-4-yl)-1-thiophen-2-ylmethylethyl]benzamide
3-Bromo-N-[2-oxo-2-(3-oxo-hexahydrofuro[3,2-b]pyrrol-4-yl)-1-thiophen-2-ylmethylethyl]benzamide
N-[2-Oxo-2-(3-oxo-hexahydrofuro[3,2-b]pyrrol-4-yl)-1-thiophen-2-ylmethylethyl]-4-vinylbenzamide
Naphthalene-2-carboxylic acid [2-oxo-2-(3-oxo-hexahydrofuro[3,2-b]pyrrol-4-yl)-1-thiophen-2-ylmethylethyl]amide
Naphthalene-1-carboxylic acid [2-oxo-2-(3-oxo-hexahydrofuro[3,2-b]pyrrol-4-yl)-1-thiophen-2-ylmethylethyl]amide
Quinoline-4-carboxylic acid [2-oxo-2-(3-oxo-hexahydrofuro[3,2-b]pyrrol-4-yl)-1-thiophen-2-ylmethylethyl]amide
Benzo[b]thiophene-2-carboxylic acid [2-oxo-2-(3-oxo-hexahydrofuro[3,2-b]pyrrol-4-yl)-1-thiophen-2-ylmethylethyl]amide
Benzo[b]thiophene-3-carboxylic acid [2-oxo-2-(3-oxo-hexahydrofuro[3,2-b]pyrrol-4-yl)-1-thiophen-2-ylmethylethyl]amide
Benzothiazole-5-carboxylic acid [2-oxo-2-(3-oxo-hexahydrofuro[3,2-b]pyrrol-4-yl)-1-thiophen-2-ylmethylethyl]amide
Biphenyl-4-carboxylic acid [2-oxo-2-(3-oxo-hexahydrofuro[3,2-b]pyrrol-4-yl)-1-thiophen-2-ylmethylethyl]amide
N-[2-Oxo-2-(3-oxo-hexahydrofuro[3,2-b]pyrrol-4-yl)-1-thiophen-2-ylmethylethyl]-4-phenoxybenzamide N-[2-Oxo-2-(3-oxo-hexahydrofuro[3,2-b]pyrrol-4-yl)-1-thiophen-2-ylmethylethyl]-3-phenoxybenzamide
N-[2-Oxo-2-(3-oxo-hexahydrofuro[3,2-b]pyrrol-4-yl)-1-thiophen-2-ylmethylethyl]-4-imidazol-1-ylbenzamide
N-[2-Oxo-2-(3-oxo-hexahydrofuro[3,2-b]pyrrol-4-yl)-1-thiophen-2-ylmethylethyl]-4-thiophen-2-ylbenzamide
N-[2-Oxo-2-(3-oxo-hexahydrofuro[3,2-b]pyrrol-4-yl)-1-thiophen-2-ylmethylethyl]-4-oxazol-5-ylbenzamide
N-[2-Oxo-2-(3-oxo-hexahydrofuro[3,2-b]pyrrol-4-yl)-1-thiophen-2-ylmethylethyl]-4-[1,2,3]thiadiazol-5-ylbenzamide
N-[2-Oxo-2-(3-oxo-hexahydrofuro[3,2-b]pyrrol-4-yl)-1-thiophen-2-ylmethylethyl]-4-pyrazol-1-ylbenzamide
N-[2-Oxo-2-(3-oxo-hexahydrofuro[3,2-b]pyrrol-4-yl)-1-thiophen-2-ylmethylethyl]-5-thiophen-2-ylnicotinamide
N-[2-Oxo-2-(3-oxo-hexahydrofuro[3,2-b]pyrrol-4-yl)-1-thiophen-2-ylmethylethyl]-6-phenylnicotinamide
2-Phenylthiazole-4-carboxylic acid [2-oxo-2-(3-oxo-hexahydrofuro[3,2-b]pyrrol-4-yl)-1-thiophen-2-ylmethylethyl]amide
2-Pyridin-3-ylthiazole-4-carboxylic acid [2-oxo-2-(3-oxo-hexahydrofuro[3,2-b]pyrrol-4-yl)-1-thiophen-2-ylmethylethyl]amide
5-Phenylthiophene-2-carboxylic acid [2-oxo-2-(3-oxo-hexahydrofuro[3,2-b]pyrrol-4-yl)-1-thiophen-2-ylmethylethyl]amide
5-Pyridin-3-ylthiophene-2-carboxylic acid [2-oxo-2-(3-oxo-hexahydrofuro[3,2-b]pyrrol-4-yl)-1-thiophen-2-ylmethylethyl]amide
2-Methyl-5-phenylfuran-3-carboxylic acid [2-oxo-2-(3-oxo-hexahydrofuro[3,2-b]pyrrol-4-yl)-1-thiophen-2-ylmethylethyl]amide
4-Phenylthiophene-2-carboxylic acid [2-oxo-2-(3-oxo-hexahydrofuro[3,2-b]pyrrol-4-yl)-1-thiophen-2-ylmethylethyl]amide
4-Pyridin-3-ylthiophene-2-carboxylic acid [2-oxo-2-(3-oxo-hexahydrofuro[3,2-b]pyrrol-4-yl)-1-thiophen-2-ylmethylethyl]amide
2-Thiophen-2-ylthiazole-4-carboxylic acid [2-oxo-2-(3-oxo-hexahydrofuro[3,2-b]pyrrol-4-yl)-1-thiophen-2-ylmethylethyl]amide
2-Methyl-5-(pyrrolidine-1-sulfonyl)furan-3-carboxylic acid [2-oxo-2-(3-oxo-hexa hydrofuro[3,2-b]pyrrol-4-yl)-1-thiophen-2-ylmethylethyl]amide
3-Phenylpyrrole-1-carboxylic acid [2-oxo-2-(3-oxo-hexahydrofuro[3,2-b]pyrrol-4-yl)-1-thiophen-2-ylmethylethyl]amide
N-[1-(4-Aminobenzyl)-2-oxo-2-(3-oxo-hexahydrofuro[3,2-b]pyrrol-4-yl)ethyl]benzamide
4-tert-Butyl-N-[1-(4-aminobenzyl)-2-oxo-2-(3-oxo-hexahydrofuro[3,2-b]pyrrol-4-yl)ethyl]benzamide
N-[1-(4-Aminobenzyl)-2-oxo-2-(3-oxo-hexahydrofuro[3,2-b]pyrrol-4-yl)ethyl]-4-trifluoromethoxybenzamide
4-Dimethylamino-N-[1-(4-aminobenzyl)-2-oxo-2-(3-oxo-hexahydrofuro[3,2-b]pyrrol-4-yl)ethyl]benzamide
N-[1-(4-Aminobenzyl)-2-oxo-2-(3-oxo-hexahydrofuro[3,2-b]pyrrol-4-yl)ethyl]-4-isopropylbenzamide
4-Difluoromethoxy-N-[1-(4-aminobenzyl)-2-oxo-2-(3-oxo-hexahydrofuro[3,2-b]pyrrol-4-yl)ethyl]benzamide
N-[1-(4-Aminobenzyl)-2-oxo-2-(3-oxo-hexahydrofuro[3,2-b]pyrrol-4-yl)ethyl]-4-trifluoromethylbenzamide
4-Bromo-N-[1-(4-aminobenzyl)-2-oxo-2-(3-oxo-hexahydrofuro[3,2-b]pyrrol-4-yl)ethyl]benzamide
3-Bromo-N-[1-(4-aminobenzyl)-2-oxo-2-(3-oxo-hexahydrofuro[3,2-b]pyrrol-4-yl)ethyl]benzamide
N-[1-(4-Aminobenzyl)-2-oxo-2-(3-oxo-hexahydrofuro[3,2-b]pyrrol-4-yl)ethyl]-4-vinylbenzamide
Naphthalene-2-carboxylic acid [1-(4-aminobenzyl)-2-oxo-2-(3-oxo-hexahydrofuro[3,2-b]pyrrol-4-yl)ethyl]amide
Naphthalene-1-carboxylic acid [1-(4-aminobenzyl)-2-oxo-2-(3-oxo-hexahydrofuro[3,2-b]pyrrol-4-yl)ethyl]amide
Quinoline-6-carboxylic acid [1-(4-aminobenzyl)-2-oxo-2-(3-oxo-hexahydrofuro[3,2-b]pyrrol-4-yl)ethyl]amide
Benzo[b]thiophene-2-carboxylic acid [1-(4-aminobenzyl)-2-oxo-2-(3-oxo-hexa hydrofuro[3,2-b]pyrrol-4-yl)ethyl]amide
Benzo[b]thiophene-3-carboxylic acid [1-(4-aminobenzyl)-2-oxo-2-(3-oxo-hexa hydrofuro[3,2-b]pyrrol-4-yl)ethyl]amide
Benzothiazole-5-carboxylic acid [1-(4-aminobenzyl)-2-oxo-2-(3-oxo-hexahydro furo[3,2-b]pyrrol-4-yl)ethyl]amide
Biphenyl-4-carboxylic acid [1-(4-aminobenzyl)-2-oxo-2-(3-oxo-hexahydrofuro[3,2-b]pyrrol-4-yl)ethyl]amide
N-[1-(4-Aminobenzyl)-2-oxo-2-3-oxo-hexahydrofuro[3,2-b]pyrrol-4-yl)ethyl]-4-phenoxybenzamide
N-[1-(4-Aminobenzyl)-2-oxo-2-(3-oxo-hexahydrofuro[3,2-b]pyrrol-4-yl)ethyl]-3-phenoxybenzamide
N-[1-(4-Aminobenzyl)-2-oxo-2-(3-oxo-hexahydrofuro[3,2-b]pyrrol-4-yl)ethyl]-4-imidazol-1-ylbenzamide
N-[1-(4-Aminobenzyl)-2-oxo-2-(3-oxo-hexahydrofuro[3,2-b]pyrrol-4-yl)ethyl]-4-thiophen-2-ylbenzamide
N-[1-(4-Aminobenzyl)-2-oxo-2-(3-oxo-hexahydrofuro[3,2-b]pyrrol-4-yl)ethyl]-4-oxazol-5-ylbenzamide
N-[1-(4-Aminobenzyl)-2-oxo-2-(3-oxo-hexahydrofuro[3,2-b]pyrrol-4-yl)ethyl]-4-[1,2,3]thiadiazol-5-ylbenzamide
N-[1-(4-Aminobenzyl)-2-oxo-2-(3-oxo-hexahydrofuro[3,2-b]pyrrol-4-yl)ethyl]-4-pyrazol-1-ylbenzamide
N-[1-(4-Aminobenzyl)-2-oxo-2-(3-oxo-hexahydrofuro[3,2-b]pyrrol-4-yl)ethyl]-5-thiophen-2-ylnicotinamide
N-[1-(4-Aminobenzyl)-2-oxo-2-(3-oxo-hexahydrofuro[3,2-b]pyrrol-4-yl)ethyl]-6-phenylnicotinamide
2-Phenylthiazole-4-carboxylic acid [1-(4-aminobenzyl)-2-oxo-2-(3-oxo-hexa hydrofuro[3,2-b]pyrrol-4-yl)ethyl]amide
2-Pyridin-3-ylthiazole-4-carboxylic acid [1-(4-aminobenzyl)-2-oxo-2-(3-oxo-hexa hydrofuro[3,2-b]pyrrol-4-yl)ethyl]amide
5-Phenylthiophene-2-carboxylic acid [1-(aminobenzyl)-2-oxo-2-(3-oxo-hexa hydrofuro[3,2-b]pyrrol-4-yl)ethyl]amide
5-Pyridin-3-ylthiophene-2-carboxylic acid [1-(4-aminobenzyl)-2-oxo-2-(3-oxo-hexahydrofuro[3,2-b]pyrrol-4-yl)ethyl]amide
2-Methyl-5-phenylfuran-3-carboxylic acid [1-(4-aminobenzyl)-2-oxo-2-(3-oxo-hexahydrofuro[3,2-b]pyrrol-4-yl)ethyl]amide
4-Phenylthiophene-2-carboxylic acid [1-(4-aminobenzyl)-2-oxo-2-(3-oxo-hexa hydrofuro[3,2-b]pyrrol-4-yl)ethyl]amide
4-Pyridin-3-ylthiophene-2-carboxylic acid [1-(4-aminobenzyl)-2-oxo-2-(3-oxo-hexahydrofuro[3,2-b]pyrrol-4-yl)ethyl]amide
2-Thiophen-2-ylthiazole-4-carboxylic acid [1-(4-aminobenzyl)-2-oxo-2-(3-oxo-hexahydrofuro[3,2-b]pyrrol-4-yl)ethyl]amide
2-Methyl-5-(pyrrolidine-1-sulfonyl)furan-3-carboxylic acid [1-(4-aminobenzyl)-2-oxo-2-(3-oxo-hexahydrofuro[3,2-b]pyrrol-4-yl)ethyl]amide
3-Phenylpyrrole-1-carboxylic acid [1-(4-aminobenzyl)-2-oxo-2-(3-oxo-hexahydrofuro[3,2-b]pyrrol-4-yl)ethyl]amide
N-[1-Benzyl-2-oxo-2-(3-oxo-hexahydrofuro[3,2-b]pyrrol-4-yl)ethyl]benzamide 4-tert-Butyl-N-[1-benzyl-2-oxo-2-(3-oxo-hexahydrofuro[3,2-b]pyrrol-4-yl) ethyl]benzamide
N-[1-Benzyl-2-oxo-2-(3-oxo-hexahydrofuro[3,2-b]pyrrol-4-yl)ethyl]-4-trifluoro methoxybenzamide
4-Dimethylamino-N-[1-benzyl-2-oxo-2-(3-oxo-hexahydrofuro[3,2-b]pyrrol-4-yl)ethyl]benzamide
N-[1-Benzyl-2-oxo-2-(3-oxo-hexahydrofuro[3,2-b]pyrrol-4-yl)ethyl]-4-isopropyl benzamide
4-Difluoromethoxy-N-[1-benzyl-2-oxo-2-(3-oxo-hexahydrofuro[3,2-b]pyrrol-4-yl)ethyl]benzamide
N-[1-Benzyl-2-oxo-2-(3-oxo-hexahydrofuro[3,2-b]pyrrol-4-yl)ethyl]-4-trifluoro methylbenzamide
4-Bromo-N-[1-benzyl-2-oxo-2-(3-oxo-hexahydrofuro[3,2-b]pyrrol-4-yl)ethyl]benzamide
3-Bromo-N-[1-benzyl-2-oxo-2-(3-oxo-hexahydrofuro[3,2-b]pyrrol-4-yl)ethyl]benzamide
N-[1-Benzyl-2-oxo-2-(3-oxo-hexahydrofuro[3,2-b]pyrrol-4-yl)ethyl]-4-vinyl benzamide
Naphthalene-2-carboxylic acid [1-benzyl-2-oxo-2-(3-oxo-hexahydrofuro[3,2-b]pyrrol-4-yl)ethyl]amide
Naphthalene-1-carboxylic acid [1-benzyl-2-oxo-2-(3-oxo-hexahydrofuro[3,2-b]pyrrol-4-yl) ethyl]amide
Quinoline-6-carboxylic acid [1-benzyl-2-oxo-2-(3-oxo-hexahydrofuro[3,2-b]pyrrol-4-yl)ethyl]amide
Benzo[b]thiophene-2-carboxylic acid [1-benzyl-2-oxo-2-(3-oxo-hexahydrofuro[3,2-b]pyrrol-4-yl)ethyl]amide
Benzo[b]thiophene-3-carboxylic acid [1-benzyl-2-oxo-2-(3-oxo-hexahydrofuro[3,2-b]pyrrol-4-yl)ethyl]amide
Benzothiazole-5-carboxylic acid [1-benzyl-2-oxo-2-(3-oxo-hexahydrofuro[3,2-b]pyrrol-4-yl)ethyl]amide
Biphenyl-4-carboxylic acid [1-benzyl-2-oxo-2-(3-oxo-hexahydrofuro[3,2-b]pyrrol-4-yl)ethyl]amide
N-[1-Benzyl-2-oxo-2-(3-oxo-hexahydrofuro[3,2-b]pyrrol-4-yl)ethyl]-4-phenoxy benzamide
N-[1-Benzyl-2-oxo-2-(3-oxo-hexahydrofuro[3,2-b]pyrrol-4-yl)ethyl]-3-phenoxy benzamide
N-[1-Benzyl-2-oxo-2-(3-oxo-hexahydrofuro[3,2-b]pyrrol-4-yl)ethyl]-4-imidazol-1-ylbenzamide
N-[1-Benzyl-2-oxo-2-(3-oxo-hexahydrofuro[3,2-b]pyrrol-4-yl)ethyl]-4-thiophen-2-ylbenzamide
N-[1-Benzyl-2-oxo-2-(3-oxo-hexahydrofuro[3,2-b]pyrrol-4-yl)ethyl]-4-oxazol-5-ylbenzamide
N-[1-Benzyl-2-oxo-2-(3-oxo-hexahydrofuro[3,2-b]pyrrol-4-yl)ethyl]-4-[1,2,3]thiadiazol-5-ylbenzamide
N-[1-Benzyl-2-oxo-2-(3-oxo-hexahydrofuro[3,2-b]pyrrol-4-yl)ethyl]-4-pyrazol-1-ylbenzamide
N-[1-Benzyl-2-oxo-2-(3-oxo-hexahydrofuro[3,2-b]pyrrol-4-yl)ethyl]-5-thiophen-2-ylnicotinamide
N-[1-Benzyl-2-oxo-2-(3-oxo-hexahydrofuro[3,2-b]pyrrol-4-yl)ethyl]-6-phenyl nicotinamide
2-Phenylthiazole-4-carboxylic acid [1-benzyl-2-oxo-2-(3-oxo-hexahydrofuro[3,2-b]pyrrol-4-yl)ethyl]amide
2-pyridin-3-ylthiazole-4-carboxylic acid [1-benzyl-2-oxo-2-(3-oxo-hexahydrofuro[3,2-b]pyrrol-4-yl)ethyl]amide
5-Phenylthiophene-2-carboxylic acid [1-benzyl-2-oxo-2-(3-oxo-hexahydrofuro[3,2-b]pyrrol-4-yl)ethyl]amide
5-Pyridin-3-ylthiophene-2-carboxylic acid [1-benzyl-2-oxo-2-(3-oxo-hexahydrofuro[3,2-b]pyrrol-4-yl)ethyl]amide
2-Methyl-5-phenylfuran-3-carboxylic acid [1-benzyl-2-oxo-2-(3-oxo-hexahydrofuro[3,2-b]pyrrol-4-yl)ethyl]amide
4-Phenylthiophene-2-carboxylic acid [1-benzyl-2-oxo-2-(3-oxo-hexa hydrofuro[3,2-b]pyrrol-4-yl)ethyl]amide
4-Pyridin-3-ylthiophene-2-carboxylic acid [1-benzyl-2-oxo-2-(3-oxo-hexahydrofuro[3,2-b]pyrrol-4-yl)ethyl]amide
2-Thiophen-2-ylthiazole-4-carboxylic acid [1-benzyl-2-oxo-2-(3-oxo-hexahydrofuro[3,2-b]pyrrol-4-yl)ethyl]amide
2-Methyl-5-(pyrrolidine-1-sulfonyl)furan-3-carboxylic acid [1-benzyl-2-oxo-2-(3-oxo-hexahydrofuro[3,2-b]pyrrol-4-yl)ethyl]amide
3-Phenylpyrrole-1-carboxylic acid [1-benzyl-2-oxo-2-(3-oxo-hexahydrofuro[3,2-b]pyrrol-4-yl)ethyl]amide
4-[2-(4-tert-Butyl-benzylsulfanyl)-4-methyl-pentanoyl]-tetrahydrofuro[3,2-b]pyrrol-3-one
4-[2-(4-tert-Butyl-benzylsulfanyl)-3-(4-hydroxy-phenyl)-propionyl]-tetrahydro-furo[3,2-b]pyrrol-3-one
2-Isobutyl-1-(3-oxo-hexahydrofuro[3,2-b]pyrrol-4-yl)-4-(3-phenyl-pyrrol-1-yl)-butane-1,4-dione
2-Isobutyl-1-(3-oxo-hexahydrofuro[3,2-b]pyrrol-4-yl)-4-(3-phenyl-pyrrolidin-1-yl)-butane-4-dione
2-(4-Hydroxybenzyl)-1-(3-oxo-hexahydrofuro[3,2-b]pyrrol-4-yl)-4-(3-phenyl-pyrrol-1-yl)-butane-1,4-dione
2-(4-Hydroxybenzyl)-1-(3-oxo-hexahydrofuro[3,2-b]pyrrol-4-yl)-4-(3-phenyl-pyrrolidin-1-yl)-butane-1,4-dione
4-(1,3-Dihydro-isoindol-2-yl)-2-isobutyl-1-(3-oxo-hexahydrofuro[3,2-b]pyrrol-4-yl)-butane-1,4-dione
4-(1,3-Dihydro-isoindol-2-yl)-2-(4-hydroxybenzyl)-1-(3-oxo-hexahydrofuro[3,2-b]pyrrol-4-yl)-butane-1,4-dione
4-(3,4-Dihydro-1H-isoquinolin-2-yl)-2-isobutyl-1-(3-oxo-hexahydrofuro[3,2-b]pyrrol-4-yl)-butane-1,4-dione
4-(3,4-Dihydro-1H-isoquinolin-2-yl)-2-(4-hydroxybenzyl)-1-(3-oxo-hexahydrofuro[3,2-b]pyrrol-4-yl)-butane-1,4-dione Further compounds of the invention include, but are not limited to, the following examples that are the (3aS,7aR) or (3aR,7aS) isomer of general formula (II), where Z='O' and R$^1$='H' and also include the equivalent analogues included in the full definition of Z and R$^1$ N-[1-(4-Hydroxybenzyl)-2-oxo-2-(3-oxo-hexahydrofuro[3,2-b]pyridin yl)ethyl]benzamide
4-tert-Butyl-N-[1-(4-hydroxybenzyl)-2-oxo-2-(3-oxo-hexahydrofuro[3,2-b]pyridin-4-yl)ethyl]benzamide
N-[1-(4-Hydroxybenzyl)-2-oxo-2-(3-oxo-hexahydrofuro[3,2-b]pyridin-4-yl)ethyl]-4-trifluoromethoxybenzamide
4-Dimethylamino-N-[1-(4-hydroxybenzyl)-2-oxo-2-(3-oxo-hexahydrofuro[3,2-b]pyridin-4-yl)ethyl]benzamide
N-[1-(4-Hydroxybenzyl)-2-oxo-2-(3-oxo-hexahydrofuro[3,2-b]pyridinyl-4-yl)ethyl]-4-isopropylbenzamide
4-Difluoromethoxy-N-[1-(4-hydroxybenzyl)-2-oxo-2-(3-oxo-hexahydrofuro[3,2-b]pyridin-4-yl)ethyl]benzamide
N-[1-(4-Hydroxybenzyl)-2-oxo-2-(3-oxo-hexahydrofuro[3,2-b]pyridin-4-yl)ethyl]-4-trifluoromethylbenzamide
4-Bromo-N-[1-(4-hydroxybenzyl)-2-oxo-2-(3-oxo-hexahydrofuro[3,2-b]pyridin-4-yl)ethyl]benzamide
3-Bromo-N-[1-(4-hydroxybenzyl)-2-oxo-2-(3-oxo-hexahydrofuro[3,2-b]pyridin-4-yl)ethyl]benzamide
N-[1-(4-Hydroxybenzyl)-2-oxo-2-(3-oxo-hexahydrofuro[3,2-b]pyridin-4-yl)ethyl]-4-vinylbenzamide
Naphthalene-2-carboxylic acid [1-(4-hydroxybenzyl)-2-oxo-2-(3-oxo-hexahydrofuro[3,2-b]pyridinyl)ethyl]amide
Naphthalene-1-carboxylic acid [1-(4-hydroxybenzyl)-2-oxo-2-(3-oxo-hexahydrofuro[3,2-b]pyridin-4-yl)ethyl]amide
Quinoline-6-carboxylic acid [1-(4-hydroxybenzyl)-2-oxo-2-(3-oxo-hexahydrofuro[3,2-b]pyridinyl)ethyl]amide
Benzo[b]thiophene-2-carboxylic acid [1-(4-hydroxybenzyl)-2-oxo-2-(3-oxo-hexa hydrofuro[3,2-b]pyridinyl-4-yl)ethyl]amide
Benzo[b]thiophene-3-c=boxylic acid [1-(4-hydroxybenzyl)-2-oxo-2-(3-oxo-hexa hydrofuro[3,2-b]pyridin-4-yl)ethyl]amide Benzothiazole-5-carboxylic acid [1-(4-hydroxybenzyl)-2-oxo-2-(3-oxo-hexahydro furo[3,2-b]pyridin-4-yl)ethyl]amide Biphenyl-4-carboxylic acid [1-(4-hydroxybenzyl)-2-oxo-2-(3-oxo-hexahydrofuro[3,2-b]pyridin-4-yl)ethyl]amide N-[1-(4-Hydroxybenzyl)-2-oxo-2-(3-oxo-hexahydrofuro[3,2-b]pyridin-4-yl)ethyl]-4-phenoxybenzamide N-[1-(4-Hydroxybenzyl)-2-oxo-2-(3-oxo-hexahydrofuro[3,2-b]pyridin-4-yl)ethyl]-3-phenoxybenzamide N-[1-(4-Hydroxybenzyl)-2-oxo-2-(3-oxo-hexahydrofuro[3,2-b]pyridin-4-yl)ethyl]-4-imidazol-1-ylbenzamide N-[1-(4-Hydroxybenzyl)-2-oxo-2-(3-oxo-hexahydrofuro[3,2-b]pyridin-4-yl)ethyl]-4-thiophen-2-ylbenzamide N-[1-(4-Hydroxybenzyl)-2-oxo-2-(3-oxo-hexahydrofuro[3,2-b]pyridin-4-yl)ethyl]-4-oxazol-5-ylbenzamide N-[1-(4-Hydroxybenzyl)-2-oxo-2-(3-oxo-hexahydrofuro[3,2-b]pyridin-4-yl)ethyl]-4-[1,2,3]thiadiazol-5-ylbenzamide N-[1-(4-Hydroxybenzyl)-2-oxo-2-(3-oxo-hexahydrofuro[3,2-b]pyridin-4-yl)ethyl]-4-pyrazol-1-ylbenzamide N-[1-(4-Hydroxybenzyl)-2-oxo-2-(3-oxo-hexahydrofuro[3,2-b]pyridin-4-yl)ethyl]-5-thiophen-2-ylnicotinamide N-[1-(4-Hydroxybenzyl)-2-oxo-2-(3-oxo-hexahydrofuro[3,2-b]pyridin-4-yl)ethyl]-6-phenylnicotinamide 2-Phenylthiazole-4-carboxylic acid [1-(4-hydroxybenzyl)-2-oxo-2-(3-oxo-hexa hydrofuro[3,2-b]pyridin-4-yl)ethyl]amide 2-Pyridin-3-ylthiazole-4-carboxylic acid [1-(4-hydroxybenzyl)-2-oxo-2-(3-oxo-hexa hydrofuro[3,2-b]pyridin-4-yl)ethyl]amide 5-Phenylthiophene-2-carboxylic acid [1-(4-hydroxybenzyl)-2-oxo-2-(3-oxo-hexa hydrofuro[3,2-b]pyridin-4-yl)ethyl]amide 5-Pyridin-3-ylthiophene-2-carboxylic acid [1-(4-hydroxybenzyl)-2-oxo-2-(3-oxo-hexahydrofuro[3,2-b]pyridin-4-yl)ethyl]amide 2-Methyl-5-phenylfuran-3-carboxylic acid [1-(4-hydroxybenzyl)-2-oxo-2-(3-oxo-hexahydrofuro[3,2-b]pyridin-4-yl)ethyl]amide 4-Phenylthiophene-2-carboxylic acid [1-(4-hydroxybenzyl)-2-oxo-2-(3-oxo-hexa hydrofuro[3,2-b]pyridinyl)ethyl]amide 4-Pyridin-3-ylthiophene-2-carboxylic acid [1-(4-hydroxybenzyl)-2-oxo-2-(3-oxo-hexahydrofuro[3,2-b]pyridin-4-yl)ethyl]amide 2-Thiophen-2-ylthiazole-4-carboxylic acid [1-(4-hydroxybenzyl)-2-oxo-2-(3-oxo-hexahydrofuro[3,2-b]pyridin-4-yl)ethyl]amide 2-Methyl-5-(pyrrolidine-1-sulfonyl)furan-3-carboxylic acid [1-(4-hydroxybenzyl)-2-oxo-2-(3-oxo-hexahydrofuro[3,2-b]pyridinyl-4-yl)ethyl]amide 3-Phenylpyrrole-1-carboxylic acid [1-(4-hydroxybenzyl)-2-oxo-2-(3-oxo-hexahydrofuro[3,2-b]pyridin-4-yl)ethyl]amide N-[3-Methyl-1-(3-oxo-hexahydrofuro[3,2-b]pyridine-4-carbonyl)butyl]benzamide 4-tert-Butyl-N-[3-methyl-1-(3-oxo-hexahydrofuro[3,2-b]pyridine-4-carbonyl)butyl]benzamide N-[3-Methyl-1-(3-oxo-hexahydrofuro[3,2-b]pyridine-4-carbonyl)butyl]-4-trifluoro methoxybenzamide 4-Dimethylamino-N-[3-methyl-1-(3-oxo-hexahydrofuro[3,2-b]pyridine-4-carbonyl) butyl]benzamide 4-Isopropyl-N-[3-methyl-1-(3-oxo-hexahydrofuro[3,2-b]pyridine-4-carbonyl)butyl]benzamide 4-Difluoromethoxy-N-[3-methyl-1-(3-oxo-hexahydrofuro[3,2-b]pyridine-4-carbonyl)butyl]benzamide N-[3-Methyl-1-(3-oxo-hexahydrofuro[3,2-b]pyridine-4-carbonyl)butyl]-4-trifluoro methylbenzamide 4-Bromo-N-[3-methyl-1-(3-oxo-hexahydrofuro[3,2-b]pyridine-4-carbonyl)butyl]benzamide 3-Bromo-N-[3-methyl-1-(3-oxo-hexahydrofuro[3,2-b]pyridine-4-carbonyl)butyl]benzamide N-[3-Methyl-1-(3-oxo-hexahydrofuro[3,2-b]pyridine-4-carbonyl)butyl]-4-vinyl benzamide Naphthalene-2-carboxylic acid [3-methyl-1-(3-oxo-hexahydrofuro[3,2-b]pyridine-4-carbonyl)butyl]amide Naphthalene-1-carboxylic acid [3-methyl-1-(3-oxo-hexahydrofuro[3,2-b]pyridine-4-carbonyl)butyl]amide Quinoline-6-carboxylic acid [3-methyl-1-(3-oxo-hexahydrofuro[3,2-b]pyridine-4-carbonyl)butyl]amide Benzo[b]thiophene-2-carboxylic acid [3-methyl-1-(3-oxo-hexahydrofuro[3,2-b]pyridine-4-carbonyl)butyl]amide Benzo[b]thiophene-3-carboxylic acid [3-methyl-1-(3-oxo-hexahydrofuro[3,2-b]pyridine-4-carbonyl)butyl]amide Benzothiazole-5-carboxylic acid [3-methyl-1-(3-oxo-hexahydrofuro[3,2-b]pyridine-4-carbonyl)butyl]amide Biphenyl-4-carboxylic acid [3-methyl-1-(3-oxo-hexahydrofuro[3,2-b]pyridine-4-carbonyl)butyl]amide N-[3-Methyl-1-(3-oxo-hexahydrofuro[3,2-b]pyridine-4-carbonyl)butyl]-4-phenoxy benzamide N-[3-Methyl-1-(3-oxo-hexahydrofuro[3,2-b]pyridine-4-carbonyl)butyl]-3-phenoxy benzamide 4-Imidazol-1-yl-N-[3-methyl-1-(3-oxo-hexahydrofuro[3,2-b]pyridine-4-carbonyl) butyl]benzamide N-[3-Methyl-1-(3-oxo-hexahydrofuro[3,2-b]pyridine-4-carbonyl)butyl]-4-thiophen-2-ylbenzamide N-[3-Methyl-1-(3-oxo-hexahydrofuro[3,2-b]pyridine-4-carbonyl)butyl]-4-oxazol-5-ylbenzamide N-[3-Methyl-1-(3-oxo-hexahydrofuro[3,2-b]pyridine-4-carbonyl)butyl]-4-[1,2,3]thiadiazol-4-ylbenzamide N-[3-Methyl-1-(3-oxo-hexahydrofuro[3,2-b]pyridine-4-carbonyl)butyl]-4-pyrazol-1-ylbenzamide N-[3-Methyl-1-(3-oxo-hexahydrofuro[3,2-b]pyridine-4-carbonyl)butyl]-5-thiophen-2-ylnicotinamide N-[3-Methyl-1-(3-oxo-hexahydrofuro[3,2-b]pyridine-4-carbonyl)butyl]-6-phenyl nicotinamide 2-Phenylthiazole-4-carboxylic acid [3-methyl-1-(3-oxo-hexahydrofuro[3,2-b]pyridine-4-carbonyl)butyl]amide 2-Pyridin-3-ylthiazole-4-carboxylic acid [3-methyl-1-(3-oxo-hexahydrofuro[3,2-b]pyridine-4-carbonyl)butyl]amide 5-Phenylthiophene-2-carboxylic acid [3-methyl-1-(3-oxo-hexahydrofuro[3,2-b]pyridine-4-carbonyl)butyl]amide 5-Pyridin-3-ylthiophene-2-carboxylic acid [3-methyl-1-(3-oxo-hexahydrofuro[3,2-b]pyridine-4-carbonyl)butyl]amide 2-Methyl-5-phenylfuran-3-carboxylic acid [3-methyl-1-(3-oxo-hexahydrofuro[3,2-b]pyridine-4-carbonyl)butyl]amide 4-Phenylthiophene-2-carboxylic acid [3-methyl-1-(3-oxo-hexahydrofuro[3,2-b]pyridine-4-carbonyl)butyl]amide 4-Pyridin-3-ylthiophene-2-carboxylic acid [3-methyl-1-(3-oxo-hexahydrofuro[3,2-b]pyridine-4-carbonyl)butyl]amide 2-Thiophen-2-ylthiazole-4-carboxylic acid [3-methyl-1-(3-oxo-hexahydrofuro[3,2-b]pyridine-4-carbonyl)butyl]amide 2-Methyl-5-(pyrrolidine-1-sulfonyl)furan-3-carboxylic acid [3-methyl-1-(3-oxo-hexahydrofuro[3,2-b]pyridine-4-carbonyl)butyl]amide 3-Phenylpyrrole-1-carboxylic acid [3-methyl-1-(3-oxo-hexahydrofuro[3,2-b]pyridine-4-carbonyl)butyl]amide Additional compounds of the invention include, but are not limited to, the following examples that are the (3aS,6aR) isomer of general formula (I), where Z='O' and R¹='H', and also include the equivalent analogues included in the fill definition of Z and R$^1$ N-[1-Cyclopropylmethyl-2-oxo-2-(3-oxo-hexahydrofuro[3,2-b]pyrrol-4-yl)ethyl]benzamide 4-tert-Butyl-N-[1-Cyclopropylmethyl-2-oxo-2-(3-oxo-hexahydrofuro[3,2-b]pyrrol-4-yl)ethyl]benzamide N-[1-Cyclopropylmethyl-2-oxo-2-(3-oxo-hexahydrofuro[3,2-b]pyrrol-4-yl)ethyl]-4-trifluoromethoxybenzamide 4-Dimethylamino-N-[1-Cyclopropylmethyl-2-oxo-2-(3-oxo-hexahydrofuro[3,2-b]pyrrol-4-yl)ethyl]benzamide 4-Isopropyl-N-[1-Cyclopropylmethyl-2-oxo-2-(3-oxo-hexahydrofuro[3,2-b]pyrrol-4-yl)ethyl]benzamide 4-Difluoromethoxy-N-[1-Cyclopropylmethyl-2-oxo-2-(3-oxo-hexahydrofuro[3,2-b]pyrrol-4-yl)ethyl]benzamide N-[1-Cyclopropylmethyl-2-oxo-2-(3-oxo-hexahydrofuro[3,2-b]pyrrol-4-yl)ethyl]-4trifluoromethylbenzamide 4-Bromo-N-[1-Cyclopropylmethyl-2-oxo-2-(3-oxo-hexahydrofuro[3,2-b]pyrrol-4-yl)ethyl]benzamide 3-Bromo-N-[1-Cyclopropylmethyl-2-oxo-2-(3-oxo-hexahydrofuro[3,2-b]pyrrol-4-yl)ethyl]benzamide N-[1-Cyclopropylmethyl-2-oxo-2-(3-oxo-hexahydrofuro[3,2-b]pyrrol-4-yl)ethyl]-4-vinylbenzamide Naphthalene-2-carboxylic acid [1-Cyclopropylmethyl-2-oxo-2-(3-oxo-hexahydrofuro[3,2-b]pyrrol-4-yl)ethyl]amide Naphthalene-1-carboxylic acid [1-Cyclopropylmethyl-2-oxo-2-(3-oxo-hexahydrofuro[3,2-b]pyrrol-4-yl)ethyl]amide Quinoline-6-carboxylic acid [1-Cyclopropylmethyl-2-oxo-2-(3-oxo-hexahydrofuro[3,2-b]pyrrol-4-yl)ethyl]amide Benzo[b]thiophene-2-carboxylic acid [1-Cyclopropylmethyl-2-oxo-2-(3-oxo-hexahydrofuro[3,2-b]pyrrol-4-yl)ethyl]amide Benzo[b]thiophene-3-carboxylic acid [1-Cyclopropylmethyl-2-oxo-2-(3-oxo-hexahydrofuro[3,2-b]pyrrol-4-yl)ethyl]amide Benzothiazole-5-carboxylic acid [1-Cyclopropylmethyl-2-oxo-2-(3-oxo-hexahydrofuro[3,2-b]pyrrol-4-yl)ethyl]amide Biphenyl-4-carboxylic acid [1-Cyclopropylmethyl-2-oxo-2-(3-oxo-hexahydrofuro[3,2-b]pyrrol-4-yl)ethyl]amide N-[1-Cyclopropylmethyl-2-oxo-2-(3-oxo-hexahydrofuro[3,2-b]pyrrol-4-yl)ethyl]-4-phenoxy benzamide N-[1-Cyclopropylmethyl-2-oxo-2-(3-oxo-hexahydrofuro[3,2-b]pyrrol-4-yl)ethyl]-3-phenoxy benzamide 4-Imidazol-1-yl-N-[1-Cyclopropylmethyl-2-oxo-2-(3-oxo-hexahydrofuro[3,2-b]pyrrol-4-yl)ethyl]benzamide N-[1-Cyclopropylmethyl-2-oxo-2-(3-oxo-hexahydrofuro[3,2-b]pyrrol-4-yl)ethyl]-4-thiophen-2-ylbenzamide N-[1-Cyclopropylmethyl-2-oxo-2-(3-oxo-hexahydrofuro[3,2-b]pyrrol-4-yl)ethyl]-4-oxazol-5-ylbenzamide N-[1-Cyclopropylmethyl-2-oxo-2-(3-oxo-hexahydrofuro[3,2-b]pyrrol-4-yl)ethyl]-4-[1,2,3]thiadiazol-4-ylbenzamide N-[1-Cyclopropylmethyl-2-oxo-2-(3-oxo-hexahydrofuro[3,2-b]pyrrol-4-yl)ethyl]-4-pyrazol-1-ylbenzamide N-[1-Cyclopropylmethyl-2-oxo-2-(3-oxo-hexahydrofuro[3,2-b]pyrrol-4-yl)ethyl]-5-thiophen-2-ylnicotinamide N-[1-Cyclopropylmethyl-2-oxo-2-(3-oxo-hexahydrofuro[3,2-b]pyrrol-4-yl)ethyl]-6-phenyl nicotinamide 2-Phenylthiazole-4-carboxylic acid [1-Cyclopropylmethyl-2-oxo-2-(3-oxo-hexahydrofuro[3,2-b]pyrrol-4-yl)ethyl]amide 2-Pyridin-3-ylthiazole-4-carboxylic acid [1-Cyclopropylmethyl-2-oxo-2-(3-oxo-hexahydrofuro[3,2-b]pyrrol-4-yl)ethyl]amide 5-Phenylthiophene-2-carboxylic acid [1-Cyclopropylmethyl-2-oxo-2-(3-oxo-hexahydrofuro[3,2-b]pyrrol-4-yl)ethyl]amide 5-Pyridin-3-ylthiophene-2-carboxylic acid [1-Cyclopropylmethyl-2-oxo-2-(3-oxo-hexahydrofuro[3,2-b]pyrrol-4-yl)ethyl]amide 2-Methyl-5-phenylfuran-3-carboxylic acid [1-Cyclopropylmethyl-2-oxo-2-(3-oxo-hexahydrofuro[3,2-b]pyrrol-4-yl)ethyl]amide 4-Phenylthiophene-2-carboxylic acid [1-Cyclopropylmethyl-2-oxo-2-(3-oxo-hexahydrofuro[3,2-b]pyrrol-4-yl)ethyl]amide 4-Pyridin-3-ylthiophene-2-carboxylic acid [1-Cyclopropylmethyl-2-oxo-2-(3-oxo-hexahydrofuro[3,2-b]pyrrol-4-yl)ethyl]amide 2-Thiophen-2-ylthiazole-4-carboxylic acid [1-Cyclopropylmethyl-2-oxo-2-(3-oxo-hexahydrofuro[3,2-b]pyrrol-4-yl)ethyl]amide 2-Methyl-5-(pyrrolidine-1-sulfonyl)furan-3-carboxylic acid [1-Cyclopropylmethyl-2-oxo-2-(3-oxo-hexahydrofuro[3,2-b]pyrrol-4-yl)ethyl]amide 3-Phenylpyrrole-1-carboxylic acid [1-Cyclopropylmethyl-2-oxo-2-(3-oxo-hexahydrofuro[3,2-b]pyrrol-4-yl)ethyl]amide N-[1-(3-Oxo-hexahydrofuro[3,2-b]pyrrole-4-carbonyl)butyl]benzamide 4-tert-Butyl-N-[1-(3-oxo-hexahydrofuro[3,2-b]pyrrol-4-carbonyl)butyl]benzamide N-[1-(3-Oxo-hexahydrofuro[3,2-b]pyrrole-4-carbonyl)butyl]-4-trifluoromethoxy benzamide 4-Dimethylamino-N-[1-(3-oxo-hexahydrofuro[3,2-b]pyrrole-4-carbonyl) butyl]benzamide 4-Isopropyl-N-[1-(3-oxo-hexahydrofuro[3,2-b]pyrrole-4-carbonyl)butyl]benzamide 4-Difluoromethoxy-N-[1-(3-oxo-hexahydrofuro[3,2-b]pyrrole-4-carbonyl) butyl]benzamide N-[1-(3-Oxo-hexahydrofuro[3,2-b]pyrrole-4-carbonyl)butyl]-4-trifluoromethyl benzamide 4-Bromo-N-[1-(3-oxo-hexahydrofuro[3,2-b]pyrrole-4-carbonyl)butyl]benzamide 3-Bromo-N-[1-(3-oxo-hexahydrofuro[3,2-b]pyrrole-4-carbonyl)butyl]benzamide N-[1-(3-Oxo-hexahydrofuro[3,2-b]pyrrole-4-carbonyl)butyl]-4-vinyl benzamide Naphthalene-2-carboxylic acid [1-(3-oxo-hexahydrofuro[3,2-b]pyrrole-4-carbonyl) butyl]amide Naphthalene-1-carboxylic acid [1-(3-oxo-hexahydrofuro[3,2-b]pyrrole-4-carbonyl) butyl]amide Quinoline-6-carboxylic acid [1-(3-oxo-hexahydrofuro[3,2-b]pyrrole-4-carbonyl) butyl]amide Benzo[b]thiophene-2-carboxylic acid [1-(3-oxo-hexahydrofuro[3,2-b]pyrrole-4-carbonyl)butyl]amide Benzo[b]thiophene-3-carboxylic acid [1-(3-oxo-hexahydrofuro[3,2-b]pyrrole-4-carbonyl)butyl]amide Benzothiazole-5-carboxylic acid [1-(3-oxo-hexahydrofuro[3,2-b]pyrrol-4-carbonyl) butyl]amide Biphenyl-4-carboxylic acid [1-(3-oxo-hexahydrofuro[3,2-b]pyrrole-4-carbonyl) butyl]amide N-[1-(3-Oxo-hexahydrofuro[3,2-b]pyrrole-4-carbonyl)butyl]-4-phenoxy benzamide N-[1-(3-Oxo-hexahydrofuro[3,2-b]pyrrole-4-carbonyl)butyl]-3-phenoxy benzamide 4-Imidazol-1-yl-N-[1-(3-oxo-hexahydrofuro[3,2-b]pyrrole-4-carbonyl)butyl]benzamide N-[1-(3-Oxo-hexahydrofuro[3,2-b]pyrrole-4-carbonyl)butyl]-4-thiophen-2-y lbenzamide
N-[1-(3-Oxo-hexahydrofuro[3,2-b]pyrrole-4-carbonyl)butyl]-4-oxazol-5-yl benzamide
N-[1-(3-Oxo-hexahydrofuro[3,2-b]pyrrole 4-carbonyl)butyl]-4-[1,2,3]thiadiazol-4-yl benzamide
N-[1-(3-Oxo-hexahydrofuro[3,2-b]pyrrole-4-carbonyl)butyl]-4-pyrazol-1-yl benzamide
N-[1-(3-Oxo-hexahydrofuro[3,2-b]pyrrole-4-carbonyl)butyl]-5-thiophen-2-yl nicotinamide
N-[1-(3-Oxo-hexahydrofuro[3,2-b]pyrrole-4-carbonyl)butyl]-6-phenylnicotinamide
2-Phenylthiazole-4-carboxylic acid [1-(3-oxo-hexahydrofuro[3,2-b]pyrrole-4-carbonyl)butyl]amide
2-Pyridin-3-ylthiazole-4-carboxylic acid [1-(3-oxo-hexahydrofuro[3,2-b]pyrrole-4-carbonyl)butyl]amide
5-Phenylthiophene-2-carboxylic acid [1-(3-oxo-hexahydrofuro[3,2-b]pyrrole-4-carbonyl)butyl]amide
5-Pyridin-3-ylthiophene-2-carboxylic acid [1-(3-oxo-hexahydrofuro[3,2-b]pyrrole-4-carbonyl)butyl]amide
2-Methyl-5-phenylfuran-3-carboxylic acid [1-(3-oxo-hexahydrofuro[3,2-b]pyrrole-4-carbonyl)butyl]amide
4-Phenylthiophene-2-carboxylic acid [1-(3-oxo-hexahydrofuro[3,2-b]pyrrole-4-carbonyl)butyl]amide
4-Pyridin-3-ylthiophene-2-carboxylic acid [1-(3-oxo-hexahydrofuro[3,2-b]pyrrole-4-carbonyl)butyl]amide
2-Thiophen-2-ylthiazole-4-carboxylic acid [1-(3-oxo-hexahydrofuro[3,2-b]pyrrole-4-carbonyl)butyl]amide
2-Methyl-5-(pyrrolidine-1-sulfonyl)furan-3-carboxylic acid [1-(3-oxo-hexahydro furo[3,2-b]pyrrole-4-carbonyl)butyl]amide
3-Phenylpyrrole-1-carboxylic acid [1-(3-oxo-hexahydrofuro[3,2-b]pyrrole-4-carbonyl)butyl]amide
4-Methyl-N-[3-methyl-1-(3-oxo-hexahydrofuro[3,2-b]pyrrole-4-carbonyl)butyl]benzamide
4-Methoxy-N-[3-methyl-1-(3-oxo-hexahydrofuro[3,2-b]pyrrole-4-carbonyl)butyl]benzamide
N-[3-Methyl-1-(3-oxo-hexahydrofuro[3,2-b]pyrrole-4-carbonyl)butyl]-4-morpholin-4-ylbenzamide
4-tert-Butyl-N-[1-(4-methoxybenzyl)-2-oxo-2-(3-oxo-hexahydrofuro[3,2-b]pyrrol-4-yl)ethyl]benzamide
Naphthalene-2-carboxylic acid [1-(4-methoxybenzyl)-2-oxo-2-(3-oxo-hexahydro furo[3,2-b]pyrrol-4-yl)ethyl]amide
Biphenyl-4-carboxylic acid [1-(4-methoxybenzyl)-2-oxo-2-(3-oxo-hexahydrofuro[3,2-b]pyrrol 4-yl)ethyl]amide
4-tert-Butyl-N-[1-(4-hydroxymethylbenzyl)-2-oxo-2-(3-oxo-hexahydrofuro[3,2-b]pyrrol-4-yl)ethyl]benzamide
Naphthalene-2-carboxylic acid [1-(4-hydroxymethylbenzyl)-2-oxo-2-(3-oxo-hexahydrofuro[3,2-b]pyrrol-4-yl)ethyl]amide
Biphenyl-4-carboxylic acid [1-(4-hydroxymethylbenzyl)-2-oxo-2-(3-oxo-hexahydrofuro[3,2-b]pyrrol-4-yl)ethyl]amide
Furan-2-carboxylic acid [1-(4-hydroxybenzyl)-2-oxo-2-(3-oxo-hexahydrofuro[3,2-b]pyrrol-4-yl)ethyl]amide
Furan-3-carboxylic acid [1-(4-hydroxybenzyl)-2-oxo-2-(3-oxo-hexahydrofuro[3,2-b]pyrrol-4-yl)ethyl]amide
Thiophene-2-carboxylic acid [1-(4-hydroxybenzyl)-2-oxo-2-(3-oxo-hexahydrofuro[3,2-b]pyrrol-4-yl)ethyl]amide
Thiophene-3-carboxylic acid [1-(4-hydroxybenzyl)-2-oxo-2-(3-oxo-hexahydrofuro[3,2-b]pyrrol-4-yl)ethyl]amide
Morpholine-4-carboxylic acid [1-(4-hydroxybenzyl)-2-oxo-2-(3-oxo-hexahydro furo[3,2-b]pyrrol-4-yl)ethyl]amide
N-[1-(4-Hydroxybenzyl)-2-oxo-2-3-oxo-hexahydrofuro[3,2-b]pyrrol-4-yl)ethyl]-2-phenylacetamide
N-[1-(4-Hydroxybenzyl)-2-oxo-2-(3-oxo-hexahydrofuro[3,2-b]pyrrol-4-yl)ethyl]-3-phenylpropionamide
Furan-2-carboxylic acid [3-methyl-1-(3-oxo-hexahydrofuro[3,2-b]pyrrole-4-carbonyl)butyl]amide
Furan-3-carboxylic acid [3-methyl-1-(3-oxo-hexahydrofuro[3,2-b]pyrrole-4-carbonyl)butyl]amide
Thiophene-2-carboxylic acid [3-methyl-1-(3-oxo-hexahydrofuro[3,2-b]pyrrole-4-carbonyl)butyl]amide
Thiophene-3-carboxylic acid [3-methyl-1-(3-oxo-hexahydrofuro[3,2-b]pyrrole-4-carbonyl)butyl]amide
Morpholine-carboxylic acid [3-methyl-1-(3-oxo-hexahydrofuro[3,2-b]pyrrole-4-carbonyl)butyl]amide
N-[3-Methyl-1-(3-oxo-hexahydrofuro[3,2-b]pyrrole-4-carbonyl)butyl]-2-phenyl acetamide
N-[3-Methyl-1-(3-oxo-hexahydrofuro[3,2-b]pyrrole-4-carbonyl)butyl]-3-phenyl propionamide
Furan-2-carboxylic acid [1-cyclohexylmethyl-2-oxo-(3-oxo-hexahydrofuro[3,2-b]pyrrol-4-yl)ethyl]amide
Furan-3-carboxylic acid [1-cyclohexylmethyl-2-oxo-(3-oxo-hexahydrofuro[3,2-b]pyrrol-4-yl)ethyl]amide
Thiophene-2-carboxylic acid [1-cyclohexylmethyl-2-oxo-(3-oxo-hexahydro furo[3,2-b]pyrrol-4-yl)ethyl]amide
Thiophene-3-carboxylic acid [1-cyclohexylmethyl-2-oxo-(3-oxo-hexahydro furo[3,2-b]pyrrol-4-yl)ethyl]amide
Morpholine-4-carboxylic acid [1-cyclohexylmethyl-2-oxo-(3-oxo-hexahydro furo[3,2-b]pyrrol-4-yl)ethyl]amide
N-[1-Cyclohexylmethyl-2-oxo-(3-oxo-hexahydrofuro[3,2-b]pyrrol-4-yl)ethyl]-2-phenylacetamide
N-[1-Cyclohexylmethyl-2-oxo-(3-oxo-hexahydrofuro[3,2-b]pyrrol-4-yl)ethyl]-3-phenylpropionamide
N-[1-Cyclohexylmethyl-2-oxo-2-(3-oxo-hexahydrofuro[3,2-b]pyrrol-4-yl)ethyl]benzamide
Naphthalene-1-carboxylic acid [1-cyclohexylmethyl-2-oxo-2-(3-oxo-hexahydro furo[3,2-b]pyrrol-4-yl)ethyl]amide
Benzo[b]thiophene-2-carboxylic acid [1-cyclohexylmethyl-2-oxo-2-(3-oxo-hexa hydrofuro[3,2-b]pyrrol-4-yl)ethyl]amide
Furan-2-carboxylic acid [3,3-dimethyl-1-(3-oxo-hexahydrofuro[3,2-b]pyrrole-4-carbonyl)butyl]amide
Furan-3-carboxylic acid [3,3-dimethyl-1-(3-oxo-hexahydrofuro[3,2-b]pyrrole-4-carbonyl)butyl]amide
Thiophene-2-carboxylic acid [3,3-dimethyl-1-(3-oxo-hexahydrofuro[3,2-b]pyrrole-4-carbonyl)butyl]amide
Thiophene-3-carboxylic acid [3,3-dimethyl-1-(3-oxo-hexahydrofuro[3,2-b]pyrrole-4-carbonyl)butyl]amide
Morpholine-4-carboxylic acid [3,3-dimethyl-1-(3-oxo-hexahydrofuro[3,2-b]pyrrole-4-carbonyl)butyl]amide
N-[3,3-Dimethyl-1-(3-oxo-hexahydrofuro[3,2-b]pyrrole-4-carbonyl)butyl]-2-phenyl acetamide
N-[3,3-Dimethyl-1-(3-oxo-hexahydrofuro[3,2-b]pyrrole-4-carbonyl)butyl]-3-phenyl propionamide
Benzo[b]thiophene-2-carboxylic acid [3,3-dimethyl-1-(3-oxo-hexahydrofuro[3,2-b]pyrrole-4-carbonyl)butyl]amide
N-[3,3-Dimethyl-1-(3-oxo-hexahydrofuro[3,2-b]pyrrole-4-carbonyl)butyl]benzamide
Furan-2-carboxylic acid [1-benzyl-2-oxo-2-(3-oxo-hexahydrofuro[3,2-b]pyrrol-4-yl) ethyl]amide
Furan-3-carboxylic acid [1-benzyl-2-oxo-2-(3-oxo-hexahydrofuro[3,2-b]pyrrol-4-yl) ethyl]amide
Thiophene-2-carboxylic acid [1-benzyl-2-oxo-2-(3-oxo-hexahydrofuro[3,2-b]pyrrol-4-yl)ethyl]amide
Thiophene-3-carboxylic acid [1-benzyl-2-oxo-2-(3-oxo-hexahydrofuro[3,2-b]pyrrol-4-yl)ethyl]amide
Morpholine-4-carboxylic acid [1-benzyl-2-oxo-2-(3-oxo-hexahydrofuro[3,2-b]pyrrol-4-yl)ethyl]amide N-[1-Benzyl-2-oxo-2-(3-oxo-hexahydrofuro[3,2-b]pyrrol-4-yl)ethyl]-2-phenyl acetamide
N-[1-Benzyl-2-oxo-2-(3-oxo-hexahydrofuro[3,2-b]pyrrol-4-yl)ethyl]-3-phenyl propionamide
Benzo[b]thiophene-2-carboxylic acid [1-benzyl-2-oxo-2-(3-oxo-hexahydrofuro[3,2-b]pyrrol-4-yl)ethyl]amide
N-[1-Benzyl-2-oxo-2-(3-oxo-hexahydrofuro[3,2-b]pyrrol-4-yl)ethyl]benzamide
Furan-2-carboxylic acid [1-cyclopentylmethyl-2-oxo-(3-oxo-hexahydrofuro[3,2-b]pyrrol-4-yl)ethyl]amide
Furan-3-carboxylic acid [1-cyclopentylmethyl-2-oxo-(3-oxo-hexahydro furo[3,2-b]pyrrol-4-yl)ethyl]amide
Thiophene-2-carboxylic acid [1-cyclopentylmethyl-2-oxo-(3-oxo-hexahydro furo[3,2-b]pyrrol-4-yl)ethyl]amide
Thiophene-3-carboxylic acid [1-cyclopentylmethyl-2-oxo-(3-oxo-hexahydro furo[3,2-b]pyrrol-4-yl)ethyl]amide
Morpholine-4-carboxylic acid [1-cyclopentylmethyl-2-oxo-(3-oxo-hexahydro furo[3,2-b]pyrrol-4-yl)ethyl]amide
N-[1-Cyclopentylmethyl-2-oxo-(3-oxo-hexahydrofuro[3,2-b]pyrrol-4-yl)ethyl]-2-phenylacetamide
N-[1-Cyclopentylmethyl-2-oxo-(3-oxo-hexahydrofuro[3,2-b]pyrrol-4-yl)ethyl]-3-phenylpropionamide
N-[1-Cyclopentylmethyl-2-oxo-2-(3-oxo-hexahydrofuro[3,2-b]pyrrol-4-yl)ethyl]benzamide
Naphthalene-1-carboxylic acid [1-cyclopentylmethyl-2-oxo-2-(3-oxo-hexahydro furo[3,2-b]pyrrol-4-yl)ethyl]amide
Benzo[b]thiophene-2-carboxylic acid [1-cyclopentylmethyl-2-oxo-2-(3-oxo-hexa hydrofuro[3,2-b]pyrrol-4-yl)ethyl]amide
Furan-2-carboxylic acid [1-benzylsulfanylmethyl-2-oxo-2-(3-oxo-hexahydro furo[3,2-b]pyrrol-4-yl)ethyl]amide
Furan-3-carboxylic acid [1-benzylsulfanylmethyl-2-oxo-2-(3-oxo-hexahydro furo[3,2-b]pyrrol-4-yl)ethyl]amide
Thiophene-2-carboxylic acid [1-benzylsulfanylmethyl-2-oxo-2-(3-oxo-hexahydro furo[3,2-b]pyrrol-4-yl)ethyl]amide
Thiophene-3-carboxylic acid [1-benzylsulfanylmethyl-2-oxo-2-(3-oxo-hexahydro furo[3,2-b]pyrrol-4-yl)ethyl]amide
Morpholine-4-carboxylic acid [1-benzylsulfanylmethyl-2-oxo-2-(3-oxo-hexahydro furo[3,2-b]pyrrol-4-yl)ethyl]amide
N-[1-Benzylsulfanylmethyl-2-oxo-2-3-oxo-hexahydrofuro[3,2-b]pyrrol-4-yl)ethyl]-2-phenylacetamide
N-[1-Benzylsulfanylmethyl-2-oxo-2-(3-oxo-hexahydrofuro[3,2-b]pyrrol-4-yl)ethyl]-3-phenylpropionamide
Benzo[b]thiophene-2-carboxylic acid [1-benzylsulfanylmethyl-2-oxo-2-(3-oxo-hexahydrofuro[3,2-b]pyrrol-4-yl)ethyl]amide
N-[1-Benzylsulfanylmethyl-2-oxo-2-(3-oxo-hexahydrofuro[3,2-b]pyrrol-4-yl) ethyl]benzamide
Naphthalene-1-carboxylic acid [1-benzylsulfanylmethyl-2-oxo-2-(3-oxo-hexahydro furo[3,2-b]pyrrol-4-yl)ethyl]amide
Furan-2-carboxylic acid [2-oxo-2-(3-oxo-hexahydrofuro[3,2-b]pyrrol-4-yl)-1-(phenylmethanesulfonylmethyl)ethyl]amide
Furan-3-carboxylic acid [2-oxo-2-(3-oxo-hexahydrofuro[3,2-b]pyrrol-4-yl)-1-(phenylmethanesulfonylmethyl)ethyl]amide
Thiophene-2-carboxylic acid [2-oxo-2-(3-oxo-hexahydrofuro[3,2-b]pyrrol-4-yl)-1-(phenylmethanesulfonylmethyl)ethyl]amide
Thiophene-3-carboxylic acid [2-oxo-2-(3-oxo-hexahydrofuro[3,2-b]pyrrol-4-yl)-1-(phenylmethanesulfonylmethyl)ethyl]amide
Morpholine-4-carboxylic acid [2-oxo-2-(3-oxo-hexahydrofuro[3,2-b]pyrrol-4-yl)-1-(phenylmethanesulfonylmethyl)ethyl]amide
N-[2-Oxo-2-(3-oxo-hexahydrofuro[3,2-b]pyrrol-4-yl)-1-(phenylmethanesulfonyl methyl)ethyl]-2-phenylacetamide
N-[2-Oxo-2-(3-oxo-hexahydrofuro[3,2-b]pyrrol-4-yl)-1-(phenylmethanesulfonyl methyl)ethyl]-3-phenylpropionamide
Benzo[b]thiophene-2-carboxylic acid [2-oxo-2-(3-oxo-hexahydrofuro[3,2-b]pyrrol-4-yl)-1-(phenylmethanesulfonylmethyl)ethyl]amide
N-[2-Oxo-2-(3-oxo-hexahydrofuro[3,2-b]pyrrol-4-yl)-1-(phenymethanesulfonyl methyl)ethyl]benzamide
Naphthalene-1-carboxylic acid [2-oxo-2-(3-oxo-hexahydrofuro[3,2-b]pyrrol-4-yl)-1-(phenylmethanesulfonylmethyl)ethyl]amide
4-(2-Benzyloxy-3-cyclohexyl-propionoyl)tetrahydrofuro[3,2-b]pyrrol-3-one
4-[2-(4-tert-Butylbenzyloxy)-4-methyl-pentanoyl]tetrahydrofuro[3,2-b]pyrrol-3-one
4-[2-(Naphthalen-1-ylmethoxy)-3-phenyl-propionyl]-tetrahydro-furo[3,2-b]pyrrol-3-one
4-[3-Cyclohexyl-2-(furan-2-ylmethanesulfanyl)propionoyl]tetrahydrofuro[3,2-b]pyrrol-3-one
4-[3-Cyclohexyl-2-(furan-3-ylmethanesulfanyl)propionoyl]tetrahydrofuro[3,2-b]pyrrol-3-one
4-[3-Cyclohexyl-2-(furan-2-ylmethanesulphonyl)propionoyl]tetrahydrofuro[3,2-b]pyrrol-3-one
4-[3-Cyclohexyl-2-(furan-3-ylmethanesulphonyl)propionoyl]tetrahydrofuro[3,2-b]pyrrol-3-one
Morpholine-4-carboxylic acid 1-cyclohexylmethyl-2-oxo-2-(3-oxo-hexahydro-furo[3,2-b]pyrrol-4-yl)-ethyl ester
Morpholine-4-carboxylic acid 3-methyl-1-(3-oxo-hexahydrofuro[3,2-b]pyrrole-4-carbonyl)-butyl ester
Morpholine-4-carboxylic acid 3,3-dimethyl-1-(3-oxo-hexahydrofuro[3,2-b]pyrrole-4-carbonyl)-butyl ester
2-Cyclohexylmethyl-4-morpholin-4-yl-1-(3-oxo-hexahydrofuro[3,2-b]pyrrol-4-yl)butane-1,4-dione
2-Isobutyl-4-morpholin-4-yl-1-(3-oxo-hexahydrofuro[3,2-b]pyrrol-4-yl)-butane-1,4-dione
2-(2,2-Dimethyl-propyl)-4-morpholin-4-yl-1-(3-oxo-hexahydrofuro[3,2-b]pyrrol-4-yl)-butane-1,4-dione
4-(2-Biphenyl-3-yl-4-methylpentanoyl)tetrahydrofuro[3,2-b]pyrrol-3-one Further additional compounds of the invention include, but are not limited to, the following examples that are the (3 aS, 7aR) or (3aR,7aS) isomer of general formula (II) where Z='O' and $R^1$='H', and also include the equivalent analogues included in the full definition of Z and $R^1$ Furan-2-carboxylic acid [1-(4-hydroxybenzyl)-2-oxo-2-(3-oxo-hexahydrofuro[3,2-b]pyridin-4-yl)ethyl]amide
Furan-3-carboxylic acid [1-(4-hydroxybenzyl)-2-oxo-2-(3-oxo-hexahydrofuro[3,2-b]pyridin-4-yl)ethyl]amide
Thiophene-2-carboxylic acid [1-(4-hydroxybenzyl)-2-oxo-2-(3-oxo-hexahydrofuro[3,2-b]pyridin-4-yl)ethyl]amide
Thiophene-3-carboxylic acid [1-(4-hydroxybenzyl)-2-oxo-2-(3-oxo-hexahydrofuro[3,2-b]pyridin-4-yl)ethyl]amide
Morpholine-4-carboxylic acid [1-(4-hydroxybenzyl)-2-oxo-2-(3-oxo-hexahydro furo[3,2-b]pyridinyl-4-yl)ethyl]amide
N-[1-(4-Hydroxybenzyl)-2-oxo-2-(3-oxo-hexahydrofuro[3,2-b]pyridin-4-yl)ethyl]-2-phenylacetamide
N-[1-(4-Hydroxybenzyl)-2-oxo-2-(3-oxo-hexahydrofuro[3,2-b]pyridin-4-yl)ethyl]-3-phenylpropionamide
N-[1-(4-Hydroxybenzyl)-2-oxo-2-(3-oxo-hexahydrofuro[3,2-b]pyridin-4-yl)ethyl]benzamide Furan-2-carboxylic acid [3-methyl-1-(3-oxo-hexahydrofuro[3,2-b]pyridine-4-carbonyl)butyl]amide
Furan-3-carboxylic acid [3-methyl-1-(3-oxo-hexahydrofuro[3,2-b]pyridine-4-carbonyl)butyl]amide
Thiophene-2-carboxylic acid [3-methyl-1-(3-oxo-hexahydrofuro[3,2-b]pyridine-4-carbonyl)butyl]amide
Thiophene-3-carboxylic acid [3-methyl-1-(3-oxo-hexahydrofuro[3,2-b]pyridine-4-carbonyl)butyl]amide
Morpholine-4-carboxylic acid [3-methyl-1-(3-oxo-hexahydrofuro[3,2-b]pyridine-4-carbonyl)butyl]amide
N-[3-Methyl-1-(3-oxo-hexahydrofuro[3,2-b]pyridine-4-carbonyl)butyl]-2-phenyl acetamide
N-[3-Methyl-1-(3-oxo-hexahydrofuro[3,2-b]pyridine-4-carbonyl)butyl]-3-phenyl propionamide
Furan-2-carboxylic acid [1-cyclohexylmethyl-2-oxo-(3-oxo-hexahydrofuro[3,2-b]pyridin-4-yl)ethyl]amide
Furan-3-carboxylic acid [1-cyclohexylmethyl-2-oxo-(3-oxo-hexahydrofuro[3,2-b]pyridin-4-yl)ethyl]amide
Thiophene-2-carboxylic acid [1-cyclohexylmethyl-2-oxo-(3-oxo-hexahydro furo[3,2-b]pyridin-4-yl)ethyl]amide
Thiophene-3-carboxylic acid [1-cyclohexylmethyl-2-oxo-(3-oxo-hexahydro furo[3,2-b]pyridin-4-yl)ethyl]amide
Morpholine-4-carboxylic acid [1-cyclohexylmethyl-2-oxo-(3-oxo-hexahydro furo[3,2-b]pyridin-4-yl)ethyl]amide
N-[1-Cyclohexylmethyl-2-oxo-(3-oxo-hexahydrofuro[3,2-b]pyridin-4-yl)ethyl]-2-phenylacetamide
N-[1-Cyclohexylmethyl-2-oxo-(3-oxo-hexahydrofuro[3,2-b]pyridin-4-yl)ethyl]-3-phenylpropionamide
N-[1-Cyclohexylmethyl-2-oxo-2-(3-oxo-hexahydrofuro[3,2-b]pyridin-4-yl)ethyl]benzamide
Naphthalene-1-carboxylic acid [1-cyclohexylmethyl-2-oxo-2-(3-oxo-hexahydro furo[3,2-b]pyridin-4-yl)ethyl]amide
Benzo[b]thiophene-2-carboxylic acid [1-cyclohexylmethyl-2-oxo-2-(3-oxo-hexa hydrofuro[3,2-b]pyridin-4-yl)ethyl]amide
Furan-2-carboxylic acid [3,3-dimethyl-1-(3-oxo-hexahydrofuro[3,2-b]pyridine-4-carbonyl)butyl]amide
Furan-3-carboxylic acid [3,3-dimethyl-1-(3-oxo-hexahydrofuro[3,2-b]pyridine-4-carbonyl)butyl]amide
Thiophene-2-carboxylic acid [3,3-dimethyl-1-(3-oxo-hexahydrofuro[3,2-b]pyridine-4-carbonyl)butyl]amide
Thiophene-3-carboxylic acid [3,3-dimethyl-1-(3-oxo-hexahydrofuro[3,2-b]pyridine-4-carbonyl)butyl]amide
Morpholine-4-carboxylic acid [3,3-dimethyl-1-(3-oxo-hexahydrofuro[3,2-b]pyridine-4-carbonyl)butyl]amide
N-[3,3-Dimethyl-1-(3-oxo-hexahydrofuro[3,2-b]pyridine-4-carbonyl)butyl]-2-phenyl acetamide
N-[3,3-Dimethyl-1-(3-oxo-hexahydrofuro[3,2-b]pyridine-4-carbonyl)butyl]-3-phenyl propionamide
Benzo[b]thiophene-2-carboxylic acid [3,3-dimethyl-1-(3-oxo-hexahydrofuro[3,2-b]pyridine-4-carbonyl)butyl]amide
N-[3,3-Dimethyl-1-(3-oxo-hexahydrofuro[3,2-b]pyridine-4-carbonyl)butyl]benzamide
Furan-2-carboxylic acid [1-benzyl-2-oxo-2-(3-oxo-hexahydrofuro[3,2-b]pyridin-4-yl) ethyl]amide
Furan-3-carboxylic acid [1-benzyl-2-oxo-2-(3-oxo-hexahydrofuro[3,2-b]pyridin-4-yl) ethyl]amide
Thiophene-2-carboxylic acid [1-benzyl-2-oxo-2-(3-oxo-hexahydrofuro[3,2-b]pyridin-4-yl)ethyl]amide
Thiophene-3-carboxylic acid [1-benzyl-2-oxo-2-(3-oxo-hexahydrofuro[3,2-b]pyrrol-4-yl)ethyl]amide
Morpholine-4-carboxylic acid [1-benzyl-2-oxo-2-(3-oxo-hexahydrofuro[3,2-b]pyridin-4-yl)ethyl]amide
N-[1-Benzyl-2-oxo-2-(3-oxo-hexahydrofuro[3,2-b]pyridin-4-yl)ethyl]-2-phenyl acetamide
N-[1-Benzyl-2-oxo-2-(3-oxo-hexahydrofuro[3,2-b]pyridin-4-yl)ethyl]-3-phenyl propionamide
Benzo[b]thiophene-2-carboxylic acid [1-benzyl-2-oxo-2-(3-oxo-hexahydrofuro[3,2-b]pyridinyl)ethyl]amide
N-[1-benzyl-2-oxo-2-(3-oxo-hexahydrofuro[3,2-b]pyridin-4-yl)ethyl]benzamide
Furan-2-carboxylic acid [1-cyclopentylmethyl-2-oxo-(3-oxo-hexahydrofuro[3,2-b]pyridin-4-yl)ethyl]amide
Furan-3-carboxylic acid [1-cyclopentylmethyl-2-oxo-(3-oxo-hexahydro furo[3,2-b]pyridinyl)ethyl]amide
Thiophene-2-carboxylic acid [1-cyclopentylmethyl-2-oxo-(3-oxo-hexahydro furo[3,2-b]pyridin-4-yl)ethyl]amide
Thiophene-3-carboxylic acid [1-cyclopentylmethyl-2-oxo-(3-oxo-hexahydro furo[3,2-b]pyridin-4-yl)ethyl]amide
Morpholine-4-carboxylic acid [1-cyclopentylmethyl-2-oxo-(3-oxo-hexahydro furo[3,2-b]pyridin-4-yl)ethyl]amide
N-[1-Cyclopentylmethyl-2-oxo-(3-oxo-hexahydrofuro[3,2-b]pyridin-4-yl)ethyl]-2-phenylacetamide
N-[1-Cyclopentylmethyl-2-oxo-(3-oxo-hexahydrofuro[3,2-b]pyridin-4-yl)ethyl]-3-phenylpropionamide
N-[1-Cyclopentylmethyl-2-oxo-2-(3-oxo-hexahydrofuro[3,2-b]pyridinyl-4-yl)ethyl]benzamide
Naphthalene-1-carboxylic acid [1-cyclopentylmethyl-2-oxo-2-(3-oxo-hexahydro furo[3,2-b]pyridin-4-yl)ethyl]amide
Benzo[b]thiophene-2-carboxylic acid [1-cyclopentylmethyl-2-oxo-2-(3-oxo-hexa hydrofuro[3,2-b]pyridin-4-yl)ethyl]amide
Furan-2-carboxylic acid [1-benzylsulfanylmethyl-2-oxo-2-(3-oxo-hexahydro furo[3,2-b]pyridin-4-yl)ethyl]amide
Furan-3-carboxylic acid [1-benzylsulfanylmethyl-2-oxo-2-(3-oxo-hexahydro furo[3,2-b]pyridin-4-yl)ethyl]amide
Thiophene-2-carboxylic acid [1-benzylsulfanylmethyl-2-oxo-2-(3-oxo-hexahydro furo[3,2-b]pyridin-4-yl)ethyl]amide
Thiophene-3-carboxylic acid [1-benzylsulfanylmethyl-2-oxo-2-(3-oxo-hexahydro furo[3,2-b]pyridin-4-yl)ethyl]amide
Morpholine-4-carboxylic acid [1-benzylsulfanylmethyl-2-oxo-2-(3-oxo-hexahydro furo[3,2-b]pyridin-4-yl)ethyl]amide
N-[1-Benzylsulfanylmethyl-2-oxo-2-(3-oxo-hexahydrofuro[3,2-b]pyridin-4-yl)ethyl]-2-phenylacetamide
N-[1-Benzylsulfanylmethyl-2-oxo-2-(3-oxo-hexahydrofuro[3,2-b]pyridin-4-yl)ethyl]-3-phenylpropionamide
Benzo[b]thiophene-2-carboxylic acid [1-benzylsulfanylmethyl-2-oxo-2-(3-oxo-hexahydrofuro[3, 2-b]pyridin-4-yl)ethyl]amide
N-[1-Benzylsulfanylmethyl-2-oxo-2-(3-oxo-hexahydrofuro[3,2-b]pyridin-4-yl) ethyl]benzamide
Naphthalene-1-carboxylic acid [1-benzylsulfanylmethyl-2-oxo-2-(3-oxo-hexahydro furo[3,2-b]pyridin-4-yl)ethyl]amide
Furan-2-carboxylic acid [2-oxo-2-(3-oxo-hexahydrofuro[3,2-b]pyridin-4-yl)-1-(phenylmethanesulfonylmethyl)ethyl]amide
Furan-3-carboxylic acid [2-oxo-2-(3-oxo-hexahydrofuro[3,2-b]pyridin-4-yl)-1-(phenylmethanesulfonylmethyl)ethyl]amide
Thiophene-2-carboxylic acid [2-oxo-2-(3-oxo-hexahydrofuro[3,2-b]pyridin-4-yl)-1-(phenylmethanesulfonylmethyl)ethyl]amide
Thiophene-3-carboxylic acid [2-oxo-2-(3-oxo-hexahydrofuro[3,2-b]pyridin-4-yl)-1-(phenylmethanesulfonylmethyl)ethyl]amide
Morpholine-4-carboxylic acid [2-oxo-2-(3-oxo-hexahydrofuro[3,2-b]pyridin-4-yl)-1-(phenylmethanesulfonylmethyl)ethyl]amide N-[2-Oxo-2-(3-oxo-hexahydrofuro[3,2-b]pyridin-4-yl)-1-(phenylmethanesulfonyl methyl)ethyl]-2-phenylacetamide N-[2-Oxo-2-(3-oxo-hexahydrofuro[3,2-b]pyridin-4-yl)-1-(phenylmethanesulfonyl methyl)ethyl]-3-phenylpropionamide Benzo[b]thiophene-2-carboxylic acid [2-oxo-2-(3-oxo-hexahydrofuro[3,2-b]pyridin-4-yl)-1-(phenylmethanesulfonylmethyl)ethyl]amide N-[2-Oxo-2-(3-oxo-hexahydrofuro[3,2-b]pyridin-4-yl)-1-(phenylmethanesulfonyl methyl)ethyl]benzamide Naphthalene-1-carboxylic acid [2-oxo-2-(3-oxo-hexahydrofuro[3,2-b]pyridin-4-yl)-1-(phenylmethanesulfonylmethyl)ethyl]amide Morpholine-4-carboxylic acid 1-cyclohexylmethyl-2-oxo-2-(3-oxo-hexahydrofuro[3,2-b]pyridinyl)ethyl ester 4-[3-Cyclohexyl-2-(furan-2-ylmethanesulfanyl)propionyl]hexahydrofuro[3,2-b]pyridin-3-one 4-[3-Cyclohexyl-2-(furan-2-ylmethanesulphonyl)propionyl]hexahydrofuro[3,2-b]pyridin-3-one 4-[3-Cyclohexyl-2-(furan-3-ylmethanesulfanyl)propionyl]hexahydrofuro[3,2-b]pyridin-3-one 4-[3-Cyclohexyl-2-(furan-3-ylmethanesulphonyl)propionyl]hexahydrofuro[3,2-b]pyridin-3-one 2-Cyclohexylmethyl-4-morpholin-4-yl-1-(3-oxo-hexahydrofuro[3,2-b]pyridin-4-yl)butane-1,4-dione Considering all of the above examples, it is also intended to include the oxidised analogues of capping groups that contain a readily oxidised nitrogen to give the N-oxide or a readily oxidised sulphur to give the sulphone. The following structures are illustrative examples;

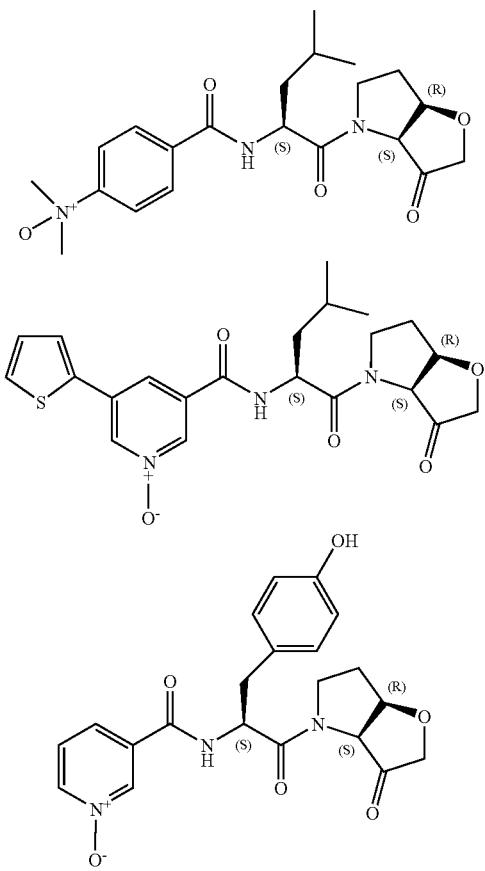

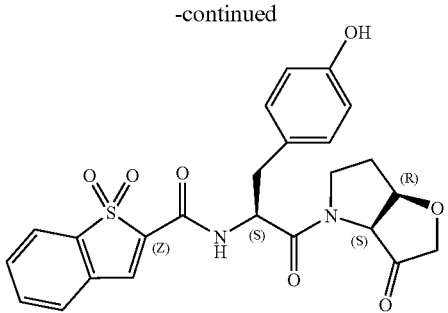

To those skilled in the practices of organic chemistry, compounds of general formulae (I) and (II) may be readily synthesised by a number of chemical strategies, performed either in solution or on the solid phase (see Atherton, E. and Sheppard, R C. In '*Solid Phase Peptide Synthesis: A Practical Approach*', Oxford University Press, Oxford, U.K. 1989, for a general review of solid phase synthesis principles). The solid phase strategy is attractive in being able to generate many thousands of analogues, typically on a 5-100 mg scale, through established parallel synthesis methodologies (e.g. see (a) Bastos, M.; Maeji, N. J.; Abeles, R. H. *Proc. Natl. Acad. Sci. USA,* 92, 6738-6742, 1995).

Therefore, one strategy for the synthesis of compounds of general formulae (I) and (II) comprises:

(a) Preparation of an appropriately functionalised and protected bi-cyclic ketone building block in solution.

(b) Attachment of the building block (a) to the solid phase through a linker that is stable to the conditions of synthesis, but readily labile to cleavage at the end of a synthesis (see James, I. W., *Tetrahedron,* 55(*Report N°* 489), 4855-4946, 1999, for examples of the 'linker' function as applied to solid phase synthesis).

(c) Solid phase organic chemistry (see Brown, R. D. *J. Chem. Soc., Perkin Trans.*1, 19, 3293-3320, 1998), to construct the remainder of the molecule.

(d) Compound cleavage from the solid phase into solution.

(e) Cleavage work-up and compound analysis.

The first stage in a synthesis of compounds of general formulae (I) and (II) is the preparation in solution of a functionalised and protected building block. A typical scheme towards the tetrahydrofuro[3,2-b]pyrrol-3-one (19) is detailed in Scheme 1. The following descriptions detailed in Schemes 1-13 could equally be applied using alternative scaffolds of general formulae (I) and (II).

Scheme 1.

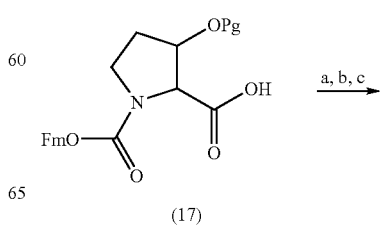

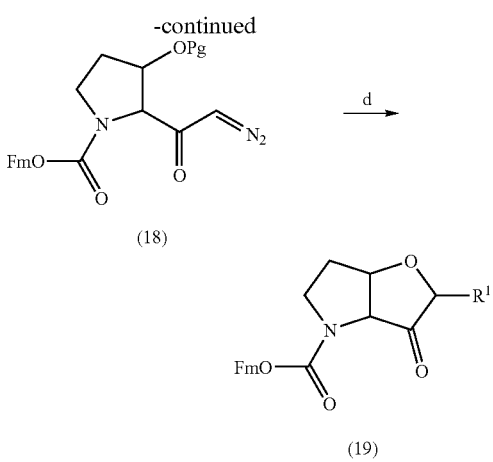

a ᶦBuOCOCl, NMM, DCM, -15° C., 10 mins, under argon.
b Diazomethane in diethyl ether, -15° C. to RT over 1 hr.
c Acetic acid
d LiCl (10 eq) in 80% aq acetic acid, 5° C. to RT over 1 hr.

FmOC(O) denotes the well known amine protecting group 9-fluorenyl methoxycarbonyl (Fmoc, see Atherton, E. and Sheppard, R. C., 1989) and 'Pg' denotes either a free hydroxyl or an hydroxylprotecting group such as tert-butyl ether. In the illustrated case, condensation with diazomethane provides $R^1$=H. Although formation of the diazoketone is clearly observed at 1 hr reaction, an overall improvement in isolated yield is obtained by leaving the reaction with ethereal diazomethane for 24 hr.

Considering step (a), synthesis may commence from suitably protected β-hydroxyproline (17) (or protected β-hydroxypipecolic acid), which are accessible through a variety of literature methods e.g. (a) Heffaer, R J., et al, *J. Am. Chem. Soc*, 114, 10181-10189, 1992; (b) Hughes, P. Cardy, J., *J. Org. Chem*, 54, 3260-3264, 1989, (c) Heffner, R. J., Jouille, M. M., *Tet. Lett*, 30, 7021-7024, 1989, (d) Ewing, W. R., Joujile, M. M., *Heterocycles*, 27, 2843-2850, 1988. (e) Kolodziej, S. A., Marshall, G. R, *Int. J. Pept. Prot. Res.*, 48, 274-280, 1996, (f) Evans, D. A., Weber, A, E., *J. Am. Chem. Soc*, 109, 7151-7157, 1987, (g) Langlois, N., Rakotondradany, F., *Tetrahedron*, 56, 2437-2448, 2000, (h) Sugisaki, C. H., et al, *Tet. Lett.*, 39, 3413-3416, 1998, (i) Greek, C., et al, *Tet. Lett.*, 37, 2031-, 1996, (j) Agami, C., et al, *Tet. Lett.*, 37, 4001-, 1996.

Activation of the suitably protected β-hydroxyproline (17) via isobutyl chloroformate mixed anhydride, followed by condensation with diazomethane, yields the diazomethylketone intermediates (18). Treatment of diazomethylketone intermediates (18) with lithium chloride in aqueous acetic acid provides the protected tetrahydrofuro[3,2-b]pyrrol-3-one (19). Introduction of simple $R^1$ substituents may be achieved by condensation of activated (17) with alternatives to diazomethane such as diazoethane ($R^1$=CH$_3$), or 1-phenyloxydiazoethane ($R^1$=CH$_2$OPh).

The protected building blocks (synthesis exemplified by the tetrahydrofuro[3,2-b]-pyrrol-3-one (19)) detailed in Scheme 1 may be utilised in a solid phase synthesis of inhibitor molecules (steps (b) to (e)). Step (b), the solid phase linkage of an aldehyde or ketone, has previously been described by a variety of methods (e.g. see (a) James, I. W., 1999, (b) Lee, A., Huang, L., Ellman, J. A., *J. Am. Chem. Soc*, 121(43), 9907-9914, 1999, (c) Murphy, A. M., et al, J. Am. Chem. Soc, 114, 3156-3157, 1992). A suitable method amenable to the reversible linkage of an alkyl ketone functionality such as (19) is through a combination of the previously described chemistries. The semicarbazide, 4-[[(hydrazinocarbonyl)amino]methyl]cyclohexane carboxylic acid. trifluoroacetate (20) (Murphy, A. M., et al, J. Am. Chem. Soc, 114, 3156-3157, 1992), may be utilised as illustrated in Scheme 2, exemplified by linkage of the tetrahydrofuro[3,2-b]pyrrol-3-one (19).

Scheme 2.

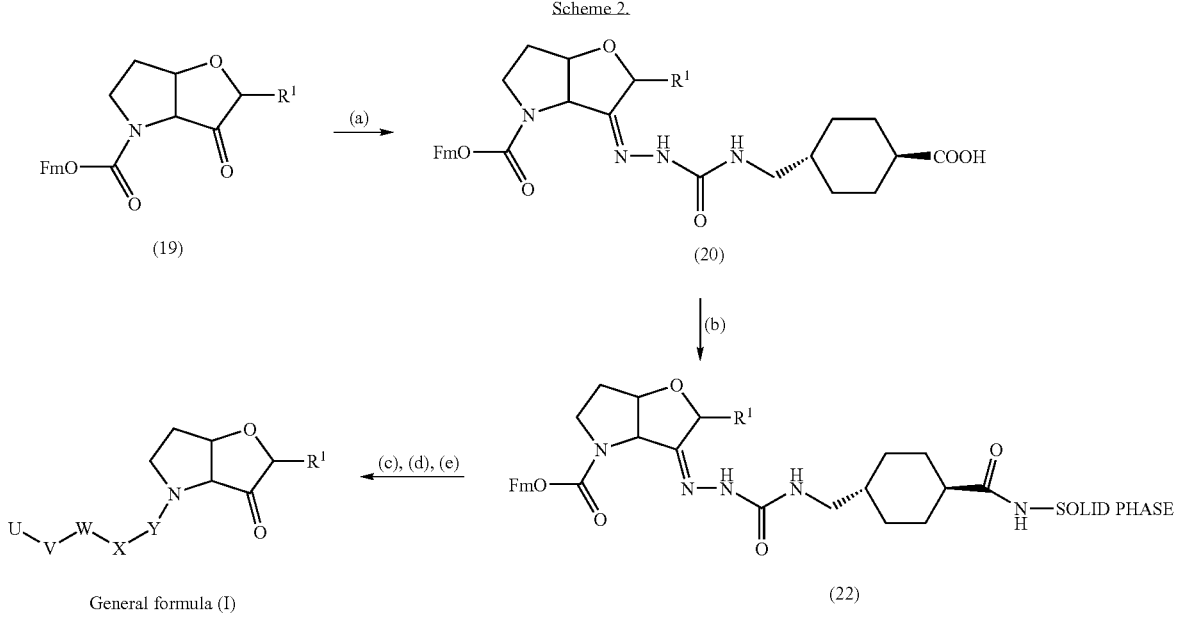

General formula (I)

(a) (19) in 90% EtOH/H₂O/1.5 eq NaOAc/4-[[hyrazinocarbonyl)amino]methyl]-cyclohexane carboxylic acid trifluoroacetate (20), 2 hr reflux.
(b) 3 eq construct (21)/3 eq HBTU/3 eq HOBt/6 eq NMM, NH₂-SOLID PHASE, DMF, RT, o/n.
(c) 20% piperdine/DMF, 30 mins.
(d) Range of chemistries to introduce U—V—W—X—Y
(e) TFA/H₂O (95:5, v/v), RT, 2 hr Construct (21) is prepared through reaction of the linker molecule (20) and the tetrahydrofuro[3,2-b]pyrrol-3-one (19) by reflux in aqueous ethanol/sodium acetate. Standard solid phase techniques (e.g. see Atherton, E. and Sheppard, R. C., 1989) are used to anchor the construct to an amino-functionalised solid phase through the free carboxylic acid functionality of (21), providing the loaded construct (22).

Loaded construct (22) may be reacted with a wide range of carboxylic acids available commercially or in the literature, to introduce the left-hand portion 'U-V-W-X-Y' in general formula (I). In the simplest example, the entire left hand portion of an inhibitor of general formula (I) comprises a capped aminoacid (Scheme 3), providing for example analogues of general formula (I) where $R^{12}=$'H', $(X)_o=$'-', $(W)_n=$'NH', $R^{16}=$'H', n=1, $(V)_m=$'CO', m=1 and U=aryl Scheme 3.

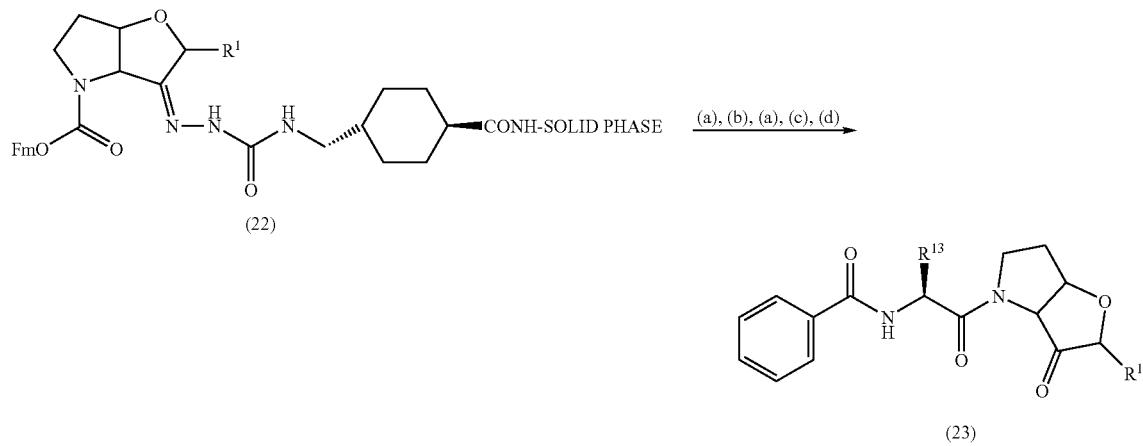

(a) 20% piperidine/DMF, 30 mins
(b) 20 eq Fmoc-aminoacid/20e q HBTU/20 eq HOBt/40 eq NMM, DMF, o/n
(c) 5eq carboxylic acid/5 eq HBTU/5 eq HOBt/10 eq NMM, DMF, RT, o/n
(d) TFA/H$_2$O (95;5, v/v), RT, 2 hr.

General formula (I) where
$R^{12}$ = 'H'
$(X)_o$ = '-'
$(W)_n$ = 'NH', n = 1
$(V)_m$ = 'CO', m = 1
U = phenyl
Z = 'O'

Alternatively, carboxylic acids can be prepared in solution by traditional organic chemistry methods and coupled to construct (22) on the solid phase (Schemes 4-8). For example (Scheme 4), treatment in solution of an amino acid, exemplified by (24) with sodium nitrite/H$_2$SO$_4$, provides the α-hydroxyacid, exemplified by (25) (Degerbeck, F. et al, *J. Chem. Soc, Perkin Trans.* 1, 11-14, 1993). Treatment of α-hydroxyacid, (25) with sodium hydride in a dimethylformamide/dichloromethane mixture followed by addition of benzyl bromide, provides 2RS-benzyloxy-3-cyclohexylpropionic acid (26). Coupling of (26) to the solid phase construct (22) followed by cleavage, provides (27), an example of general formula (I) where $R^{12}=$'H', $(X)_o=$'-', $(W)_n=$'O', n=1, $(V)_m=$'CH$_2$', i.e. $R^{17}$, $R^{18}=$'H', m=1 and U=phenyl. To those skilled in the practices of organic synthesis, a wide variety of aminoacids such as (24) may be converted to the corresponding α-hydroxyacid such as (25) following the general conditions detailed. Additionally, benzylbromide may be replaced by any reasonable Ar—CR$^{17}$R$^{18}$-halide, providing many variations of carboxylic acid (26) following the general conditions detailed. In certain instances, it may be advantageous to temporarily protect the carboxylic acid as the methyl ester (for example compound (32), Scheme 6) prior to reaction with the alkylhalide. The ester intermediate is then simply hydrolysed to acid (26). Analogues of (27), exploring a wide range of (V)$_m$ and U in general formula (I) may be prepared through the general conditions detailed in Scheme 4. Since the final synthetic step involves a trifluoroacetic acid (TFA) mediated cleavage of the solid phase bound compound, analogues where the substituted ether is labile to TFA may be prepared in solution by an alternative route (see Scheme 11).

Scheme 4.

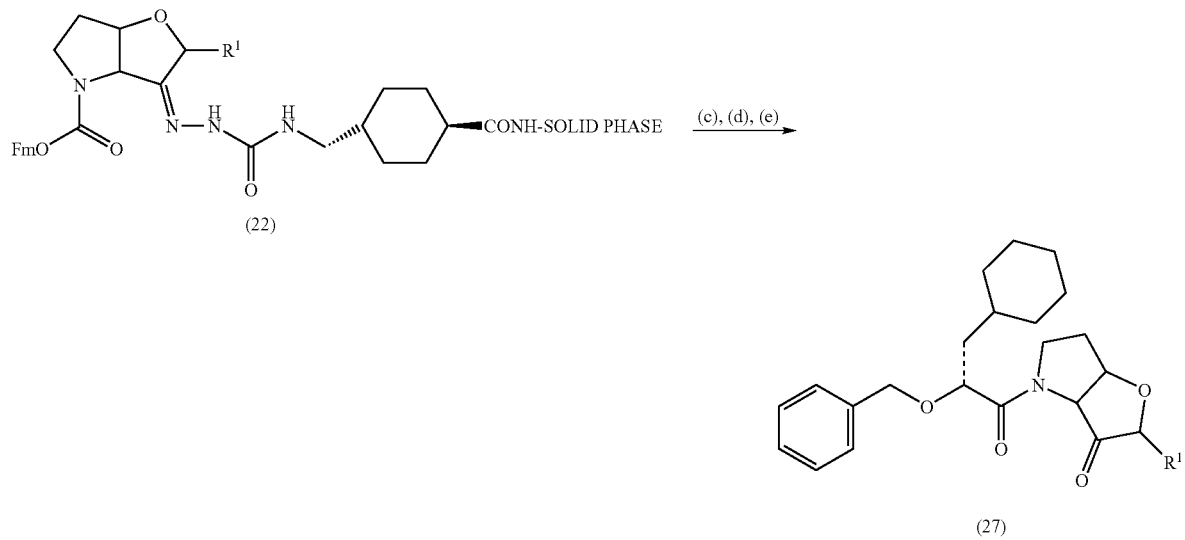

General formula (I) where
$R^{12}$ = 'H'
$(X)_o$ = '-'
$(W)_n$ = 'O', n = 1
$(V)_m$ = 'CH$_2$', i.e. $r^{17}, r^{18}$ = 'H', m = 1
U = phenyl
Z = 'O'

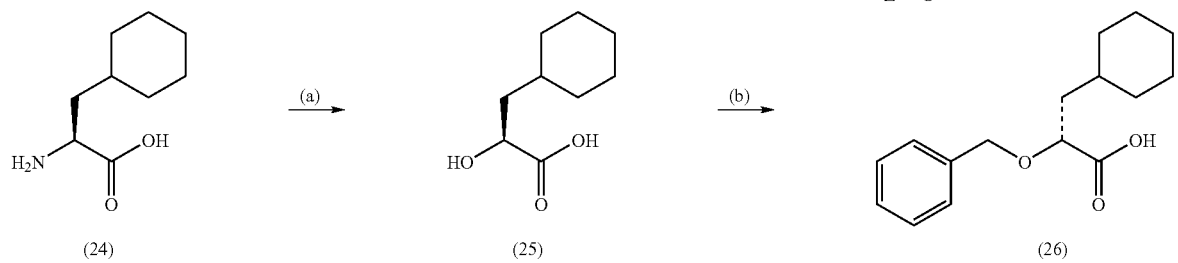

(a) NaNO$_2$/H$_2$SO$_4$, 0° C.→ RT, 2 hr
(b) 2.3 eq NaH, 1:1 DMF/DCM, 1.4 eq benzylbromide, o/n
(c) 20% piperidine/DMF, 30 mins.
(d) 10 eq (26)/10 eq HBTU/10 eq HOBt/20 eq NMM, DMF, RT, o/n
(e) TFA/H$_2$O (95:5, v/v), RT, 2 hr.

Alternatively, coupling of construct (22) (following removal of Fmoc) with the α-hydroxyacid (25), provides a versatile solid phase bound intermediate 'Y' substituent in general formula (I) that may be reacted with many reagents. For example, the α-hydroxyl can be reacted under Mitsunobu conditions (Hughes, D. L. Org. React. (N.Y.), 42, 335-656, 1992) to give ethers (i.e. X='-', W='O', in general formula (I)) (see Grabowska, U. et al, J Comb. Chem., 2(5), 475-490, 2000, for an example of Mitsunobu reaction on the solid phase). Alternatively, the α-hydroxyl can be reacted with a carbamoyl chloride to give a carbamate (i.e. X='-', W='O', V='NHC(O)', in general formula (I)).

Alternatively, (Scheme 5), treatment in solution of an amino acid, exemplified by (24) with sodium nitrite/H$_2$SO$_4$/potassium bromide provides the α-bromoacid, exemplified by (28) (Souers, A. J. et al, Synthesis, 4, 583-585, 1999) with retention of configuration. Treatment of α-bromoacid (28) with an alkylthiol exemplified by 4-tert-butylphenyl-methanethiol (29) in dimethylformamide/triethylamine, provides 2S-(4-tert-butylbenzylsulfanyl)-4-methylpropionic acid (30), with inversion of configuration. Coupling of (30) to the solid phase construct (22) followed by cleavage, provides (31), an example of general formula (I) where $R^{12}$='H', $(X)_o$='-', $(W)_n$='S', n=1, $(V)_m$='CH$_2$', i.e. $R^{17}$, $R^{18}$='H', m=1 and U=4-tert-butylphenyl. To those skilled in the practices of organic synthesis, a wide variety of aminoacids such as (24) may be converted to the corresponding α-bromoacid such as (28) following the general conditions detailed. Additionally, starting with the S-isomer of (24) gives the S-bromoacid analogue of (28) and R-thioether analogue of (30). Additionally, (4-tert-butylphenyl)methanethiol (29) may be replaced by any reasonable Ar—CR$^{17}$R$^{18}$—SH, providing many variations of carboxylic acid (30) following the general conditions detailed. Thus analogues of (31) exploring a wide range of $(V)_m$ and U in general formula (I) may be prepared through the general conditions detailed in Scheme 5.

Scheme 5.

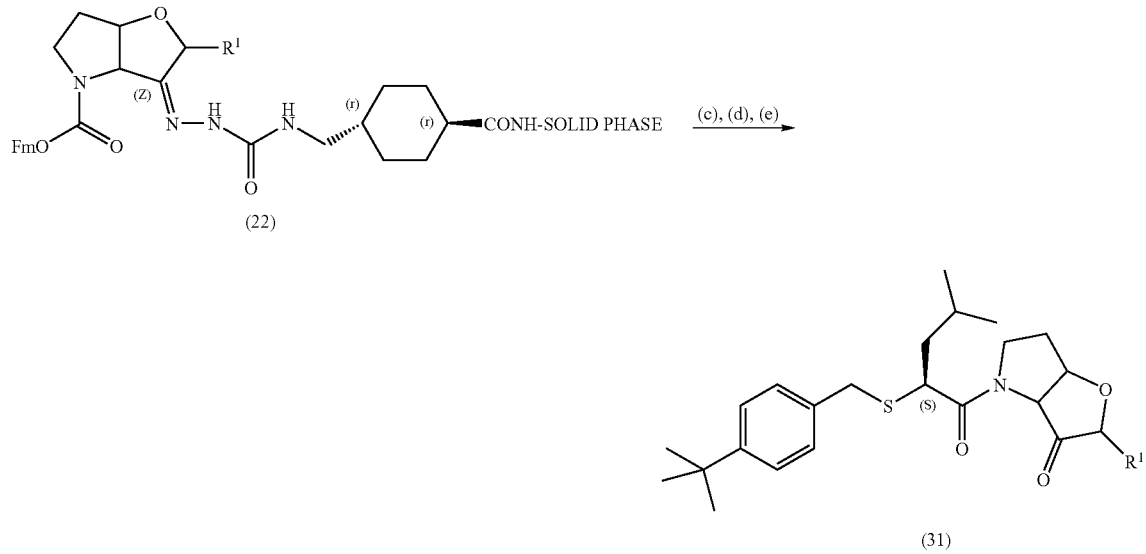

General formula (I) where
$R^{12}$ = 'H'
$(X)_o$ = '-'
$(W)_n$ = 'S', n = 1
$(V)_m$ = '$CH_2$', i.e. $R^{17}$, $R^{18}$ = 'H', m = 1
U = 4-teri-butylphenyl
Z = 'O'

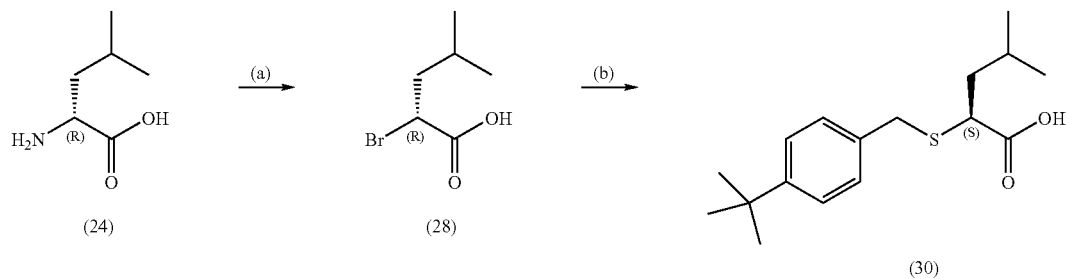

(a) $NaNO_2/H_2SO_4$, KBr 0° C.→ RT, 2 hr
(b) Alkylthiol (29)/DMF/$NEt_3$, o/n
(c) 20% piperidine/DMF, 30 mins.
(d) 10 eq (30)/10 eq HBTU/10 eq HOBt/20 eq NMM, DMF, RT, o/n
(e) $TFA/H_2O$ (95:5, v/v), RT, 2 hr.

Alternatively, coupling of construct (22) (following removal of Fmoc) with an α-bromoacid e.g. (28), provides a versatile intermediate 'Y' substituent in general formula (I) that may be reacted with many reagents. For example, the α-bromide can be displaced with nucleophiles e.g. alcohols, thiols, carbanions etc, to give ethers (i.e. X='-', W='O', in general formula (I)), thioethers (i.e. X='-', W='S', in general formula (I)). The thioethers may optionally be oxidised to the sulphone (see Scheme 9, i.e. X='-', W='$SO_2$', in general formula (I)) (see Grabowska, U. et al, *J Comb. Chem*, 2(5), 475-490, 2000, for an example of bromide displacement and thioether oxidation on the solid phase).

Alternatively, (Scheme 6), treatment of an α-hydroxyacid, exemplified by (25) with trimethylsilylchloride and methanol provides the methyl ester (32). Activation of the free hydroxyl to the chloroformate with phosgene in dichloromethane followed by addition of morpholine, then hydrolysis, provides morpholine-4-carboxylic acid-1S-carboxy-2-cyclohexyl ethyl ester (33). Coupling of (33) to the solid phase construct (22) followed by cleavage, provides (34), an example of general formula (I) where $R^{12}$='H', $(X)_o$='-', $(W)_n$='O', n=1, $(V)_m$='CO' and U=morpholino. To those skilled in the practices of organic synthesis, a wide variety of α-hydroxyacid esters such as (32) could be converted to the activated chloroformate following the general conditions detailed. Additionally, morpholine may be replaced by any reasonable amine, providing many variations of carboxylic acid (33) following the general conditions detailed. Thus analogues of (34) exploring a wide range of $(V)_m$ and U in general formula (I) may be prepared through the general conditions detailed in Scheme 6.

Scheme 6.

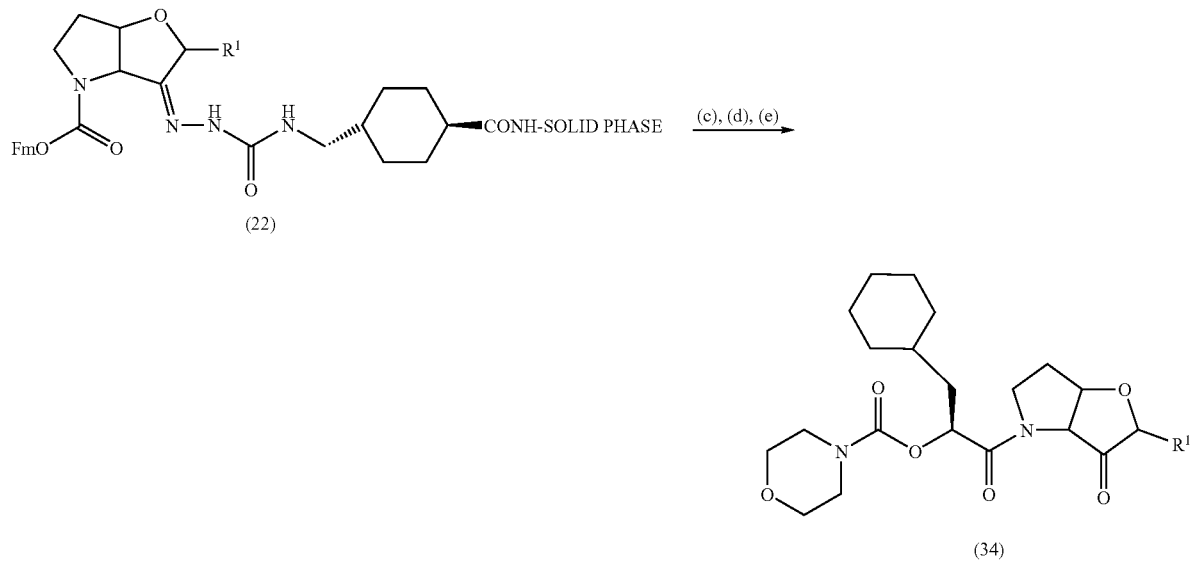

General formula (I) where
$R^{12}$ = 'H'
$(X)_o$ = '-'
$(W)_n$ = 'O', n = 1
$(V)_m$ = 'CO', m = 1
U = morpholino
Z = 'O'

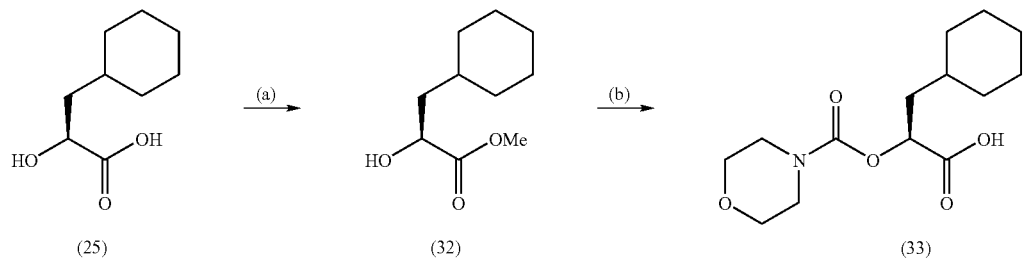

(a) Me$_3$SiCl, MeOH, RT, o/n.
(b) i. COCl$_2$/DCM/o/n, ii. Morpholine/DCM 0° C., 2 hr, iii. LiOH in H$_2$O/dioxan, 0° C.
(c) 20% piperidine/DMF, 30 mins. (d) 10 eq (33)/10 eq HBTU/10 eq HOBt/20 eq NMM, DMF, RT, o/n
(e) TFA/H$_2$O (95:5, v/v), RT, 2 hr.

Alternatively, (Scheme 7), a wide range of alkylsuccinate esters exemplified by 2R-cyclohexylmethylsuccinic acid 1-methyl ester (35) are commercially available or readily prepared by known methods (see (a) Azam et al, *J. Chem. Soc. Perkin Trans.* 1, 621-, 1996; (b) Evans et al, *J Chem Soc. Perkin Trans.* 1, 103, 2127, 1981; (c) Oikawa et al, *Tet. Lett,* A37, 6169, 1996). Carboxyl activation of alkylsuccinate ester (35) followed by addition of morpholine in dimethylformamide and subsequent ester hydroylsis, provides 2R-cyclohexylmethyl-4-morpholin-4-yl-4-oxo-butyric acid (36). Coupling of (36) to the solid phase construct (22) followed by cleavage, provides (37), an example of general formula a) where $R^{12}$='H', $(X)_o$='CH$_2$' i.e. $R^{14}$, $R^{15}$='H', o=1, $(W)_n$='CO', n=1, $(V)_m$='-' and U=morpholino. To those skilled in the practices of organic synthesis, a wide variety of alkylsuccinate esters such as (35) may be prepared and converted to the corresponding substituted alkylsuccinate acid such as (36) following the general conditions detailed. Additionally, morpholine may be replaced by any reasonable amine, providing many variations of carboxylic acid (36) following the general conditions detailed. Thus analogues of (37) exploring a wide range of $(X)_o$, $(V)_m$ and U in general formula (I) may be prepared through the general conditions detailed in Scheme 7.

Scheme 7.

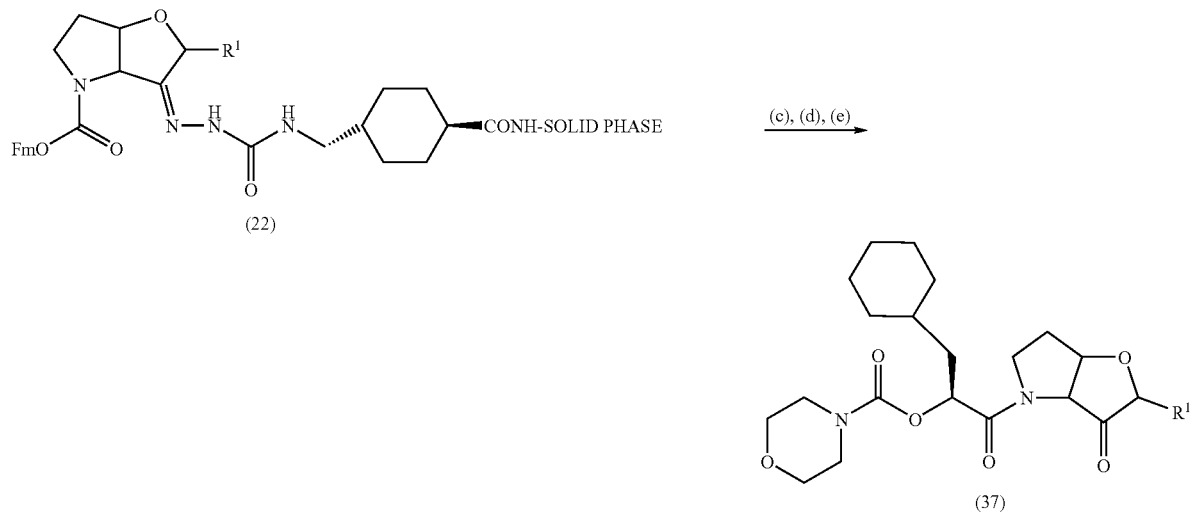

(a) i. EDC/1-hydroxybenzotriazole/DMF, 0° C., 30 mins. ii. Morpholine, RT, o/n
(b) LiOH in H$_2$O/dioxan, 0° C.
(c) 20% piperidine/DMF, 30 mins.
(d) 10eq (36)/10 eq HBTU/10 eq HOBt/20 eq NMM, DMF, RT, o/n
(e) TFA/H$_2$O (95:5, v/v), RT, 2 hr.

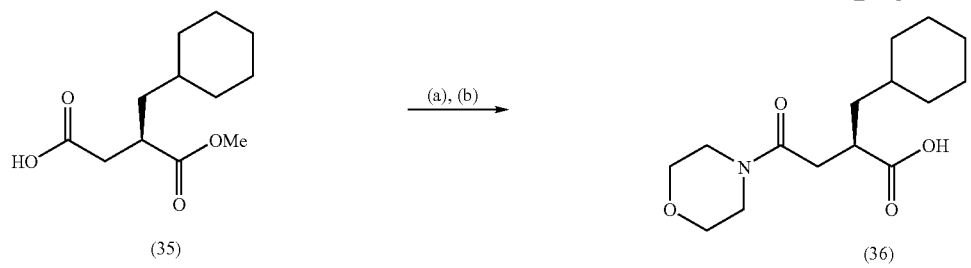

Alternatively, (Scheme 8), a wide range of biarylalkylacetic acids, exemplified by 2RS-biphenyl-3-yl-4-methylpentanoic acid (39) are readily available by known methods (see (a) DesJarlais, R. L. et al, *J. Am. Chem. Soc*, 120, 9114-9115, 1998; (b) Oballa, R. M. et al, WO 0149288). Coupling of biarylalkylacetic acid (39) to the solid phase construct (22) followed by cleavage, provides (40), an example of general formula (I) where R$^{12}$='H', (X)$_o$='-', (W)$_n$='-', (V)$_m$='-' and U=m-biphenyl. To those skilled in the practices of organic synthesis, a wide variety of biarylalkylacetic acids such as (39) may be prepared by alkylation of the α-anion of the free acid analogue of (38), which in turn is prepared by Suzuki coupling of phenylboronic acid and 3-bromophenylacetic acid methyl ester. Phenylboronic acid may be replaced by a wide range of arylboronic acids in the Suzuki coupling, providing many variations of carboxylic acid (39) following the general conditions detailed. Thus analogues of (40) exploring a wide range of group 'U' in general formula (I) may be prepared through the general conditions detailed in Scheme 8.

Scheme 8.

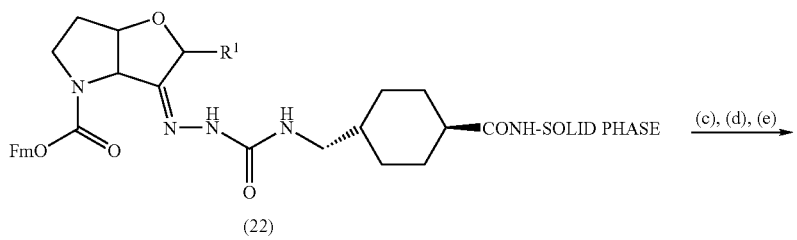

-continued

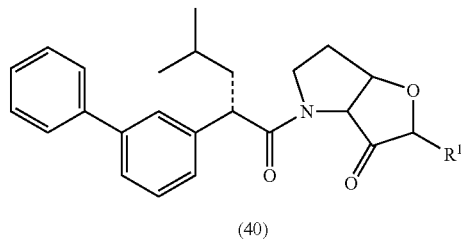

(40)

General formula (I) where
R$^{12}$ = 'H'
(X)$_o$ = '-'
(W)$_n$ = '-'
(V)$_m$ = '-'
U = m-biphenyl
Z = 'O'

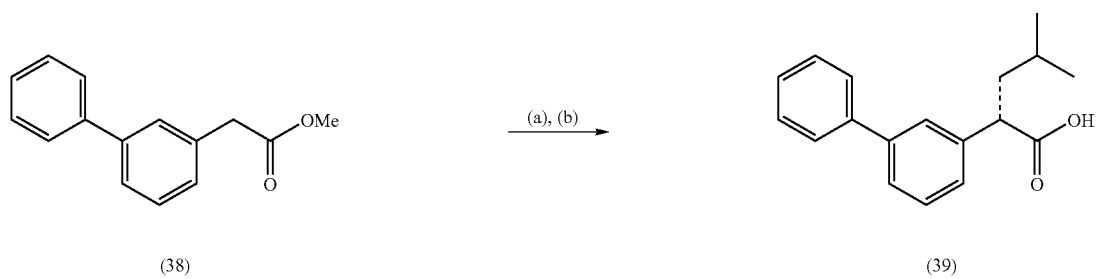

(38) → (a), (b) → (39)

(a) LiOH in H$_2$O/dioxan, 0° C.
(b) i.LDA, THF, 2-methylpropenylbromide, ii. Pd/C, EtOH, H$_2$
(c) 20% piperidine/DMF, 30 mins.
(d) 10 eq (39)/10 eq HBTU/10 eq HOBt/20 eq NMM, DMF, RT, o/n
(e) TFA/H$_2$O (95:5), v/v), RT, 2 hr.

Many other possibilities for solid phase organic chemistry (e.g. see Brown, R. D. *J Chem. Soc., Perkin Trans.*1, 19, 3293-3320, 1998, for a review of recent SPOC publications) can be used to derivatise construct (22) towards compounds of general formula (I) (and similarly, through the appropriate loaded derivative, compounds of general formula (II)). For example, the left-hand portion 'U-V-W-X-Y' in general formulae (I) can be partially constructed in solution, coupled to construct (22) and further modified on the solid phase. For example (Scheme 9), a simple extension of Scheme 5 is through the oxidation of the intermediate solid phase bound species, with m-chloroperbenzoic acid in dichloromethane prior to cleavage, to give the sulphone analogue (42). Commencing from a variation of carboxylic acid (30), 3-cyclohexyl-2S-(furan-2-ylmethylsulfanyl)propionic acid (41), sulphone (42) is prepared, an example of general formula (I) where R$^{12}$='H', (X)$_o$='-', (W)$_n$='SO$_2$', n=1, (V)$_m$='CH$_2$', i.e. R$^{17}$,R$^{18}$='H', m=1 and U=2-furanyl. As described in Scheme 5, many variations of carboxylic acid (30) may be prepared following the general conditions detailed e.g. (41). Thus analogues of (42) exploring a wide range of (V)$_m$ and U in general formula (I) may be prepared through the general conditions detailed in Schemes 5 and 9.

Scheme 9.

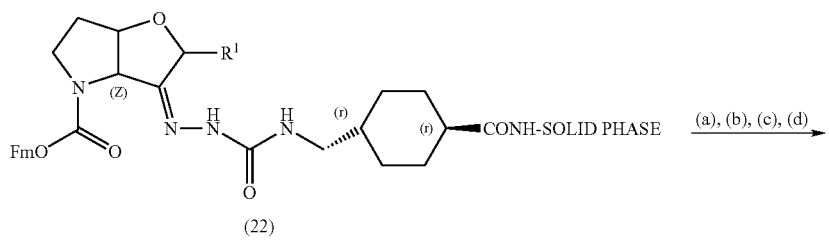

(22) → (a), (b), (c), (d) →

-continued

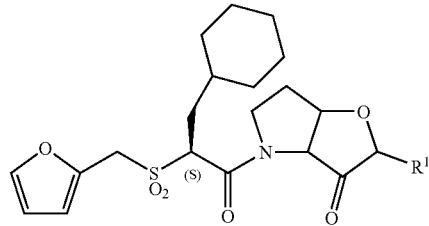

(42)

General formula (I) where
R$^{12}$ = 'H'
(X)$_o$ = '-'
(W)$_n$ = 'SO$_2$', n = 1
(V)$_m$ = 'CH$_2$', i.e. R$^{17}$, R$^{18}$ = 'H', m = 1
U = 2-furanyl
Z = 'O'

(a) 20% piperidine/DMF, 30 mins.
(b) 5 eq (41)/5 eq HBTU/5 eq HOBt/10 eq NMM, DMF, RT, o/n
(c) 5 eq m-chloroperbenzoic acid/DCM, RT, 5 hr.
(d) TFA/H$_2$O (95:5, v/v), RT, 2 hr.

Compounds of general formulae (I) and (II) are finally released from the solid phase by treatment with trifluoroacetic acid/water, followed by evaporation, lyophylis and standard analytical characterisation.

A second strategy for the synthesis of compounds of general formulae (I) and (II) comprises:

(a) Preparation of an appropriately functionalised and protected tetrahydrofuro[3,2-b]pyrrol-3-one, tetrahydrothieno[3,2-b]pyrrol-3-one, hexahydropyrrolo[3,2-b]pyrrol-3-one, hexahydrocyclopenta[b]pyrrol-6-one, tetrahydrofuro[3,2-c]pyrazol-6-one, tetrahydrothieno[3,2-c]pyrazol-6-one, hexahydropyrrolo[3,2-c]pyrazol-6-one, hexahydrocyclopentapyrazol-6-one, hexahydrofuro[3,2-b]pyridin-3-one, hexahydrothieno[3,2-b]pyridin-3-one, octahydropyrrolo[3,2-b]pyridin-3-one, octahydrocyclopenta[b]pyridin-7-one, hexahydrofuro[3,2-c]pyridazin-7-one, hexahydrothieno[3,2-c]pyridazin-7-one, octahydropyrrolo[3,2-c]pyridazin-7-one or octahydrocyclopenta[c]pyridazin-7-one building block in solution.

Preferred protecting groups for solution phase chemistry are the Nα-tert-butoxycarbonyl group and the Na-benzyloxycarbonyl group.

(b) Standard organic chemistry methods for the conversion of building block (a) towards compounds of general formulae (I) and (II).

In the simplest example, the entire left hand portion of an inhibitor of general formulae (I) and (II) can be prepared in solution by traditional organic chemistry methods and coupled to building block (a) (see Scheme 10 exemplified by preparation and use of the 3-oxo-hexahydrofuro[3,2-b]pyrrole-4-carboxylic acid tert-butyl ester (45)).

Scheme 10.

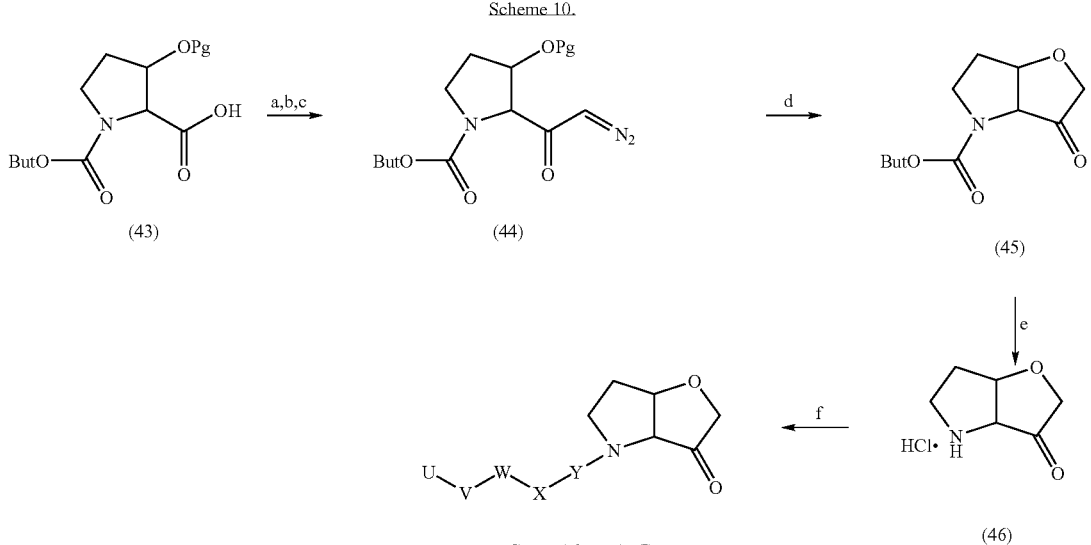

General formula (I)

(a) $^t$BuOCOCl, NMM, DCM, -15° C., 10 mins, under argon.
(b) Diazomethane in diethyl ether, -15° C. to RT over 24 hr.
(c) Acetic acid
(d) LiCl (10 eq) in 80% aq acetic acid, 5° C. to RT over 1 hr.
(e) 4M HCl in dioxan, 0° C., 2 hrs.
(f) Pre-prepared U—V—W—X—Y—COOH/activation e.g. HATU/HOAt/NMM, DMF, RT, o/n.

The general strategy detailed in Scheme 10 is particularly useful when the compound of general formula (I) contains a substituent that is labile to trifluoroacetic acid, this being the final reagent used in each of the solid phase Schemes 4-9. For example (Scheme 11), treatment in solution of α-hydroxy-acid (47) with sodium hydride in a dimethylformamide/dichloromethane mixture followed by addition of 4-tert-butylbenzyl bromide, provides 2RS-(4-tert-butylbenzyloxy)-4-methylpentanoic acid (48). Coupling of (48) to hydrochloride salt (46), provides (49), an example of general formula (I) where $R^{12}$='H', $(X)_o$='-', $(W)_n$='O', n=1, $(V)_m$='$CH_2$', i.e. $R^{17}$, $R^{18}$='H', m=1 and U=4-tert-butylphenyl. To those skilled in the practices of organic synthesis, 4-tert-butylbenzyl bromide may be replaced by any reasonable Ar—$CR^{17}R^{18}$-halide, providing many variations of carboxylic acid (48) under the conditions shown. Thus analogues of (49) exploring a wide range of $(V)_m$ and U in general formula (I) may be prepared through the conditions detailed in Scheme 11.

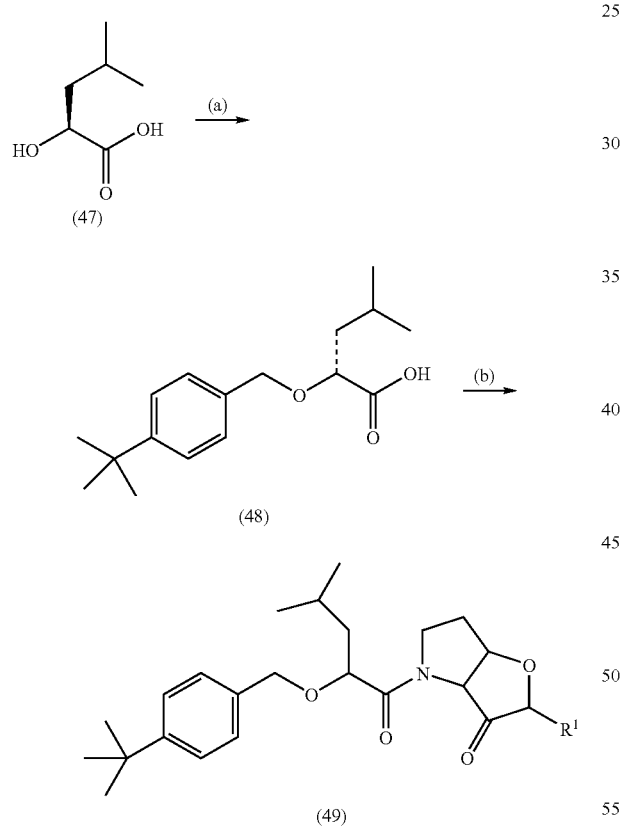

Scheme 11.

(47)

(48)

(49)
General formula (I) where
$R^{12}$ = 'H'
$(X)_o$ = '-'
$(W)_n$ = 'O', n = 1
$(V)_m$ = '$CH_2$', I.E. $R^{17}$, $R^{18}$ = 'H', m = 1
U = 4-tert-butylphenyl
Z = 'O'

(a) 2.2 eq NaH, 1:1 DMF/DCM, 1.25eq 4-tert-benzylbromide, 2 hr
(b) 1 eq (48), 1 eq $^i$BuOCOCl, 2 eq NMM, DCM, -15° C., 1 hr, under nitrogen, then 1 eq, (46), RT, o/n.

A third strategy for the synthesis of compounds of general formulae (I) and (II) where the addition of U-V-W-X-Y to the protected building block involves multistep organic reactions comprises:

(a) Preparation of an appropriately functionalised and protected tetrahydrofuro[3,2-b]pyrrol-3-one, tetrahydrothieno[3,2-b]pyrrol-3-one, hexahydropyrrolo[3,2-b]pyrrol-3-one, hexahydrocyclopenta[b]pyrrol-6-one, tetrahydrofuro[3,2-c]pyrazol-6-one, tetrahydrothieno[3,2-c]pyrazol-6-one, hexahydropyrrolo[3,2-c]pyrazol-6-one, hexahydrocyclopentapyrazol-6-one, hexahydrofuro[3,2-b]pyridin-3-one, hexahydrothieno[3,2-b]pyridin-3-one, octahydropyrrolo[3,2-b]pyridin-3-one, octahydrocyclopenta[b]pyridin-7-one, hexahydrofuro[3,2-c]pyridazin-7-one, hexahydrothieno[3,2-c]pyridazin-7-one, octahydropyrrolo[3,2-c]pyridazin-7-one or octahydrocyclopenta[c]pyridazin-7-one building block in solution.

Preferred protecting groups for solution phase chemistry are the Nα-tert-butoxycarbonyl group and the Nα-benzyloxycarbonyl group.

(b) Protection of the ketone functionality of the tetrahydrofuro[3,2-b]pyrrol-3-one, tetrahydrothieno[3,2-b]pyrrol-3-one, hexahydropyrrolo[3,2-b]pyrrol-3-one, hexahydrocyclopenta[b]pyrrol-6-one, tetrahydrofuro[3,2-c]pyrazol-6-one, tetrahydrothieno[3,2-c]pyrazol-6-one, hexahydropyrrolo[3,2-c]pyrazol-6-one, hexahydrocyclopentapyrazol-6-one, hexahydrofuro[3,2-b]pyridin-3-one, hexahydrothieno[3,2-b]pyridin-3-one, octahydropyrrolo[3,2-b]pyridin-3-one, octahydrocyclopenta[b]pyridin-7-one, hexahydrofuro[3,2-c]pyridazin-7-one, hexahydrothieno[3,2-c]pyridazin-7-one, octahydropyrrolo[3,2-c]pyridazin-7-one or octahydrocyclopenta[c]pyridazin-7-one building block e.g. as a dimethylacetal. Alternatively, the ketone may be reduced to the achiral secondary alcohols and re-oxidised as the final synthetic step.

(c) Standard organic chemistry methods for the conversion of building block (b) towards compounds of general formulae (I) and (II).

(d) Intermediates may be prepared in solution, followed by coupling to building block (b) and further derivitisation towards compounds of general formulae (I) and (II) (see Scheme 12 exemplified by preparation and use of the 3-hydroxyhexahydrofuro[3,2-b]pyrrole-4-carboxylic acid tert-butyl ester (50)).

Scheme 12.

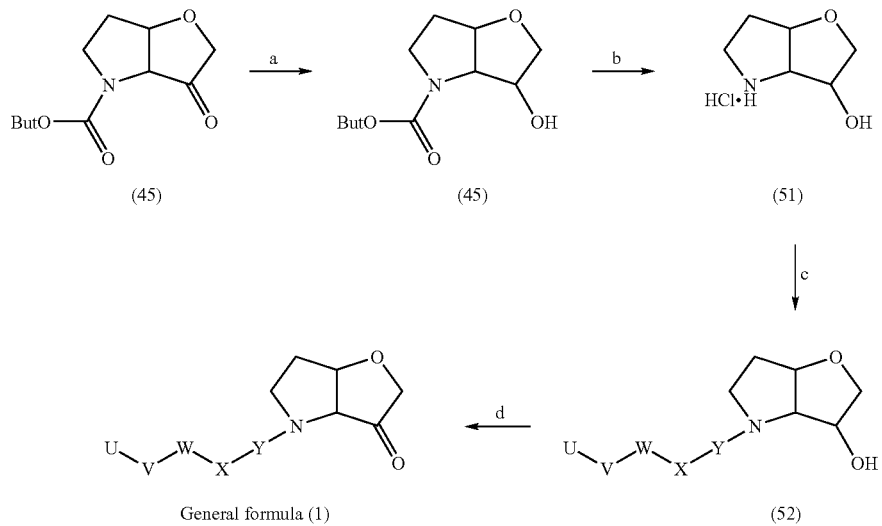

a Reduction, e.g. NaBH₄
b 4M HCl in dioxan, 0° C., 2 hrs.
c Stepwise reaction with intermediates of Y, then X, then W etc., to stepwise construct compounds (52).
d Oxidation, e.g. Dess-Martin periodane, CH₂Cl₂.

Alternatively, depending upon the types of chemistry used to construct the left hand side U-V-W-X-Y of compounds of general formula (I) and (II), the ketone may require protection e.g. as the dimethyl acetal. Such a method is detailed and exemplified in Scheme 13 by the preparation and use of 3,3-dimethoxyhexahydrofuro[3,2-b]pyrrole-4-carboxylic acid benzyl ester (54).

The invention extends to novel intermediates as described above, and to processes for preparing compounds of general formulae (I) or (II) from each of their immediate precursors. In turn, processes for preparing intermediates from their immediate precursors also form part of the invention.

Compounds of general formulae (I) and (II) are useful both as laboratory tools and as therapeutic agents. In the laboratory Scheme 13.

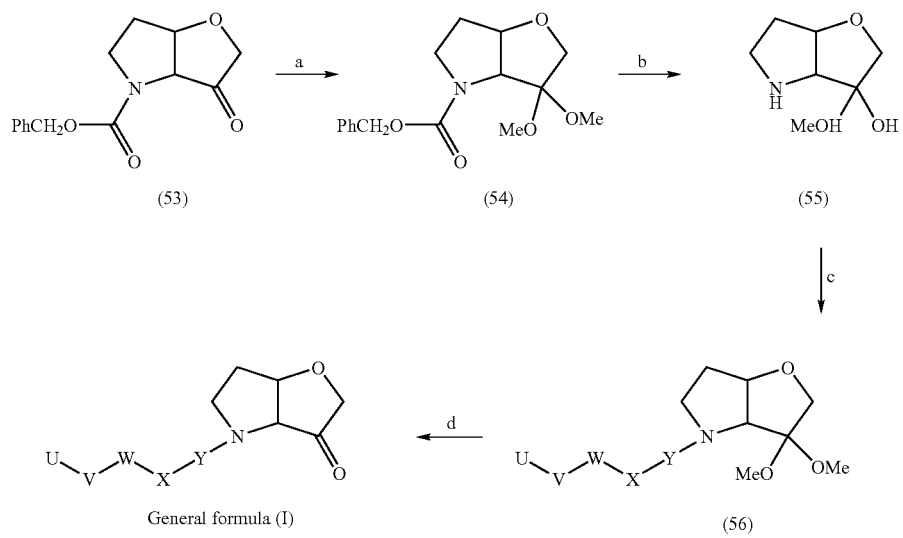

a Triethylorthoformate / pTSA / MeOH.
b H₂, Pd—C.
c Stepwise reaction with intermediates of Y, then W etc., to stepwise construct compounds (56).
d Trifluoroacetic acid / CH₂Cl₂ / H₂O.

certain compounds of the invention are useful in establishing whether a known or newly discovered cysteine protease contributes a critical or at least significant biochemical function during the establishment or progression of a disease state, a process commonly referred to as 'target validation'.

According to a second aspect of the invention, there is provided a method of validating a known or putative cysteine protease inhibitor as a therapeutic target, the method comprising:
(a) assessing the in vitro binding of a compound as described above to an isolated known or putative cysteine protease, providing a measure of potency; and optionally, one or more of the steps of:
(b) assessing the binding of the compound to closely related homologous proteases of the target and general housekeeping proteases (e.g. trypsin) to provides a measure of selectivity;
(c) monitoring a cell-based functional marker of a particular cysteine protease activity, in the presence of the compound; and
(d) monitoring an animal model-based functional marker of a particular cysteine protease activity in the presence of the compound.

The invention therefore provides a method of validating a known or putative cysteine protease inhibitor as a therapeutic target. Differing approaches and levels of complexity are appropriate to the effective inhibition and 'validation' of a particular target. In the first instance, the method comprises assessing the in vitro binding of a compound of general formulae (I) or (II) to an isolated known or putative cysteine protease, providing a measure of 'potency'. An additional assessment of the binding of a compound of general formulae (I) or (II) to closely related homologous proteases of the target and general house-keeping proteases (e.g. trypsin) provides a measure of 'selectivity'. A second level of complexity may be assessed by monitoring a cell-based functional marker of a particular cysteine protease activity, in the presence of a compound of general formulae (I) or (II). For example, a 'human osteoclast resorption assay' has been utilised as a cell-based secondary in vitro testing system for monitoring the activity of cathepsin K and the biochemical effect of protease inhibitors (e.g. see WO-A-9850533). An 'MHC-II processing—T-cell activation assay' has been utilised as a cell-based secondary in vitro testing system for monitoring the activity of cathepsin S and the biochemical effect of protease inhibitors (Shi, G-P., et al, Immunity, 10, 197-206, 1999). When investigating viral or bacterial infections such a marker could simply be a functional assessment of viral (e.g. count of mRNA copies) or bacterial loading and assessing the biochemical effect of protease inhibitors. A third level of complexity may be assessed by monitoring an animal model-based functional marker of a particular cysteine protease activity, in the presence of a compound of general formulae (I) or (II). For example, murine models of Leishmania infection, P. vinckei infection, malaria (inhibition of falcipain) and T. cruzi infection (cruzipain), indicate that inhibition of cysteine proteases that play a key role in pathogen propagation is effective in arresting disease symptoms, 'validating' said targets.

The invention therefore extends to the use of a compound of general formulae (I) or (II) in the validation of a known or putative cysteine protease inhibitor as a therapeutic target.

Compounds of general formulae (I) and (II) are useful for the in vivo treatment or prevention of diseases in which participation of a cysteine protease is implicated.

According to a third aspect of the invention, there is provided a compound of general formulae (I) or (II) for use in medicine, especially for preventing or treating diseases in which the disease pathology may be modified by inhibiting a cysteine protease.

According to a fourth aspect of the invention, there is provided the use of a compound of general formulae (I) or (II) in the preparation of a medicament for preventing or treating diseases in which the disease pathology may be modified by inhibiting a cysteine protease.

Certain cysteine proteases function in the normal physiological process of protein degradation in animals, including humans, e.g. in the degradation of connective tissue. However, elevated levels of these enzymes in the body can result in pathological conditions leading to disease. Thus, cysteine proteases have been implicated in various disease states, including but not limited to, infections by Pneumocystis carinii, Trypsanoma cruzi, Trypsanoma brucei brucei and Crithidia fisiculata; as well as in osteoporosis, autoimmunity, schistosomiasis, malaria, tumour metastasis, metachromatic leukodystrophy, muscular dystrophy, amytrophy, and the like. See WO-A-9404172 and EP-A-0603873 and references cited in both of them. Additionally, a secreted bacterial cysteine protease from S. Aureus called staphylopain has been implicated as a bacterial virulence factor (Potempa, J., et al. J. Biol. Chem, 262(6), 2664-2667, 1998).

The invention is useful in the prevention and/or treatment of each of the disease states mentioned or implied above. The present invention also is useful in a methods of treatment or prevention of diseases caused by pathological levels of cysteine proteases, particularly cysteine proteases of the papain superfamily, which methods comprise administering to an animal, particularly a mammal, most particularly a human, in need thereof a compound of the present invention. The present invention particularly provides methods for treating diseases in which cysteine proteases are implicated, including infections by Pneumocystis carinii, Trypsanoma cruzi, Trypsanoma brucei, Leishmania mexicana, Clostridium histolyticum, Staphylococcus aureus, foot-and-mouth disease virus and Crithidia fisiculata; as well as in osteoporosis, autoimmunity, schistosomiasis, malaria, tumour metastasis, metachromatic leukodystrophy, muscular dystrophy and amytrophy.

Inhibitors of cruzipain, particularly cruzipain-specific compounds, are useful for the treatment of Chagas' disease.

In accordance with this invention, an effective amount of a compound of general formulae (I) or (II) may be administered to inhibit the protease implicated with a particular condition or disease. Of course, this dosage amount will further be modified according to the type of administration of the compound. For example, to achieve an "effective amount" for acute therapy, parenteral administration of a compound of general formulae (I) or (II) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a cysteine protease. The compounds may be administered one to four times daily at a level to achieve a total daily dose of about 0.4 to about 400 mg/kg/day. The precise amount of an inventive-compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method. For those compounds in which the prodrug moiety is a ketone functionality, specifically ketals and/or hemiacetals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

According to a fifth aspect of the invention, there is provided a pharmaceutical or veterinary composition comprising one or more compounds of general formulae (I) or (II) and a pharmaceutically or veterinarily acceptable carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formulae (I) or (II) in conjunction or association with a pharmaceutically or veterinarily acceptable carrier or vehicle.

Formulations for oral administration in the present invention may be presented as: discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica Flavouring agents such as peppermint, oil of wintergreen, cherry flavouring and the like can also be used. It may be desirable to add a colouring agent to make the dosage form readily identifiable. Tablets may also be coated by methods well known in the art. A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Parenteral formulations will generally be sterile.

According to a sixth aspect of the invention, there is provided a process for the preparation of a pharmaceutical or veterinary composition as described above, the process comprising bringing the active compound(s) into association with the carrier, for example by admixture.

Preferred features for each aspect of the invention are as for each other aspect *mutatis mutandis*.

The invention will now be illustrated with the following examples:

Solution Phase Chemistry-General Methods

All solvents were purchased from ROMIL Ltd (Waterbeach, Cambridge, UK) at SpS or Hi-Dry grade unless otherwise stated. General peptide synthesis reagents were obtained from Chem-Impex Intl. Inc. (Wood Dale Ill. 60191. USA). Thin layer chromatography (TLC) was performed on pre-coated plates (Merck aluminium sheets silica 60 F254, part no. 5554). Visualisation of compounds was achieved under ultraviolet light (254 nm) or by using an appropriate staining reagent Flash column purification was performed on silica gel 60 (Merck 9385). All analytical HPLC were obtained on Phenomenex Jupiter $C_4$, 5µ, 300A, 250×4.6 mm, using mixtures of solvent A=0.1% aq trifluoroacetic acid (TFA) and solvent B=90% acetonitrile/10% solvent A on automated Agilent systems with 215 and/or 254 nm UV detection. Unless otherwise stated a gradient of 10-90% B in A over 25 minutes at 1.5 mL/min was performed for full analytical HPLC analysis. HPLC-MS analysis was performed on an Agilent 1100 series LC/MSD, using automated Agilent HPLC systems, with a gradient of 10-90% B in A over 10 minutes on Phenomenex Columbus $C_8$, 5µ, 300A, 50×2.0 mm at 0.4 mL/min. Nuclear magnetic resonance (NMR) were obtained on a Bruker DPX400 (400 MHz 1 H frequency; QXI probe) in the solvents and temperature indicated. Chemical shifts are expressed in parts per million (δ) and are referenced to residual signals of the solvent. Coupling constants (J) are expressed in Hz.

Solid Phase Chemistry-General Methods

Example inhibitors (1-156) were prepared through a combination of solution and solid phase Fmoc-based chemistries (see 'Solid Phase Peptide Synthesis', Atherton, E. and Sheppard, R. C., IRL Press Ltd, Oxford, UK, 1989, for a general description). An appropriately protected and functionalised building block was prepared in solution (e.g. general compound (19), Scheme 1), then reversibly attached to the solid phase through an appropriate linker. Rounds of coupling/ deprotection/chemical modification e.g. oxidation were then performed until the full length desired molecule was complete (Scheme 2). Example inhibitors (1-156) were then released (cleaved) from the solid phase, analysed, purified and assayed for inhibition verses a range of proteases.

Generally, multipins (polyamide 1.2→10 μmole loadings, see www.mimotopes.com) were used for the solid phase synthesis, although any suitable solid phase surface could be chosen. In general, the 1.2 μmole gears were used to provide small scale crude examples for preliminary screening, whilst the 10 μmole crowns were used for scale-up synthesis and purification of preferred examples. Standard coupling and Fmoc deprotection methods were employed (see Grabowska, U. et al, *J Comb. Chem.* 2(5), 475-490, 2000. for a thorough description of solid phase multipin methodologies).

Preparation of Initial Assembly

Building Block-linker constructs (e.g.(21), typically 100 mg to 2 g) were carboxyl activated with 2-(1H-benzotriazole-1-yl)-1,1,3,3-tetramethyluronium hexafluoro phosphate (HBTU, 1 mole equivalent), 1-hydroxybenzotriazole.hydrate (HOBT, 1 mole equivalent) and N-methylmorpholine (NMM, 2 mole equivalents) in dimethylformamide (DMF, typically 1 to 10 mL) for 5 minutes. Amino functionalised DA/MDA crowns or HEMA gears (10 μmole per crown/1.2 μmole per gear, 0.33 mole equivalent of total surface amino functionalisation compared to activated construct) were added, followed by additional DMF to cover the solid phase surface. The loading reaction was left overnight. Following overnight loading, crowns/gears were taken through standard cycles washing, Fmoc deprotection and loading quantification (see Grabowska, U. et al to provide loaded Building Block-linker constructs (e.g.(22)). Analysis indicated virtually quantitative loading in all examples.

Coupling Cycles

The coupling of standard Fmoc-aminoacids (10 or 20 mole equivalent) were performed via carboxyl activated with 2-(1H-benzotriazole-1-yl)-1,1,3,3-tetramethyluronium hexafluoro phosphate (HBTU, 10 or 20 mole equivalent), 1-hydroxybenzotriazole.hydrate (HOBT, 10 or 20 mole equivalent) and N-methylmorpholine (NMM, 20 or 40 mole equivalents) in dimethylformamide, with pre-activation for 5 minutes. Activated species were dispensed to the appropriate wells of a polypropylene 96-well plate (Beckman, 1 mL wells, 500 μL solution per well for crowns or 250 μL solution per well for gears) in a pattern required for synthesis. Loaded free amino Building Block-linker constructs (e.g.(22)) were added and the coupling reaction left overnight. Following overnight coupling, crowns/gears were taken through standard cycles washing and Fmoc deprotection (see Grabowska, U. et al). Identical activation and coupling conditions were used for the coupling of a range of carboxylic acids (R—COOH). Alternatively, chloroformates e.g. morpholine-4-carbonylchloride (10 mole equivalent), were coupled in DMF with the addition of NMM (10 mole equivalents).

Acidolytic Cleavage Cycle

A mixture of 95% TFA/5% water was pre-dispensed into two polystyrene 96-well plates (Beckman, 1 mL wells, 600 μL solution per well for crowns or 300 μL solution per well for gears) in a pattern corresponding to that of the synthesis. The completed multipin assembly was added to the first plate (mother plate), the block covered in tin foil and cleaved for 2 hours. The cleaved multipin assembly was then removed from the first plate and added to the second plate (washing plate) for 15 minutes. The spent multipin assembly was then discarded and the mother/washing plates evaporated on an HT-4 GeneVac plate evaporator.

Analysis and Purification of Cleaved Examples (a) Ex 1.2 μmole Gears. 100 μL dimethylsulphoxide (DMSO) was added to each post cleaved and dried washing plate well, thoroughly mixed, transferred to the corresponding post cleaved and dried mother plate well and again thoroughly mixed. 10 μL of this DMSO solution was diluted to 100 μL with a 90% acetonitrile/10% 0.1% aq TFA mixture. 20 μL aliquots were analysed by HPLC-MS and full analytical HPLC. In each case the crude example molecules gave the expected [M+H]$^+$ ion and an HPLC peak at>80% (by 215 nm UV analysis). This provided an approximately 10 mM DMSO stock solution of good quality crude examples for preliminary protease inhibitory screening.

(b) Ex 10 μmole Crowns. 500 μL of a 90% acetonitrile/10% 0.1% aq TFA mixture was added to each washing plate well, thoroughly mixed, transferred to the corresponding mother plate well and again thoroughly mixed. 5 μL of this solution was diluted to 100 μL with a 90% acetonitrile/10% 0.1% aq TFA mixture. 20 μL aliquots were analysed by HPLC-MS and full analytical HPLC. In each case the crude example molecules gave the expected [M+H]$^+$ion and an HPLC peak at>80% (by 215 nm UV analysis). The polystyrene blocks containing crude examples were then lyophilised.

(c) Individual examples (ex (b)) were re-dissolved in a 1:1 mixture of 0.1% aq TFA/acetonitrile (1 mL) and purified by semi-preparative HPLC (Phenomenex Jupiter $C_4$, 5μ, 300A, 250×10 mm, a 25-90% B in A gradient over 25 mins, 4.0 mL/min, 215 nm UV detection). Fractions were lyophilised into pre-tarred glass sample vials to provide purified examples (typically 2 to 4 mg, 40 to 80% yield).

(d) Purified examples were dissolved in an appropriate volume of DMSO to provide a 10 mM stock solution, for accurate protease inhibitory screening.

EXAMPLE 1

(An Example of General Formula (I)). (3aS, 6aR) N-[1S-(4-hydroxybenzyl)-2-oxo-2-(3-oxo-hexahydrofuro[3,2-b]pyrrol-4-yl)ethyl]benzamide

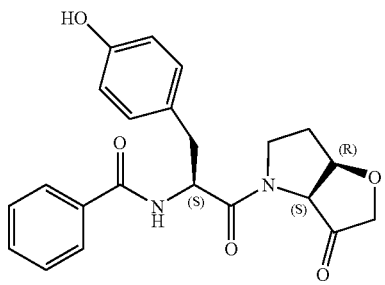

Following the general details from Scheme 1, the required bicycle building block (3aS, 6aR) 3-oxo-hexahydrofuro[3,2-b]pyrrole-4-carboxylic acid 9H-fluoren-9-yl methyl ester (19) was prepared in 8 steps as follows.

(1) Preparation of (2S,3S) (3-hydroxy)pyrrolidine-1,2-dicarboxylic acid 1-(9H-fluoren-9-ylmethyl)ester. Trans-3-hydroxy-L-proline (10.0 g, 76.3 mmole) was added to a vigorously stirred, ice-cooled solution of sodium carbonate (16.90 g, 160.2 mmole) in water (100 mL). 1,4-Dioxan (75 mL) was added providing an opaque but mobile mixture. 9-Fluorenylmethyl chloroformate (20.31 g, 80 mmole) in 1,4-dioxan (75 mL) was added over 1 hr, then the ice-cooling removed and the mixture stirred at RT for an additional 2 hr. Additional water (300 mL) was added, the reaction mixture washed with chloroform (2×250 mL) and the combined organic layers discarded. The aqueous phase was acidified with 1N HCl to ~pH 2, providing a thick opaque mixture. The acidified aqueous mixture was extracted with chloroform (2×500 mL) and the now clear aqueous phase discarded. The opaque combined chloroform layers were dried (Na$_2$SO$_4$), filtered and reduced in vacuo to provide batch 1 (5.70 g). The residual precipitate (a mixture of product and drying agent) was triturated with hot methanol (2×250 mL) and the combined methanol solutions reduced in vacuo to provide batch 2 (10.25 g). Batch 1 and 2 were individually analysed by TLC (single UV spot, Rf=0.15, 20% MeOH in CHCl$_3$), and HPLC-MS (single main UV peak with Rt=7.069 mins, 354.2 [M+H]$^+$, 376.2 [M+Na]$^+$) and found to be identical, giving a combined yield of 15.95 g (45.2 mmole, 59.2%). Analysis by $^1$H and $^{13}$C NMR showed the presence of cis and trans geometrical isomers around the 3° amide bond. $_\delta$H (DMSO-d$_6$ at 298K); 1.80-2.02 (2H$_\gamma$, m), 3.49-3.62 (2H$_\delta$, m), 4.12 4.38 (H$_\alpha$, H$_\beta$, Fmoc H-9 and CH$_2$, m), 5.55/5.62 (OH), 7.30-7.31 (2H aromatic, Fmoc H-2 and H-7), 7.35-7.37 (2H aromatic, Fmoc H-3 and H-6), 7.43-7.45 (2H aromatic, Fmoc H-1 and H-8), 7.63-7.65 (2H aromatic, Fmoc H-4 and H-5), 12.8-13.0 (COOH). $_\delta$C (DMSO-d$_6$ at 298K); 31.70/32.70 (d, C$_\gamma$), 44.68/45.32 (d, C$_\delta$), 46.94/46.97 (u, Fmoc C-9), 67.04/67.33 (d, Fmoc CH$_2$), 68.24/68.51 (u, C$_\alpha$), 73.12/74.23 (u, C$_\beta$), 120.49/120.52 (u, Fmoc C-4 and C-5), 125.49/125.58 (U, Fmoc C-1 and C-8), 127.50 (u, Fmoc C-2 and C-7), 128.04 (u, Fmoc C-3 and C-6), 140.99/141.09 (q, Fmoc C-4' and C-5'), 144.02/144.16 (q, Fmoc C-1' and C-8'), 154.33/154.54 (q, OCON), 172.10/172.39 (COOH).

(2) Preparation of (2S,3S) (3-hydroxy)pyrrolidine-1,2-dicarboxylic Acid 2-allyl ester 1-(9H-fluoren-9-ylmethyl)ester. (2S,3S) (3-hydroxy)pyrrolidine-1,2-dicarboxylic acid 1-(9H-fluoren-9-ylmethyl)ester (10.9 g, 30.8 mmole) was dissolved in toluene (75 mL) in a Dean-Stark apparatus. Allyl alcohol (20 mL) was added followed by p-toluenesulphonic acid.hydrate (6.05 g, 31.4 mmole). The mixture was refluxed for 1 hr, cooled and CHCl$_3$ (300 mL) added. The organic layer was washed with NaHCO$_3$ (300 mL), 0.1N HCl (300 mL) and brine (300 mL), then dried (Na$_2$SO$_4$). Filtration and reduction in vacuo gave a pale yellow foam (13.5 g). The crude foam was purified over silica gel (150 g) eluting with a gradient of heptane:ethyl acetate 3:1→1:1. Desired fractions were combined and reduced in vacuo to a colourless gum yield 10.34 g (26.3 mmole, 85.4%). TLC (single UV spot, Rf=0.30, heptane: ethyl acetate 1:1), analytical HPLC Rt=18.849 mins, HPLC-MS (single main UV peak with Rt=8.354 mins, 394.2 [M+H]$^+$, 416.2 [M+Na]$^+$). Analysis by $^1$H and $^{13}$C NMR showed the presence of cis and trans geometrical isomers around the 3° amide bond. $_\delta$H (CDCl$_3$ at 298K); 2.00-2.21 (2H$_\gamma$, m), 2.70/2.85 (OH, b), 3.72-3.81 (2H$_\delta$, m), 4.12-4.67 (H$_\alpha$, H$_\beta$, Fmoc H-9 and CH$_2$ , 2×COOCH$_2$CH=CH$_2$, m), 5.20-5.40 (2×COOCH$_2$CH=CH$_2$, m), 5.82-5.99 (1×COOCH$_2$CH=CH$_2$, m), 7.28-7.33 (2H aromatic, Fmoc H-2 and H-7), 7.34-7.41 (2H aromatic, Fmoc H-3 and H-6), 7.53-7.66 (2H aromatic, Fmoc H-1 and H-8), 7.77-7.81 (2H aromatic, Fmoc H-4 and H-5). $_\delta$C (CDCl$_3$ at 298K); 32.28/33.04 (d, C$_\gamma$), 44.98/45.32 (d, C$_\delta$), 47.56/47.63 (u, Fmoc C-9), 66.44 (d, COOCH$_2$CH=CH$_2$), 68.01/68.11 (d, Fmoc CH$_2$), 68.32/68.72 (u, C$_\alpha$), 74.49/75.67 (u, C$_\beta$), 119.20/119.48 (d, COOCH$_2$CH=CH$_2$), 120.34/120.37 (u, Fmoc C-4 and C-5), 125.36/125.60 (u, Fmoc C-1 and C-8), 127.47 (u, Fmoc C-2 and C-7), 128.06/128.12 (u, Fmoc C-3 and C-6), 131.79/131.94 (u, COOCH$_2$CH=CH$_2$), 141.65/141.71 (q, Fmoc C4' and C-5'), 144.12/144.34 (q, Fmoc C-1' and C-8'), 155.13/155.59 (q, OCON), 170.53/170.55 (COOCH$_2$CH=CH$_2$).

(3) Preparation of (2S,3R) (3-formyloxy)pyrrolidine-1,2-dicarboxylic Acid 2-allyl Ester 1-(9H-fluoren-9-ylmethyl)ester. Triphenylphosphine (2.76 g, 10.5 mmole, TPP) was dissolved in dry tetrahydrofuran (75 mL), under a nitrogen blanket with stirring and ice-cooled. Diisopropylazodicarboxylate (2.12 g, 2.07 mL, 10.5 mmole, DIAD) was added dropwise over 15 mins to give a precipitous white mixture. (2S,3S) (3-hydroxy)pyrrolidine-1,2-dicarboxylic acid 2-allyl ester 1-(9H-fluoren-9-ylmethyl)ester (4.15 g, 10.5 mmole) and formic acid (0.97 g, 0.79 mL, 21.0 mmole) were mixed in dry tetrahydrofuran (30 mL) and added over 15 mins to the TPP/DIAD mixture. The reaction was stirred for a further 1 hr at 0° C., then overnight at RT. The solvents were removed in vacuo to give a viscous pale yellow oil (11.1 g). The crude oil was purified over silica gel (250 g) eluting with a gradient of heptane: ethyl acetate 4:1→1: 1. Product fractions were identified and reduced in vacuo to give (2S,3R) (3-formyloxy)pyrrolidine-1,2-dicarboxylic acid 2-allyl ester 1-(9H-fluoren-9-ylmethyl) ester/Bis-hydrazide of DIAD, a white solid, yield 4.0 g. TLC (single UV spot, Rf=0.50, heptane: ethyl acetate 1:1), analytical HPLC Rt=19.064-mins, HPLC-MS (single main UV peak with Rt=9.721 mins, 422.2 [M+H]$^+$, 444.1 [M+Na]$^+$ and a non-UV peak with Rt=5.057 mins, 205.1 [M+H]$^+$, 431.2 [2M+Na]$^+$).

(4) Preparation of (2S,3R) (3-hydroxy)pyrrolidine-1,2-dicarboxylic Acid 2-allyl ester 1-(9H-fluoren-9-ylmethyl)ester. (2S,3R) (3-formyloxy)pyrrolidine-1,2-dicarboxylic acid 2-allyl ester 1-(9H-fluoren-9-ylmethyl)ester/Bis-hydrazide of DIAD mixture (4.0 g) was dissolved in allyl alcohol (18 mL), cH$_2$SO$_4$ (75 μL) added and heated to reflux for 90 mins. The mixture was cooled, EtOAc (200 mL) added and washed with NaHCO$_3$ (200 mL), brine (200 mL) and dried (Na$_2$SO$_4$). The solvents were removed in vacuo to give a viscous tan oil (4.2 g). The crude oil was purified over silica gel (150 g) eluting with a gradient of heptane:ethyl acetate 2:1→1:1. Desired fractions were combined and reduced in vacuo to a colourless gum yield 1.75 g (4.44 mmole, 42.4%). TLC (single UV spot, Rf=0.25, heptane:ethyl acetate 1:1), analytical HPLC Rt=17.795 mins, HPLC-MS (single main UV peak with Rt=8.574-mins, 394.2 [M+H]$^+$, 416.2 [M+Na]$^+$). Analysis by $^1$H and $^{13}$C NMR showed the presence of cis and trans geometrical isomers around the 3° amide bond. $_\delta$H (CDCl$_3$ at 298K); 2.09-2.19 (2H$_\gamma$, m), 2.52 (OH, dd, J 1.0, 6.0), 3.54-3.65/3.70-3.82 (2H$_\delta$, m), 4.14-4.20/4.22-4.30 (Fmoc H-9, dm), 4.30-4.39 (1×Fmoc CH$_2$, m), 4.43-4.58 (H$_\alpha$+1×Fmoc CH$_2$, m), 4.60 4.65 (H$_\beta$, m) 4.65-4.76 (2×COOCH$_2$CH=CH$_2$, m), 5.23-5.36 (2×COOCH$_2$CH=CH$_2$, m), 5.81-6.00 (1×COOCH$_2$CH=CH$_2$, m), 7.28-7.38 (2H aromatic, Fmoc H-2 and H-7), 7.39-7.46 (2H aromatic, Fmoc H-3 and H-6), 7.53-7.69 (2H aromatic, Fmoc H-1 and H-8), 7.73-7.81 (2H aromatic, Fmoc H-4 and H-5). $_\delta$C (CDCl$_3$ at 298K); 32.34/33.22 (d, C$_\gamma$), 44.65/44.90 (d, C$_\delta$), 47.57/47.63 (u, Fmoc C-9), 63.89/64.22 (u, C$_\alpha$), 66.38/66.41 (d, COOCH$_2$CH=CH$_2$), 68.02 (d, Fmoc CH$_2$), 71.84/72.80 (u, C$_\beta$), 119.08/119.31 (d, COOCH$_2$CH=CH$_2$), 120.39 (u, Fmoc C-4 and C-5), 125.32/125.46/125.56 (u, Fmoc C-1 and C-8), 127.46 (u, Fmoc C-2 and C-7), 128.12 (u, Fmoc C-3 and C-6), 132.03/132.14 (u, COOCH$_2$CH=CH$_2$), 141.65/141.69 (q, Fmoc C-4' and C-5'), 144.00/144.16/144.43/144.48 (q, Fmoc C-1' and C-8'), 154.88/155.25 (q, OCON), 169.94/169.99 (COOCH$_2$CH=CH$_2$).

(5) Preparation of (2S,3R) (3-tert-butoxy)pyrrolidine-1,2-dicarboxylic acid 2-allyl ester 1-(9H-fluoren-9-ylmethyl)ester. (2S,3R) (3-hydroxy)pyrrolidine-1,2-dicarboxylic acid 2-allyl ester 1-(9H-fluoren-9-ylmethyl) ester (1.75 g, 4.45 mmole) was dissolved in dry dichloromethane (20 mL) in a 50 mL glass pressure tube and cooled to −78° C. Isobutylene gas (~10 mL) was condensed into the solution and $cH_2SO_4$ (100 μL) added. A stirrer bar was added, the tube was sealed, the cooling removed and stirred at RT for 72 hr. The sealed tube was cooled to −78° C., N-methylmorpholine (200 μL, 1 eq w.r.t. $cH_2SO_4$) and allowed to warm to RT, unsealed, with stirring over 2 hr. Dichloromethane (75 mL) was added and the organics washed with $NaHCO_3$ (75 mL), then brine (75 mL) and dried ($Na_2SO_4$). The solvents were removed in vacuo to give a mobile pale tan oil (2.41 g). The crude oil was purified over silica gel (150 g) eluting with a gradient of heptane:ethyl acetate 4:1→3:1. Desired fractions were combined and reduced in vacuo to a thick clear oil yield 1.66 g (3.69 mmole, 83.0%). TLC (single UV spot, Rf=0.45, heptane:ethyl acetate 2:1), analytical HPLC Rt=22.811 mins, HPLC-MS (single main UV peak with Rt=11.193 mins, 450.2 [M+H]$^+$, 472.2 [M+Na]$^+$, 921.4 [2M+Na]$^+$).

(6) Preparation of (2S,3R) (3-tert-butoxy)pyrrolidine-1,2-dicarboxylic acid 1-(9H-fluoren-9-ylmethyl)ester. (2S,3R) (3-tert-butoxy)pyrrolidine-1,2-dicarboxylic acid 2-allyl ester 1-(9H-fluoren-9-ylmethyl)ester (1.60 g, 3.56 mmole) was dissolved in dry dichloromethane (20 mL) with stirring. Tetrakistriphenylphosphine palladium (0) (83 mg, 0.071 mmole, 0.02eq) was added, followed by phenyltrihydrosilane (0.77 g, 0.674 mL, 7.12 mmole, 2eq). After 2 hr, dichloromethane (150 mL) was added and the organics washed with 0.01N HCl (150 mL), brine (150 mL) and dried ($Na_2SO_4$). The solvents were removed in vacuo to give a dark grey solid (2.14-g). The crude solid was purified over silica gel (75 g) eluting with a gradient of heptane:ethyl acetate 2:1→1:6. Desired fractions were combined and reduced in vacuo to a white crystalline yield 0.89 g (2.17 mmole, 61.1%). TLC (single UV spot, Rf=0.30, heptane:ethyl acetate 1:2), analytical HPLC Rt=19.135 mins, HPLC-MS (single main UV peak with Rt=9.386 mins, 354.1 [M+H-Bu$^t$]$^+$, 410.2 [M+H]$^+$, 432.1 [M+Na]$^+$, 841.1 [2M+Na]$^+$). Analysis by $^1$H and $^{13}$C NMR showed the presence of cis and trans geometrical isomers around the 3° amide bond. $_\delta$H (CDCl$_3$ at 298K); 1.23 (9H, s), 1.98-2.28 (2H$_\gamma$, m), 3.40-3.50 (1H$_\delta$, m), 3.68-3.81 (1H$_\delta$, m), 4.10-4.50 (H$_\alpha$+H$_\beta$+Fmoc H-9+2×Fmoc C$\underline{H}_2$, m), 7.29-7.40 (2H aromatic, Fmoc H-2 and H-7), 7.42-7.47 (2H aromatic, Fmoc H-3 and H-6), 7.55-7.70 (2H aromatic, Fmoc H-1 and H-8), 7.73-7.85 (2H aromatic, Fmoc H-4 and H-5), 6.30-8.30 (COO$\underline{H}$, b). $_\delta$C (CDCl$_3$ at 298K); 28.285 (u, (C$\underline{H}_3$)C), 31.47/32.29 (d, C$_\gamma$), 44.13/44.38 (d, C$_\delta$), 47.51/47.60 (u, Fmoc C-9), 62.73/62.95 (u, C$_\alpha$), 67.96/68.13 (d, Fmoc C$\underline{H}_2$), 71.77/72.67 (u, C$_\beta$), 120.33 (u, Fmoc C-4 and C-5), 125.39/125.50/125.55/125.61 (u, Fmoc C-1 and C-8), 127.46 (u, Fmoc C-2 and C-7), 128.01/128.07 (u, Fmoc C-3 and C-6), 141.58/141.66 (q, Fmoc C-4' and C-5'), 144.04/144.23/144.46 (q, Fmoc C-1' and C-8'), 154.95/155.32 (q, O$\underline{C}$ON), 175.19/175.65 ($\underline{C}$OOH).

(7) Preparation of (2S,3R) (3-tert-butoxy)-2-(2-diazoacetyl)pyrrolidine-1-carboxylic acid 9H-fluoren-9-ylmethyl ester. (2S,3R) (3-tert-butoxy)pyrrolidine-1,2-dicarboxylic acid 1-(9H-fluoren-9-ylmethyl)ester (615 mg, 1.5 mmole) was dissolved with stirring in dry dichloromethane (15 mL). The reaction was flushed with nitrogen and cooled to −15° C. Isobutylchloroformate (225 mg, 1.6 mmole in dry dichloromethane (2.5 mL) and N-methylmorpholine (303 mg, 3.0 mmole in dry dichloromethane (2.5 mL) were added simultaneously in 0.5 mL aliquots over 15 mins. Etheral diazomethane (generated from diazald (4.7 g, 15 mmole in diethyl ether (75 mL)) onto sodium hydroxide (5.25 g) in water (7.5 mL)/ethanol (15 mL) at 60° C.). was added to the activated aminoacid solution and stirred at RT for 24 hr. Acetic acid (~2 mL) was added to quench the reaction, then tert-butylmethylether (150 mL) was added, the organics washed with water (3×200 mL), then dried ($Na_2SO_4$). The solvents were removed in vacuo to give a thick yellow oil (890 g). The crude oil was purified over silica gel (75 g) eluting with a gradient of heptane: ethyl acetate 3:1→2:1. Desired fractions were combined and reduced in vacuo to give (2S,3R) (3-tert-butoxy)-2-(2-diazoacetyl)pyrrolidine-1-carboxylic acid 9H-fluoren-9-ylmethyl ester, a pale yellow solid, yield 270 mg (0.624 mmole, 41.6%). TLC (single UV spot Rf=0.55, heptane: ethyl acetate 1:1), analytical HPLC Rt=20.085 mins, HPLC-MS (2 main UV peaks with Rt=7.48 mins, 350.1 [M+H]$^+$, 372.1 [M+Na]$^+$, 721.0 [2M+Na]$^+$ and Rt=9.949 mins, 406.2 [M+H−N$_2$]$^+$, 456.2 [M+Na]$^+$, 889.3 [2M+Na]$^+$). Note that upon HPLC-MS analysis, m/z 350.1 corresponds to the desired bicycle product (3aS, 6aR) 3-oxo-hexahydrofuro[3,2-b]pyrrole-4-carboxylic acid 9H-fluoren-9-ylmethyl ester (19).

(8) Cyclisation to (3aS, 6aR) 3-oxo-hexahydrofuro[3,2-b]pyrrole-4-carboxylic acid 9H-fluoren-9-ylmethyl ester (19). A solution of lithium chloride (205 mg, 4.8 mmole) in water (1.25 mL) and acetic acid (5.0 mL) was added to (2S,3R) (3-tert-butoxy)-2-(2-diazoacetyl)pyrrolidine-1-carboxylic acid 9H-fluoren-9-ylmethyl ester (209 mg, 0.483 mmole). Gas was evolved and the yellow oily solid dissolved over 1 hr to give a virtually colourless solution. After 90 mins, chloroform (150 mL) was added and the organics washed with NaHCO$_3$ (2×150 mL), brine (150 mL) and dried (Na$_2$SO$_4$). The solvents were removed in vacuo to give a thick yellow gum (200 mg). The crude gum was purified over silica gel (40 g) eluting with a gradient of heptane: ethyl acetate 3:2→1:1. Desired fractions were combined and reduced in vacuo to a white crystalline solid, yield 133 mg (0.38 mmole, 18.6% from starting acid). TLC (single UV spot, Rf=0.25, heptane:ethyl acetate 1:1), analytical HPLC broad peak Rt=15.2-17.6 mins, HPLC-MS (single broad UV peak with Rt=7.45-8.56 mins, 350.1 [M+H]$^+$, 372.1 [M+Na]$^+$, 721.2 [2M+Na]$^+$). Analysis by $^1$H and $^{13}$C NMR showed the presence of cis and trans geometrical isomers around the 3° amide bond. $_\delta$H (CDCl$_3$ at 298K); 1.61-1.97 (2H$_\gamma$, m), 3.32-3.45 (1H$_\delta$, m), 3.66-3.75/3.85-3.95 (½H$_\delta$+½H$_\delta$, dm), 3.95/4.10 (1×COC$\underline{H}_{2\alpha}$+1×COC$\underline{H}_{2\beta}$, dm), 4.15-4.30 (Fmoc H-9+2×Fmoc C$\underline{H}_2$, m), 4.40-4.60/4.80-4.92 (H$_\alpha$+H$_\beta$, complex), 7.20-7.30 (2H aromatic, Fmoc H-2 and H-7), 7.31-7.42 (2H aromatic, Fmoc H-3 and H-6), 7.50-7.57/7.60-7.66 (2H aromatic, Fmoc H-1 and H-8), 7.68-7.76 (2H aromatic, Fmoc H-4 and H-5). $_\delta$C (CDCl$_3$ at 298K); 31.76/32.28 (d, C$_\gamma$), 45.59/45.95 (d, C$_\delta$), 47.64 (u, Fmoc C-9), 62.26/62.77 (u, C$_\alpha$), 68.03/68.65 (d, Fmoc C$\underline{H}_2$), 71.28 (d, CO$\underline{C}$H$_2$), 82.17/83.11 (u, C$_\beta$), 120.38 (u, Fmoc C-4 and C-5), 125.41/125.59/125.88 (u, Fmoc C-1 and C-8), 127.45/127.49 (u, Fmoc C-2 and C-7), 128.13 (u, Fmoc C-3 and C-6), 141.73 (q, Fmoc C-4' and C-5'), 144.16/144/37/144.88 (q, Fmoc C-1' and C-8'), 155.33 (q, O$\underline{C}$ON), 209.32 ($\underline{C}$OCH$_2$).

Following the general details from Scheme 2, the required bicycle building block (3 aS, 6aR) 3-oxo-hexahydrofuro[3,2-b]pyrrole-4-carboxylic acid 9H-fluoren-9-ylmethyl ester (19) was converted to building block-linker construct (21) as follows:

(3aS, 6aR) 3-oxo-hexahydrofuro[3,2-b]pyrrole-4-carboxylic acid 9H-fluoren-9-ylmethyl ester (19) (100 mg, 0.286 mmole) was dissolved in a mixture of ethanol (5.0 mL) and water (0.75 mL) containing sodium acetate.trihydrate (59 mg, 0.428 mmole, 1.5eq). 4-[[(hydrazinocarbonyl)amino]methyl]cyclohexanecarboxylic acid. trifluoroacetate (95 mg, 0.286 mmole, 1.0 eq, Murphy, A. M. et al, *J. Am. Chem. Soc.*, 114, 3156-3157, 1992) was added and the mixture refluxed for 90 mins. Chloroform (50 mL) was added and the organics washed with HCl (50 mL, ~pH3), dried ($Na_2SO_4$) and reduced in vacuo to provide crude building block-linker construct (21) as a colourless gum. Yield 172 mg, analytical HPLC 2 peaks Rt=16.477 and 18.512 mins (cis/trans geometrical isomers), HPLC-MS (2×UV peak with Rt=7.75 and 8.82 mins, 547.3 $[M+H]^+$, 569.3 $[M+Na]^+$). Crude (21) was used directly for construct loading.

Following the general details from Scheme 2, the required building block-linker construct (21) was attached to the solid phase providing loaded building block-linker construct (22) as follows:

Building block-linker construct (21) (0.26 mmoles), 2-(1H-benzotriazole-1-yl)-1,1,3,3-tetramethyluronium-hexafluoro phosphate (HBTU, 98.6 mg, 0.26 mmole), 1-hydroxybenzotriazole.hydrate and (HOBT, 39.8 mg, 0.26 mmole) were dissolved in dimethylformamide (3 mL) and N-methylmorpholine (NMM, 58 µL, 0.52 mmole) added. After pre-activation for 5 minutes, free amine gears (72×1.2 µmole) were added, followed by dimethylformamide (5.5 mL) and left overnight. The spent coupling solution was then added to free amine crowns (10×10 µmole) and left overnight. Standard washing and analyses indicated quantitative loading.

Following the general details from Scheme 2, the required loaded building block-linker construct (22) was elaborated on the solid phase as follows:

Loaded construct (22) was elaborated to EXAMPLE 1 (3aS, 6aR) N-[1S-(4-hydroxybenzyl)-2-oxo-2-(3-oxo-hexahydrofuro[3,2-b]pyrrol-4-yl)ethyl]benzamide by standard Fmoc deprotection and sequential coupling with Fmoc-Tyr(OBut)-OH then benzoic acid. The crude example was cleaved and analysed (see general techniques). HPLC Rt=10.15 mins (>95%), HPLC-MS 395.1 $[M+H]^+$.

The following examples (2-82) were prepared as detailed for EXAMPLE 1, coupling with the required reagents to provide the full length molecule.

EXAMPLE 2

(3aS, 6aR) Biphenyl-4-carboxylic Acid [1S-(4-hydroxybenzyl)-2-oxo-2-(3-oxo-hexahydrofuro[3,2-b]pyrrol-4-yl)ethyl]amide

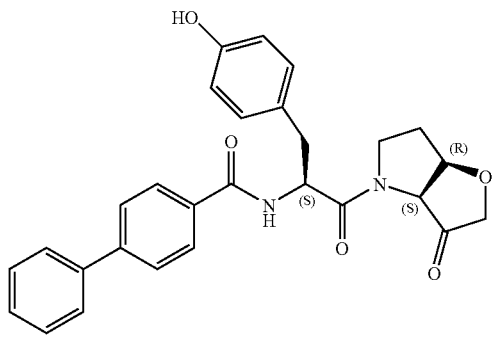

HPLC Rt=14.94-15.46 mins (>90%), HPLC-MS 471.2 $[M+H]^+$.

EXAMPLE 3

(3aS, 6aR) 4-tert-Butyl-N-[1S-(4-hydroxybenzyl)-2-oxo-2-(3-oxo-hexahydrofuro[3,2-b]pyrrol-4-yl)ethyl]benzamide

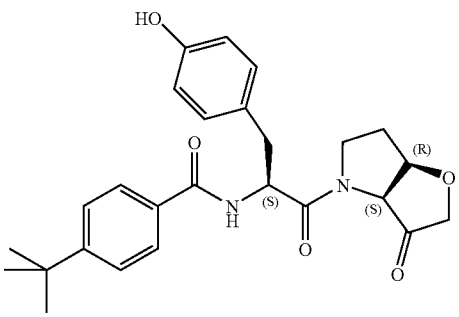

HPLC Rt=15.29-15.89 mins (>90%), HPLC-MS 451.3 $[M+H]^+$

EXAMPLE 4

(3aS, 6aR) N-[1S-(4-hydroxybenzyl)-2-oxo-2-(3-oxo-hexahydrofuro[3,2-b]pyrrol-4-yl)ethyl]-5-thiophen-2-ylnicotinamide

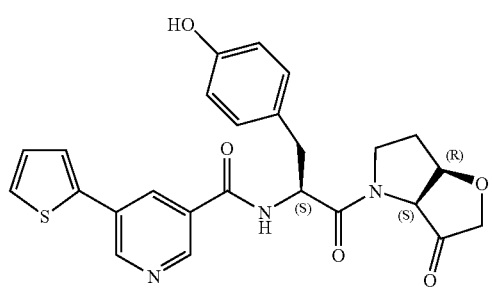

HPLC Rt=11.12 mins (>90°/0), HPLC-MS 478.2 $[M+H]^+$

EXAMPLE 5

(3aS, 6aR) 2-Pyridin-3-ylthiazole-4-carboxylic Acid [1S-(4-hydroxy benzyl)-2-oxo-2-(3-oxo-hexahydrofuro[3,2-b]pyrrol-4-yl)ethyl]amide

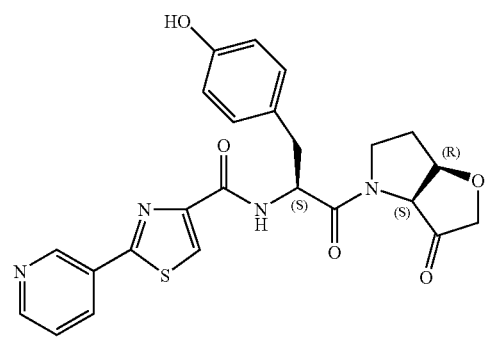

HPLC Rt=8.58 mins (>90%), HPLC-MS 479.2$[M+H]^+$

EXAMPLE 6

(3aS, 6aR) N-[1S-(4-hydroxybenzyl)-2-oxo-2-(3-oxo-hexahydrofuro[3,2-b]pyrrol-4-yl)ethyl]-4-thiophen-2-ylbenzamide

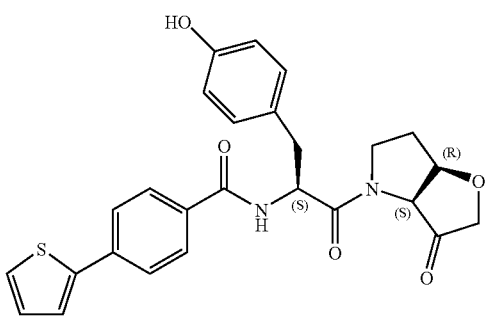

HPLC Rt=14.77-15.311 mins (>90%), HPLC-MS 477.2 [M+H]+

EXAMPLE 7

(3aS, 6aR) N-[1S-(4-hydroxybenzyl)-2-oxo-2-(3-oxo-hexahydrofuro[3,2-b]pyrrol-4-yl)ethyl]-4-trifluoromethoxybenzamide

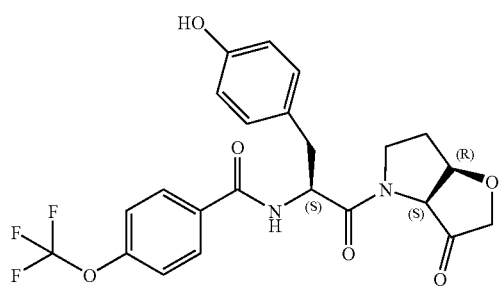

HPLC Rt=14.68 mins (>90%), HPLC-MS 479.2 [M+H]+

EXAMPLE 8

(3aS, 6aR) Biphenyl-4-carboxylic Acid [3-methyl-1S-(3-oxo-hexahydrofuro[3,2-b]pyrrole-4-carbonyl)butyl]amide

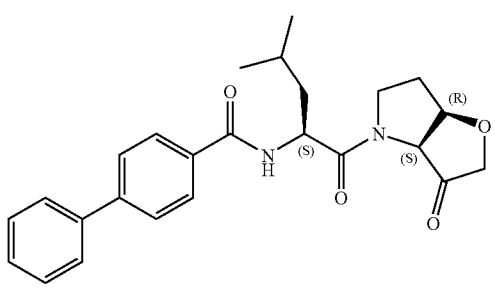

HPLC Rt=16.90-18.04 mins (>90%), HPLC-MS 421.3 [M+H]+

EXAMPLE 9

(3aS, 6aR) 4-tert-Butyl-N-[3-methyl-1S-(3-oxo-hexahydrofuro[3,2-b]pyrrole-4-carbonyl)butyl]benzamide

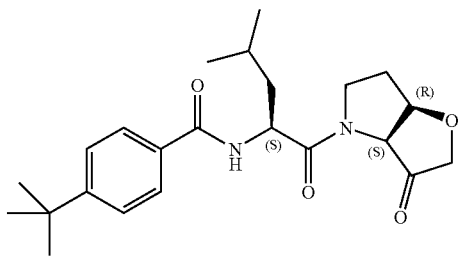

HPLC Rt=17.45-18.62 mins (>90%), HPLC-MS 401.2 [M+H]+

EXAMPLE 10

(3aS, 6aR) N-[3-methyl-1S-(3-oxo-hexahydrofuro[3,2-b]pyrrole-4-carbonyl)butyl]-4-phenoxybenzamide

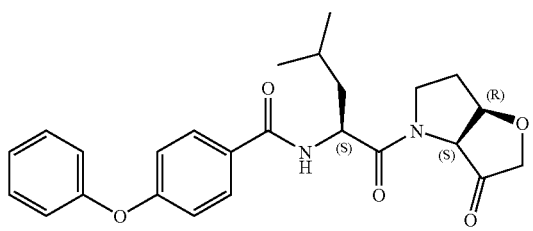

HPLC Rt=17.26-18.38 mins (>90%), HPLC-MS 437.2 [M+H]+

EXAMPLE 11

(3aS, 6aR) N-[3-methyl-1S-(3-oxo-hexahydrofuro[3,2-b]pyrrole-4-carbonyl)butyl]-3-phenoxybenzamide

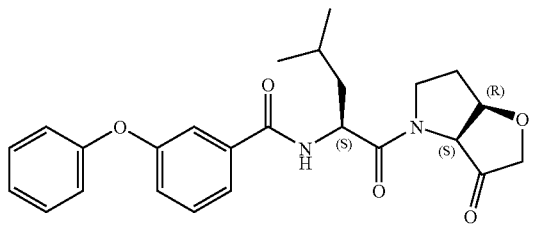

HPLC Rt=17.34-18.52 mins (>90%), HPLC-MS 437.2 [M+H]+

EXAMPLE 12

(3aS, 6aR) 4-Bromo-N-[3-methyl-1S-(3-oxo-hexahydrofuro[3,2-b]pyrrole-4-carbonyl)butyl]benzamide

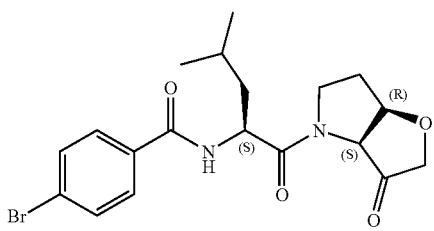

HPLC Rt=14.81 mins (>90%), HPLC-MS 423.2/425.2 [M+H]$^+$

EXAMPLE 13

(3aS, 6aR) 3-Bromo-N-[3-methyl-1S-(3-oxo-hexahydrofuro[3,2-b]pyrrole-4-carbonyl)butyl]benzamide

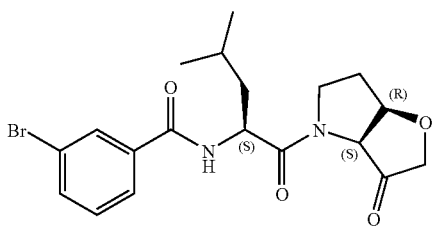

HPLC Rt=14.85-16.20 mins (>90%), HPLC-MS 423.2/425.2 [M+H]$^+$

EXAMPLE 14

(3aS, 6aR) 4-Isopropyl-N-[3-methyl-1S-(3-oxo-hexahydrofuro[3,2-b]pyrrole-4-carbonyl)butyl]benzamide

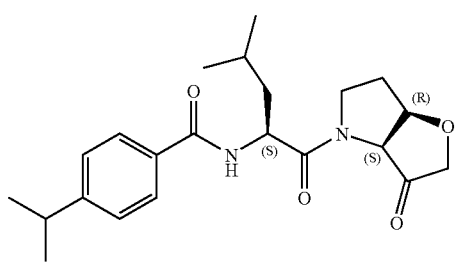

HPLC Rt=16.41-17.65 mins (>90%), HPLC-MS 387.2 [M+H]$^+$

EXAMPLE 15

(3aS, 6aR) N-[3-methyl-1S-(3-oxo-hexahydrofuro[3,2-b]pyrrole-4-carbonyl)butyl]-4-vinylbenzamide

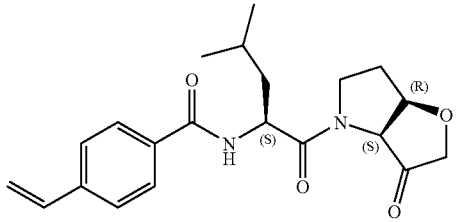

HPLC Rt=14.63 mins (>90%), HPLC-MS 371.1 [M+H]$^+$

EXAMPLE 16

(3aS, 6aR) 4-Imidazol-1-yl-N-[3-methyl-1S-(3-oxo-hexahydrofuro[3,2-b]pyrrole-4-carbonyl)butyl]benzamide

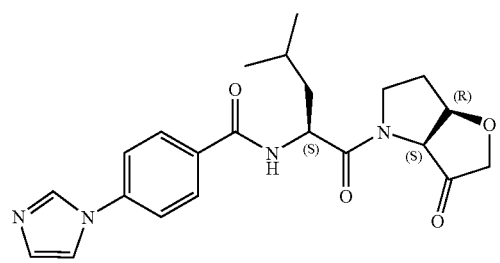

HPLC Rt=9.20 mins (>90%), HPLC-MS 411.2 [M+H]$^+$

EXAMPLE 17

(3aS, 6aR) N-[3-methyl-1S-(3-oxo-hexahydrofuro[3,2-b]pyrrole-4-carbonyl)butyl]-4-thiophen-2-ylbenzamide

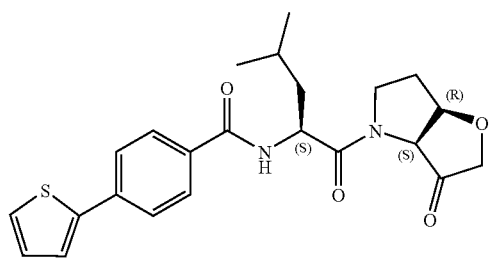

HPLC Rt=16.49-18.34-mins (>90%), HPLC-MS 427.2 [M+H]$^+$

EXAMPLE 18

(3aS, 6aR) N-[3-methyl-1S-(3-oxo-hexahydrofuro[3,2-b]pyrrole-4-carbonyl)butyl]-4-oxazol-5-ylbenzamide

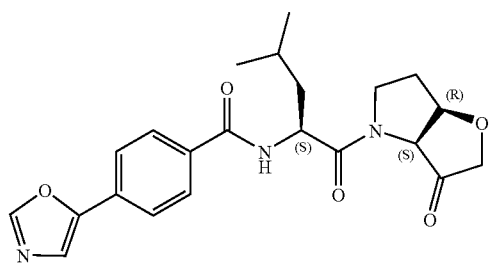

HPLC Rt=12.79 mins (>90%), HPLC-MS 412.2 [M+H]$^+$

EXAMPLE 19

(3aS, 6aR) 2-Phenylthiazole-4-carboxylic Acid [3-methyl-1S-(3-oxo-hexahydrofuro[3,2-b]pyrrole-4-carbonyl)butyl]amide

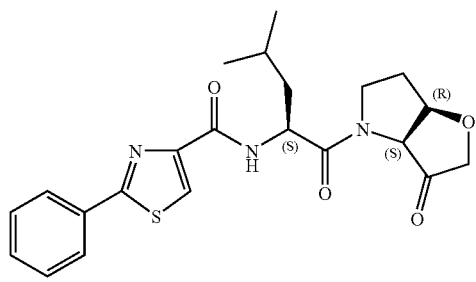

HPLC Rt=16.41-17.80 mins (>90%), HPLC-MS 428.2 [M+H]+

EXAMPLE 20

(3aS, 6aR) 5-Phenylthiophene-2-carboxylic Acid [3-methyl-1S-(3-oxo-hexahydrofuro[3,2-b]pyrrole-4-carbonyl)butyl]amide

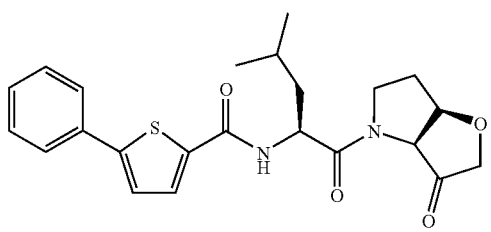

HPLC Rt=16.89 mins (>90%), HPLC-MS 427.2 [M+H]+

EXAMPLE 21

(3aS, 6aR) Quinoline-6-carboxylic Acid [3-methyl-1S-(3-oxo-hexahydrofuro[3,2-b]pyrrole-4-carbonyl)butyl]amide

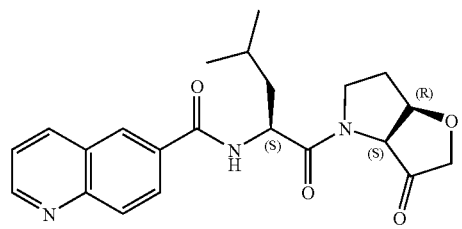

HPLC Rt=9.08 mins (>90%), HPLC-MS 396.2 M+H]+

EXAMPLE 22

(3aS, 6aR) N-[3-methyl-1S-(3-oxo-hexahydrofuro[3,2-b]pyrrole-4-carbonyl)butyl]-4-[1,2,3]thiadiazol-4-ylbenzamide

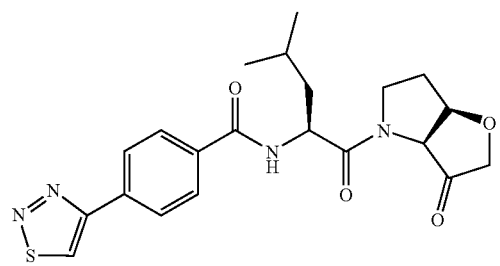

HPLC Rt=13.41 mins (>90%), HPLC-MS 429.2 [M+H]+

EXAMPLE 23

(3aS, 6aR) N-[3-methyl-1S-(3-oxo-hexahydrofuro[3,2-b]pyrrole-4-carbonyl)butyl]-5-thiophen-2-ylnicotinamide

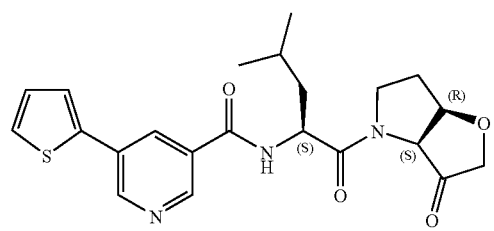

HPLC Rt=13.24 mins (>90%), HPLC-MS 428.2 [M+H]+

EXAMPLE 24

(3aS, 6aR) 2-Pyridin-3-ylthiazole-4-carboxylic Acid [3-methyl-1S-(3-oxo-hexahydrofuro[3,2-b]pyrrole-4-carbonyl)butyl]amide

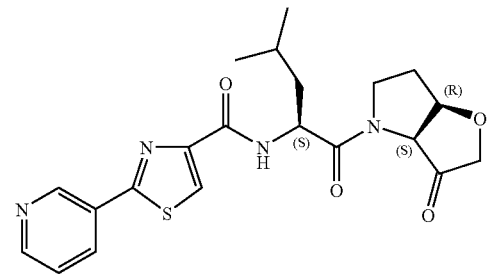

HPLC Rt=10.22 mins (>90%), HPLC-MS 429.2 [M+H]+

EXAMPLE 25

(3aS, 6aR) N-[3-methyl-1S-(3-oxo-hexahydrofuro[3,2-b]pyrrole-4-carbonyl)butyl]-4-trifluoromethoxy-benzamide

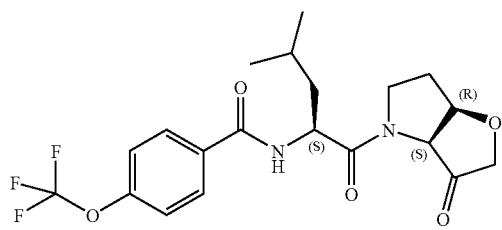

HPLC Rt=16.90-18.34-mins (>90%), HPLC-MS 429.2 [M+H]+

EXAMPLE 26

(3aS, 6aR) 4-tert-Butyl-N-[1S-(3-hydroxybenzyl)-2-oxo-2-(3-oxo-hexahydrofuro[3,2-b]pyrrol-4-yl)ethyl]benzamide

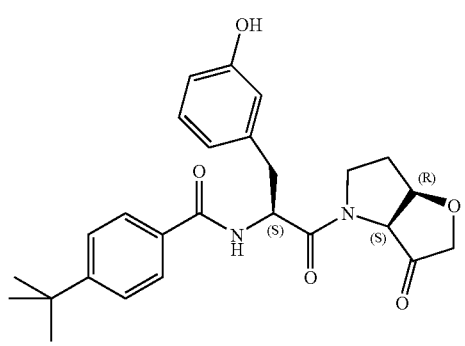

HPLC Rt=16.1417.02 mins (>90%), HPLC-MS 451.2 [M+H]+

EXAMPLE 27

(3aS, 6aR) N-[1S-(3-hydroxybenzyl)-2-oxo-2-(3-oxo-hexahydrofuro[3,2-b]pyrrol-4-yl)ethyl]thiophen-2-ylbenzamide

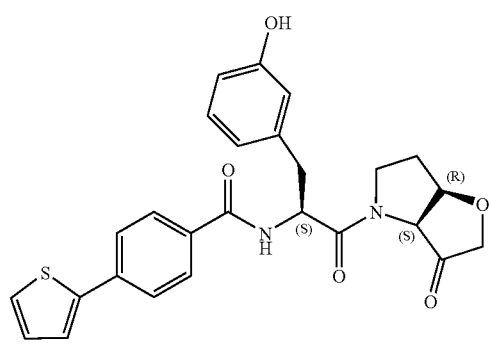

HPLC Rt=15.31-16.07 mins (>90%), HPLC-MS 477.2 [M+H]+

EXAMPLE 28

(3aS, 6aR) 4-tert-Butyl-N-[1S-(4-fluorobenzyl)-2-oxo-2-(3-oxo-hexahydrofuro[3,2-b]pyrrol-4-yl)ethyl]benzamide

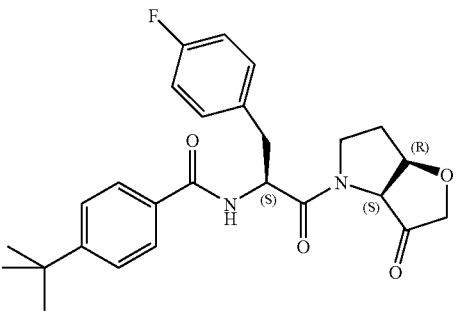

HPLC Rt=18.37-19.63 mins (>90%), HPLC-MS 453.1 [M+H]+

EXAMPLE 29

(3aS, 6aR) N-[1S-(4-fluorobenzyl)-2-oxo-2-(3-oxo-hexahydrofuro[3,2-b]pyrrol-4-yl)ethyl]-4-thiophen-2-ylbenzamide

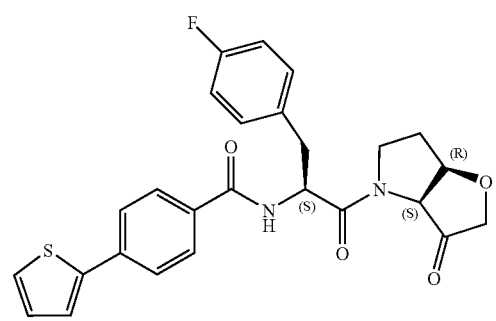

HPLC Rt=17.45-18.59 mins (>90%), HPLC-MS 479.2 [M+H]+

EXAMPLE 30

(3aS, 6aR) Morpholine-4-carboxylic Acid [1S-(4-hydroxybenzyl)-2-oxo-2-(3-oxo-hexahydrofuro[3,2-b]pyrrol-4-yl)ethyl]amide

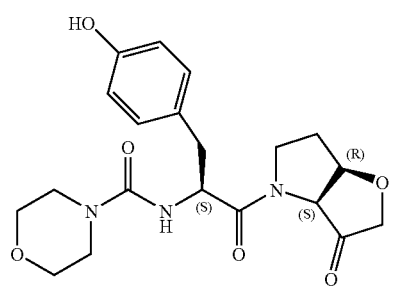

HPLC Rt=7.38 mins (>95%), HPLC-MS 404.2 [M+H]+.

EXAMPLE 31

(3aS, 6aR) Morpholine-4-carboxylic Acid [3-methyl-1S-(3-oxo-hexa hydrofuro[3,2-b]pyrrole-4-carbonyl)butyl]amide

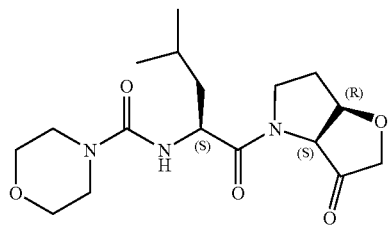

HPLC-MS 354.2 [M+H]⁺.

EXAMPLE 32

(3aS, 6aR) Morpholine-4-carboxylic Acid [1S-cyclohexylmethyl-2-oxo-2-(3-oxo-hexahydrofuro[3,2-b]pyrrol-4-yl)ethyl]amide

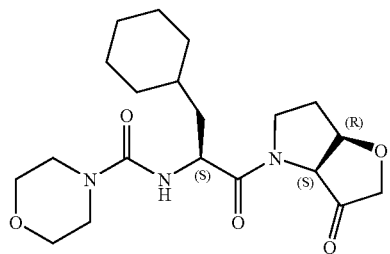

HPLC-MS 394.2 [M+H]⁺.

EXAMPLE 33

(3aS, 6aR) Morpholine-4-carboxylic Acid [1S-benzyl-2-oxo-2-(3-oxo-hexahydrofuro[3,2-b]pyrrol-4-yl)ethyl]amide

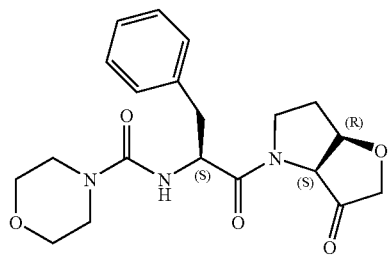

HPLC Rt=10.07 mins (>95%), HPLC-MS 388.1 [M+H]⁺.

EXAMPLE 34

(2RS, 3aS, 6aR) 4-(2-Benzyloxy-3-[cyclohexyl]propionoyl)tetra hydrofuro[3,2-b]pyrrol-3-one

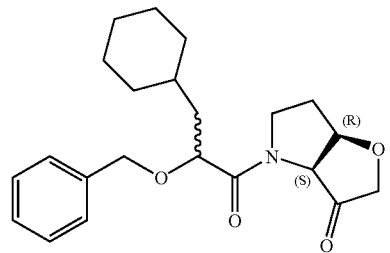

HPLC Rt=17.5-19.7 mins (>90%), HPLC-MS 372.4 [M+H]⁺, 390.3 [M+H+18]⁺.

(a) Preparation of 3-Cyclohexyl-2S-hydroxypropionic Acid (Compound (25) Scheme 4)

A solution of sodium nitrite (12.1 g, 175 mmol) in water (40 ml) was added dropwise to a stirred suspension of (S)-α-aminocyclohexanepropionic acid hydrate (5 g, 26.5 mmol) in 0.5M sulphuric acid (120 ml, 60 mmol) at 0° C. over 1.5 hours. The mixture was allowed to warm to ambient temperature over 20 hours. The product was extracted into diethyl ether (2×25 ml) then the ethereal layers were washed with saturated aqueous sodium chloride solution (2×25 ml), dried ($Na_2SO_4$) and the solvents removed in vacuo. The residue (5.3 g) was recrystallized from diethyl ether (10 ml) and heptane (25 ml) to give 3-cyclohexyl-2S-hydroxypropionic acid as a white solid, yield 2.4 g, (53%).

$\delta_H$ (400 MHz, $CDCl_3$ at 298K), 0.89-1.35 (5H, m) and 1.51-1.86 (7H, m) (OCHC$\underline{H}_2$ and cyclohexyl), 4.32 (1H, OC$\underline{H}CH_2$, m)

(b) Preparation of 2RS-Benzyloxy-3-cyclohexylpropionic Acid (Compound (26) Scheme 4)

Sodium hydride (265 mg of 60% dispersion in oil, 6.6 mmol) was added in two portions to a stirred mixture of 3-cyclohexyl-2S-hydroxypropionic acid (0.52 g, 3.0 mmol), dimethylformamide (5 ml) and dichloromethane (5 ml) at 0° C. over 5 minutes. The mixture was stirred at 0° C. for 5 minutes then at ambient temperature for 45 minutes. Benzyl bromide (0.45 ml, 3.8 mmol) was added then the mixture stirred for 1 hour before adding dimethylformamide (5 ml). After stirring for 4 hours potassium iodide (50 mg, 0.3 mmol) was added. The mixture was stirred for 20 hours then heated at 55° C. for 1 hour then allowed to cool to ambient temperature and poured into water (15 ml). A saturated aqueous sodium chloride solution (5 ml) was added then the mixture was extracted with dichloromethane (5 ml then 10 ml) that was discarded. The aqueous layer was acidified using 1M hydrochloric acid (10 ml) then extracted with dichloromethane (2×10 ml). The dichloromethane layer was dried ($MgSO_4$) and the solvent removed in vacuo. The residue (0.55 g) was dissolved in dimethylformamide (8 ml) then cooled to 0° C. before adding sodium hydride (190 mg of 60% dispersion in oil, 4.75 mmol). The mixture was stirred for 30 minutes then polymer bound isocyanate (380 mg, 2 mmol Ng⁻¹) added. The mixture was stirred for 2 hours at ambient temperature then poured into water (15 ml). 1M Hydrochloric acid (10 ml) was added then the product was extracted into dichloromethane (2×10 ml), dried ($Na_2SO_4$) and the solvent removed in vacuo. The residue was purified by flash chromatography over silica gel eluting with a gradient of methanol:dichloromethane 0:1→1:20. Appropriate fractions were combined and the solvents removed in vacuo to give 2RS-benzyloxy-3-cyclohexylpropionic acid as a colourless oil, yield 41 mg (5.2%).

HPLC-MS (Single Main UV Peak with Rt=9.47 mins, 261.2 [M–H]⁻, 285.2[M+Na]⁺, 547.3[2M+Na]⁺).

$\delta_H$ (400 MHz, $CDCl_3$ at 298K), 0.72-1.03 (2H, cyclohexane, m), 1.08-1.38 (3H, cyclohexane, m), 1.45-1.93 (6H+2Hβ, cyclohexane, m), 3.93-4.18 (1Hα, OC$\underline{H}$CO), 4.35-4.53 (1H, C$\underline{H}_2$O, d, J=11.52 Hz), 4.68-4.88 (1H C$\underline{H}_2$°, d, J=11.54 Hz), 7.20-7.47 (5H, ArH, m), 9.36 (1H, O$\underline{H}$, brs).

Compound (26) was coupled under standard conditions to loaded building block-linker construct (22), then cleaved to provide EXAMPLE 34.

EXAMPLE 35

(3aS, 6aR) Morpholine-4-carboxylic Acid [1R-benzylsulfanylmethyl-2-oxo-2-(3-oxo-hexahydrofuro[3,2-b]pyrrol-4-yl)ethyl]amide

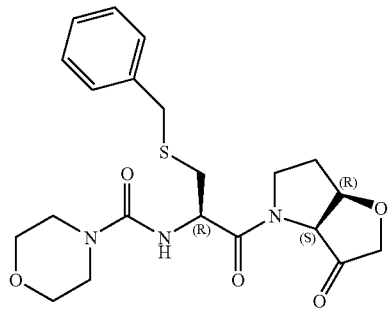

HPLC Rt=12.15 mins (>95%), HPLC-MS 434.1 [M+H]$^+$.

EXAMPLE 36

(3aS, 6aR) N-[3-methyl-1S-(3-oxo-hexahydrofuro[3,2-b]pyrrole-4-carbonyl)butyl]benzamide

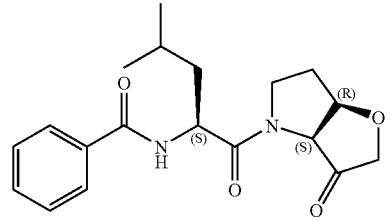

HPLC Rt=12.43 mins (>95%), HPLC-MS 345.2 [M+H]$^+$.

EXAMPLE 37

(3aS, 6aR) N-[1R-benzylsulfanylmethyl-2-oxo-2-(3-oxo-hexahydro furo[3,2-b]pyrrol-4-yl)ethyl]benzamide

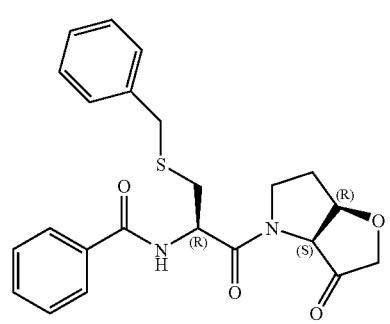

HPLC Rt=15.09 mins (>95%), HPLC-MS 425.1 [M+H]$^+$.

EXAMPLE 38

(3aS, 6aR) N-[1S-cyclohexylmethyl-2-oxo-2-(3-oxo-hexahydrofuro[3,2-b]pyrrol-4-yl)ethyl]benzamide

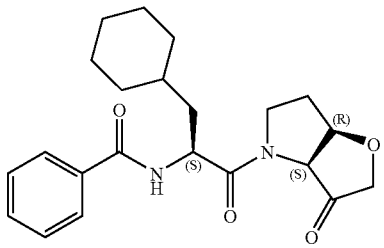

HPLC Rt=15.63 mins (>90%), HPLC-MS 385.3 [M+H]$^+$, 791.3 [2M+Na]$^+$.

EXAMPLE 39

(3aS, 6aR) N-[1S-benzyl-2-oxo-2-(3-oxo-hexahydrofuro[3,2-b]pyrrol-4-yl)ethyl]benzamide

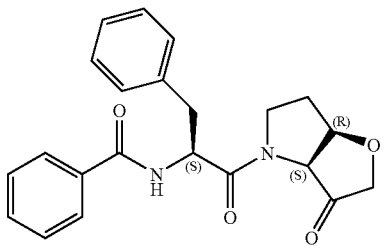

HPLC Rt=12.85 mins (>90%), HPLC-MS 379.1 [M+H]$^+$.

EXAMPLE 40

(3aS, 6aR) Furan-3-carboxylic Acid [1S-cyclopentylmethyl-2-oxo-2-(3-oxo-hexahydrofuro[3,2-b]pyrrol-4-yl)ethyl]amide

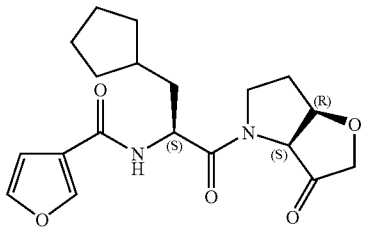

HPLC Rt=13.23 mins (>95%), HPLC-MS 361.2 [M+H]$^+$.

EXAMPLE 41

(3aS, 6aR) N-[1S-(4-hydroxybenzyl)-2-oxo-2-(3-oxo-hexahydro furo[3,2-b]pyrrol-4-yl)ethyl]-2-phenylacetamide

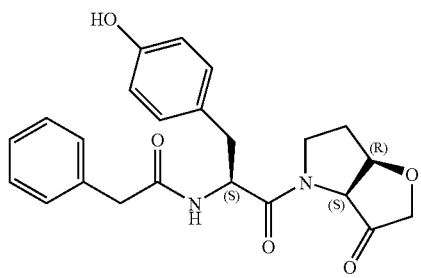

HPLC Rt=10.71 mins (>95%), HPLC-MS 409.1 [M+H]$^+$.

EXAMPLE 42

(3aS, 6aR) N-[3-methyl-1S-(3-oxo-hexahydrofuro[3,2-b]pyrrole-4-carbonyl)butyl]-2-phenylacetamide

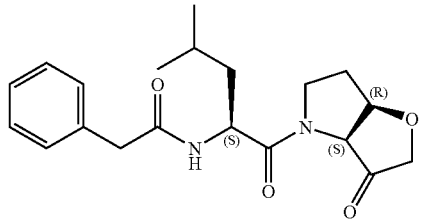

HPLC Rt=13.00 mins (>95%), HPLC-MS 359.2 [M+H]$^+$.

EXAMPLE 43

(3aS, 6aR) N-[1R-benzylsulfanylmethyl-2-oxo-2-(3-oxo-hexahydro furo[3,2-b]pyrrol-4-yl)ethyl]-2-phenylacetamide

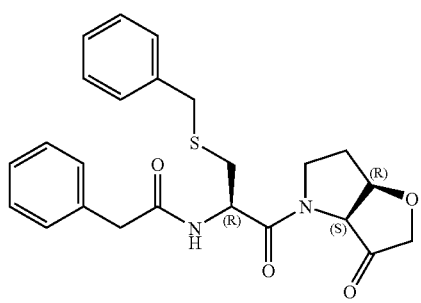

HPLC Rt=15.53 mins (>90%), HPLC-MS 439.1 [M+H]$^+$.

EXAMPLE 44

(3aS, 6aR) N-[1S-cyclohexylmethyl-2-oxo-2-(3-oxo-hexahydrofuro[3,2-b]pyrrol-4-yl)ethyl]-2-phenylacetamide

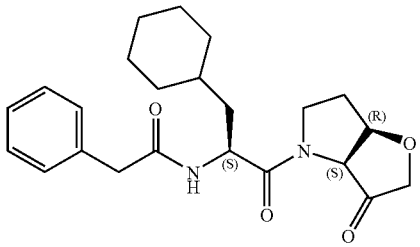

HPLC Rt=18.5 mins (>90%), HPLC-MS 399.2 [M+H]$^+$.

EXAMPLE 45

(3aS, 6aR) N-[1S-benzyl-2-oxo-2-(3-oxo-hexahydrofuro[3,2-b]pyrrol-4-yl)ethyl]-2-phenylacetamide

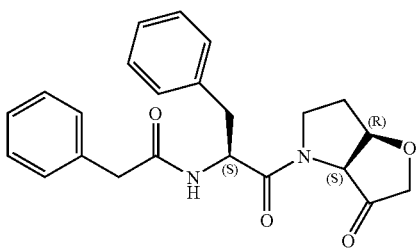

HPLC Rt=13.2 mins (>90%), HPLC-MS 393.2 [M+H]$^+$.

EXAMPLE 46

(3aS, 6aR) Furan-3-carboxylic Acid [1S-(4-hydroxybenzyl)-2-oxo-2-(3-oxo-hexahydrofuro[3,2-b]pyrrol-4-yl)ethyl]amide

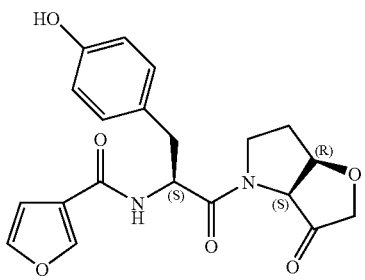

HPLC Rt=8.65 mins (>95%), HPLC-MS 385.2 [M+H]$^+$.

EXAMPLE 47

(3aS, 6aR) Furan-3-carboxylic Acid [3-methyl-1S-(3-oxo-hexahydro furo[3,2-b]pyrrol-carbonyl)butyl]amide

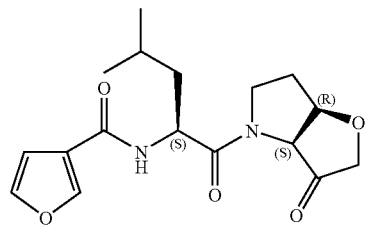

HPLC Rt=10.95 mins (>90%), HPLC-MS 335.1 [M+H]$^+$, 357.1 [M+Na]$^+$.

EXAMPLE 48

(3aS, 6aR) Furan-3-carboxylic Acid [1R-benzylsulfanylmethyl-2-oxo-2-(3-oxo-hexahydrofuro[3,2-b]pyrrol-4-yl)ethyl]amide

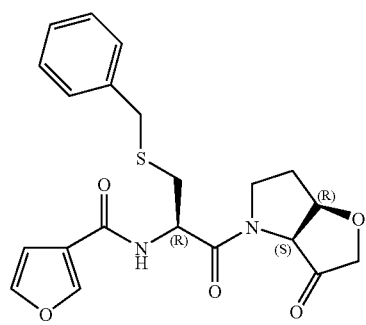

HPLC Rt=13.68 mins (>90%), HPLC-MS 415.1 [M+H]$^+$.

EXAMPLE 49

(3aS, 6aR) Furan-3-carboxylic Acid [1S-cyclohexylmethyl-2-oxo-2-(3-oxo-hexahydrofuro[3,2-b]pyrrol-4-yl)ethyl]amide

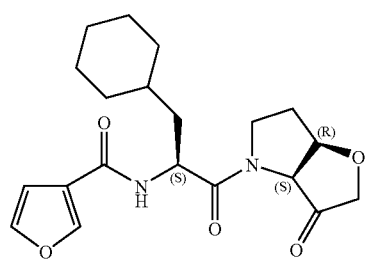

HPLC Rt=14.39 mins (>90%), HPLC-MS 375.2 [M+H]$^+$, 771.3 [2M+Na]$^+$.

EXAMPLE 50

(3aS, 6aR) Furan-3-carboxylic Acid [1S-benzyl-2-oxo-2-(3-oxo-hexa hydrofuro[3,2-b]pyrrol-4-yl)ethyl]amide

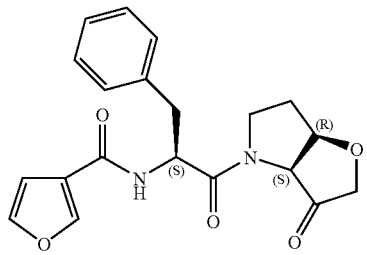

HPLC Rt=11.51 mins (>90%), HPLC-MS 369.1 [M+H]$^+$.

EXAMPLE 51

(3aS, 6aR) Thiophene-3-carboxylic Acid [1S-cyclopentylmethyl-2-oxo-2-(3-oxo-hexahydrofuro[3,2-b]pyrrol-4-yl)ethyl]amide

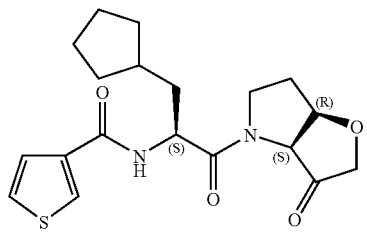

HPLC Rt=14.07 mins (>95%), HPLC-MS 377.3 [M+H]$^+$.

EXAMPLE 52

(3aS, 6aR) Thiophene-3-carboxylic Acid [1S-(4-hydroxybenzyl)-2-oxo-2-(3-oxo-hexahydrofuro[3,2-b]pyrrol-4-yl)ethyl]amide

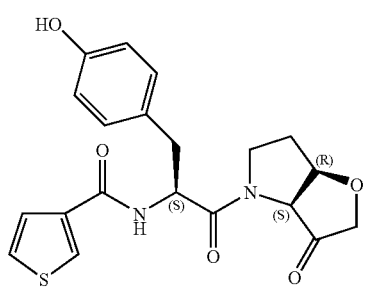

HPLC Rt=11.75 mins (>95%), HPLC-MS 401.3 [M+H]$^+$.

EXAMPLE 53

(3aS, 6aR) Thiophene-3-carboxylic Acid [3-methyl-1S-(3-oxo-hexa hydrofuro[3,2-b]pyrrole-4-carbonyl)butyl]amide

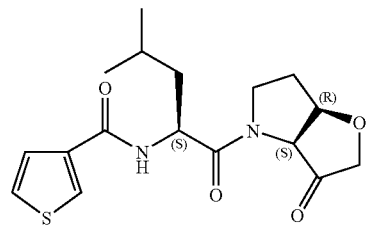

HPLC Rt=14.01 mins (>90%), HPLC-MS 351.1 [M+H]$^+$, 373.1 [M+Na]$^+$.

EXAMPLE 54

(3aS, 6aR) Thiophene-3-carboxylic Acid [1R-benzylsulfanylmethyl-2-oxo-2-(3-oxo-hexahydrofuro[3,2-b]pyrrol-4-yl)ethyl]amide

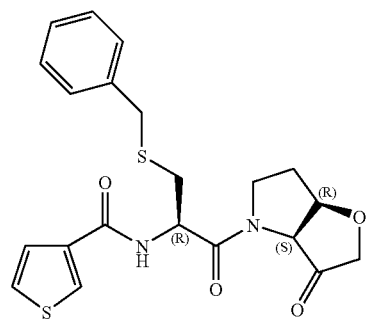

HPLC Rt=14.51 mins (>95%), HPLC-MS 431.1 [M+H]$^+$.

EXAMPLE 55

(3aS, 6aR) Thiophene-3-carboxylic Acid [1S-cyclohexylmethyl-2-oxo-2-(3-oxo-hexahydrofuro[3,2-b]pyrrol-4-yl)ethyl]amide

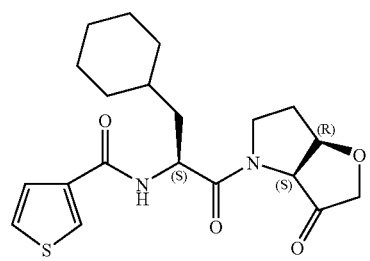

HPLC Rt=15.11 mins (>90%), HPLC-MS 391.1 [M+H]$^+$, 803.3 [2M+Na]$^+$.

EXAMPLE 56

(3aS, 6aR) Thiophene-3-carboxylic Acid [1S-benzyl-2-oxo-2-(3-oxo-hexahydrofuro[3,2-b]pyrrol-4-yl)ethyl]amide

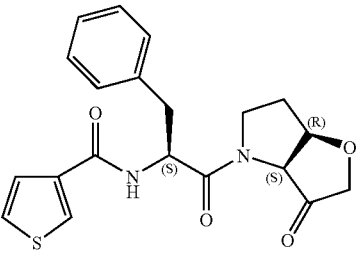

HPLC Rt=12.27 mins (>95%), HPLC-MS 385.1[M+H]$^+$, 407.1 [M+Na]$^+$, 791.2 [2M+Na]$^+$.

EXAMPLE 57

(3aS, 6aR) Furan-3-carboxylic Acid [3,3-dimethyl-1S-(3-oxo-hexa hydrofuro[3,2-b]pyrrole-4-carbonyl)butyl]amide

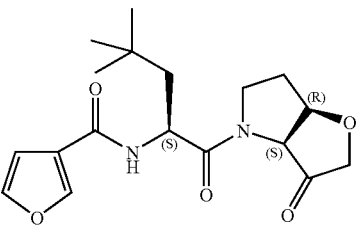

HPLC Rt=12.50 mins (>95%), HPLC-MS 349.2 [M+H]$^+$.

EXAMPLE 58

(3aS, 6aR) N-[1S-(4-hydroxybenzyl)-2-oxo-2-(3-oxo-hexahydrofuro[3,2-b]pyrrol-4-yl)ethyl]-3-phenylpropionamide

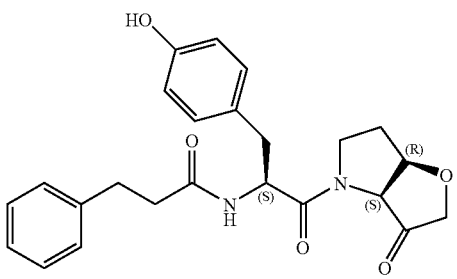

HPLC Rt=11.72 mins (>90%), HPLC-MS 423.2 [M+H]$^+$.

EXAMPLE 59

(3aS, 6aR) N-[3-methyl-1S-(3-oxo-hexahydrofuro[3,2-b]pyrrole-4-carbonyl)butyl]-3-phenylpropionamide

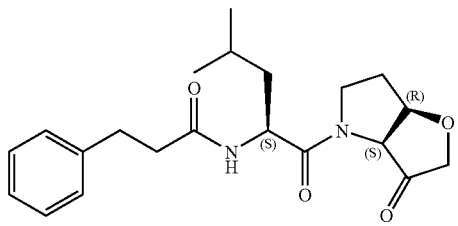

HPLC Rt=13.46 mins (>90%), HPLC-MS 373.1 [M+H]$^+$, 767.3 [2M+Na]$^+$.

EXAMPLE 60

(3aS, 6aR) N-[1R-benzylsulfanylmethyl-2-oxo-2-(3-oxo-hexahydro furo[3,2-b]pyrrol-4-yl)ethyl]-3-phenylpropionamide

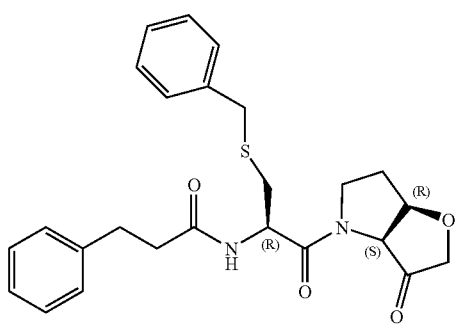

HPLC Rt=16.22 mins (>90%), HPLC-MS 453.2 [M+H]$^+$, 475.0 [M+Na]$^+$.

EXAMPLE 61

(3aS, 6aR) N-[1S-cyclohexylmethyl-2-oxo-2-(3-oxo-hexahydrofuro[3,2-b]pyrrol-4-yl)ethyl]-3-phenylpropionamide

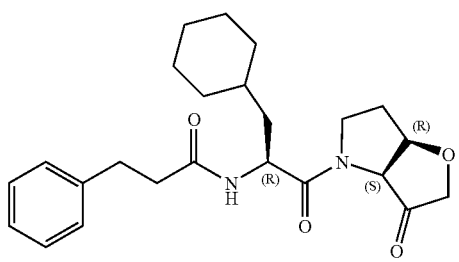

HPLC-MS 413.2 [M+H]$^+$.

EXAMPLE 62

(3aS, 6aR) N-[1S-benzyl-2-oxo-2-(3-oxo-hexahydrofuro[3,2-b]pyrrol-4-yl)ethyl]-3-phenylpropionamide

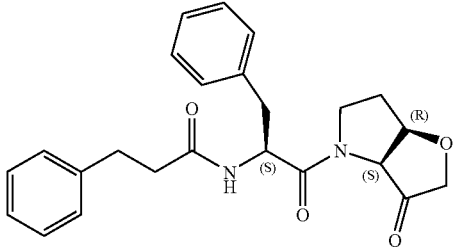

HPLC Rt=16.68 mins (>90%), HPLC-MS 407.2 [M+H]$^+$, 835.2 [2M+Na]$^+$.

EXAMPLE 63

(3aS, 6aR) Thiophene-3-carboxylic Acid [3,3 dimethyl-1S-(3-oxo-hexahydrofuro[3,2-b]pyrrole-4-carbonyl)butyl]amide

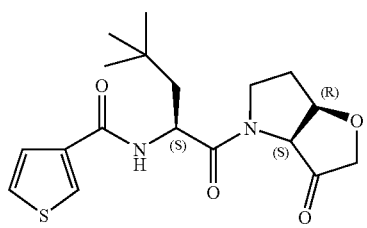

HPLC Rt=13.24-mins (>95%), HPLC-MS 365.2 [M+H]$^+$.

EXAMPLE 64

(3aS, 6aR) Benzo[b]thiophene-2-carboxylic Acid [1S-(4-hydroxy benzyl)-2-oxo-2-(3-oxo-hexahydrofuro[3,2-b]pyrrol-4-yl)ethyl]amide

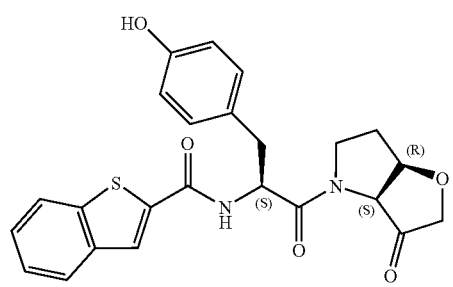

HPLC Rt=13.10 mins (>85%), HPLC-MS 451.1 [M+H]$^+$, 923.2 [2M+Na]$^+$.

EXAMPLE 65

(3aS, 6aR) Benzo[b]thiophene-2-carboxylic Acid [3-methyl-1S-(3-oxo-hexahydrofuro[3,2-b]pyrrole-4-carbonyl)butyl]amide

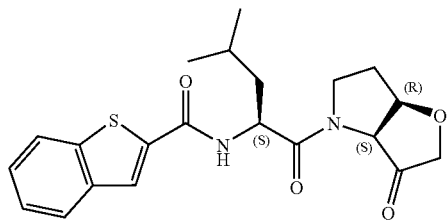

HPLC Rt=15.62 mins (>90%), HPLC-MS 401.1 [M+H]$^+$, 823.2 [2M+Na]$^+$.

EXAMPLE 66

(3aS, 6aR) Benzo[b]thiophene-2-carboxylic Acid [1R-benzylsulfanyl methyl-2-oxo-2-(3-oxo-hexahydrofuro[3,2-b]pyrrol-4-yl)ethyl]amide

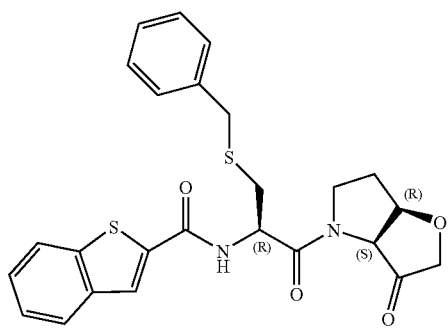

HPLC Rt=17.47 mins (>90%), HPLC-MS 481.1 [M+H]$^+$, 983.2 [2M+Na]$^+$.

EXAMPLE 67

(3aS, 6aR) Benzo[b]thiophene-2-carboxylic Acid [1S-cyclohexyl methyl-2-oxo-2-(3-oxo-hexahydrofuro[3,2-b]pyrrol-4-yl)ethyl]amide

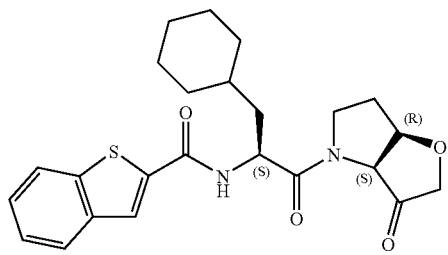

HPLC Rt=18.15 mins (>90%), HPLC-MS 441.2 [M+H]$^+$, 903.2 [2M+Na]$^+$.

EXAMPLE 68

(3aS, 6aR) Benzo[b]thiophene-2-carboxylic Acid [1S-benzyl-2-oxo-2-(3-oxo-hexahydrofuro[3,2-b]pyrrol-4-yl)ethyl]amide

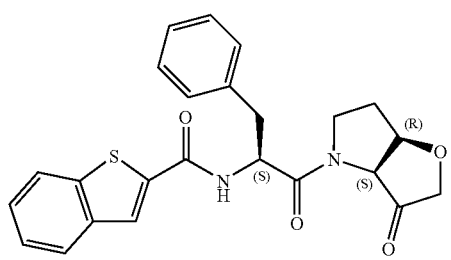

HPLC Rt=15.58 mins (>85%), HPLC-MS 435.1 [M+H]$^+$, 891.2 [2M+Na]$^+$.

EXAMPLE 69

(3aS, 6aR) Naphthalene-1-carboxylic Acid [1S-(4-hydroxybenzyl)-2-oxo-2-(3-oxo-hexahydrofuro[3,2-b]pyrrol-4-yl)ethyl]amide

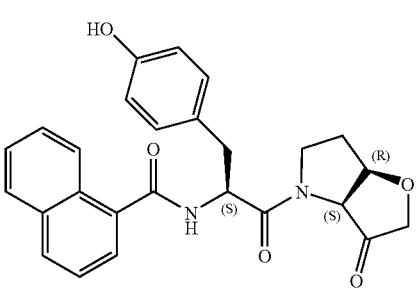

HPLC Rt=12.42 mins (>85%), HPLC-MS 445.1 [M+H]$^+$, 911.3 [2M+Na]$^+$.

EXAMPLE 70

(3aS, 6aR) Naphthalene-1-carboxylic Acid [3-methyl-1S-(3-oxo-hexa hydrofuro[3,2-b]pyrrol-4-carbonyl)butyl]amide

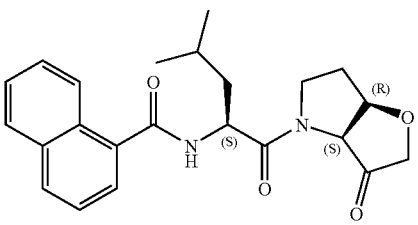

HPLC Rt=14.81 mins (>85%), HPLC-MS 395.2 [M+H]$^+$, 811.3 [2M+Na]$^+$.

EXAMPLE 71

(3aS, 6aR) Naphthalene-1-carboxylic Acid [1R-benzylsulfanylmethyl-2-oxo-2-(3-oxo-hexahydrofuro[3,2-b]pyrrol-4-yl)ethyl]amide

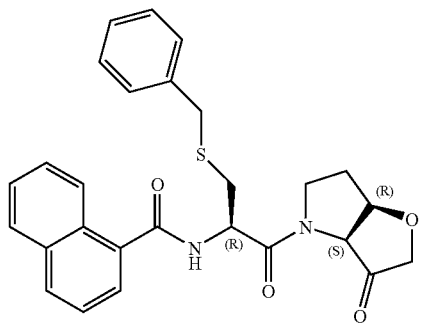

HPLC Rt=17.10 mins (>90%), HPLC-MS 475.2 [M+H]⁺.

EXAMPLE 72

(3aS, 6aR) Naphthalene-1-carboxylic Acid [1S-cyclohexylmethyl-2-oxo-2-(3-oxo-hexahydrofuro[3,2-b]pyrrol-4-yl)ethyl]amide

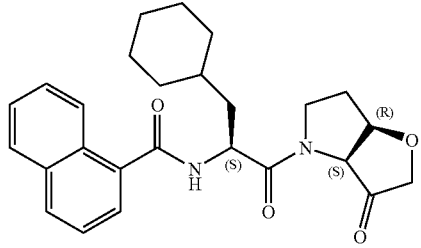

HPLC Rt=17.45 mins (>90%), HPLC-MS 435.2 [M+H]⁺, 891.4 [2M+Na]⁺.

EXAMPLE 73

(3aS, 6aR) Naphthalene-1-carboxylic Acid [1S-benzyl-2-oxo-2-(3-oxo-hexahydrofuro[3,2-b]pyrrol-4-yl)ethyl]amide

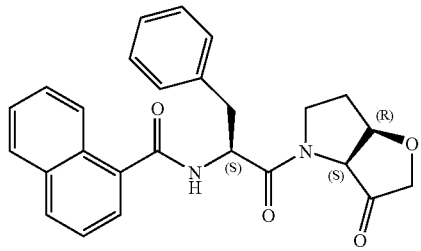

HPLC Rt=15.17 mins (>90%), HPLC-MS 429.1 [M+H]⁺, 879.3 [2M+Na]⁺.

EXAMPLE 74

(1S, 3aS, 6aR) Morpholine-4-carboxylic Acid 1-cyclohexylmethyl-2-oxo-2-(3-oxo-hexahydrofuro[3,2-b]pyrrol-4-yl)ethyl Ester

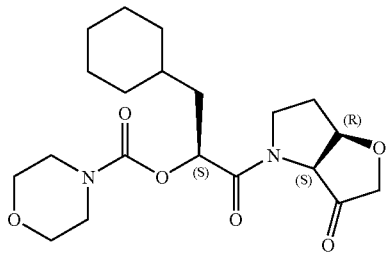

HPLC-MS 395.2 [M+H]⁺, 811.4 [2M+Na]⁺.

(a) Preparation of 3-cyclohexyl-2S-hydroxypropionic Acid Methyl Ester. (Compound (32), Scheme 6)

Trimethylsilyl chloride (1.78 ml, 14.0 mmol) was added dropwise to a stirred solution of 3-cyclohexyl-2S-hydroxypropionic acid (compound (25) 1.31 g, 7.6 mmol) in methanol (35 ml). The mixture was stirred at room temperature for 20 hours then the solvents were removed in vacuo to leave a pale yellow oil (1.38 g). The crude oil was purified by chromatography over silica gel eluting with a gradient of n-heptane:ethyl acetate (4:1) Appropriate fractions were combined and the solvents removed in vacuo to give 3-cyclohexyl-2S-hydroxypropionic acid methyl ester as a colourless oil, yield 1.26 g, (89%). HPLC-MS (single main peak with Rt=7.43 mins, 187.14 [M+H]⁺, 395.2 [2M+Na]⁺).

$\delta_H$ (400 MHz, CDCl₃ at 298K), 0.84-1.04 (2H, CH₂(cyclohexane), m), 1.09-1.36 (3H, CH₂(cyclohexane), CH(cyclohexane), m), 1.45-1.77 (7H, CH₂(cyclohexane), CH(cyclohexane), m), 1.80-1.90 (1Hβ, m), 2.72 (1H, OH, d, J=5.99 Hz), 3.80 (3H, CH₃O, s), 4.20-4.31 (1Hα, m).

(b) Preparation of morpholine-4-carboxylic Acid 1-carboxy-2-cyclohexylethyl Ester (Compound (33), Scheme 6)

A solution of phosgene (33.6 ml, 20% in toluene) was added to 3-cyclohexyl-2S-hydroxypropionic acid methyl ester (compound (32), 0.7 g, 4.03 mmol) followed by 6 drops of dimethylformamide. The mixture was stirred at ambient temperature for 16 hours then the solvents removed in vacuo. The residue was azeotroped with toluene (3×20 ml), and dissolved in anhydrous dichloromethane (1 ml). The solution was cooled to 0° C. then morpholine (0.86 g, 9.85 mmol) added. The mixture was stirred for 2 hours then partitioned between dichloromethane (30 ml) and 0.5M hydrochloric acid (30 ml). The dichloromethane layer was washed with saturated aqueous sodium hydrogen carbonate solution (30 ml), saturated aqueous sodium chloride solution (30 ml), dried (Na₂SO₄) and the solvent removed in vacuo. The residue was purified by chromatography over silica gel eluting with ethyl acetate:heptane 1:1. Appropriate fractions were combined and the solvents removed in vacuo to leave morpholine-4-carboxylic acid 2-cyclohexyl-1-methoxycarbonylethyl ester (0.13 g, 10%) as an oil. A solution of lithium hydroxide monohydrate (17.5 mg, 0.418 mmol) in water (0.76 ml) was added to an iced-water chilled solution of morpholine-4-carboxylic acid 2-cyclohexyl-1-methoxycarbonylethyl ester (110 mg, 0.367 mmol) in dioxane (1.5 ml). The mixture was stirred at ambient temperature for 1 hour then diluted with water (10 ml). The aqueous layer was extracted with diethyl ether (2×10 ml) which was discarded, then acidified to pH=2 with 6M hydrochloric acid. The product was extracted into diethyl ether (2×10 ml), then the combined ethereal layers washed with saturated aqueous sodium chloride (10 ml), dried (MgSO$_4$) and the solvent removed in vacuo to give morpholine-4-carboxylic acid 1-carboxy-2S-cyclohexylethyl ester as a white solid, yield 0.11 g, (100% from ester). TLC (single spot, Rf=0.20, methanol:dichloromethane 1:9), HPLC-MS (single main peak with Rt=7.614-mins, 286.2 [M+H]$^+$, 287.2 [M+2H]$^+$, 593.3 [2M+Na]$^+$).

$\delta_H$ (400 MHz, CDCl$_3$ at 298K), 0.75-1.00 (2H, CH$_2$(cyclohexane), m), 1.02-1.28 (4-H, CH$_2$(cyclohexane), m), 1.33-1.46 (1H, CH(cyclohexane), m), 1.50-1.79 (6H, CH$_2$(cyclohexane), m), 3.28-3.73 (8H, CH$_2$OCH$_2$ and CH$_2$NH, m), 4.92-5.02 (1Hα, m), 5.99 (1H, OH, brs).

Compound (33) was coupled under standard conditions to loaded building block-linker construct (22), then cleaved to provide EXAMPLE 74.

EXAMPLE 75

(3aS, 6aR) 4-[2-(4-tert-butylbenzylsulfanyl)-4-methylpentanoyl]tetrahydrofuro[3,2-b]pyrrol-3-one

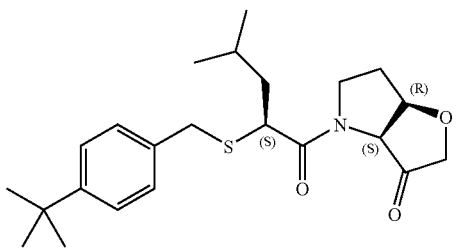

HPLC Rt=21.3-23.4-mins (>80%), HPLC-MS 404.4 [M+H]$^+$.

(a) Preparation of 2R-Bromo-4-methylpentanoic Acid (Compound (28), Scheme 5)

A solution of sodium nitrite (5.1 g, 73 mmol) in water (15 ml) was added drop-wise at 0° C. over 5 hours to a stirred mixture of D-leucine (8.75 g, 67 mmol), potassium bromide (29.75 g, 0.25 mol) and concentrated sulphuric acid (8.6 ml) in water (100 ml). The mixture was stirred for 30 minutes at 0° C. then at ambient temperature for 20 hours. The product was extracted into diethyl ether (2×150 ml) then the combined ethereal layers were washed with saturated aqueous sodium chloride solution (2×100 ml), dried (MgSO$_4$) and the solvent removed in vacuo. The residue was purified by flash chromatography over silica gel eluting with a gradient of methanol:dichloromethane 1:50→1:20. Appropriate fractions were combined and the solvents removed in vacuo to leave 2R-bromo-4-methylpentanoic acid (28) as a colourless oil, yield 1.60 g, (12.3%). TLC (single spot, Rf=0.2, methanol:dichloromethane 1:20). Additionally, a second crop (5.2 g, 40%) of slightly impure product was obtained $\delta_H$ (400 MHz, CDCl$_3$ at 298K), 0.95 and 0.99 (both 3H, CH$_3$CH, d, J=6.55 Hz), 1.77-1.89 (1H, CH$_3$CH, m), 1.93 (2Hβ, m), 4.31 (1Hα, t, J=7.7 Hz), 9.3 (1H, CO$_2$H, brs).

(b) Preparation of 2S-(4-tert-butylbenzylsulfanyl)-4-methylpentanoic Acid (Compound (30), Scheme 5)

A solution of 2R-bromo-4-methylpentanoic acid (compound (28), 1.1 g, 5.6 mmol) and (4-(tert-butyl)phenyl)methanethiol (1.0 g, 5.6 mmol) in dimethylformamide (15 ml) was purged with nitrogen for 5 minutes then cooled to 0° C. Triethylamine (0.79 ml, 5.7 mmol) was added drop-wise over 1 minute then the mixture was stirred for two days at ambient temperature. The solvents were removed in vacuo and residue purified by flash chromatography over silica gel eluting with a gradient of methanol:dichloromethane 0:1→1:20. Appropriate fractions were combined and the solvents removed in vacuo to leave a residue which was purified by flash chromatography over silica gel eluting with ethyl acetate:heptane 2:5. Appropriate fractions were combined and the solvents removed in vacuo to give 2S-(4-tert-butylbenzylsulfanyl)-4-methylpentanoic acid (30) as a colourless oil, yield 150 mg, (9%). TLC (single spot, Rf=0.2, heptane:ethyl acetate 5:2), analytical HPLC with main peak Rt=22.117 mins, HPLC-MS (main UV peak with Rt=11.072 mins, 317.2 [M+Na]$^+$).

$\delta_H$ (400 MHz, CDCl$_3$ at 298K), 0.70 and 0.85 (both 3H, CH$_3$CH, d, J=6.3), 1.29 (9H, (CH$_3$)$_3$C, s), 1.44-1.51 (1H, CH$_3$CH, m), 1.62-1.75 (2H$_\beta$, m), 3.15-3.20 (1H$_\alpha$, m), 3.81 and 3.88 (both 1H, SCH$_2$, d, J=13.2 Hz), 7.25-7.35 (4-H, aromatic).

Compound (30) was coupled under standard conditions to loaded building block-linker construct (22), then cleaved to provide EXAMPLE 75.

EXAMPLE 76

(3aS, 6aR) 4-[3-Cyclohexyl-2S-(furan-2-ylmethanesulphonyl) propionyl]tetrahydrofuro[3,2-b]pyrrol-3-one

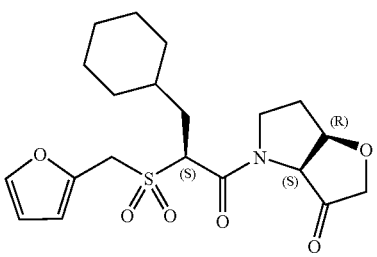

HPLC Rt=12.8-15.1 mins (>90%), HPLC-MS 410.1 [M+H]$^+$, 841.2 [2M+Na]$^+$.

(a) Preparation of (R)-α-bromocyclohexanepropionic Acid

A solution of sodium nitrite (0.45 g, 6.5 mmol) in water (1.2 ml) was added dropwise at 0° C. over 4 hours to a stirred mixture of (R)-α-aminocyclohexanepropionic acid (1 g, 5.8 mmol), potassium bromide (2.3 g, 19.2 mmol) and concentrated sulphuric acid (0.66 ml) in water (7 ml). The mixture was stirred for 5 hours at 0° C. then at ambient temperature for 16 hours. The product was extracted into diethyl ether (4×20 ml) then the combined ethereal layers were washed with saturated aqueous sodium chloride solution (2×50 ml), dried (MgSO$_4$) and the solvent removed in vacuo. The residue was purified by chromatography over silica gel eluting with a gradient of methanol: dichloromethane 1:50→1:20. Appropriate fractions were combined and the solvents removed in vacuo to give (R)-α-bromocyclohexanepropionic acid as a pale yellow oil 0.374 g, (27%). TLC (single spot, Rf=0.45, 10% methanol in dichloromethane), HPLC-MS (single main peak with Rt=8.88 mins, 234.1/236.1 [M+H]$^+$, 257.2/259.2 [M+Na]$^+$).

$\delta_H$ (400 MHz, CDCl$_3$ at 298K), 0.83-1.88 (11H, CH(cyclohexane), CH$_2$ (cyclohexane), m), 1.89-2.05 (2Hβ, m), 4.32-4.44 (1Hα, m).

(b) Preparation of 3-cyclohexyl-2S-(furan-2-ylmethylsulfanyl)propionic acid (Compound (41), Scheme 9)

(R)-α-bromocyclohexanepropionic (0.37 g, 1.58 mmol) and furan-2-yl methanethiol (0.18 g, 1.58 mmol) were dissolved in dimethylformamide (10 ml) and purged with nitrogen for 10 minutes. The solution was cooled to 0° C. then triethylamine (0.22 ml, 1.58 mmol) was added drop-wise over 1 minute. The mixture was stirred at 0° C. for 30 minutes then at ambient temperature for 16 hours. The solvent was removed in vacuo, and the residue purified by chromatography over gel silica using methanol:dichloromethane 1:100 as eluent. Appropriate fractions were combined and the solvents removed in vacuo to give 3-cyclohexyl-2S-(furan-2-ylmethyl sulfanyl)propionic acid (41) as a light brown oil, yield 142 mg, (33%). Analytical HPLC peak Rt=18.68 mins. TLC (single spot, Rf=0.45, 10% methanol in dichloromethane), HPLC-MS (single main peak with Rt=9.53 mins, 291.0 [M+Na]$^+$).

$\delta_H$ (400 MHz, CDCl$_3$ at 298K), 0.68-0.89 (2H, CH$_2$(cyclohexane), m), 0.97-1.77 (11H, CH(cyclohexane), CH$_2$(cyclohexane), m), 3.21-3.32 (1Hα, t, J=7.79 Hz), 3.69-3.79 (1H, CH$_2$S, d, J=14.79 Hz), 3.84-3.94 (1H, CH$_2$S, d, J=14.8 Hz), 6.15-6.28 (2H, furan H-3 and H-4, d, J=27.34 Hz), 7.30 (1H, furan H-5, s).

Compound (41) was coupled under standard conditions to loaded building block-linker construct (22). The intermediate loaded thioether (1.2 μmole gear) was oxidised with m-chloroperbenzoic acid (5eq, 65% reagent, 1.6 mg) in dichloromethane (200 μL) for 5 hrs, followed by standard washing and then cleaved to provide EXAMPLE 76.

EXAMPLE 77

(3aS, 6aR) 2R-Cyclohexylmethyl-4-morpholin-4-yl-1-(3-oxo-hexa hydrofuro[3,2-b]pyrrol-4-yl)butane-1,4-dione

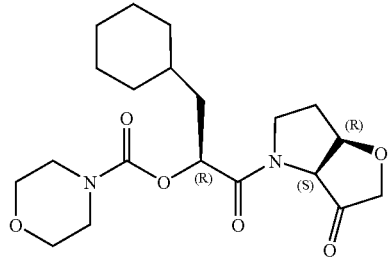

HPLC-MS 393.1 [M+H]$^+$, 807.3 [2M+Na]$^+$.

(a) Preparation of 2R-cyclohexylmethyl-4-morpholin-4-yl-4-oxo-butyric Acid Methyl Ester.

1-(3-dimethylaminopropyl)-3-ethylcarbodiimide.HCl (1.12 g, 5.69 mmol) then 1-hydroxybenzotriazole monohydrate (0.87 g, 5.69 mmol) were added to a stirred solution of 2R-(cyclohexylmethyl)succinic acid 1-methyl ester (compound (35), 1.0 g, 4.38 mmol) in dimethylformamide (10 ml) at 0° C. under argon. The mixture was stirred for 25 minutes then morpholine (0.7 ml, 8.76 mmol) was added drop-wise over 1 minute and stirring continued at ambient temperature for 16 hours. The product was extracted into ethyl acetate (200 ml) then washed with 1.0M hydrochloric acid (3×100 ml), saturated aqueous sodium hydrogen carbonate solution (3×100 ml), water (100 ml), then saturated aqueous sodium chloride solution (100 ml), dried (MgSO$_4$), and the solvent removed in vacuo to give 2R-cyclohexylmethyl-4-morpholin-4-yl-4-oxo-butyric acid methyl ester as an off-white solid, yield 1.22 g, (94%). HPLC-MS (single peak with Rt=7.91 mins, 298.1 [M+H]$^+$, 617.3 [2M+Na]).

(b) Preparation of 2R-cyclohexylmethyl-4-morpholin-4-yl-4-oxo-butyric Acid (Compound (36), Scheme 7).

A solution of lithium hydroxide monohydrate (0.51 g, 12.18 mmol) in water (27 ml) was added a stirred solution of 2R-cyclohexylmethyl-4-morpholinyl-4-oxo-butyric acid methyl ester (1.21 g, 4.06 mmol) in tetrahydrofuran (55 ml) and methanol (27 ml) at 0° C. The mixture was stirred at ambient temperature for 1 hours then diluted with water (100 ml). The aqueous layer was extracted with diethyl ether (2×50 ml) which was discarded, then acidified to pH=1-2 with 1M hydrochloric acid. The product was extracted into dichloromethane (3×50 ml), then the combined ethereal layers washed with water (2×50 ml), saturated aqueous sodium chloride solution (2×50 ml), dried (MgSO$_4$) and the solvent removed in vacuo to leave a residue. The residue was purified by chromatography over silica gel eluting with a gradient of methanol:dichloromethane 1:100→3:100. Appropriate fractions were combined and the solvents removed in vacuo was to give 2R-cyclohexylmethyl-4-morpholin-4-yl-4-oxo-butyric acid (36) as a white solid, yield 0.82 g, (71%). HPLC-MS (single peak with Rt=6.769 mins, 284.2 [M+H]$^+$, 589.2 [2M+Na]$^+$).

$\delta_H$ (400 MHz, CDCl$_3$ at 298K), 0.77-0.90 (2H, CH$_2$(cyclohexane), m), 1.05-1.40 (4-H, CH$_2$(cyclohexane), m), 1.50-1.90 (7H, CH(cyclohexane), CH$_2$(cyclohexane), m), 2.30-2.44 (2Hβ, m), 2.64-2.77 (1Hα, m), 2.96-3.10 (1H, OH, brs), 3.40-3.78 (8H, CH$_2$OCH$_2$ and CH$_2$NCH$_2$, m).

Compound (36) was coupled under standard conditions to loaded building block-linker construct (22), then cleaved to provide EXAMPLE 77.

EXAMPLE 78

(3aS, 6aR) 4-(2-Biphenyl-3-yl-4-methylpentanoyl)tetrahydrofuro[3,2-b]pyrrol-3-one

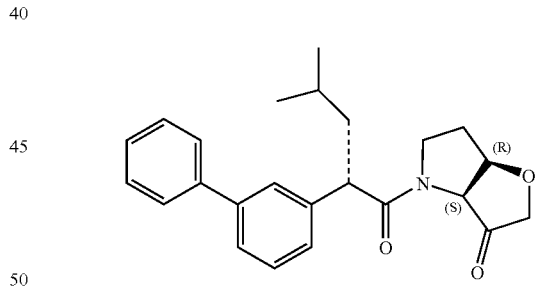

HPLC Rt=19.09-20.76 mins (>90%), HPLC-MS 378.4 [M+H]$^+$ (a) Preparation of Biphenyl-3-yl-acetic Acid Methyl Ester (Compound (38), Scheme 8)

Concentrated sulphuric acid (588 μL) was added to a solution of 3-bromophenyl acetic acid (10 g, 46.5 mmol) in methanol (100 mL). The mixture was refluxed for 1.5 h and then cooled to ambient temperature and evaporated under reduced pressure to afford a residue. The residue was redissolved in diethyl ether (500 mL), washed with water (2×100 mL), brine (100 mL), dried (MgSO$_4$) and then evaporated under reduced pressure to afford 3-bromophenyl acetic acid methyl ester (10.65 g). The 3-bromophenyl acetic acid methyl ester was dissolved in toluene (17 mL) then phenyl boronic acid (6.8 g, 55.69 mmol) added, followed by a aqueous solution of sodium carbonate (93 mL, 2M) and tetrakis(triphenylphosphine)palladium (1.6 g, 1.41 mmol). The mixture was stirred overnight then cooled to ambient temperature and an aqueous solution of saturated ammonium chloride (100 mL) added. The mixture was extracted with ethyl acetate (2×200 mL), died (Na$_2$SO$_4$) and evaporated under reduced pressure to afford a residue. Flash chromatography of the residue over silica (200 g) using ethyl acetate:heptane (3:48) as the eluent gave biphenyl-3-yl acetic acid methyl ester, yield 10.5 g, (99%), TLC (single UV spot, R$_f$=0.24, 10% ethyl acetate in heptane), analytical HPLC R$_t$=19.55 min, HPLC-MS (single main UV peak with R$_t$=9.35 min, 227.1 [M+H]$^+$).

δ$_H$ (400 MHz, CDCl$_3$ at 298K) 3.76 (2H, s, CH$_2$CO$_2$CH$_3$), 3.77 (3H, s, OCH$_3$), 7.34-7.66 (9H, m, biphenyl-3-yl).

(b)Preparation of Biphenyl-3-yl-acetic Acid

Water (39 mL), followed by lithium hydroxide monohydrate (4.2 g, 101.5 mmol) were added to a solution of biphenyl-3-yl acetic acid methyl ester (11.43 g, 50.57 mmol) in methanol (265 mL). The mixture was stirred at ambient temperature for 2 h then the organics were removed under reduced pressure. The mixture was acidified with dilute hydrochloric acid (1M, 80 mL), extracted with chloroform (2×100 mL), dried (MgSO4) and evaporated under reduced pressure to afford biphenyl-3-yl acetic acid as a white solid, yield 10.6 g, (99%), analytical HPLC R$_t$=16.565 min, HPLC-MS (single main UV peak with R$_t$=7.91 min, 213.1 [M+H]$^+$).

δ$_H$ (400 MHz, CDCl$_3$ at 298K) 3.77 (2H, s, CH$_2$CO$_2$CH$_3$), 7.28-7.52 (9H, m, biphenyl-3-yl).

(c)Preparation of 2RS-Biphenyl-3-ylmethylpent-4-enoic Acid

A solution of biphenyl-3-yl acetic acid (7.0 g, 33 mmol) in anhydrous tetrahydrofuran (84 mL) was added dropwise to a solution of lithium diisopropyl amide (36.4 mL, 2M solution in hexanes) in anhydrous tetrahydrofuran (84 mL) at −78° C. The mixture was allowed to warm to 0° C. and stirred for 40 min. The mixture was then cooled to −78° C. and 3-bromo-2-methylpropene (4.97 mL) rapidly added. The mixture was stirred for 1 h at −78° C. then water (28 mL) added and the organics removed under reduced pressure. The mixture was then acidified with hydrochloric acid (6M, 14 ml), extracted with ethyl acetate (3×100 ml), dried (MgSO4) and evaporated under reduced pressure to afford a residue. Flash chromatography of the residue over silica (400 g) using methanol:dichloromethane (3:97) as the eluent afforded impure 2-biphenyl-3-yl-4-methylpent-4-enoic acid (8.3 g). Flash chromatography over silica (400 g) using methanol:dichloromethane (1.5:98.5) afforded pure 2-biphenyl-3-yl-4-methylpent-4-enoic acid, yield 5.27 g, (60%), TLC (single UV spot, R$_f$=0.28, 5% methanol in dichloromethane), analytical HPLC R$_t$=19.99 min, HPLC-MS (single main UV peak with R$_t$=9.57 min, 267.1 [M+H]$^+$).

δ$_H$ (400 MHz, CDCl$_3$ at 298K), 1.765 (3H, s, CH$_3$), 2.53 (1H, dd, J=6.6 and 14.7 Hz, 3-H$_1$), 2.91 (1H, dd, J=8.9 and 14.7 Hz, 3-H$_1$), 3.92 (1H, dd, J=6.6 and 8.9 Hz, 2-H), 4.79 (2H, d, J=10.7 Hz, 5-H$_2$), 7.30-7.62 (9H, m, biphenyl-3-yl).

(d)Preparation of 2RS-Biphenyl-3-yl-4-methylpentanoic Acid (Compound (39), Scheme 8)

Palladium on carbon (10%, 300 mg) was added portionwise to a solution of 2RS-biphenyl-3-yl-4-methylpent-4-enoic acid (1 g, 3.76 mmol) in ethanol (40 mL) at 0° C. A hydrogen atmosphere was then introduced and the mixture allowed to warm to ambient temperature. The mixture was stirred for 18 h, then the hydrogen atmosphere removed and the mixture filtered over Celite and the catalyst washed with ethanol (40 mL). The combined organic filtrate was concentrated under reduced pressure to afford a residue, which was flash chromatographed over silica (150 g) using methanol:dichloromethane (1:99) as the eluent to afford 2RS-biphenyl-3-yl-4-methylpentanoic acid, yield 980 mg, (98%), TLC (single UV spot, R$_f$=0.45, 5% methanol in dichloromethane), analytical HPLC R$_t$=20.92 min, HPLC-MS (single main UV peak with R$_t$=10.15 min, 269.1 [M+H]$^+$, 291.1 [M+Na]3).

δ$_H$ (400 MHz, CDCl$_3$ at 298K), 0.93 (6H, d, J=6.6 Hz, 2×CH$_3$), 1.52-1.57 (1H, m, 4-H$_1$), 1.71-1.76 (1H, m, 3-H$_1$), 1.97-2.05 (1H, m, 3-H$_1$), 3.66 (1H, t, J=7.8 Hz, 2-H$_1$), 7.32-7.60 (9H, m, biphenyl-3-yl).

Compound (39) was coupled under standard conditions to loaded building block-linker construct (22), then cleaved to provide EXAMPLE 78.

EXAMPLE 79

(3aS, 6aR) 4-Methyl-N-[3-methyl-1S-(3-oxo-hexahydrofuro[3,2-b]pyrrole-4-carbonyl)butyl]benzamide

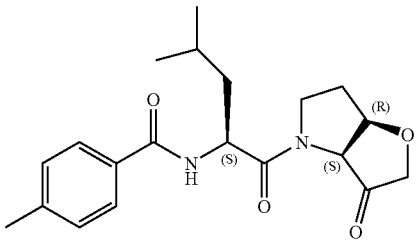

HPLC Rt=13.74-14.85 mins (>90%), HPLC-MS 359.2 [M+H]$^+$.

EXAMPLE 80

(3aS, 6aR) 4-Methoxy-N-[3-methyl-1S-(3-oxo-hexahydrofuro[3,2-b]pyrrole-4-carbonyl)butyl]benzamide

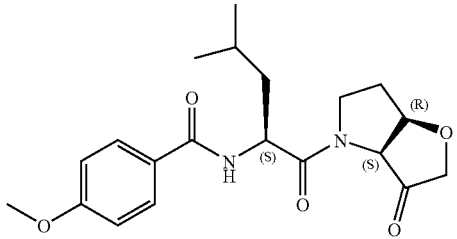

HPLC Rt=12.95-13.87 mins (>90%), HPLC-MS 375.2 [M+H]$^+$.

EXAMPLE 81

(3aS, 6aR) 4-tert-Butyl-N-[1S-(4-bromobenzyl)-2-oxo-2-(3-oxo-hexahydrofuro[3,2-b]pyrrol-4-yl)ethyl]benzamide

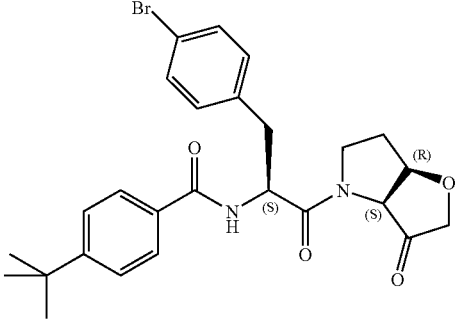

HPLC Rt=18.40-19.10 mins (>90%), HPLC-MS 513.2/515.2 [M+H]$^+$.

EXAMPLE 82

(3aS, 6aR) 4-tert-Butyl-N-[1S-(4-methoxybenzyl)-2-oxo-2-(3-oxo-hexahydrofuro[3,2-b]pyrrol-4-yl)ethyl]benzamide

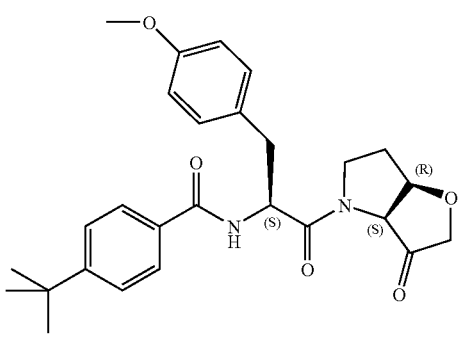

HPLC Rt=17.50-18.31 mins (>90%), HPLC-MS 465.2 [M+H]$^+$.

EXAMPLE 83

(An Example of General Formula (II)). (3aS, 7aR) Morpholine-4-carboxylic Acid [1R-benzylsulfanylmethyl-2-oxo-2-(3-oxo-hexahydrofuro[3,2-b]pyridin-4-yl)ethyl]amide

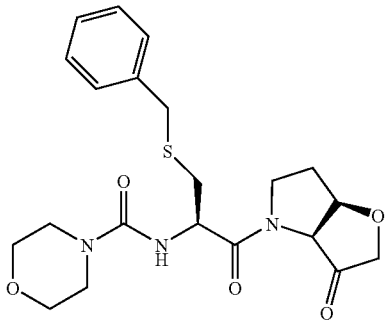

The required bicycle building block (3aS, 7aR) 3-oxo-hexahydrofuro[3,2-b]pyridine-4-carboxylic acid 9H-fluoren-9-ylmethyl ester was prepared in 8 steps as follows.

(1) Preparation of Cis-rac-(3-hydroxy)pyrrolidine-1,2-dicarboxylic Acid 1-(9H-fluoren-9-ylmethyl)ester.

Cis-rac-(3-hydroxy)piperidine-2-carboxylic acid (obtained by hydrogenation of commercially available 3-hydroxypicolinic acid, see Drummond, J. et al, *J. Med. Chem.*, 32, 2116-2128, 1989) (15.0 g, 103.4 mmole) was added to a vigorously stirred, ice-cooled solution of sodium carbonate (22.90 g, 217.1 mmole) in water (200 mL). 1,4-Dioxan (100 mL) was added providing a clear pale yellow solution. 9-Fluorenylmethyl chloroformate (27.52 g, 108.4 mmole) in 1,4-dioxan (100 mL) was added over 1 hr, then the ice-cooling removed and the mixture stirred at RT for an additional 1 hr. Additional water (150 mL) was added, the reaction mixture washed with chloroform (2×250 mL) and the combined organic layers discarded. The aqueous phase was acidified with 1N HCl to~pH 2, providing a thick opaque mixture. The acidified aqueous mixture was extracted with chloroform (2×500 mL) and the now clear aqueous phase discarded. The opaque combined chloroform layers were dried (Na$_2$SO$_4$), filtered and reduced in vacuo to provide a white foam, yield 30.2 g (82.2 mmole, 79.5%). TLC (Minor UV spot, Rf=0.58, major UV spot Rf=0.25, methanol:chloroform 1:4), analytical HPLC major peak Rt=16.990 mins, HPLC-MS (single major UV peak with Rt=7.976 mins, 368.0 [M+H]$^+$, 390.0 [M+Na]$^+$. Analysis by $^1$H and $^{13}$C NMR showed the presence of cis and trans geometrical isomers around the 3° amide bond.

$\delta$C (DMSO-d$_6$ at 298K); 23.29/23.57 (d, C$_\delta$), 28.89 (d, C$_\gamma$), 40.19 (d, C$_\epsilon$), 47.59 (u, Fmoc C-9), 59.11/59.43 (u, C$_\alpha$), 67.34 (u, C$_\beta$), 67.75/67.87 (d, Fmoc CH$_2$), 121.13 (u, Fmoc C-4 and C-5), 126.90/127.02 (u, Fmoc C-1 and C-8), 128.11 (u, Fmoc C-2 and C-7), 128.68 (u, Fmoc C-3 and C-6), 141.73 (q, Fmoc C-4' and C-5'), 144.58/144.76 (q, Fmoc C-1' and C-8'), 155.71/156.23 (q, OCON), 172.37/172.63 (COOH).

(2) Preparation of Cis-rac-(3-hydroxy)pyrrolidine-1,2-dicarboxylic Acid 2-allyl Ester 1-(9H-fluoren-9-ylmethyl)ester.

Cis-rac-(3-hydroxy)pyrrolidine-1,2-dicarboxylic acid 1-(9H-fluoren-9-yl methyl)ester (28.2 g, 76.7 mmole) was dissolved in toluene (200 mL) in a Dean-Stark apparatus. Allyl alcohol (50 mL) was added followed by p-toluenesulphonic acid.hydrate (15.1 g, 78.2 mmole). The mixture was refluxed for 1 hr, cooled and CHCl$_3$ (500 mL) added. The organic layer was washed with NaHCO$_3$ (2×250 mL), 0.1N HCl (250 mL) and brine (250 mL), then dried (Na$_2$SO$_4$). Filtration and reduction in vacuo gave a pale yellow mobile oil (35 g). The crude oil was purified over silica gel (240 g) eluting with a gradient of heptane:ethyl acetate 3:1→1:1. Desired fractions were combined and reduced in vacuo to a colourless gum yield 20.4 g (50.1 mmole, 65.3%). TLC (single UV spot, Rf=0.20, heptane:ethyl acetate 2:1), analytical HPLC Rt=20.003 mins, HPLC-MS (single main UV peak with Rt=9.473 mins, 408.1 [M+H]$^+$, 430.1 [M+Na]$^+$). Analysis by $^1$H and $^{13}$C NMR showed the presence of cis and trans geometrical isomers around the 3° amide bond.

$\delta$H (CDCl$_3$ at 298K); 1.55 (2H$_\gamma$ or 2H$_\delta$, d, J9.3), 1.81 (1H$_\gamma$ or 1H$_\delta$, d, J3.2), 2.06 (1H$_\gamma$ or 1H$_\delta$, d, J3.2), 2.78/2.92 (1H$_\epsilon$, dbt), 3.55 (1H$_\beta$, dd, J12.6, 9.2), 3.78 (OH, b), 3.95/4.11 (1 Hz, d, J13), 4.31 Fmoc H-9, m), 4.49 (Fmoc CH$_2$, m), 4.71 (2×COOCH$_2$CH=CH$_2$, m), 4.99/5.17 (H., d, J4.8), 5.31 (2×COOCH$_2$CH=CH$_2$, m), 5.87 (1×COOCH$_2$CH=CH$_2$, m), 7.37 (2H aromatic, Fmoc H-2 and H-7), 7.47 (2H aromatic, Fmoc H-3 and H-6), 7.62 (2H aromatic, Fmoc H-1 and H-8), 7.83 (2H aromatic, Fmoc H-4 and H-5).

$\delta$C (CDCl$_3$ at 298K); 23.87/24.11 (d, C$_\delta$), 30.59 (d, C$_\gamma$), 41.26/41.56 (d, C$_\epsilon$), 47.62 (u, Fmoc C-9), 58.29/59.54 (u, CM, 66.44/66.54 (d, COOCH$_2$CH=CH$_2$), 68.28 (d, Fmoc CH$_2$), 69.14/69.42 (u, C$_\beta$), 119.67/119.90 (d, COOCH$_2$CH=CH$_2$), 120.43 (u, Fmoc C-4 and C-5), 125.22/125.35 (u, Fmoc C-1 and C-8), 127.48 (u, Fmoc C-2 and C-7), 128.15 (u, Fmoc C-3 and C-6), 131.43/131.57 (u, COOCH$_2$CH=CH$_2$), 141.73 (q, Fmoc C-4' and C-5'), 144.19/144.38 (q, Fmoc C-1' and C-8'), 155.67/156.27 (q, OCON), 171.56 (COOCH$_2$CH=CH$_2$).

(3) Enzymic Resolution of Cis-rac-(3-hydroxy)pyrrolidine-1,2-dicarboxylic Acid 2-allyl ester 1-(9H-fluoren-9-ylmethyl)ester to (2R,3S) (3-hydroxy) pyrrolidine-1,2-dicarboxylic acid 2-allyl ester 1-(9H-fluoren-9-ylmethyl) ester and (2S, 3R) (3-acetoxy) pyrrolidine-1,2-dicarboxylic acid 2-allyl ester 1-(9H-fluoren-9-ylmethyl)ester.

Cis-rac-(3-hydroxy)pyrrolidine-1,2-dicarboxylic acid 2-allyl ester 1-(9H-fluoren-9-ylmethyl)ester (19.6 g, 48.1 mmole), Lipase PS (25 g, ex Amano Enzyme Inc.), vinyl acetate (300 mL) and isopropyl ether (200 mL) were stirred at 38° C. After 5 days, HPLC indicated equilibration of 2 peaks (52%:48%, indicating 95% conversion) and the reaction mixture was filtered through celite (3 cm×10 cm bed). The celite bed was washed with chloroform (3×250 mL) and the combined organic filtrate reduced in vacuo to a viscous tan oil (23.0 g). The crude oil was purified over silica gel (300 g) eluting with a gradient of heptane: ethyl acetate 3:1→1:2. Two major fractions were identified and reduced in vacuo.

Product 1. (2S, 3R) (3-acetoxy)pyrrolidine-1,2-dicarboxylic acid 2-allyl Ester 1-(9H-fluoren-9-ylmethyl)ester.

A viscous very pale yellow oil, yield 9.5 g (21.1 mmole, 43.9%). TLC (single UV spot, Rf=0.40, heptane:ethyl acetate 2:1), analytical HPLC Rt=22.633 mins, HPLC-MS (single main UV peak with Rt=10.714-mins, 450.1 [M+H]$^+$, 472.1 [M+Na]). Analysis by $^1$H and $^{13}$C NMR showed the presence of cis and trans geometrical isomers around the 3° amide bond.

$\delta$H (CDCl$_3$ at 298K); 1.25-1.32/1.52-1.70/1.72-2.00 (2H$_\gamma$+2 H$_\delta$, bm), 2.05-2.15 (OCOC$\underline{H}_3$, bs), 3.35-3.58 (1H$_\epsilon$, m), 3.98-4.10/4.18-4.22 (1H, dd), 4.24-4.31 (Fmoc H-9, m), 4.32-4.52 (Fmoc C$\underline{H}_2$, m), 4.60-4.82 (2×COOC$\underline{H}_2$CH=CH$_2$, m), 4.92-4.99 (H$_\beta$, m), 5.22-5.32 (He, m), 5.28-5.32/5.34-5.41 (2×COOCH$_2$CH=C$\underline{H}_2$, dd, J17.2), 5.89-6.00 (1×COOCH$_2$C$\underline{H}$=CH$_2$, m), 7.30-7.37 (2H aromatic, Fmoc H-2 and H-7), 7.38-7.46 (2H aromatic, Fmoc H-3 and H-6), 7.59-7.76 (2H aromatic, Fmoc H-1 and H-8), 7.78-7.80 (2H aromatic, Fmoc H-4 and H-5, d, J7.5).

$\delta$C (CDCl$_3$ at 298K); 21.22 (u, OCOC$\underline{H}_3$), 23.01 (d, C$_\delta$), 25.54 (d, C$_\gamma$), 40.51/40.88 (d, C$_\epsilon$), 47.44 (u, Fmoc C-9), 55.55 (u, C$_\alpha$), 66.08 (d, COOC$\underline{H}_2$CH=CH$_2$), 68.30/68.65 (d, Fmoc C$\underline{H}_2$), 69.21/69.59 (u, C$_\beta$), 118.94/119.22 (d, COOCH$_2$CH=C$\underline{H}_2$), 120.31 (u, Fmoc C-4 and C-5), 125.34/125.49 (u, Fmoc C-1 and C-8), 127.43 (u, Fmoc C-2 and C-7), 128.04 (u, Fmoc C-3 and C-6), 131.93 (u, COOCH$_2$C$\underline{H}$=CH$_2$), 141.61 (q, Fmoc C-4' and C-5'), 144.15 (q, Fmoc C-1' and C-8'), 155.50/156.36 (q, OC̲ON), 169.42/169.91/170.37 (C̲OOCH$_2$CH=CH$_2$+OC̲OCH$_3$).

Product 2. (2R,3S) (3-hydroxy)pyrrolidine-1,2-dicarboxylic acid 2-allyl Ester 1-(9H-fluoren-9-ylmethyl)ester.

A white crystalline solid, yield 9.05 g (22.2 mmole, 46.1%). TLC (single UV spot, Rf=0.20, heptane:ethyl acetate 2:1), analytical HPLC Rt=19.970 mins, HPLC-MS (single main UV peak with Rt=9.450 mins, 408.1 [M+H]$^+$, 430.1 [M+Na]$^+$). Analysis by $^1$H and $^{13}$C NMR showed the presence of cis and trans geometrical isomers around the 3° amide bond.

$\delta$H (CDCl$_3$ at 298K); 1.47-1.61 (1H$_\gamma$+1H$_\delta$, m), 1.71-1.81 (1H$_\delta$, b), 2.02-2.11 (1H$_\gamma$, b), 2.71-2.81/2.84-2.94 (1H$_\epsilon$, dt), 3.54-3.59 (H$_\beta$, m), 3.70-3.82 (OH, b), 3.93-3.96/4.10-4.16/4.11 (1H$_\epsilon$, d, J10), 4.24-4.31 (Fmoc H-9, m), 4.40-4.56 (Fmoc CH$_2$, m), 4.61-4.78 (2×COOC$\underline{H}_2$CH=CH$_2$, m), 4.98/5.18 (H$_\alpha$, d, J5.0), 5.25-5.37 (2×COOCH$_2$CH=C$\underline{H}_2$, m), 5.86-5.96 (1×COOCH$_2$C$\underline{H}$=CH$_2$, m), 7.30-7.34 (2H aromatic, Fmoc H-2 and H-7), 7.41-7.48 (2H aromatic, Fmoc H-3 and H-6), 7.53-7.62 (2H aromatic, Fmoc H-1 and H-8), 7.79-7.81 (2H aromatic, Fmoc H-4 and H-5).

$\delta$C (CDCl$_3$ at 298K); 23.87/24.12 (d, C$_\delta$), 30.60 (d, C$_\gamma$), 41.27/41.57 (d, C$_\epsilon$), 47.62 (u, Fmoc C-9), 58.29/59.54 (u, Co, 66.44/66.54 (d, COOC$\underline{H}_2$CH=CH$_2$), 68.28 (d, Fmoc C$\underline{H}_2$), 69.15/69.42 (u, C$_\beta$), 119.67/119.91 (d, COOCH$_2$CH=C$\underline{H}_2$), 120.42 (u, Fmoc C-4 and C-5), 125.22/125.35 (u, Fmoc C-1 and C-8), 127.48 (u, Fmoc C-2 and C-7), 128.15 (u, Fmoc C-3 and C-6), 131.42/131.57 (u, COOCH$_2$C$\underline{H}$=CH$_2$), 141.73 (q, Fmoc C-4' and C-5'), 144.12/144.37 (q, Fmoc C-1' and C-8'), 155.67/156.26 (q, OC̲ON), 171.57 (C̲OOCH$_2$CH=CH$_2$).

(4) Preparation of (2S, 3R) (3-hydroxy)pyrrolidine-1,2-dicarboxylic Acid 2-allyl Ester 1-(9H-fluoren-9-ylmethyl)ester.

(2S, 3R) (3-acetoxy)pyrrolidine-1,2-dicarboxylic acid 2-allyl ester 1-(9H-fluoren-9-ylmethyl)ester (4.5 g, 10 mmole)) was dissolved in allyl alcohol (50 mL), cH$_2$SO$_4$ (200 µL) added and heated to reflux for 24 hrs. The mixture was cooled, EtOAc (250 mL) added and washed with NaHCO$_3$ (250 mL), brine (250 mL) and dried (Na$_2$SO$_4$). The solvents were removed in vacuo to give a tan oil (4.2 g). The crude oil was purified over silica gel (170 g) eluting with a gradient of heptane: ethyl acetate 3:1→1:1. Desired fractions were combined and reduced in vacuo to a white crystalline solid, yield 3.0 g (7.37 mmole, 73.7%). TLC (single UV spot, Rf=0.20, heptane:ethyl acetate 2:1), analytical HPLC Rt=19.474-mins, HPLC-MS (single main UV peak with Rt=9.507 mins, 408.2 [M+H]$^+$, 430.2 [M+Na]$^+$). Analysis by $^{1H}$ and $^{13}$C NMR showed the presence of cis and tans geometrical isomers around the 3° amide bond.

$\delta$H (CDCl$_3$ at 298K); 1.46-1.59 (1H$_\gamma$+1H$_\delta$, m), 1.74-1.81 (1H$_\delta$, b), 2.01-2.10 (1H$_\gamma$, b), 2.70-2.82/2.88-2.99 (1H$_\delta$, dt), 3.49-3.62 (H$_\beta$, m), 3.70-3.80 (OH, b), 3.90-3.94/4.09-4.14 (1H$_\epsilon$, dd), 4.26-4.32 (Fmoc H-9, m), 4.41-4.58 (Fmoc C$\underline{H}_\alpha$, m), 4.60-4.80 (2×COOC$\underline{H}_2$CH=CH$_2$, m), 4.96-4.98/5.17-5.18 (H$_\alpha$, dd, J4.8), 5.25-5.42 (2×COOCH$_2$CH=C$\underline{H}_2$, m), 5.82-5.97 (1×COOCH$_2$C$\underline{H}$=CH$_2$, m), 7.30-7.38 (2H aromatic, Fmoc H-2 and H-7), 7.42-7.48 (2H aromatic, Fmoc H-3 and H-6), 7.55-7.63 (2H aromatic, Fmoc H-1 and H-8), 7.79-7.84 (2H aromatic, Fmoc H-4 and H-5).

$\delta$C (CDCl$_3$ at 298K); 23.86/24.12 (d, C$_\delta$), 30.62 (d, C$_\gamma$), 41.28/41.57 (d, C$_\epsilon$), 47.62 (u, Fmoc C-9), 58.29/59.54 (u, C$_\alpha$), 66.43/66.54 (d, COOC$\underline{H}_2$CH=CH$_2$), 68.27 (d, Fmoc C$\underline{H}_2$), 69.15/69.43 (u, C$_\beta$), 119.69/119.91 (d, COOCH$_2$CH=C$\underline{H}_2$), 120.42 (u, Fmoc C-4 and C-5), 125.22/125.35 (u, Fmoc C-1 and C-8), 127.47 (u, Fmoc C-2 and C-7), 128.14 (u, Fmoc C-3 and C-6), 131.43/131.57 (u, COOCH$_2$C$\underline{H}$=CH$_2$), 141.73 (q, Fmoc C-4' and C-5'), 144.12/144.37 (q, Fmoc C-1' and C-8'), 155.67/156.26 (q, OC̲ON), 171.57 (C̲OOCH$_2$CH=CH$_2$).

(5) Preparation of (2S, 3R) (3-tert-butoxy)pyrrolidine-1,2-dicarboxylic Acid 2-allyl Ester 1-(9H-fluoren-9-ylmethyl)ester.

(2S, 3R) (3-hydoxy)pyrrolidine-1,2-dicarboxylic acid 2-allyl ester 1-(9H-fluoren-9-ylmethyl)ester (1.75 g, 4.30 mmole) was dissolved in dry dichloromethane (20 mL) in a 50 mL glass pressure tube and cooled to −78° C. Isobutylene gas (~10 mL) was condensed into the solution and cH$_2$SO$_4$ (100 µL) added. A stirrer bar was added, the tube was sealed, the cooling removed and stirred at RT for 72 hr. The sealed tube was cooled to −78° C., N-methylmorpholine (200 µL, 1 eq w.r.t.

cH$_2$SO$_4$) and allowed to warm to RT, unsealed, with stirring over 2 hr. Dichloromethane (75 mL) was added and the organics washed with NaHCO$_3$ (75 mL), then brine (75 mL) and dried (Na$_2$SO$_4$). The solvents were removed in vacuo to give a pale tan oil (1.91 g). The crude oil was purified over silica gel (10 g) eluting with a gradient of heptane:ethyl acetate 5:1→3:1. Desired fractions were combined and reduced in vacuo to a thick clear oil yield 1.59 g (3.43 mmole, 79.8%). TLC (single UV spot, Rf=0.50, heptane: ethyl acetate 2:1), analytical HPLC Rt=24.123 mins, HPLC-MS (single main UV peak with Rt=11.91 mins, 408.2 [M+H-Bu$^t$]$^+$, 486.3 [M+Na]$^+$, 949.5 [2M+Na]$^+$). Analysis by $^1$H and $^{13}$C NMR showed the presence of cis and trans geometrical isomers around the 3° amide bond.

$\delta$H (CDCl$_3$ at 298K); 1.23 (9×C(CH$_3$)$_3$, s), 1.46-1.98 (2H$_\gamma$+2H$_\delta$, m), 3.37-3.45/3.46-3.57 (1H$_\epsilon$, dt), 3.61-3.72 (H$_\beta$, b), 3.90-3.99/4.02-4.10 (1H$_\epsilon$, dd), 4.20-4.72 (Fmoc H-9+Fmoc CH$_2$+2×COOCH$_2$CH=CH$_2$, bm), 4.89/5.01 (H$_\alpha$, dd, J6.3), 5.24 (1×COOCH$_2$CH=CH$_2$, d, J10.5), 5.38 (1×COOCH$_2$CH=CH$_2$, d), 5.88-5.99 (1×COOCH$_2$CH=CH$_2$, m), 7.29-7.36 (2H aromatic, Fmoc H-2 and H-7), 7.38-7.47 (2H aromatic, Fmoc H-3 and H-6), 7.56-7.69 (2H aromatic, Fmoc H-1 and H-8), 7.76-7.81 (2H aromatic, Fmoc H-4 and H-5).

$\delta$C (CDCl$_3$ at 298K); 23.69/23.99 (d, C$_\delta$), 28.38/28.65 (u, C(CH$_3$)$_3$), 28.75 (d, C$_\gamma$), 40.40/40.72 (d, C$_\epsilon$), 47.61 (u, Fmoc C-9), 58.36/58.47 (u, C$_\alpha$), 65.67 (d, COOCH$_2$CH=CH$_2$), 67.82 (u, C$_\beta$), 67.99/68.13 (d, Fmoc CH$_2$), 74.97 (q, C(CH$_3$)$_3$), 118.44/118.57 (d, COOCH$_2$CH=CH$_2$), 120.40 (u, Fmoc C4 and C-5), 125.39/125.48 (u, Fmoc C-1 and C-8), 127.46 (u, Fmoc C-2 and C-7), 128.10 (u, Fmoc C-3 and C-6), 132.49 (u, COOCH$_2$CH=CH$_2$), 141.71 (q, Fmoc C4' and C-5'), 144.14/144.30 (q, Fmoc C-1' and C-8'), 155.44/157.00 (q, OCON), 170.43/171.05 (COOCH$_2$CH=CH$_2$).

(6) Preparation of (2S, 3R) (3-tert-butoxy)pyrrolidine-1,2-dicarboxylic Acid 1-(9H-fluoren-9-ylmethyl)ester.

(2S,3R) (3-tert-butoxy)pyrrolidine-1,2-dicarboxylic acid 2-allyl ester 1-(9H-fluoren-9-ylmethyl)ester (1.52 g, 3.29 mmole) was dissolved in dry dichloromethane (25 mL) with stirring. Tetrakistriphenylphosphine palladium (0) (76 mg, 0.066 mmole, 0.02eq) was added, followed by phenyltrihydrosilane (0.71 g, 0.622 mL, 6.58 mmole, 2eq). After 1 hr, dichloromethane (150 mL) was added and the organics washed with 0.01N HCl (150 mL), brine (150 mL) and dried (Na$_2$SO$_4$). The solvents were removed in vacuo to give a dark grey solid (2.05 g). The crude solid was purified over silica gel (75 g) eluting with a gradient of heptane: ethyl acetate 2:1→1:2. Desired fractions were combined and reduced in vacuo to a white crystalline yield 0.97 g (2.29 mmole, 69.6%). TLC (single UV spot, Rf=0.25, heptane:ethyl acetate 1:1), analytical HPLC Rt=21.310 mins, HPLC-MS (single main UV peak with Rt=10.254-mins, 368.2 [M+H-Bu$^t$]$^+$, 446.2 [M+Na]$^+$, 869.3 [2M+Na]$^+$). Analysis by $^1$H and $^{13}$C NMR showed the presence of cis and trans geometrical isomers around the 3° amide bond.

$\delta$H (CDCl$_3$ at 298K); 1.32/1.40 (9×C(CH$_3$)$_3$, ds), 1.42-1.58 (1H$_\gamma$+1H$_\delta$, m), 1.72-1.80 (1H$_\delta$, bm), 1.82-1.96 (1H$_\gamma$, bm), 2.76-2.82/2.90-2.97 (1H$_\epsilon$, dt), 3.70-3.84 (H$_\beta$, b), 3.90-4.07 (1H$_\epsilon$, dd), 4.22-4.32 (Fmoc H-9), 4.40-4.58 (Fmoc CH$_2$, bm), 4.59 4.61/5.02-5.04 (1H$_\alpha$, dd, J5.7), 7.29-7.36 (2H aromatic, Fmoc H-2 and H-7), 7.39-7.43 (2H aromatic, Fmoc H-3 and H-6), 7.53-7.67 (2H aromatic, Fmoc H-1 and H-8), 7.76-7.81 (2H aromatic, Fmoc H-4 and H-5), 10.90-11.10 (COOH, bs).

$\delta$C (CDCl$_3$ at 298K); 23.71/24.23 (d, C$_\delta$), 28.21/28.28 (u, C(CH$_3$)$_3$), 30.58/30.72 (d, C$_\gamma$), 40.49/40.79 (d, C$_\epsilon$), 47.58/47.63 (u, Fmoc C-9), 58.20/58.43 (u, C$_\alpha$), 67.78/68.32 (u, C$_\beta$), 68.69/68.88 (d, Fmoc CH$_2$), 78.48/78.67 (q, C(CH$_3$)$_3$), 120.31 (u, Fmoc C-4 and C-5), 125.16/125.27/125.50/125.53 (u, Fmoc C-1 and C-8), 127.42/127.46/127.59 (u, Fmoc C-2 and C-7), 128.03/128.10 (u, Fmoc C-3 and C-6), 141.55/141.69/141.79 (q, Fmoc C-4' and C-5'), 144.06/144.12/144.38 144.48 (q, Fmoc C-1' and C-8'), 155.73/156.49 (q, OCON), 169.26/169.52 (COOH).

(7) Preparation of (2S, 3R) (3-tert-butoxy)-2-(2-diazoacetyl)pyrrolidine-1,2-dicarboxylic Acid 1-(9H-fluoren-9-ylmethyl)ester.

(2S, 3R) (3-tert-butoxy)pyrrolidine-1,2-dicarboxylic acid 1-(9H-fluoren-9-ylmethyl)ester (830 mg, 1.96 mmole) was dissolved with stirring in dry dichloromethane (20 mL). The reaction was flushed with nitrogen and cooled to −15° C. Isobutylchloroformate (296 mg, 2.166 mmole in dry dichloromethane (2.5 mL) and N-methylmorpholine (397 mg, 3.92 mmole in dry dichloromethane (2.5 mL) were added simultaneously in 0.5 mL aliquots over 15 mins. Etheral diazomethane (generated from diazald (2.5 g, ~8 mmole in diethyl ether (40 mL)) onto sodium hydroxide (2.75 g) in water (4.3 mL)/ethanol (8.6 mL) at 60° C.). was added to the activated aminoacid solution and stirred at RT for 24 hr. Acetic acid (~2 mL) was added to quench the reaction, then tert-butylmethylether (100 mL) was added, the organics washed with water (3×150 mL), then dried (Na$_2$SO$_4$). The solvents were removed in vacuo to give a thick yellow oil (1.02 g). The crude oil was used for the next stage without purification. TLC (single main UV spot, Rf=0.40, heptane:ethyl acetate 2:1), analytical HPLC Rt=18.887 mins (50.8%) plus numerous minor peaks, HPLC-MS (2 main UV peaks with Rt=9.095 mins, 364.2 [M+H]$^+$, 749.2 [2M+Na]$^+$ and Rt=10.856 mins, 420.2 [M+H−N$_2$]$^+$, 470.2 [M+Na]$^+$, 917.3 [2M+Na]$^+$).

Note that upon HPLC-MS analysis, m/z 364.2 corresponds to the desired bicycle product (3aS, 7aR) 3-oxo-hexahydrofuro[3,2-b]pyridine-4-carboxylic acid 9H-fluoren-9-ylmethyl ester.

(8) Cyclisation to (3aS, 7aR) 3-oxo-hexahydrofuro[3,2-b] pyridine-4-carboxylic Acid 9H-fluoren-9-ylmethyl Ester.

A solution of lithium chloride (844 mg, 20 mmole) in water (5 mL) and acetic acid (20 mL) was added to (2S, 3R) (3-tert-butoxy)-2-(2-diazoacetyl)pyrrolidine-1,2-dicarboxylic acid 1-(9H-fluoren-9-ylmethyl)ester (1000 mg, ~2 mmole). Gas was evolved and the yellow oily solid dissolved over 1 hr to give a virtually colourless solution. After 90 mins, chloroform (150 mL) was added and the organics washed with NaHCO$_3$ (2×150 mL), brine (150 mL) and dried (Na$_2$SO$_4$). The solvents were removed in vacuo to give a pale yellow gum (920 mg). The crude gum was purified over silica gel (135 g) eluting with a gradient of heptane: ethyl acetate 3:1→1:1. Desired fractions were combined and reduced in vacuo to a white crystalline solid, yield 370 mg (1.02 mmole, 51.9% from starting acid). TLC (single UV spot, Rf=0.25, heptane:ethyl acetate 2:1), analytical HPLC Rt=18.734-mins, HPLC-MS (single UV peak with Rt=9.051 mins, 364.2 [M+H]$^+$, 386.2 [M+Na]$^+$). Analysis by $^1$H and $^{13}$C NMR showed the presence of cis and trans geometrical isomers around the 3° amide bond.

δH (CDCl₃ at 298K); 1.29-1.49 (1H$_\gamma$+1H$_\delta$, m), 1.61-1.80 (1H$_\delta$, bm), 2.06-2.19 (1H$_\delta$, bm), 2.50-2.62/2.63-2.80 (1H$_\epsilon$, m), 3.96 (1H$_\beta$, b), 3.97 (COC$\underline{H}_{2A}$, d, J16.3), 4.15 (Fmoc H-9, bt), 4.25-4.34 (H$_\beta$, b), 4.36-4.60 (Fmoc CH$_2$+COCH$_{2B}$, bm), 4.75-4.82/5.11-5.19 (H$_\alpha$, bd), 7.30-7.36 (2H aromatic, Fmoc H-2 and H-7), 7.41-7.49 (2H aromatic, Fmoc H-3 and H-6), 7.52-7.68 (2H aromatic, Fmoc H-1 and H-8), 7.75-7.85 (2H aromatic, Fmoc H-4 and H-5).

δC (CDCl₃ at 298K); 21.75/22.04 (d, C$_\delta$), 26.60 (d, C$_\gamma$), 41.40/41.66 (d, C$_\epsilon$), 47.59 (u, Fmoc C-9), 60.42 (u, C$_\alpha$), 67.54 (d, Fmoc C$\underline{H}_2$), 68.21/68.39 (d, COC$\underline{H}_2$O), 72.61 (u, C$_\beta$), 120.39 (u, Fmoc C-4 and C-5), 125.43 (u, Fmoc C-1 and C-8), 127.51 (u, Fmoc C-2 and C-7), 128.14 (u, Fmoc C-3 and C-6), 141.73 (q, Fmoc C4' and C-5'), 144.30 (q, Fmoc C-1' and C-8'), 155.79/156.35 (q, O $\underline{C}$ON), 211.10/211.4 (q, $\underline{C}$OCH$_2$O).

Following the general details from Scheme 2, the required bicycle building block (3aS, 7aR) 3-oxo-hexahydrofuro[3,2-b]pyridine-4-carboxylic acid 9H-fluoren-9-ylmethyl ester was converted to building block-linker construct as follows:

(3aS, 7aR) 3-oxo-hexahydrofuro[3,2-b]pyridine-4-carboxylic acid 9H-fluoren-9-ylmethyl ester (250 mg, 0.689 mmole) was dissolved in a mixture of ethanol (12.0 mL) and water (1.75 mL) containing sodium acetate.trihydrate (141 mg, 1.03 mmole, 1.5eq). 4-[[(hydrazinocarbonyl)amino]methyl]cyclo hexanecarboxylic acid. trifluoroacetate (227 mg, 0.689 mmole, 1.0eq, Murphy, A. M. et al, *J. Am. Chem. Soc.*, 114, 3156-3157, 1992) was added and the mixture refluxed for 4 hrs.

Chloroform (150 mL) was added and the organics washed with HCl (150 mL, ~pH3), dried (Na$_2$SO$_4$) and reduced in vacuo to provide crude building block-linker construct a clear viscous oil. Yield 350 mg, analytical HPLC 2 peaks Rt=17.101 (74.7%) and 18.547 mins (25.3%) (cis/trans geometrical isomers), HPLC-MS (2×UV peak with Rt=8.037 and 8.972 mins, 561.2 [M+H]$^+$). Crude construct was used directly for construct loading.

Following the general details from Scheme 2, the required building block-linker construct was attached to the solid phase providing loaded building block-linker construct as follows:

Building block-linker construct (0.595 mmoles), 2-(1H-benzotriazole-1-yl)-1,1,3,3-tetramethyluroniumhexafluoro phosphate (HBTU, 226.0 mg, 0.596 mmole), 1-hydroxybenzotriazolehydrate and (HOBT, 92 mg, 0.596 mmole) were dissolved in dimethylformamide (3 mL) and N-methylmorpholine (NMM, 131 μL, 1.197 mmole) added. After preactivation for 5 minutes, free amine gears (160×1.21 μmole) were added, followed by dimethylformamide (17.5 mL) and left overnight. The spent coupling solution was then added to free amine crowns (18×10 μmole) and left overnight. Standard washing and analyses indicated quantitative loading in both cases.

Following the general details from Scheme 2, the required loaded building block-linker construct was elaborated on the solid phase as follows:

Loaded construct was elaborated to EXAMPLE 83 (3aS, 7aR) Morpholine-4-carboxylic acid [1R-benzylsulfanylmethyl-2-oxo-2-(3-oxohexahydrofuro[3,2-b]pyridin-4-yl) ethyl]amide by standard Fmoc deprotection and sequential coupling with Fmoc-Cys(SBzl)-OH then morpholine-4-carbonylchloride. The crude example was cleaved and analysed (see general techniques). HPLC Rt=15.59 mins (>80%), HPLC-MS 449.2 [M+H]$^+$.

The following examples (84-130) were prepared as detailed for EXAMPLE 83, coupling with the required reagents to provide the full length molecule.

EXAMPLE 84

(3aS, 7aR) Naphthalene-2-carboxylic Acid [1S-(4-hydroxybenzyl)-2-oxo-2-(3-oxo-hexahydrofuro[3,2-b]pyridin-4-yl)ethyl]amide

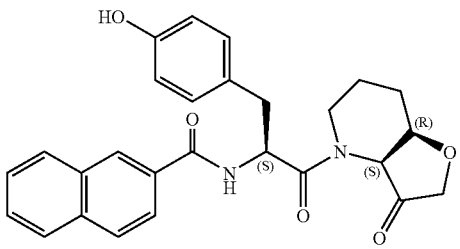

HPLC Rt=15.79 mins (>80%), HPLC-MS 459.3 [M+H]$^+$.

EXAMPLE 85

(3aS, 7aR) 4-Dimethylamino-N-[1S-(4-hydroxybenzyl)-2-oxo-2-(3-oxo-hexahydrofuro[3,2-b]pyridin-4-yl)ethyl]benzamide

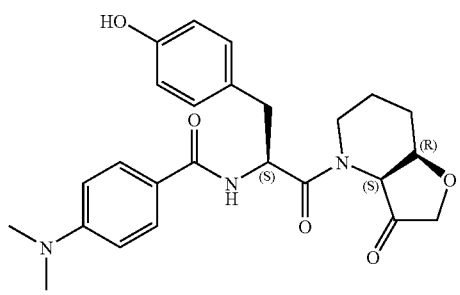

HPLC Rt=10.98 mins (>80%), HPLC-MS 452.2 [M+H]$^+$.

EXAMPLE 86

(3aS, 7aR) Naphthalene-1-carboxylic acid [3-methyl-1S-(3-oxo-hexahydrofuro[3,2-b]pyridine-4-carbonyl)butyl]amide

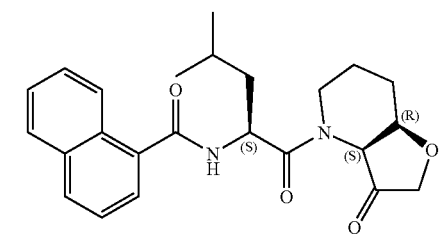

HPLC Rt=17.71 mins (>80%), HPLC-MS 409.2 [M+H]$^+$.

EXAMPLE 87

(3aS, 7aR) Naphthalene-2-carboxylic acid [3-methyl-1S-(3-oxo-hexahydrofuro[3,2-b]pyridine-4-carbonyl)butyl]amide

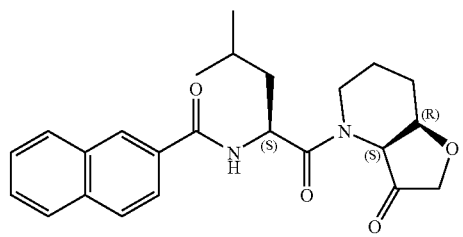

HPLC Rt=18.28 mins (>80%), HPLC-MS 409.2 [M+H]$^+$.

EXAMPLE 88

(3aS, 7aR) N-[1S-(4-hydroxybenzyl)-2-oxo-2-(3-oxo-hexahydro furo[3,2-b]pyridin-4-yl)ethyl]-5-thiophen-2-ylnicotinamide

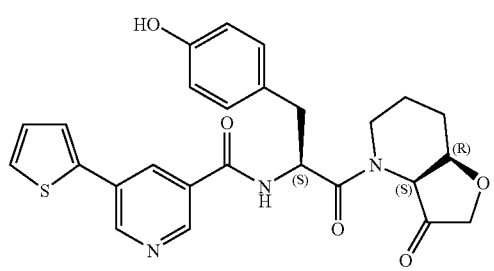

HPLC Rt=13.16 mins (>80%), HPLC-MS 492.2 [M+H]$^+$.

EXAMPLE 89

(3aS, 7aR) 2-Pyridin-3-ylthiazole-4-carboxylic acid [1S-(4-hydroxybenzyl)-2-oxo-2-(3-oxo-hexahydro-furo[3,2-b]pyridin-4-yl)ethyl]amide

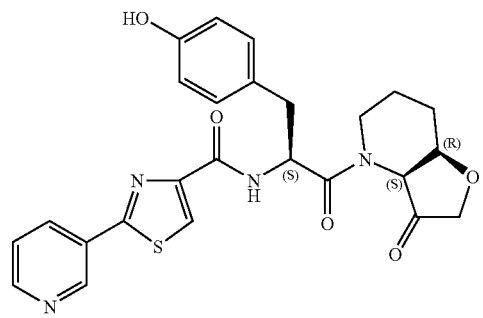

HPLC Rt=10.45 mins (>80%), HPLC-MS 493.2 [M+H]$^+$.

EXAMPLE 90

(3aS, 7aR) Biphenyl-4-carboxylic acid [1S-(4-hydroxybenzyl)-2-oxo-2-(3-oxo-hexahydrofuro[3,2-b]pyridinyl)ethyl]amide

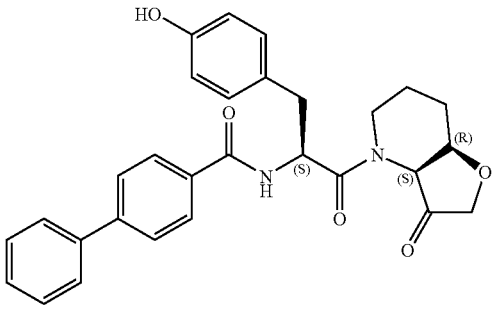

HPLC Rt=17.38 mins (>80%), HPLC-MS 485.2 [M+H]$^+$.

EXAMPLE 91

(3aS, 7aR) 4-tert-butyl-N-[1S-(hydroxybenzyl)-2-oxo-2-(3-oxo-hexahydrofuro[3,2-b]pyridinyl)ethyl]benzamide

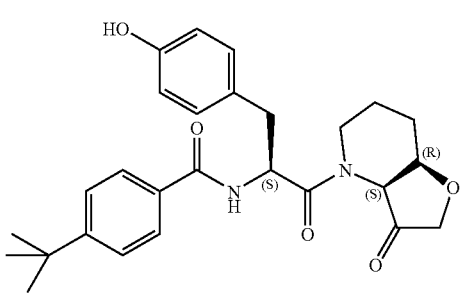

HPLC Rt=17.90 mins (>80%), HPLC-MS 485.2 [M+H]$^+$.

EXAMPLE 92

(3aS, 7aR) N-[1-(4-hydroxybenzyl)-2-oxo-2-(3-oxo-hexahydrofuro[3,2-b]pyridin-4-yl)ethyl]-4-thiophen-2-ylbenzamide

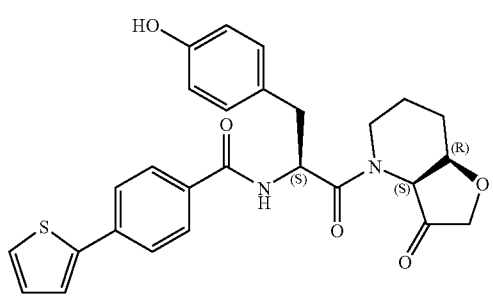

HPLC Rt=17.00 mins (>80%), HPLC-MS 491.2 [M+H]$^+$.

EXAMPLE 93

(3aS, 7aR) N-[1S-(4-hydroxybenzyl)-2-oxo-2-(3-oxo-hexahydrofuro[3,2-b]pyridin-4-yl)ethyl]-4-trifluoromethoxybenzamide

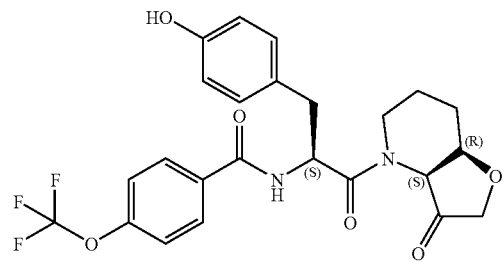

HPLC Rt=17.07 minis (>80%), HPLC-MS 493.2 [M+H]+.

EXAMPLE 94

(3aS, 7aR) N-[3-methyl-1S-(3-oxo-hexahydrofuro[3,2-b]pyridine-4-carbonyl)butyl]-5-thiophen-2-ylnicotinamide

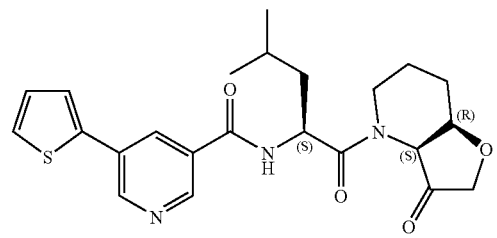

HPLC Rt=15.82 mins (>80%), HPLC-MS 442.2 [M+H]+.

EXAMPLE 95

(3aS, 7aR) 2-Pyridin-3-ylthiazole-4-carboxylic acid [3-methyl-1S-(3-oxo-hexahydrofuro[3,2-b]pyridine-4-carbonyl)butyl]amide

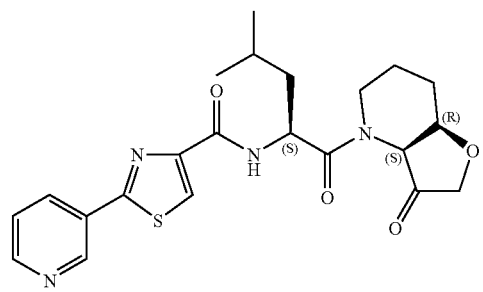

HPLC Rt=12.55 mins (>80%), HPLC-MS 443.2 [M+H]+.

EXAMPLE 96

(3aS, 7aR) Biphenyl-4-carboxylic acid [3-methyl-1S-(3-oxo-hexahydrofuro[3,2-b]pyridine-4-carbonyl)butyl]amide

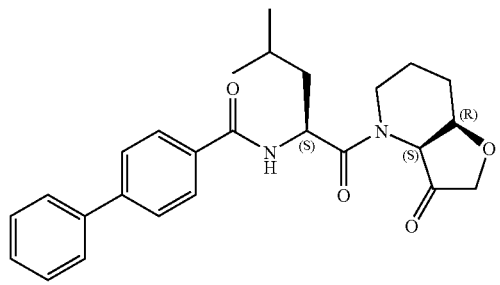

HPLC Rt=19.88 mins (>80%), HPLC-MS 435.2 [M+H]+.

EXAMPLE 97

(3aS, 7aR) 4-tert-butyl-N-[3-methyl-1S-(3-oxo-hexahydrofuro[3,2-b]pyridine-4-carbonyl)butyl]benzamide

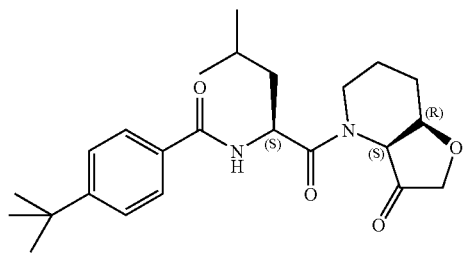

HPLC Rt=20.42 mins (>80%), HPLC-MS 415.2 [M+H]+.

EXAMPLE 98

(3aS, 7aR) N-[3-methyl-1S-(3-oxo-hexahydrofuro[3,2-b]pyridine-4-carbonyl)butyl]-4-thiophen-2-ylbenzamide

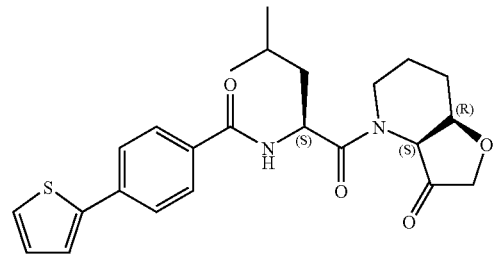

HPLC Rt=19.60 mins (>80%), HPLC-MS 441.2 [M+H]+.

EXAMPLE 99

(3aS, 7aR) N-[3-methyl-1S-(3-oxo-hexahydrofuro[3,2-b]pyridine-4-carbonyl)butyl]-4-trifluoromethoxy-benzamide

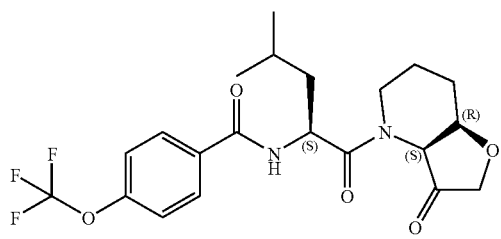

HPLC Rt=19.66 mins (>80%), HPLC-MS 443.2 [M+H]$^+$.

EXAMPLE 100

(3aS, 7aR) 2-Methyl-5-phenylfuran-3-carboxylic acid [3-methyl-1S-(3-oxo-hexahydrofuro[3,2-b]pyridine-4-carbonyl)butyl]amide

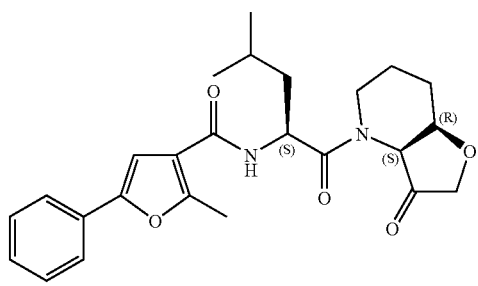

HPLC Rt=20.48 mins (>80%), HPLC-MS 439.2 [M+H]$^+$.

EXAMPLE 101

(3aS, 7aR) Morpholine carboxylic Acid [1S-(4-hydroxybenzyl)-2-oxo-2-(3-oxo-hexahydrofuro[3,2-b]pyridin-4-yl)ethyl]amide

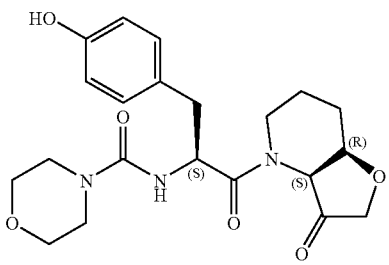

HPLC-MS 418.2 [M+H]$^+$.

EXAMPLE 102

(3aS, 7aR) N-[1S-(4-hydroxybenzyl-2-oxo-2-(3-oxo-hexahydrofuro[3,2-b]pyridin 4-yl)ethyl]benzamide

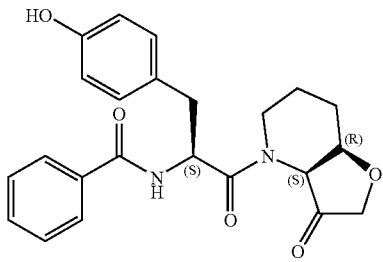

HPLC Rt=12.71 mins (>85%), HPLC-MS 409.2 [M+H].

EXAMPLE 103

(3aS, 7aR) Naphthalene-1-carboxylic acid [1S-(4-hydroxybenzyl)-2-oxo-2-(3-oxo-hexahydrofuro[3,2-b]pyridin-4-yl)ethyl]amide

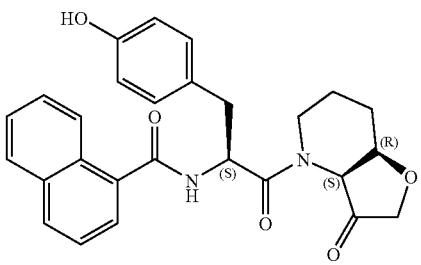

HPLC Rt=14.88 mins (>85%), HPLC-MS 459.2 [M+H]$^+$.

EXAMPLE 104

(3aS, 7&R) Furan-3-carboxylic acid [1S-(4-hydroxybenzyl)-2-oxo-2-(3-oxo-hexahydrofuro[3,2-b]pyridinyl)ethyl]amide

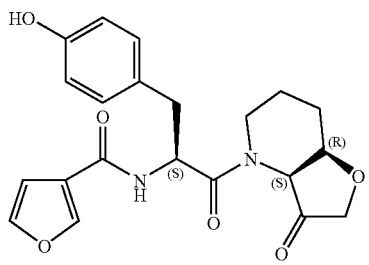

HPLC Rt=11.14-mins (>85%), HPLC-MS 399.2 [M+H]$^+$.

EXAMPLE 105

(3aS, 7aR) Benzo[b]thiophene-2-carboxylic acid [1S-(4-hydroxy benzyl)-2-oxo-2-(3-oxo-hexahydro-furo[3,2-b]pyridin-4-yl)ethyl]amide

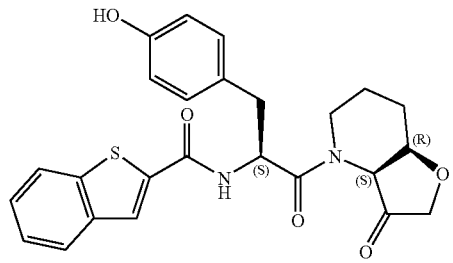

HPLC Rt=15.99 mins (>85%), HPLC-MS 465.2 [M+H]+.

EXAMPLE 106

(3aS, 7aR) Benzo[b]thiophene-3-carboxylic acid [1S-(4-hydroxy benzyl)-2-oxo-2-(3-oxo-hexahydro-furo[3,2-b]pyridin-4-yl)ethyl]amide

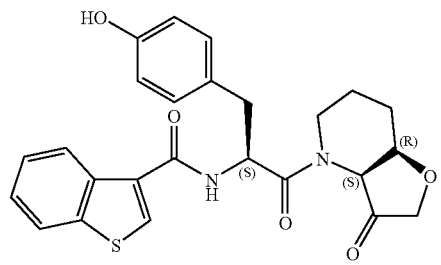

HPLC Rt=15.58 mins (>85%), HPLC-MS 465.2 [M+H]+, 951.3 [2M+Na]+.

EXAMPLE 107

(3aS, 7aR) Furan-3-carboxylic Acid [1S-benzyl-2-oxo-2-(3-oxo-hexahydrofuro[3,2-b]pyridin-4-yl)ethyl]amide

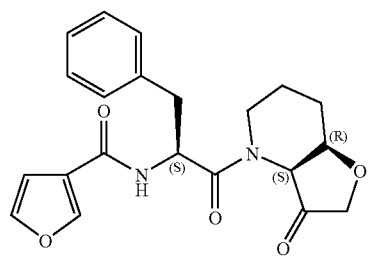

HPLC Rt=14.44-mins (>85%), HPLC-MS 383.2 -[M+H]+.

EXAMPLE 108

(3aS, 7aR) Thiophene-3-carboxylic acid [1S-benzyl-2-oxo-2-(3-oxo-hexahydrofuro[3,2-b]pyridinyl)ethyl]amide

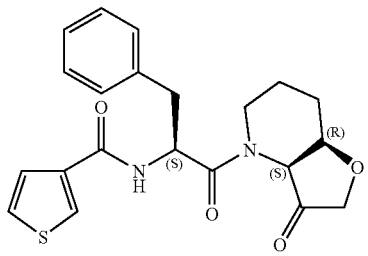

HPLC Rt=15.34-mins (>80%), HPLC-MS 399.2 [M+H]+.

EXAMPLE 109

(3aS, 7aR) Morpholine-4-carboxylic acid [3-methyl-1S-(3-oxo-hexa hydrofuro[3,2-b]pyridine-4-carbonyl)butyl]amide

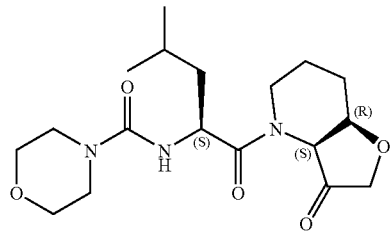

HPLC-MS 368.2 [M+H]+.

EXAMPLE 110

(3aS, 7aR) N-[3-methyl-1S-(3-oxo-hexahydrofuro[3,2-b]pyridine-4-carbonyl)butyl]benzamide

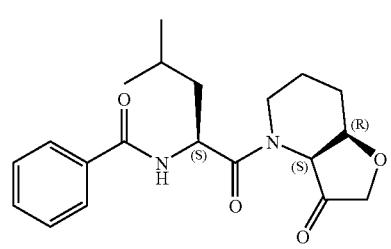

HPLC Rt=15.42 mins (>85%), HPLC-MS 359.2 [M+H]+.

EXAMPLE 111

(3aS, 7aR) Furan-3-carboxylic acid [3-methyl-1S-(3-oxo-hexahydro furo[3,2-b]pyridine-4-carbonyl)butyl]amide

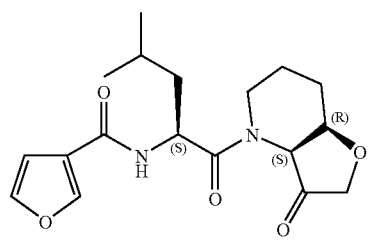

HPLC Rt=13.74-mins (>85%), HPLC-MS 349.2 [M+H]$^+$.

EXAMPLE 112

(3aS, 7aR) Benzo[b]thiophene-2-carboxylic acid [3-methyl-1S-(3-oxo-hexahydrofuro[3,2-b]pyridine-4-carbonyl)butyl]amide

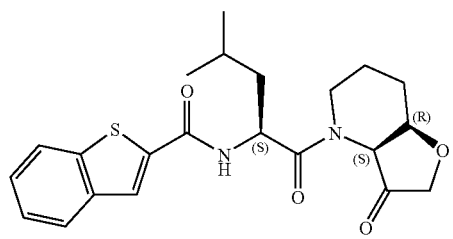

HPLC Rt=18.52 mins (>85%), HPLC-MS 415.2 [M+H]$^+$, 851.3 [2M+Na]$^+$.

EXAMPLE 113

(3aS, 7aR) 4-Dimethylamino-N-[3-methyl-1S-(3-oxo-hexahydro furo[3,2-b]pyridine-4-carbonyl)butyl]benzamide

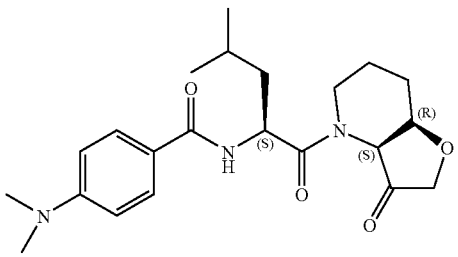

HPLC Rt=13.55 mins (>85%), HPLC-MS 402.2 [M+H]$^+$.

EXAMPLE 114

(3aS, 7aR) Benzo[b]thiophene-3-carboxylic acid [3-methyl-1S-(3-oxo-hexahydrofuro[3,2-b]pyridine-4-carbonyl)butyl]amide

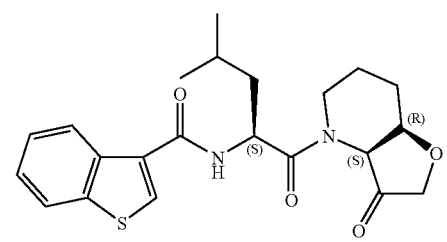

HPLC Rt=18.26 mins (>85%), HPLC-MS 415.2 [M+H]$^+$.

EXAMPLE 115

(3aS, 7aR) Thiophene-3-carboxylic acid [3-methyl-1S-(3-oxo-hexa hydrofuro[3,2-b]pyridine-4-carbonyl)butyl]amide

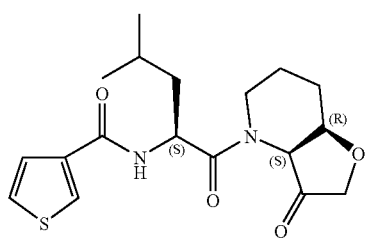

HPLC Rt=14.80 mins (>85%), HPLC-MS 365.2 [M+H]$^+$.

EXAMPLE 116

(3aS, 7aR) N-[1R-benzylsulfanylmethyl-2-oxo-2-(3-oxo-hexahydro furo[3,2-b]pyridin-4-yl)ethyl]benzamide

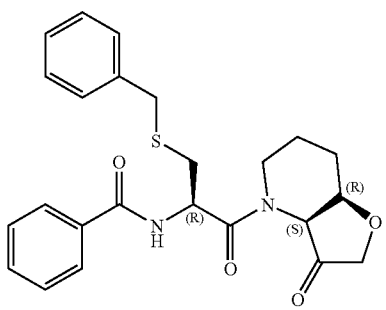

HPLC Rt=17.78 mins (>90%), HPLC-MS 439.2 [M+H]$^+$, 899.3 [2M+Na]$^+$.

EXAMPLE 117

(3aS, 7aR) Furan-3-carboxylic acid-[1R-benzylsulfanylmethyl-2-oxo-2-(3-oxo-hexahydrofuro[3,2-b]pyridin-4-yl)ethyl]amide

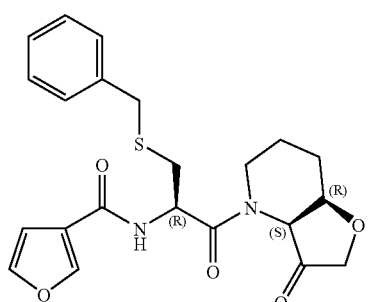

HPLC Rt=16.41 mins (>85%), HPLC-MS 429.2 [M+H]$^+$, 451.2 [M+Na]$^+$.

EXAMPLE 118

(3aS, 7aR) Thiophene-3-carboxylic acid-[1R-benzyl-sulfanylmethyl-2-oxo-2-(3-oxo-hexahydrofuro[3,2-b]pyridin-4-yl)ethyl]amide

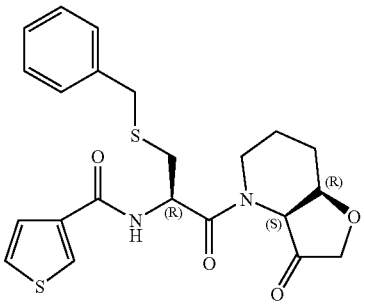

HPLC Rt=17.23 mins (>85%), HPLC-MS 445.2 [M+H]$^+$, 911.2 [2M+Na]$^+$.

EXAMPLE 119

(3aS, 7aR) Morpholine-4-carboxylic acid [1S-cyclohexylmethyl-2-oxo-2-(3-oxo-hexahydrofuro[3,2-b]pyridin-4-carbonyl)ethyl]atnide

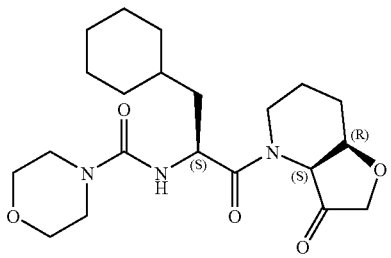

HPLC-MS 408.3 [M+H]$^+$, 430.3 [M+Na]$^+$.

EXAMPLE 120

(3aS, 7aR) N-[1S-cyclohexylmethyl-2-oxo-2-(3-oxo-hexahydrofuro[3,2-b]pyridinyl-4-yl)ethyl]benzamide

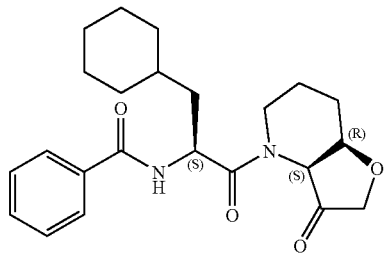

HPLC Rt=18.47 mins (>85%), HPLC-MS 399.2 [M+H]$^+$, 819.2 [2M+Na]$^+$.

EXAMPLE 121

(3aS, 7aR) Furan-3-carboxylic acid [1S-cyclohexylmethyl-2-oxo-2-(3-oxo-hexahydrofuro[3,2-b]pyridin-4-yl)ethyl]amide

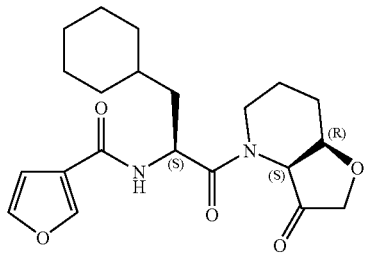

HPLC Rt=17.12 mins (>85%), HPLC-MS 389.2 [M+H]$^+$, 411.2 [2M+Na]$^+$.

EXAMPLE 122

(3aS, 7aR) Thiophene-3-carboxylic acid [1S-cyclohexylmethyl-2-oxo-2-(3-oxo-hexahydrofuro[3,2-b]pyridin-4-yl)ethyl]amide

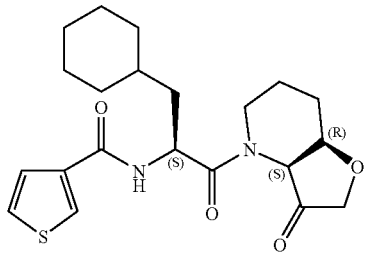

HPLC Rt=17.95 mins (>85%), HPLC-MS 405.2 [M+H]$^+$, 831.2 [2M+Na]$^+$.

EXAMPLE 123

(3aS, 7aR) Furan-3-carboxylic acid [1S-cyclopentylmethyl-2-oxo-2-(3-oxo-hexahydrofuro[3,2-b]pyridinyl-4-yl)ethyl]amide

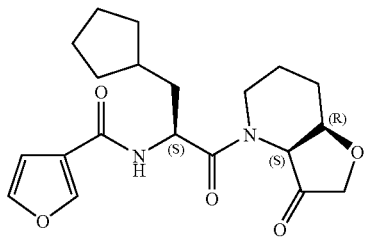

HPLC Rt=15.80 mins (>80%), HPLC-MS 375.2 [M+H]$^+$, 771.3 [2M+Na]$^+$.

EXAMPLE 124

(3aS,7aR) Thiophene-3-carboxylic acid [1S-cyclo-pentylmethyl-2-oxo-2-(3-oxo-hexahydrofuro[3,2-b]pyridin-4-yl)ethyl]amide

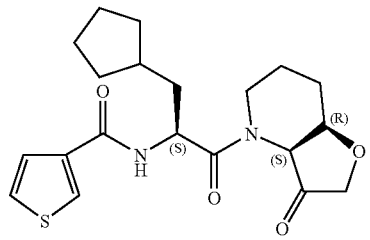

HPLC Rt=16.72 mins (>85%), HPLC-MS 391.1 [M+H]$^+$, 803.3 [2M+Na]$^+$.

EXAMPLE 125

(3aS,7aR) Furan-3-carboxylic acid [3,3-dimethyl-1S-(3-oxo-hexa hydrofuro[3,2-b]pyridine-4-carbo-nyl)butyl]amide

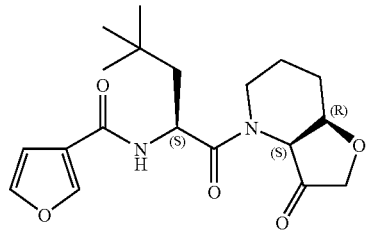

HPLC Rt=15.06 mins (>90%), HPLC-MS 363.2 [M+H]$^+$, 747.4 [2M+Na]$^+$.

EXAMPLE 126

(3aS,7aR) Thiophene-3-carboxylic acid [3,3-dim-ethyl-1S-(3-oxo-hexahydrofuro[3,2-b]pyridine-4-carbonyl)butyl]amide

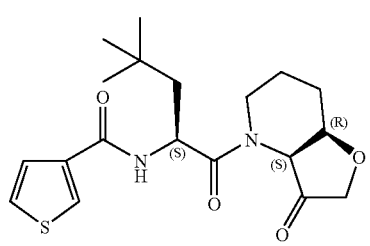

HPLC Rt=15.75 mins (>85%), HPLC-MS 379.2 [M+H]$^+$, 779.3 [2M+Na]$^+$.

EXAMPLE 127

(3aS,7aR) Morpholine-4-carboxylic acid 1S-cyclo-hexylmethyl-2-oxo-2-(3-oxo-hexahydrofuro[3,2-b]pyridin-4-yl)ethyl ester

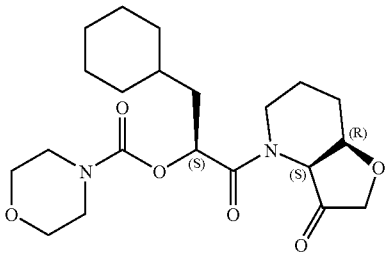

HPLC-MS 409.2 [M+H]$^+$, 839.5 [2M+Na]$^+$.

As detailed for EXAMPLE 74, compound (33) was coupled under standard conditions (following Fmoc removal) to the (3aS,7aR) 3-oxo-hexahydrofuro[3,2-b]pyridine-4-car-boxylic acid 9H-fluoren-9-ylmethyl ester equivalent of loaded building block-linker construct (22), then cleaved to provide EXAMPLE 127.

EXAMPLE 128

(2S, 3aS,7aR) 4-[3-Cyclohexyl-2-(furan-2-yl-methanesulfanyl) propionyl]hexahydrofuro[3,2-b]pyridin-3-one

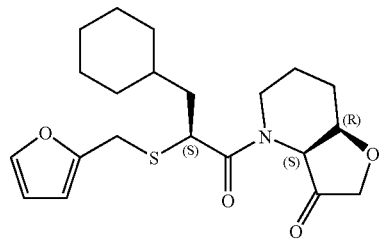

HPLC-MS 392.1 [M+H]$^+$, 805.2 [2M+Na]$^+$.

As detailed for EXAMPLE 76, compound (41) was coupled under standard conditions (following Fmoc removal) to the (3aS,7aR) 3-oxo-hexahydrofuro[3,2-b]pyridine-4-car-boxylic acid 9H-fluoren-9-ylmethyl ester equivalent of loaded building block-linker construct (22), then cleaved to provide EXAMPLE 128.

EXAMPLE 129

(2S, 3aS,7aR) 4-[3-Cyclohexyl-2-(furan-2-yl-methanesulphonyl) propionyl]hexahydrofuro[3,2-b]pyridin-3-one

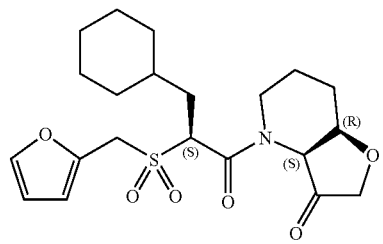

HPLC Rt=19.015 mins (>%), HPLC-MS 424.1 [M+H]⁺, 869.2 [2M+Na]⁺.

As detailed for EXAMPLE 76, compound (41) was coupled under standard conditions (following Fmoc removal) to the (3aS,7aR) 3-oxo-hexahydrofuro[3,2-b]pyridine-4-carboxylic acid 9H-fluoren-9-ylmethyl ester equivalent of loaded building block-linker construct (22). The intermediate loaded thioether (1.2 μmole gear) was oxidised with m-chloroperbenzoic acid (5eq, 65% reagent, 1.6 mg) in dichmoromethane (200 μL) for 5 hrs, followed by standard washing and then cleaved to provide EXAMPLE 129.

EXAMPLE 130

(3aS,7aR) 2R-Cyclohexylmethyl-4-morpholin-4-yl-1-(3-oxo-hexa hydrofuro[3,2-b]pyridin-4-yl)butane-1,4-dione

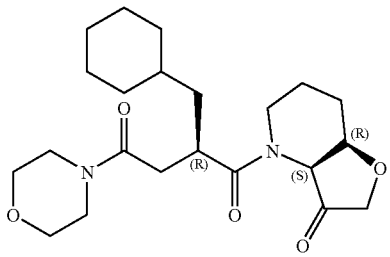

HPLC-MS 407.1 [M+H]⁺, 833.3 [2M+Na]⁺.

As detailed for EXAMPLE 77, compound (36) was coupled under standard conditions (following Fmoc removal) to the (3aS,7aR) 3-oxo-hexahydrofuro[3,2-b]pyridine-4-carboxylic acid 9H-fluoren-9-ylmethyl ester equivalent of loaded building block-linker construct (22), then cleaved to provide EXAMPLE 130.

EXAMPLE 131

(An example of general formula (II)). (3aR,7aS) Morpholine-4-carboxylic acid [1R-benzylsulfanylmethyl-2-oxo-2-(3-oxohexahydrofuro[3,2-b]pyridinyl) ethyl]amide

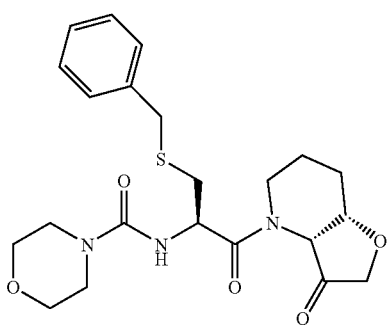

The required bicycle building block (3aR,7aS) 3-oxo-hexahydrofuro[3,2-b]pyridine-4-carboxylic acid 9H-fluoren-9-ylmethyl ester was prepared in a further 4 steps from (2R, 3s) (3-hydroxy) pyrrolidine-1,2-dicarboxylic acid 2-allyl ester 1-(9H-fluoren-9-ylmethyl)ester as follows.

(1) Preparation of (2R,3S) (3-tert-butoxy)pyrrolidine-1,2-dicarboxylic Acid 2-allyl Ester 1-(9H-fluoren-9-ylmethyl)ester.

(2R,3S) (3-hydoxy)pyrrolidine-1,2-dicarboxylic acid 2-allyl ester 1-(9H-fluoren-9-ylmethyl)ester (1.75 g, 4.30 mmole) was dissolved in dry dichloromethane (20 mL) in a 50 mL glass pressure tube and cooled to −78° C. Isobutylene gas (~10 mL) was condensed into the solution and $CH_2SO_4$ (100 μL) added. A stirrer bar was added, the tube was sealed, the cooling removed and stirred at RT for 72 hr. The sealed tube was cooled to −78° C., N-methylmorpholine (200 μL, 1 eq w.r.t. $CH_2SO_4$) and allowed to warm to RT, unsealed, with stirring over 2 hr. Dichloromethane (75 mL) was added and the organics washed with $NaHCO_3$ (75 mL), then brine (75 mL) and dried ($Na_2SO_4$). The solvents were removed in vacuo to give a pale tan oil (1.93 g). The crude oil was purified over silica gel (10 g) eluting with a gradient of heptane:ethyl acetate 5:1→3:1. Desired fractions were combined and reduced in vacuo to a thick clear oil yield 1.48 g (3.19 mmole, 74.3%). TLC (single UV spot, Rf=0.50, heptane: ethyl acetate 2:1), analytical HPLC Rt=24.083 mins, HPLC-MS (single main UV peak with Rt=11.996 mins, 408.2 [M+H-Bu$^t$]⁺, 486.3 [M+Na]⁺). Analysis by $^1$H and $^{13}$C NMR showed the presence of cis and trans geometrical isomers around the 3° amide bond.

$δ_H$ (CDCl₃ at 298K); 1.24 (9×C(C$\underline{H}_3$)₃, s), 1.51-1.90 (2H$_γ$+2H$_δ$, m), 3.38-3.48/3.49-3.58 (1H$_ε$, dt), 3.62-3.74 (H$_β$, b), 3.95-4.02/4.06-4.14 (1H$_ε$, dd), 4.24-4.78 (Fmoc H-9+Fmoc C$\underline{H}_2$+2×COOC$\underline{H}_2$CH=CH₂, bm), 4.88/5.01 (H$_α$, dd, J5.8), 5.25 (1×COOCH₂CH=C$\underline{H}_2$, d, J5.7), 5.37 (1×COOCH₂CH=C$\underline{H}_2$, d, J16.8), 5.88-6.00 (1×COOCH₂C$\underline{H}$=CH₂, m), 7.28-7.39 (2H aromatic, Fmoc H-2 and H-7), 7.39-7.46 (2H aromatic, Fmoc H-3 and H-6), 7.57-7.71 (2H aromatic, Fmoc H-1 and H-8), 7.78-7.86 (2H aromatic, Fmoc H-4 and H-5).

$δ_C$ (CDCl₃ at 298K); 23.69/24.00 (d, C$_δ$), 28.38 (u, C($\underline{C}H_3$)₃), 28.65 (d, C$_γ$), 40.41/40.72 (d, C$_ε$), 47.61 (u, Fmoc C-9), 58.46 (u, C$_α$), 65.67 (d, COO$\underline{C}H_2$CH=CH₂), 67.82 (u, C$_β$), 68.12 (d, Fmoc $\underline{C}H_2$), 74.93 (q, $\underline{C}$(CH₃)₃), 118.46/118.57 (d, COOCH₂CH=$\underline{C}H_2$), 120.40 (u, Fmoc C-4 and C-5), 125.39 (u, Fmoc C-1 and C-8), 127.46 (u, Fmoc C-2 and C-7), 128.10 (u, Fmoc C-3 and C-6), 132.49 (u, COOCH₂$\underline{C}H$=CH₂), 141.71 (q, Fmoc C-4' and C-5'), 144.12/144.35 (q, Fmoc C-1' and C-8'), 156.24 (q, O$\underline{C}$ON), 170.42/171.06 ($\underline{C}$OOCH₂CH=CH₂).

(2) Preparation of (2R,3S) (3-tert-butoxy)pyrrolidine-1,2-dicarboxylic Acid 1-(9H-fluoren-9-ylmethyl)ester.

(2R,3S) (3-tert-butoxy)pyrrolidine-1,2-dicarboxylic acid 2-allyl ester 1-(9H-fluoren-9-ylmethyl)ester (1.42 g, 3.07 mmole) was dissolved in dry dichloromethane (25 mL) with stirring. Tetrakistriphenylphosphine palladium (0) (71 mg, 0.062 mmole, 0.02eq) was added, followed by phenyltrihydrosilane (0.66 g, 0.581 mL, 6.14 mmole, 2eq). After 1 hr, dichloromethane (150 mL) was washed with 0.01N HCl (150 mL), brine (150 mL) and dried (Na₂SO₄). The solvents were removed in vacuo to give a dark grey solid (2.0 g). The crude solid was purified over silica gel (75 g) eluting with a gradient of heptane: ethyl acetate 2:1→1:2. Desired fractions were combined and reduced in vacuo to a white crystalline yield 1.07 g (2.53 mmole, 82.3%). TLC (single UV spot, Rf=0.25, heptane:ethyl acetate 1:1), analytical HPLC Rt=21.306 mins, HPLC-MS (single main UV peak with Rt=10.269 mins, 368.2 [M+H-Bu$^t$]⁺, 446.2 [M+Na]⁺, 869.3 [2M+Na]⁺). Analysis by $^1$H and $^{13}$C NMR showed the presence of cis and trans geometrical isomers around the 3° amide bond.

$_δ$H (CDCl$_3$ at 298K); 1.32/1.41 (9×C(CH$_3$)$_3$, ds), 1.43-1.59 (1H$_γ$+1H$_δ$, m), 1.70-1.81 (1H$_δ$, bm), 1.82-1.99 (1H$_γ$, bm), 2.75-2.82/2.90-2.97 (1H$_ε$, dt), 3.73-3.85 (H$_β$, b), 3.92-4.05 (1H$_ε$, dd), 4.23-4.32 (Fmoc H-9), 4.40-4.58 (Fmoc CH$_2$, bm), 4.60 4.62/5.02-5.04 (H$_α$, dd, J5.7), 7.29-7.36 (2H aromatic, Fmoc H-2 and H-7), 7.39-7.44 (2H aromatic, Fmoc H-3 and H-6), 7.54-7.67 (2H aromatic, Fmoc H-1 and H-8), 7.77-7.82 (2H aromatic, Fmoc H-4 and H-5), 10.80-11.15 (COOH, bs).

$_δ$C (CDCl$_3$ at 298K); 23.71/24.24 (d, C$_δ$), 28.20/28.27 (u, C(CH$_3$)$_3$), 30.60/30.73 (d, C$_γ$), 40.50/40.79 (d, C$_ε$), 47.58/47.63 (u, Fmoc C-9), 58.20/58.44 (u, C$_α$), 67.77/68.33 (u, C$_β$), 68.67/68.87 (d, Fmoc CH$_2$), 78.48/78.67 (q, C(CH$_3$)$_3$), 120.30 (u, Fmoc C-4 and C-5), 125.16/125.27/125.52 (u, Fmoc C-1 and C-8), 127.42/127.48/127.59 (U, Fmoc C-2 and C-7), 128.04/128.10 (u, Fmoc C-3 and C-6), 141.57/141.69/141.78 (q, Fmoc C-4' and C-5'), 144.06/144.11/144.36/144.47 (q, Fmoc C-1' and C-8'), 155.73/156.49 (q, OCON), 169.26/169.55 (COOH).

(3) Preparation of (2R,3S) (3-tert-butoxy)-2-(2-diazoacetyl)pyrrolidine-1,2-dicarboxylic Acid 1-(9H-fluoren-9-ylmethyl)ester.

(2R,3S) (3-tert-butoxy)pyrrolidine-1,2-dicarboxylic acid 1-(9H-fluoren-9-ylmethyl)ester (830 mg, 1.96 mmole) was dissolved with stirring in dry dichloromethane (20 mL). The reaction was flushed with nitrogen and cooled to −15° C. Isobutylchloroformate (296 mg, 2.16 mmole in dry dichloromethane (2.5 mL) and N-methylmorpholine (397 mg, 3.92 mmole in dry dichloromethane (2.5 mL) were added simultaneously in 0.5 mL aliquots over 15 mins. Etheral diazomethane (generated from diazald (2.5 g, 8 mmole in diethyl ether (40 mL)) onto sodium hydroxide (2.75 g) in water (4.3 mL)/ethanol (8.6 mL) at 60° C.). was added to the activated aminoacid solution and stirred at RT for 3 hr, Acetic acid (~3 mL) was added to quench the reaction, then tert-butylmethylether (100 mL) was added, the organics washed with water (3×150 mL), then dried (Na$_2$SO$_4$). The solvents were removed in vacuo to give a tacky pale yellow oil (910 mg). The crude oil was purified over silica gel (75 g) eluting with a gradient of heptane: ethyl acetate 4:1→3:1. Desired fractions were combined and reduced in vacuo to a pale yellow oil/solid, yield 560 mg (1.25 mmole, 63.9%). TLC (single main UV spot, Rf=0.35, heptane:ethyl acetate 2:1), analytical HPLC Rt=18.754 min, HHLC-MS (UV peaks with Rt=9.095 mins, 364.2 [M+H]$^+$, 386.1 [M+Na]$^+$, 749.2 [2M+Na]$^+$ and Rt=10.856 mins, 420.2 [M+H−N$_2$]$^+$, 470.2 [M+Na]$^+$, 917.3 [2M+Na]$^+$).

Note that upon HPLC-MS analysis, m/z 364.2 corresponds to the desired bicycle product (3aR,7aS) 3-oxo-hexahydrofuro[3,2-b]pyridine-4-carboxylic acid 9H-fluoren-9-ylmethyl ester.

Analysis by $^1$H and $^{13}$C NMR showed the presence of cis and trans geometrical isomers around the 3° amide bond.

$_δ$H (CDCl$_3$ at 298K); 1.29/1.46 (9×C(CH$_3$)$_3$, ds), 1.40-1.85 (2H$_γ$+2H$_ε$, bm), 3.05/3.38 (1H$_ε$, dt), 3.39-3.44/3.62-3.69 (H$_β$, dm), 3.90-3.97 (1H$_ε$, dd), 4.05-4.07/4.78 4.83 (H$_α$, bm), 4.24-4.33 (Fmoc H-9), 4.36-4.42/4.46-4.51 (1×Fmoc CH$_2$, dm), 4.61-4.68 (1×Fmoc CH$_2$, m), 4.89/5.90 (COCH=N$_2$, s+bs), 7.28-7.39 (2H aromatic, Fmoc H-2 and H-7), 7.40-7.44 (2H aromatic, Fmoc H-3 and H-6), 7.53-7.67 (2H aromatic, Fmoc H-1 and H-8), 7.76-7.81 (2H aromatic, Fmoc H-4 and H-5).

$_δ$C (CDCl$_3$ at 298K); 23.94/24.51 (d, C$_α$), 28.38/28.53 (U, C(CH$_3$)$_3$), 29.23/29.84 (d, C$_γ$), 40.83/41.45 (d, C$_ε$), 47.57/47.64 (u, Fmoc C-9), 55.50/56.38 (u, COCH=N$_2$), 61.69/62.66 (u, C$_α$), 66.85/68.20 (d, Fmoc CH$_2$), 69.35/69.61 (u, C$_β$), 75.11/75.54 (q, C(CH$_3$)$_3$), 120.29/120.32 (u, Fmoc C4 and C-5), 124.85/125.25/125.53 (u, Fmoc C-1 and C-8), 127.46/127.59 (u, Fmoc C-2 and C-7), 127.97/128.03/128.07 (u, Fmoc C-3 and C-6), 141.62/141.69/141.73 (q, Fmoc C4' and C-5'), 144.24/144.31/144.50/144.61 (q, Fmoc C-1' and C-8'), 155.68/156.89 (q, OCON), 191.90/192.37 (COCH=N$_2$).

(4) Cyclisation to (3aR,7aS) 3-oxo-hexahydrofuro[3,2-b]pyridine-4-carboxylic Acid 9H-fluoren-9-ylmethyl Ester.

A solution of lithium chloride (494 mg, 11.6 mmole) in water (3 mL) and acetic acid (12 mL) was added to (2R,3S) (3-tert-butoxy)-2-(2-diazoacetyl) pyrrolidine-1,2-dicarboxylic acid 1-(9H-fluoren-9-ylmethyl)ester (520 mg, 1.16 mmole). Gas was evolved and the yellow oily solid dissolved over 1 hr to give a virtually colourless solution. After 90 mins, chloroform (150 mL) was added and the organics washed with NaHCO$_3$ (2×150 mL), brine (150 mL) and dried (Na$_2$SO$_4$). The solvents were removed in vacuo to give a white crystalline solid (390 mg). The crude solid was purified over silica gel (75 g) eluting with a gradient of heptane: ethyl acetate 3:1→2:1. Desired fractions were combined and reduced in vacuo to a white crystalline solid, yield 340 mg (0.94 mmole, 47.7% from starting acid). TLC (single UV spot, Rf=0.25, heptane:ethyl acetate 2:1), analytical HPLC Rt=18.563 mins, HPLC-MS (single UV peak with Rt=9.074-mins, 364.2 [M+H]$^+$, 386.2 [M+Na]$^+$). Analysis by $^1$H and $^{13}$C NMR showed the presence of cis and trans geometrical isomers around the 3° amide bond.

$_δ$H (CDCl$_3$ at 298K); 1.20-1.38 (1H$_γ$+1H$_δ$, m), 1.51-1.68 (1H$_δ$, bm), 1.96-2.08 (1H$_γ$, bm), 2.40-2.52/2.53-2.67 (1Hg, m), 3.87 (COCH$_{2A}$, d, J16.5), 3.85-3.95 (1H$_ε$, b), 4.09 (Fmoc H-9, bt), 4.14 (H$_β$, b), 4.21 4.46 (Fmoc CH$_2$+COCH$_{2B}$, bm), 4.62-4.70/5.00-5.09 (H<, 2×b), 7.23-7.27 (2H aromatic, Fmoc H-2 and H-7), 7.32-7.35 (2H aromatic, Fmoc H-3 and H-6), 7.41-7.53 (2H aromatic, Fmoc H-1 and H-8), 7.69-7.71 (2H aromatic, Fmoc H-4 and H-5).

$_δ$C (CDCl$_3$ at 298K); 22.08 (d, C$_δ$), 26.61 (d, C$_γ$), 41.67 (d, C$_ε$), 47.58 (u, Fmoc C-9), 60.54 (u, C$_α$), 67.55 (d, Fmoc CH$_2$), 68.40 (d, COHH$_2$O), 72.61 (u, C$_β$), 120.39 (u, Fmoc C4 and C-5), 125.42 (u, Fmoc C-1 and C-8), 127.51 (u, Fmoc C-2 and C-7), 128.14 (u, Fmoc C-3 and C-6), 141.73 (q, Fmoc C4' and C-5'), 144.16 (q, Fmoc C-1' and C-8'), 156.20 (q, OCON), 211.64 (q, COCH$_2$O).

Following the general details from Scheme 2, the required bicycle building block (3aR,7aS) 3-oxo-hexahydrofuro[3,2-b]pyridine-4-carboxylic acid 9H-fluoren-9-yl methyl ester was converted to building block-linker construct as follows:

(3aR,7aS) 3-oxo-hexahydrofuro[3,2-b]pyridine-4-carboxylic acid 9H-fluoren-9-ylmethyl ester (290 mg, 0.80 mmole) was dissolved in a mixture of ethanol (14.0 mL) and water (2.0 mL) containing sodium acetate.trihydrate (163 mg, 1.198 mmole, 1.5eq). 4-[[(hydrazinocarbonyl)amino]methyl]cyclo hexanecarboxylic acid. trifluoroacetate (263 mg, 0.80 mmole, 1.0eq, Murphy, A. M. et al, *J. Am. Chem. Soc.*, 114, 3156-3157, 1992) was added and the mixture refluxed for 4 hrs. Chloroform (150 mL) was added and the organics washed with HCl (150 mL, ~pH3), dried (Na$_2$SO$_4$) and reduced in vacuo to provide crude building block-linker construct as an off-white crystalline solid. Yield 450 mg, analytical HPLC 2 peaks Rt=17.109 (67.6%) and 18.565 mins (26.3%) (cis/trans geometrical isomers), HPLC-MS (2×UV peak with Rt=8.069 and 9.050 mins, 561.2 [M+H]$^+$). Crude construct was used directly for construct loading.

Following the general details from Scheme 2, the required building block-linker construct was attached to the solid phase providing loaded building block-linker construct as follows:

Building block-linker construct (0.680 mmoles), 2-(1H-benzotriazole-1-yl)-1,1,3,3-tetramethyluroniumhexafluoro phosphate (HBTU, 258 mg, 0.680 mmole), 1-hydroxybenzotriazole.hydrate and (HOBT, 105 mg, 0.680 mmole) were dissolved in dimethylformamide (3 mL) and N-methylnorpholine (NMM, 150 µL, 1.36 mmole) added. After pre-activation for 5 minutes, free amine gears (190×1.2 µmole) were added, followed by dimethylformamide (17.5 mL) and left overnight. The spent coupling solution was then added to free amine crowns (18×10 µmole) and left overnight. Standard washing and analyses indicated quantitative loading in both cases.

Following the general details from Scheme 2, the required loaded building block-linker construct was elaborated on the solid phase as follows:

Loaded construct was elaborated to EXAMPLE 91 (3aR, 7aS) Morpholine-4-carboxylic acid [1R-benzylsulfanylmethyl-2-oxo-2-(3-oxohexahydrofuro[3,2-b]pyridin-4-yl) ethyl]amide by standard Fmoc deprotection and sequential coupling with Fmoc-Cys(SBzl)-OH then morpholine-4-carbonylchloride. The crude example was cleaved and analysed (see general techniques). HPLC Rt=15.59 mins (>80%), HPLC-MS 449.2 [M+H]$^+$.

The following examples (132-156) were prepared as detailed for EXAMPLE 131, coupling with the required reagents to provide the full length molecule.

EXAMPLE 132

(3aR,7aS) Morpholine-4-carboxylic acid [1S-(4-hydroxybenzyl)-2-oxo-2-(3-oxo-hexahydrofuro[3,2-b]pyridinyl)ethyl]amide

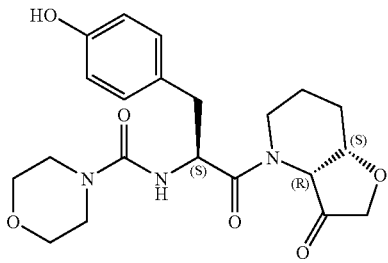

HPLC-MS 418.2 [M+H]$^+$.

EXAMPLE 133

(3aR,7aS) N-[1S-(4-hydroxybenzyl-2-oxo-2-(3-oxo-hexahydrofuro[3,2-b]pyridin-4-yl)ethyl]benzamide

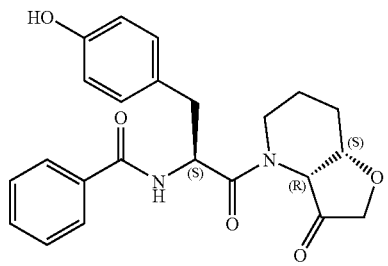

HPLC Rt=12.67 mins (>80%), HPLC-MS 409.1 [M+H]$^+$.

EXAMPLE 134

(3aR,7aS) Naphthalene-1-carboxylic acid [1S-(4-hydroxybenzyl)-2-oxo-2-(3-oxo-hexahydrofuro[3,2-b]pyridin-4-yl)ethyl]amide

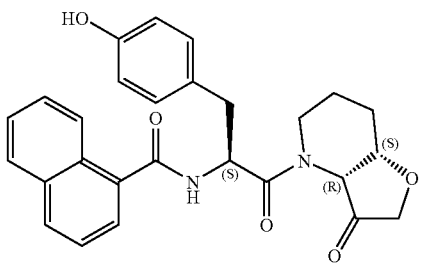

HPLC Rt=14.87 mins (>80%), HPLC-MS 459.2 [M+H]$^+$.

EXAMPLE 135

(3aR,7aS) Morpholine-4-carboxylic acid [3-methyl-1S-(3-oxo-hexa hydrofuro[3,2-b]pyridine-4-carbonyl)butyl]amide

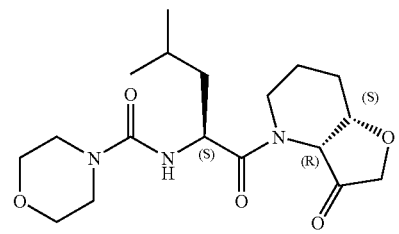

HPLC-MS 368.2 [M+H]$^+$, 390.2 [M+Na]$^+$.

EXAMPLE 136

(3aR,7aS) N-[3-methyl-1S-(3-oxo-hexahydrofuro[3,2-b]pyridine-4-carbonyl)butyl]benzamide

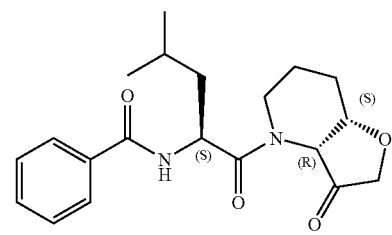

HPLC Rt=15.40 mins (>80%), HPLC-MS 359.2 [M+H]$^+$.

EXAMPLE 137

(3aR,7aS) Furan-3-carboxylic acid [3-methyl-1S-(3-oxo-hexahydro furo[3,2-b]pyridine-4-carbonyl)butyl]amide

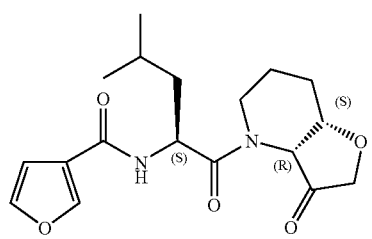

HPLC Rt=13.74-mins (>85%), HPLC-MS 349.2 [M+H]+, 371.2 [2M+Na]+.

EXAMPLE 138

(3aR,7aS) Benzo[b]thiophene-2-carboxylic acid [3-methyl-1S-(3-oxo-hexahydrofuro[3,2-b]pyridine-4-carbonyl)butyl]amide

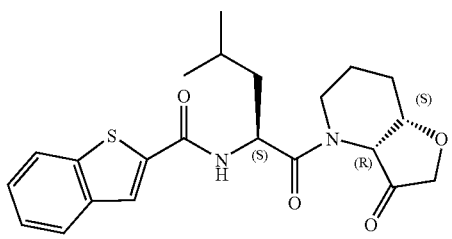

HPLC Rt=18.52 mins (>80%), HPLC-MS 415.2 [M+H]+, 851.3 [2M+Na]+.

EXAMPLE 139

(3aR,7aS) 4-Dimethylamino-N-[3-methyl-1S-(3-oxo-hexahydro furo[3,2-b]pyridine-4-carbonyl)butyl]benzamide

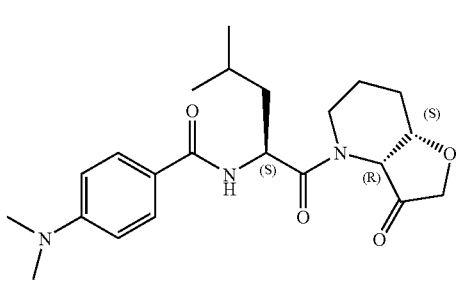

HPLC Rt=13.55 mins (>80%), HPLC-MS 402.2 [M+H]+, 825.3 [2M+Na]+.

EXAMPLE 140

(3aR,7aS) Benzo[b]thiophene-3-carboxylic acid [3-methyl-1S-(3-oxo-hexahydrofuro[3,2-b]pyridine-4-carbonyl)butyl]amide

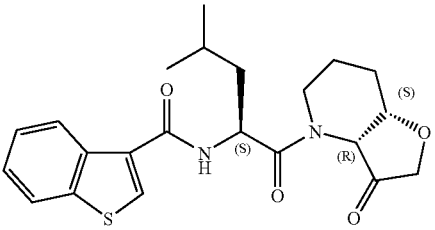

HPLC Rt=18.26 mins (>80%), HPLC-MS 415.2 [M+H]+, 851.3 [2M+Na]+.

EXAMPLE 141

(3aR,7aS) Thiophene-3-carboxylic acid [3-methyl-1S-(3-oxo-hexa hydrofuro[3,2-b]pyridine-4-carbonyl)butyl]amide

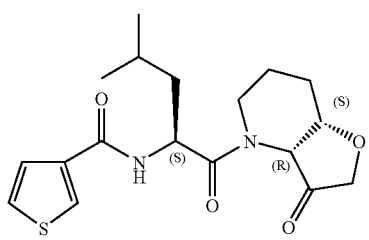

HPLC Rt=14.80 mins (>80%), HPLC-MS 365.2 [M+H]+, 387.2 [M+Na]+.

EXAMPLE 142

(3aR,7aS) N-[1R-benzylsulfanylmethyl-2-oxo-2-(3-oxo-hexahydro furo[3,2-b]pyridin-4-yl)ethyl]benzamide

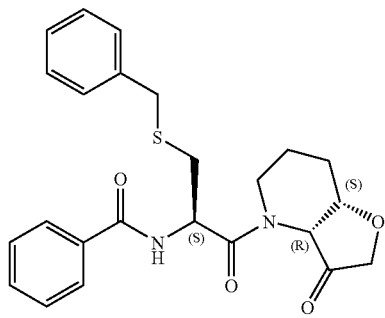

HPLC Rt=17.78 mins (>80%), HPLC-MS 439.2 M+H]+, 899.3 [2M+Na]+.

EXAMPLE 143

(3aR,7aS) Furan-3-carboxylic acid-[1R-benzylsulfanylmethyl-2-oxo-2-(3-oxo-hexahydrofuro[3,2-b]pyridin-4-yl)ethyl]amide

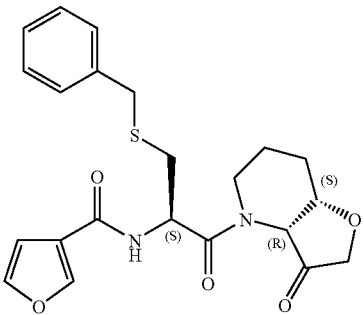

HPLC Rt=16.41 mins (>85%), HPLC-MS 429.6 [M+H]$^+$, 451.5 [M+Na]$^+$.

EXAMPLE 144

(3aR,7aS) Thiophene-3-carboxylic acid-[1R-benzylsulfanylmethyl-2-oxo-2-(3-oxo-hexahydrofuro[3,2-b]pyridin-4-yl)ethyl]amide

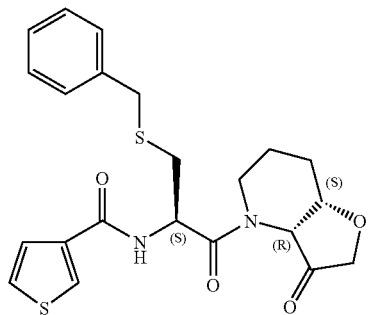

HPLC Rt=17.23 mins (>80%), HPLC-MS 445.1 [M+H]$^+$, 911.2 [2M+Na]$^+$.

EXAMPLE 145

(3aR,7aS) Morpholine-4carboxylic acid [1S-cyclohexylmethyl-2-oxo-2-(3-oxo-hexahydrofuro[3,2-b]pyridin-4-yl)ethyl]amide

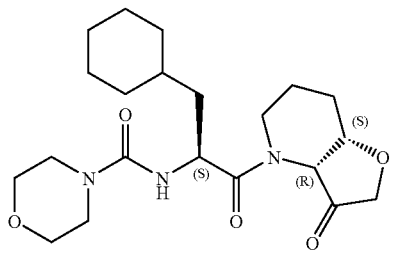

HPLC-MS 408.2 [M+H]$^+$.

EXAMPLE 146

(3aR,7aS) N-[1S-cyclohexylmethyl-2-oxo-2-(3-oxo-hexahydrofuro[3,2-b]pyridin-4-yl)ethyl]benzamide

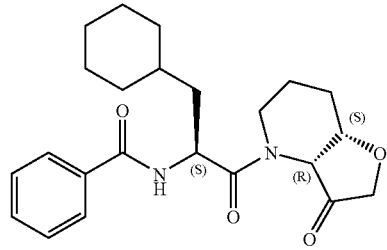

HPLC Rt=18.47 mins (>80%), HPLC-MS 399.2 [M+H]$^+$, 819.3 [2M+Na]$^+$.

EXAMPLE 147

(3aR,7aS) Furan-3-carboxylic acid [1S-cyclohexylmethyl-2-oxo-2-(3-oxo-hexahydrofuro[3,2-b]pyridin-4-yl)ethyl]amide

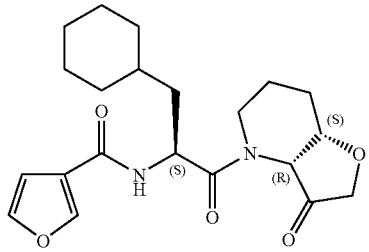

HPLC Rt=17.12 mins (>80%), HPLC-MS 389.2 [M+H]$^+$.

EXAMPLE 148

(3aR,7aS) Thiophene-3-carboxylic acid [1S-cyclohexylmethyl-2-oxo-2-(3-oxo-hexahydrofuro[3,2-b]pyridin-4-yl)ethyl]amide

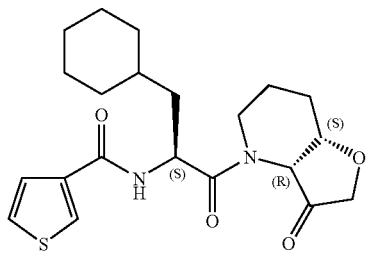

HPLC Rt=18.05 mins (>85%), HPLC-MS 405.2 [M+H]$^+$, 831.2 [2M+Na]$^+$.

EXAMPLE 149

(3aR,7aS) Furan-3-carboxylic acid [1S-cyclopentyl-methyl-2-oxo-2-(3-oxo-hexahydrofuro[3,2-b]pyridi-nyl-4-yl)ethyl]amide

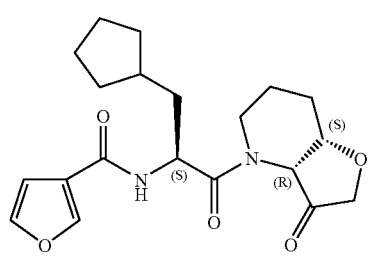

HPLC Rt=15.84-mins (>85%), HPLC-MS 375.2 [M+H]$^+$, 771.3 [2M+Na]$^+$.

EXAMPLE 150

(3aR,7aS) Thiophene-3-carboxylic acid [1S-cyclo-pentylmethyl-2-oxo-2-(3-oxo-hexahydrofuro[3,2-b]pyridin-4-yl)ethyl]amide

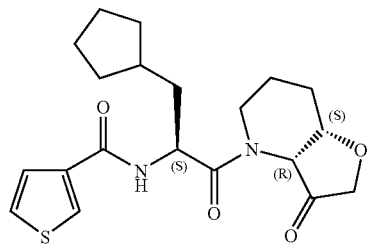

HPLC Rt=16.78 mins (>85%), HPLC-MS 391.1 [M+H]$^+$, 803.3 [2M+Na]$^+$.

EXAMPLE 151

(3aR,7aS) Furan-3-carboxylic acid [3,3-dimethyl-1S-(3-oxo-hexa hydrofuro[3,2-b]pyridine-4-carbo-nyl)butyl]amide

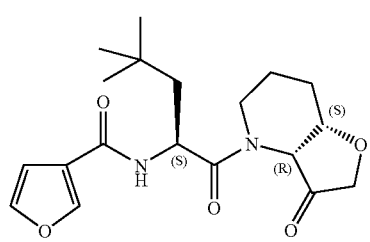

HPLC Rt=15.05 mins (>85%), HPLC-MS 363.2 [M+H]$^+$, 747.4 [2M+Na]$^+$.

EXAMPLE 152

(3aR,7aS) Thiophene-3-carboxylic acid [3,3-dim-ethyl-1S-(3-oxo-hexahydrofuro[3,2-b]pyridine-4-carbonyl)butyl]amide

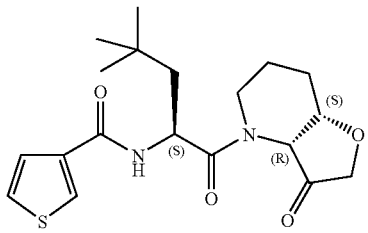

HPLC Rt=15.76 mins (>80%), HPLC-MS 379.2 [M+H]$^+$, 779.3 [2M+Na]$^+$.

EXAMPLE 153

(3aR,7aS) Morpholine-4-carboxylic acid 1S-cyclo-hexylmethyl-2-oxo-2-(3-oxo-hexahydrofuro[3,2-b]pyridin-4-yl)ethyl ester

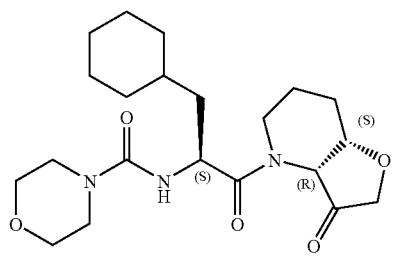

HPLC-MS 409.2 [M+H]$^+$, 839.5 [2M+Na]$^+$.

As detailed for EXAMPLE 127, compound (33) was coupled under standard conditions (following Fmoc removal) to the (3aR,7aS) 3-oxo-hexahydrofuro[3,2-b]pyridine-4-car-boxylic acid 9H-fluoren-9-ylmethyl ester equivalent of loaded building block-linker construct (22), then cleaved to provide EXAMPLE 153.

EXAMPLE 154

(2S, 3aR,7aS) 4-[3-Cyclohexyl-2-(furan-2-yl-methanesulfanyl) propionyl]hexahydrofuro[3,2-b]pyridin-3-one

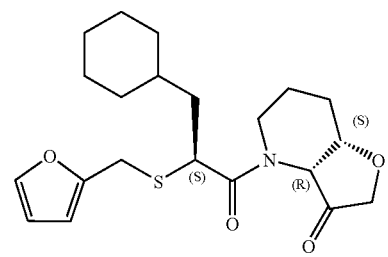

HPLC-MS 392.1 [M+H]$^+$, 805.3 [2M+Na]$^+$.

As detailed for EXAMPLE 128, compound (41) was coupled under standard conditions (following Fmoc removal) to the (3aR,7aS) 3-oxo-hexahydrofuro[3,2-b]pyridine-4-carboxylic acid 9H-fluoren-9-ylmethyl ester equivalent of loaded building block-linker construct (22), then cleaved to provide EXAMPLE 154.

EXAMPLE 155

(2S, 3aR,7aS) 4-[3-Cyclohexyl-2-(furan-2-yl-methanesulphonyl) propionyl]hexahydrofuro[3,2-b]pyridin-3-one

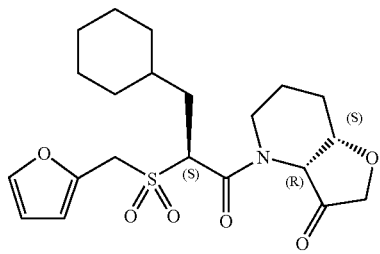

HPLC Rt=18.8-19.4-mins (>90%), HPLC-MS 424.1 [M+H]$^+$, 869.2 [2M+Na]$^+$.

As detailed for EXAMPLE 129, compound (41) was coupled under standard conditions (following Fmoc removal) to the (3aR,7aS) 3-oxo-hexahydrofuro[3,2-b]pyridine-4-carboxylic acid 9H-fluoren-9-ylmethyl ester equivalent of loaded building block-linker construct (22). The intermediate loaded thioether (1.2 µmole gear) was oxidised with m-chloroperbenzoic acid (5eq, 65% reagent, 1.6 mg) in dichloromethane (200 µL) for 5 hrs, followed by standard washing and then cleaved to provide EXAMPLE 155.

EXAMPLE 156

(3aR,7aS) 2R-Cyclohexylmethyl-4-morpholin-4-yl-1-(3-oxo-hexa hydrofuro[3,2-b]pyridin-4-yl)butane-1,4-dione

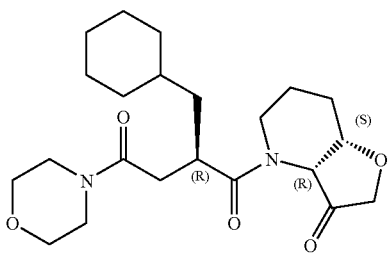

HPLC-MS 407.2 [M+H]$^+$, 833.3 [2M+Na]$^+$.

As detailed for EXAMPLE 130, compound (36) was coupled under standard conditions (following Fmoc removal) to the (3aR,7aS) 3-oxo-hexahydrofuro[3,2-b]pyridine-4-carboxylic acid 9H-fluoren-9-ylmethyl ester equivalent of loaded building block-linker construct (22), then cleaved to provide EXAMPLE 156.

EXAMPLE A

Assays for Cysteine Protease Activity

The compounds of this invention may be tested in one of a number of literature based biochemical assays that are designed to elucidate the characteristics of compound inhibition. The data from these types of assays enables compound potency and the rates of reaction to be measured and quantified. This information, either alone or in combination with other information, would allow the amount of compound required to produce a given pharmacological effect to be determined.

General Materials and Methods

Unless otherwise stated, all general chemicals and biochemicals were purchased from either the Sigma Chemical Company, Poole, Dorset, U.K. or from Fisher Scientific UK, Loughborough, Leicestershire, U.K Absorbance assays were carried out in flat-bottomed 96-well plates (Spectra; Greiner Bio-One Ltd., Stonehouse, Gloucestershire, U.K.) using a SpectraMax PLUS384 plate reader (Molecular Devices, Crawley, U.K). Fluorescence high throughput assays were carried out in either 384-well microtitre plates (Corning Costar 3705 plates, Fisher Scientific) or 96-well 'U' bottomed Microfluor W1 microtitre plates (hermo Labsystems, Ashford, Middlesex, U.K.). Fluorescence assays were monitored using a SpectraMax Gemini fluorescence plate reader (Molecular Devices). For substrates employing either a 7-amino-4-methylcoumarin (AMC) or a 7-amino-4-trifluoromethyl-coumarin (AFC) fluorophore, assays were monitored at an excitation wavelength of 365 nm and an emission wavelength of 450 nm and the fluorescence plate reader calibrated with AMC. For substrates employing a 3-amino-benzoyl (Abz) fluorophore, assays were monitored at an excitation wavelength of 310 nm and an emission wavelength of 445 nm; the fluorescence plate reader calibrated with 3-amino-benzamide (Fluka). Unless otherwise indicated, all the peptidase substrates were purchased from Bachem UK, St. Helens, Merseyside, UK. Substrates utilizing fluorescence resonance energy transfer methodology (i.e. FRET-based substrates) were synthesized at Incenta Limited using published methods (Atherton & Sheppard, *Solid Phase Peptide Synthesis*, IRL Press, Oxford, U.K., 1989) and employed Abz (2-aminobenzoyl) as the fluorescence donor and 3-nitro-tyrosine [Tyr (NO$_2$)] as the fluorescence quencher (Meldal, M. and Breddam, K, *Anal. Biochem.*, 195, 141-147, 1991). Hydroxyethylpiperazine ethanesulfonate (HEPES), tris-hydroxylmethyl aminomethane (tris) base, bis-tris-propane and all the biological detergents (e.g. CHAPS, zwittergents, etc.) were purchased from CN Biosciences UK, Beeston, Nottinghamshire, U.K Glycerol was purchased from Amersham Pharmacia Biotech, Little Chalfont, Buckinghamshire, U.K. Stock solutions of substrate or inhibitor were made up to 10 mM in 100% dimethylsulfoxide (DMSO) (Rathburns, Glasgow, U.K.) and diluted as appropriately required. In all cases the DMSO concentration in the assays was maintained at less than 1% (vol./vol.).

Assay protocols were based on literature precedent (Tablel; Barrett, A. J., Rawlings, N. D. and Woessner, J. F., 1998, *Handbook of Proteolytic Enzymes*, Academic Press, London and references therein) and modified as required to suit local assay protocols. Enzyme was added as required to initiate the reaction and the activity, as judged by the change in fluorescence upon conversion of substrate to product, was monitored over time. All assays were carried out at 25±1° C.

TABLE 1

The enzyme assays described herein were carried out according to literature precedents.

| Enzyme | Buffer | Substrate | Reference |
|---|---|---|---|
| Cathepsin B | I | Z-Phe-Arg-AMC | a, b |
| Cathepsin H | II | Bz-Phe-Val-Arg-AMC | a, b |
| Cathepsin L | I | Ac-Phe-Arg-AMC | b, c |
| Cathepsin S | I | Boc-Val-Leu-Lys-AMC | c, d |
| Caspase 1 | III | Ac-Leu-Glu-His-Asp-AMC | e |
| Caspase 2 | III | Z-Val-Asp-Val-Ala-Asp-AFC | f |
| Caspase 3 | III | Ac-Asp-Glu-Val-Asp-AMC | g, h |
| Caspase 4 | III | Suc-Tyr-Val-Ala-Asp-AMC | f |

TABLE 1-continued

The enzyme assays described herein were carried out according to literature precedents.

| Enzyme | Buffer | Substrate | Reference |
|---|---|---|---|
| Caspase 5 | III | Ac-Leu-Glu-His-Asp-AMC | |
| Caspase 6 | III | Ac-Val-Glu-Ile-Asp-AMC | i, j, k |
| Caspase 7 | III | Ac-Asp-Glu-Val-Asp-AMC | |
| Caspase 8 | III | Ac-Ile-Glu-Thr-Asp-AMC | l |
| Caspase 9 | III | Ac-Leu-Glu-His-Asp-AMC | |
| Caspase 10 | III | Ac-Ile-Glu-Thr-Asp-AMC | |
| Cruzipain | IV | D-Val-Leu-Lys-AMC | m, n |
| CPB2.8ΔCTE | XI | Pro-Phe-Arg-AMC | q |
| S. Aureus Extracellular cysteine peptidase | I | Abz-Ile-Ala-Ala-Pro-Tyr(NO$_2$)-Glu-NH$_2$ | o |
| Clostripain | | Z-Gly-Gly-Arg-AMC | p |
| FMDV LP | V | Abz-Arg-Lys-Leu-Lys-Gly-Ala-Gly-Ser-Tyr(NO$_2$)-Glu-NH$_2$ | r |
| Trypsin | VI | Z-Gly-Gly-Arg-AMC | s |
| Calpain μ | VII | Abz-Ala-Asn-Leu-Gly-Arg-Pro-Ala-Leu-Tyr(NO$_2$)-Asp-NH$_2$ | t |
| Calpain m | VIII | Abz-Lys-Leu-Cys(Bzl)-Phe-Ser-Lys-Gln-Tyr(NO$_2$)-Asp-NH$_2$ | t |
| Cathepsin K | IX | Z-Phe-Arg-AMC | u |
| Cathepsin X | X | | v, w |

I: 10 mM BTP, pH 6.5 containing 1 mM EDTA, 5 mM 2-mercaptoethanol and 1 mM CaCl$_2$
II: 10 mM BTP, pH 6.5 containing 1 mM EDTA, 142 mM NaCl, 1 mM DTT, 1 mM CaCl$_2$, 0.035 mM Zwittergent 3-16
III: 50 mM HEPES pH 7.2, 10% Glycerol, 0.1% CHAPS, 142 mM NaCl, 1 mM EDTA, 5 mM DTT
IV: 100 mM sodium phosphate, pH 6.75 containing 1 mM EDTA and 10 mM L-cysteine
V: 50 mM trisacetate, pH 8.4 containing 1 mM EDTA, 10 mM L-cysteine and 0.25% (w/v) CHAPS
VI: 10 mM HEPES, pH 8.0 containing 5 mM CaCl$_2$
VII: 10 mM HEPES, pH 7.5 containing 2 mM 2-mercaptoethanol and 100 μM CaCl$_2$
VIII: 10 mM HEPES, pH 7.5 containing 2 mM 2-mercaptoethanol and 200 μM CaCl$_2$
IX: 100 mM sodium acetate; pH 5.5 containing 10 mM L-cysteine and 1 mM EDTA
X: 100 mM sodium acetate; pH 5.5 containing 10 mM L-cysteine; 0.05% (w/v) Brij 35 and 1 mM EDTA
XI: 100 mM sodium acetate; pH 5.5 containing 10 mM L-cysteine; 142 mM sodium chloride and 1 mM EDTA
[a]Barrett, A. J., Biochem. J., 187, 909-912, 1980
[b]Barrett, A. J. and Kirschke, H., Methods Enzymol., 80, 535-561, 1981
[c]Quibell, M. and Taylor, S., WO0069855, 2000
[d]Bromme, D., Steinert, ., Freibe, S., Fittkau, S., Wiederanders, B., and Kirschke, H., Biochem. J., 264, 475-481, 1989
[e]Rano, T. A., et. al., Chem. Biol., 4, 149, 1997
[f]Talanian, R. V., et. al., J. Biol. Chem., 272, 9677, 1997
[g]Lazebnik, Y. A., Kaufmann, S. H., Desnoyers, S., Poirer, G. G. and Earnshaw, W. C., Nature., 371, 768-774, 1994
[h]Han, Z., et. al., J. Biol. Chem., 272, 13432, 1997
[i]Takahashi, A., et. al., PNAS, 93, 8395, 1996
[j]Martins, L. M., et. al., J. Biol. Chem., 272, 7421, 1997
[k]Nagata, S., Cell., 88, 355, 1997
[l]Harris, J. L., et. al., J. Biol. Chem., 273, 27364, 1998
[m]Cazzulo, J. J., Cazzulo Franke, M. C., Martinez, J. and Franke de Cazzulo, B. M., Biochim. Biophys. Acta., 1037, 186-191, 1990
[n]Cazzulo, J. J., Bravo, M., Raimondi, A., Engstrom, U., Lindeberg, G. and Hellman, U., Cell Mol. Biol., 42, 691-696, 1996
[o]Potempa, J., Dubin, A., Korzus, G. and Travis, J., Biochem. J., 263, 2664-2667, 1988
[p]Kembhavi, A. A., Buttle, D. J., Rauber, P. and Barrett, A. J., FEBS Lett., 283, 277-280, 1991
[q]Alves, L. C., et. al., Mol. Biochem. Parasitol, 116, 1-9, 2001.
[r]Guarné, et. al., J. Mol. Biol., 302, 1227-1240, 2000.
[s]Halfon and Craik, (Barret, Rawlings and Woessner, eds.), in Handbook of Proteolytic Enzymes, Academic Press, London, 12-21, 1998.
[t]Sasaki, et. al., (1984), J. Biol. Chem., 259, 12489-12494, 1984.
[u]Bossard, M. J., et. al., J. Biol. Chem., 21, 12517-12524, 1996
[v]Santamaria, I., et. al., J. Biol. Chem., 273, 16816-16823, 1998
[w]Klemencic, J, et al., Eur. J. Biochem., 267, 5404-5412, 2000

*Trypanosoma cruzi* Cruzipain Peptidase Activity Assays

Wild-type cruzipain, derived from *Trypanosoma cruzi* Dm28 epimastigotes, was obtained from Dr. Julio Scharfstein (Instituto de Biofisica Carlos Chagas Filho, Universidade Federal do R$^{10}$ de Janeiro, R$^{10}$ de Janeiro, Brazil). Activity assays were carried out in 100 mM sodium phosphate, pH 6.75 containing 1 mM EDTA and 10 mM L-cysteine using 2.5 nM enzyme. Ac-Phe-Arg-AMC ($K_M^{app} \approx 12$ μM) and D-Val-Leu-Lys-AMC ($K_M^{app} \approx 4$ μM) were used as the substrates. Routinely, Ac-FR-AMC was used at a concentration equivalent to $K_M^{app}$ and D-Val-Leu-Lys-AMC was used at a concentration of 25 μM. The rate of conversion of substrate to product was derived from the slope of the increase in fluorescence monitored continuously over time.

*Leishmania mexicana* Cysteine Protease B (CPB) Peptidase Activity Assays

Wild-type recombinant CPB without the C-terminal extention (i.e. CPB2.8ΔCTE; Sanderson, S. J., et. al., *Biochem. J,* 347 383-388, 2000) was obtained from Dr. Jeremy Mottram (Wellcome Centre for Molecular Parasitology, The Anderson College, University of Glasgow, Glasgow, U.K.). Activity assays were carried out in 100 mM sodium acetate; pH 5.5 containing 1 mM EDTA; 200 mM NaCl and 110 mM DTT (Alves, L. C., et. al., *Mol. Biochem. Parasitol,* 116, 1-9, 2001) using 0.25 nM enzyme. Pro-Phe-Arg-AMC ($K_M^{app} \approx 38$ μM) was used as the substrate at a concentration equivalent to $K_M^{app}$. The rate of conversion of substrate to product was derived from the slope of the increase in fluorescence monitored continuously over time.

Cathepsin Peptidase Activity Assays

Bovine cathepsin S, human cathepsin L, human cathepsin H and human cathepsin B were obtained from CN Biosciences. Recombinant human cathepsin S, human cathepsin K and human cathepsin X were obtained from Dr. Boris Turk (Josef Stefan Institute, Ljubljana, Slovenia). Unless otherwise stated, all peptidase activity assays were carried out in 10 mM bis-tris-propane (BTP), pH 6.5 containing 1 mM EDTA, 5 mM 2-mercaptoethanol and 1 mM CaCl$_2$. Human cathepsin H activity assays were carried out in 10 mM BTP pH 6.5, 142 mM NaCl$_2$, 1 mM CaCl$_2$, 1 mM EDTA, 1 mM DTT, 0.035 mM Zwittergent 3-16. Human cathepsin K assays were carried out in 100 mM sodium acetate; pH 5.5 containing 20 mM L-cysteine and 1 mM EDTA (Bossard, M. J., et. al., *J. Biol. Chem.*, 21, 12517-12524, 1996). Human cathepsin X assays were carried out in 100 mM sodium acetate; pH 5.5 containing 20 mM L-cysteine; 0.05% (w/v) Brij 35 and 1 mM EDTA (Santamaria, I., et. al., *J. Biol. Chem.*, 273, 16816-16823, 1998; Klemencic, J, et al., *Eur. J. Biochem.*, 267, 5404-5412, 2000). The final enzyme concentrations used in the assays were 0.5 nM bovine cathepsin S, 1 nM cathepsin L, 0.1 nM cathepsin B, 0.25 nM Cathepsin K; 1 nM cathepsin X and 10 nM cathepsin H. For the inhibition assays, the substrates used for cathepsin S, cathepsin L, cathepsin B, cathepsin K and cathepsin H were boc-Val-Leu-Lys-AMC ($K_M^{app} \approx 30$ μM), Ac-Phe-Arg-AMC ($K_M^{app} \approx 20$ μM), Z-Phe-Arg-AMC ($K_M^{app} \approx 40$ μM), Z-Leu-Arg-AMC ($K_M^{app} \sim 2$ μM); Bz-Phe-Val-Arg-AMC ($K_M^{app} \approx 150$ μM) respectively. In each case the substrate concentration used in each assay was equivalent to the $K_M^{app}$. The rate of conversion of substrate to product was derived from the slope of the increase in fluorescence monitored continuously over time.

Trypsin Peptidase Activity Assays

Human pancreatic trypsin (iodination grade; CN Biosciences) activity assays were carried out in 10 mM HEPES, pH 8.0 containing 5 mM CaCl$_2$ using 0.1 nM trypsin. For the inhibition assays, Z-Gly-Gly-Arg-AMC ($K_M^{app} \approx 84$ μM) was used as the substrate at a concentration equivalent to $K_M^{app}$. The rate of conversion of substrate to product was derived from the slope of the increase in fluorescence monitored continuously over time.

Clostripain Peptidase Activity Assays

Clostripain (Sigma) activity assays were carried out in 10 mM BTW, pH 6.5 containing 1 mM EDTA, 5 mM 2-mercaptoethanol and 1 mM $CaCl_2$ using 0.3 nM enzyme. For the inhibition assays, Z-Gly-Gly-Arg-AMC ($K_M^{app} \approx 100$ μM) was used as the substrate at a concentration equivalent to $K_M^{app}$. The rate of conversion of substrate to product was derived from the slope of the increase in fluorescence monitored continuously over time.

Calpain Peptidase Activity Assays

Calpain (human erythrocyte μ-calpain and porcine kidney m-calpain; CN Biosciences) activity assays were carried out in 10 mM HEPES, pH 7.5 containing 2 mM 2-mercaptoethanol and $CaCl_2$ using 25 nM of either enzyme (Sasaki, et. al, *J. Biol. Chem.*, 259, 12489-12494, 1984). For μ-calpain inhibition assays, the buffer contained 100 μM $CaCl_2$ and Abz-Ala-Asn-Leu-Gly-Arg-Pro-Ala-Leu-Tyr($NO_2$)-Asp-$NH_2$ ($K_M^{app} \approx 20$ μM; Incenta Limited) was used as the substrate. For μ-calpain inhibition assays, the assay buffer contained 200 μM $CaCl_2$ and Abz-Lys-Leu-Cys(Bzl)-Phe-Ser-Lys-Gln-Tyr($NO_2$)-Asp-$NH_2$ ($K_M^{app} \approx 22$ μM; Incenta Limited) was used as the substrate. In both cases the substrate concentration employed in the assays was equivalent to the $K_M^{app}$. The rate of conversion of substrate to product was derived from the slope of the increase in fluorescence monitored continuously over time.

Extracellular *S. aureus* V8 Cysteine Peptidase (Staphylopain) Peptidase Activity Assays

*S. aureus* V8 was obtained from Prof. S. Arvidson, Karolinska Institute, Stockholm, Sweden. Extracellular *S. aureus* V8 cysteine peptidase (staphylopain) activity assays were carried out using partially purified *S. aureus* V8 culture supernatant (obtained from Dr. Peter Lambert, Aston University, Birmingham, U.K.). Activity assays were carried out in 10 mM BTP, pH 6.5 containing 1 mM EDTA, 5 mM 2-mercaptoethanol and 1 mM $CaCl_2$ using two-times diluted partially purified extract. For the inhibition assays, Abz-Ile-Ala-Ala-Pro-Tyr($NO_2$)-Glu-$NH_2$ ($K_M^{app} \approx 117$ μM; Incenta Limited) was used as the substrate at a concentration equivalent to $K_M^{aPP}$. The rate of conversion of substrate to product was derived from the slope of the increase in fluorescence monitored continuously over time.

Foot-and-Mouth Disease Leader Peptidase (FMDV-LP) Activity Assays

Recombinant wild-type FMDV-LP was obtained from Dr. Tim Skern (Institut fur Medizinische Biochemie, Abteilung fur Biochemie, Universtait Wien, Wien, Austria). Activity assays were carried out in 50 mM trisacetate, pH 8.4 containing 1 mM EDTA, 10 mM L-cysteine and 0.25% (w/v) CHAPS using 10 nM enzyme. For the inhibition assays, Abz-Arg-Lys-Leu-Lys-Gly-Ala-Gly-Ser-Tyr($NO_2$)-Glu-$NH_2$ ($K_M^{app} \approx 51$ μM, Incenta Limited) was used as the substrate at a concentration equivalent to $K_M^{app}$. The rate of conversion of substrate to product was derived from the slope of the increase in fluorescence monitored continuously over time.

Caspase Peptidase Activity Assays

Caspases 1-10 were obtained from CN Biosciences or Bio-Vision Inc. (Mountain View, Calif., USA) and all assays were carried out in 50 mM HEPES; pH 7.2, 10% (v/v) glycerol, 0.1% (w/v) CHAPS, 142 mM NaCl, 1 mM EDTA, 5 mM dithiothreitol (DTT) using 0.1-1 U per assay. For caspase 1, Ac-Leu-Glu-His-Asp-AMC was used as the substrate; for caspase 2, Z-Val-Asp-Val-Ala-Asp-AFC was used as the substrate; for caspase 3, Ac-Asp-Glu-Val-Asp-AMC was used as the substrate; for caspase 4, Suc-Tyr-Val-Ala-Asp-AMC was used as the substrate; for caspase 5, Ac-Leu-Glu-His-Asp-AMC was used as the substrate; for caspase 6, Ac-Val-Glu-Ile-Asp-AMC was used as the substrate; for caspase 7, Ac-Asp-Glu-Val-Asp-AMC was used as the substrate; for caspase 8, Ac-Ile-Glu-Thr-Asp-AMC was used as the substrate; for caspase 9, Ac-Leu-Glu-His-Asp-AMC was used as the substrate; for caspase 10, Ac-Ile-Glu-Thr-Asp-AMC was used as the substrate (Nicholson, D. W. and Thornberry, N. A., *TIBS*, 22 299-306, 1997; Stennicke, H. R. and Salvesen, G. S., *J. Biol. Chem.*, 272(41), 25719-25723, 1997; Talanian, R. V., et. al., *J. Biol. Chem.*, 272(15), 9677-9682, 1997; Wolf, B. B. and Green, D. R., *J. Biol. Chem.*, 274(29), 20049-20052, 1999). The rate of conversion of substrate to product was derived from the slope of the increase in fluorescence monitored continuously over time.

Measurement of the Apparent Macroscopic Binding (Michaelis) Constants ($K_M^{app}$) for Substrates The apparent macroscopic binding constant ($K_M^{app}$) for each substrate was calculated, from the dependence of enzyme activity as a function of substrate concentration. The observed rates were plotted on the ordinate against the related substrate concentration on the abscissa and the data fitted by direct regression analysis (Prism v 3.02; GraphPad, San Diego, USA) using Equation 1 (Cornish-Bowden, A. *Fundamentals of enzyme kinetics Portland Press;* 1995, 93-128.).

$$v_i = \frac{V_{max}^{app} \cdot [S_o]}{[S_o] + K_M^{app}} \quad (1)$$

In Equation 1 '$v_1$' is the observed initial rate, '$V_{max}^{app}$' is the observed maximum activity at saturating substrate concentration, '$K_M^{app}$' is the apparent macroscopic binding (Michaelis) constant for the substrate, '$[S_o]$' is the initial substrate concentration.

Measurement of the Inhibition Constants

The apparent inhibition constant ($K_i$) for each compound was determined on the basis that inhibition was reversible and occurred by a pure-competitive mechanism. The $K_i$ values were calculated, from the dependence of enzyme activity as a function of inhibitor concentration, by direct regression analysis (Prism v 3.02) using Equation 2 (Cornish-Bowden, A., 1995.).

$$v_i = \frac{V_{max}^{app} \cdot [S]}{[S] + \{K_M^{app} \cdot ([I]/K_i)\}} \quad (2)$$

In Equation 2 '$v_1$' is the observed residual activity, '$V_{max}^{app}$' is the observed maximum activity (i.e. in the absence of inhibitor), '$K_M^{app}$' is the apparent macroscopic binding Michaelis) constant for the substrate, '[S]' is the initial substrate concentration, '$K_i$' is the apparent dissociation constant and '[I]' is the inhibitor concentration.

In situations where the apparent dissociation constant ($K_i^{app}$) approached the enzyme concentrations, the $K_i^{app}$ values were calculated using a quadratic solution in the form described by Equation 3 (Morrison, J. F. *Trends Biochem. Sci.*, 7, 102-105, 1982; Morrison, J. F. *Biochim. Biophys. Acta*, 185, 269-286, 1969; Stone, S. R. and Hofsteenge, *J. Biochemistry*, 25, 4622-4628, 1986).

$$v_i = \frac{F\{E_o - I_o - K_i^{app} + \sqrt{(E_o - I_o - K_i^{app})^2 + 4 \cdot K_i^{app} \cdot E_o}\}}{2} \quad (3)$$

$$K_i^{app} = K_i(1 + [S_o]/K_M^{app}) \quad (4)$$

In Equation 3 '$v_i$' is the observed residual activity, 'F' is the difference between the maximum activity (ie. in the absence of inhibitor) and minimum enzyme activity, '$E_o$' is the total enzyme concentration, '$K_1^{app}$' is the apparent dissociation constant and '$I_o$' is the inhibitor concentration. Curves were fitted by non-linear regression analysis (Prism) using a fixed value for the enzyme concentration. Equation 4 was used to account for the substrate kinetics, where '$K_1$' is the inhibition constant, '$[S_o]$' is the initial substrate concentration and '$K_M^{app}$' is the apparent macroscopic binding (Michaelis) constant for the substrate (Morrison, 1982).

The Second-Order Rate of Reaction of Inhibitor with Enzyme

Where applicable, the concentration dependence of the observed rate of reaction ($k_{obs}$) of each compound with enzyme was analysed by determining the rate of enzyme inactivation under pseudo-first order conditions in the presence of substrate (Morrison, J. F., *TIBS*, 102-105, 1982; Tian, W. X. and Tsou, C. L., *Biochemistry*, 21, 1028-1032, 1982; Morrson, J. F. and Walsh, C. T., from Meister (Ed.), *Advances in Enzymol.*, 61, 201-301, 1988; Tsou, C. L., from Meister (Ed.), *Advances in Enzymol.*, 61, 381-436, 1988;). Assays were carried out by addition of various concentrations of inhibitor to assay buffer containing substrate. Assays were initiated by the addition of enzyme to the reaction mixture and the change in fluorescence monitored over time. During the course of the assay less than 10% of the substrate was consumed.

$$F = v_s t + \frac{(v_o - v_s)[1 - e^{(k_{obs} \cdot t)}]}{k_{obs}} + D \quad (5)$$

The activity fluorescence progress curves were fitted by non-linear regression analysis (Prism) using Eq. 5 (Morrison, 1969; Morrison, 1982); where 'F' is the fluorescence response, 't' is time, '$v_o$' is the initial velocity, '$v_s$' is the equilibrium steady-state velocity, '$k_{obs}$' is the observed pseudo first-order rate constant and 'D' is the intercept at time zero (i.e. the ordinate displacement of the curve). The second order rate constant was obtained from the slope of the line of a plot of $k_{obs}$ versus the inhibitor concentration (i.e. $k_{obs}/[I]$) To correct for substrate kinetics, Eq. 6 was used, where '$[S_o]$' is the initial substrate concentration and '$K_M^{app}$' is the apparent macroscopic binding (Michaelis) constant for the substrate.

$$k_{inact} = \frac{k_{obs}(1 + [S_o]/K_M^{app})}{[I]} \quad (6)$$

Compounds of the invention were tested by the above described assays and observed to exhibit cruzipain inhibitory activity or inhibitory activity against an alternative CA C1 cysteine protease with an in vitro Ki inhibitory constant of less than or equal to 100 μM. Exemplary inhibition data for a number of example compounds of the invention are given in table 2.

TABLE 2

Exemplary inhibition data (Ki expressed as μM).

| EXAMPLE No | Cruzipain | Bovine Cathepsin S | Human Cathepsin L | Human Cathepsin K |
|---|---|---|---|---|
| 3 | 0.2 | >100 | >35 | >5 |
| 10 | >5 | >10 | >25 | 0.1 |
| 48 | >25 | 0.3 | >100 | >10 |
| 69 | >5 | >10 | 0.8 | >100 |

What is claimed is:

1. A compound according to general formula (I) or general formula (II):

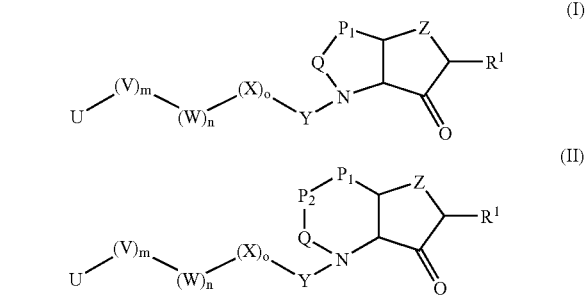

wherein: $R^1=C_{0-7}$-alkyl (when C=0, $R^1$ is hydrogen), $C_{3-6}$-cycloalkyl or Ar—$C_{0-7}$-alkyl;

Ar is an aromatic moiety which is a 5- or 6-membered monocyclic or 9- or 10-membered bicyclic ring, which is unsaturated, wherein the aromatic ring is optionally substituted with $R^{19}$;

Z=O, S, $CR^2R^3$ or $NR^4$, where $R^4$ is chosen from $C_{0-7}$-alkyl, $C_{3-6}$-cycloalkyl or Ar—$C_{0-7}$-alkyl;

$P_1=CR^5R^6$, $P_2=CR^7R^8$, $Q=CR^9R^{10}$ or $NR^{11}$, where $R^{11}$ is chosen from $C_{0-7}$-alkyl, $C_{3-6}$-cycloalkyl or Ar—$C_{0-7}$-alkyl;

Each of $R^2$, $R^3$, $R^5$, $R^6$, $R^7$, $R^8$, $R^9$ and $R^{10}$ is independently chosen from $C_{0-7}$-alkyl, $C_{3-6}$-cycloalkyl, Ar—$C_{0-7}$-alkyl, O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N($C_{0-7}$-alkyl)$_2$, N($C_{3-6}$-cycloalkyl)$_2$ or N(Ar—$C_{0-7}$-alkyl)$_2$;

Y=$CR^{12}R^{13}$—CO, where $R^{12}$, $R^{13}$ are chosen from $C_{0-7}$-alkyl, $C_{3-6}$-cycloalkyl or Ar—$C_{0-7}$-alkyl;

in the group (X)$_o$, X=$CR^{14}R^{15}$, where $R^{14}$ and $R^{15}$ are independently chosen from $C_{0-7}$-alkyl, $C_{3-6}$-cycloalkyl and Ar—$C_{0-7}$-alkyl and o is a number from zero to three;

in the group (W)$_n$, W=O, S, C(O), S(O) or S(O)$_2$ or $NR^{16}$, where $R^{16}$ is chosen from $C_{0-7}$-alkyl, $C_{3-6}$-cycloalkyl and Ar—$C_{0-7}$-alkyl and n is zero or one;

in the group (V)$_m$, V=C(O), C(S), S(O), S(O)$_2$, S(O)$_2$NH, OC(O), NHC(O), NHS(O), NHS(O)$_2$, OC(O)NH, C(O)NH or $CR^{17}R^{18}$, where $R^{17}$ and $R^{18}$ are independently chosen from $C_{0-7}$-alkyl, $C_{3-6}$-cycloalkyl, Ar—$C_{0-7}$-alkyl and m is a number from zero to three, provided that when m is greater than one, $(V)_m$ contains a maximum of one carbonyl or sulphonyl group;

U=a 5- to 7-membered monocyclic ring selected from the group consisting of:

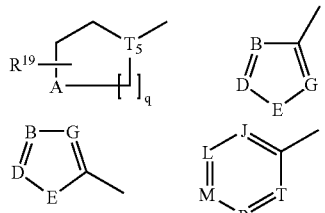

wherein $R^{19}$ is:
$C_{0-7}$-alkyl, $C_{3-6}$-cycloalkyl, Ar—$C_{0-7}$-alkyl, O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH-$C_{3-6}$-cycloalkyl, NH—Ar—$C_{0-7}$-alkyl, N($C_{0-7}$-alkyl)$_2$, N($C_{3-6}$-cycloalkyl)$_2$ or N(Ar—$C_{0-7}$-alkyl)$_2$; or, when part of a $CHR^{19}$ or $CR^{19}$ group, $R^{19}$ may be halogen;

A is chosen from:
$CH_2$, $CHR^{19}$, O, S and $NR^{20}$;
where $R^{19}$ is as defined above; and $R^{20}$ is chosen from:
$C_{0-7}$-alkyl, $C_{3-6}$-cycloalkyl and Ar—$C_{0-7}$-alkyl;

B, D and G are independently chosen from:
$CR^{19}$, where $R^{19}$ is as defined above, N and N-oxide;

E is chosen from:
$CH_2$, $CHR^{19}$, O, S and $NR^{20}$, where $R^{19}$ and $R^{20}$ are defined as above;

J, L, M, R, and T are independently chosen from:
—$CR^{19}$, N and N-oxide, where $R^{19}$ is as defined above;

$T_5$ is chosen from:
CH or N;

q is a number from one to three, thereby defining a 5-, 6- or 7-membered ring or a salt thereof.

2. A compound as claimed in claim 1 wherein independently or in combination:
Z is O, S, $CH_2$, NH or $NR^4$, where $R^4$ is a Ar—$C_{1-4}$-alkyl or a substituted carbonyl or sulphonyl group;
$P^1$ and $P^2$ are $CH_2$; and
Q is $CH_2$, or NH.

3. A compound as claimed in claim 1 wherein $R^1$ is $C_{0-7}$-alkyl or Ar—$C_{0-7}$-alkyl.

4. A compound as claimed in claim 3 wherein $R^1$ is selected from hydrogen or one of the following moieties:

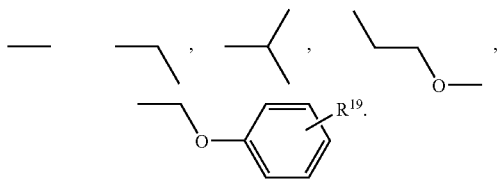

5. A compound as claimed in claim 1 wherein Y is $CR^{12}R^{13}CO$ where $R^{12}$, $R^{13}$ are selected from $C_{0-7}$-alkyl, $C_{3-6}$-cycloalkyl or Ar—$C_{0-7}$-alkyl.

6. A compound as claimed in claim 5 where Y is selected from one of the following moieties:

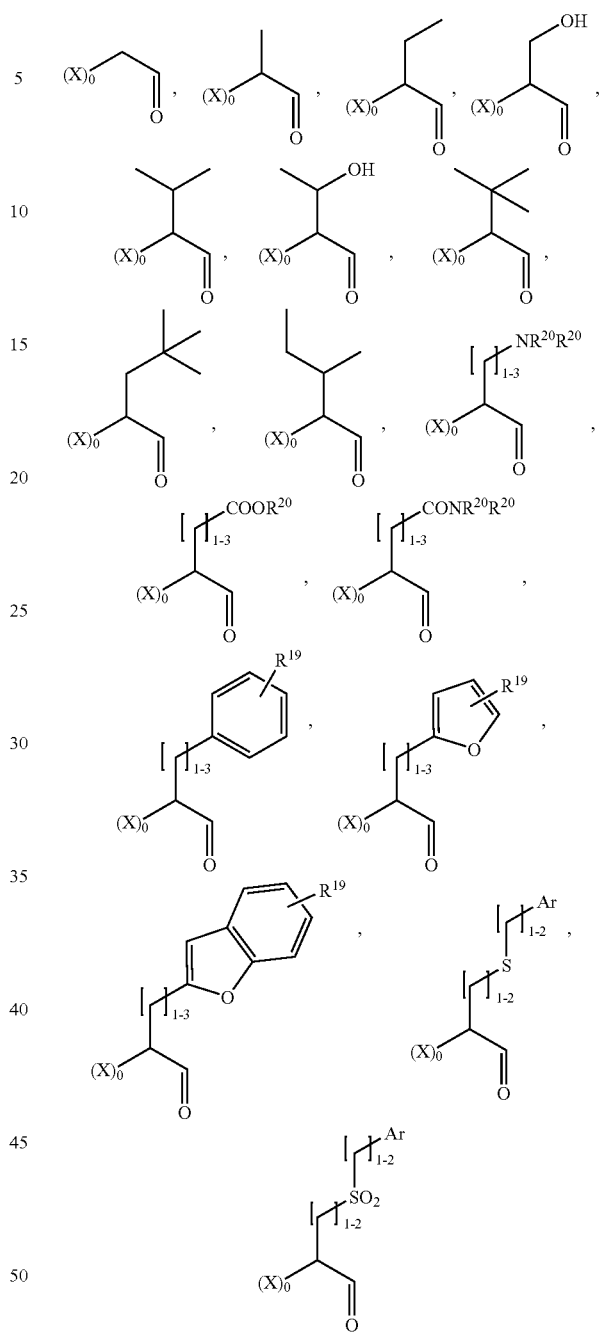

wherein $R^{19}$, $R^{20}$ and Ar are as defined in claim 1.

7. A compound as claimed in claim 1 wherein Y is $CHR^{13}CO$ where $R^{13}$ is Ar—$CH_2$—, where the aromatic ring is an optionally substituted phenyl or monocyclic heterocycle.

8. A compound as claimed in claim 1 wherein Y is $CHR^{13}CO$ where $R^{13}$ is a simple branched alkyl group or a straight heteroalkyl chain.

9. A compound as claimed in claim 1 wherein Y is $CHR^{13}CO$ where $R^{13}$ comprises cyclohexylmethyl.

10. A compound as claimed in claim 1 wherein Y is selected from the following:

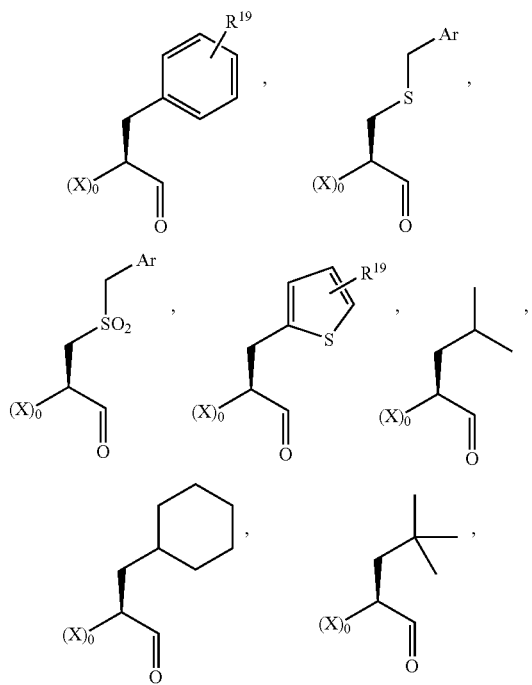

wherein $R^{19}$ and Ar are as defined in claim 1.

11. A compound as claimed in claim 1 wherein, in the group $(X)_o$, X is $CR^{14}R^{15}$ and each of $R^{14}$ and $R^{15}$ is selected from $C_{0-7}$-alkyl or Ar—$C_{0-7}$-alkyl.

12. A compound as claimed in claim 1, wherein $(X)_o$ is one of the following moieties:

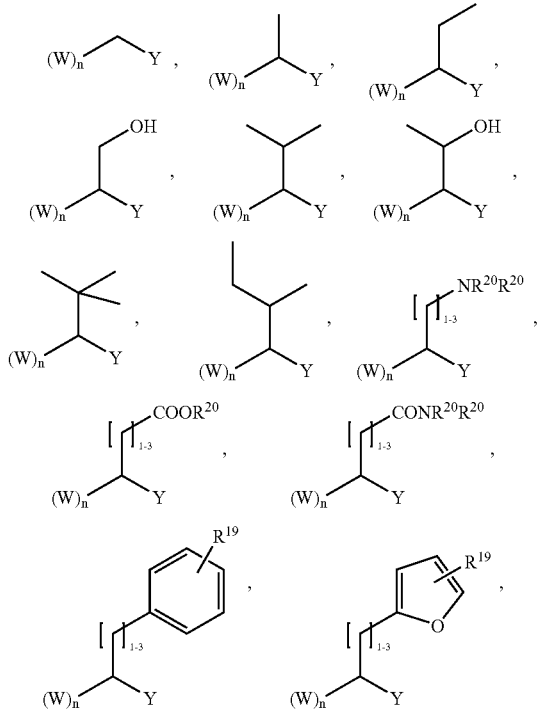

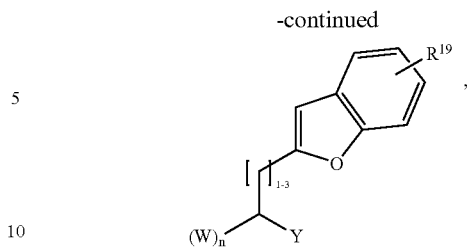

wherein $R^{19}$ and $R^{20}$ are as defined in claim 1.

13. A compound as claimed in claim 1, wherein $(X)_o$ is a simple alkyl group and where o=0 or 1.

14. A compound as claimed in claim 1 wherein, in the group $(W)_n$:

W is O, S, $SO_2$, SO, C(O) or $NR^{16}$, where $R^{16}$ is $C_{0-4}$-alkyl; and n is 0 or 1.

15. A compound as claimed in claim 1 wherein, in the group $(W)_n$:

W is O, S, $SO_2$, C(O) or NH where n is 0 or 1.

16. A compound as claimed in claim 1 wherein, in the group $(W)_n$:

W is NH where n is 1.

17. A compound as claimed in claim 1 wherein, in the group $(V)_m$:

V is C(O), C(O)NH or $CHR^{18}$, where $R^{18}$ is $C_{0-4}$-alkyl; and m is 0 or 1.

18. A compound as claimed in claim 1 wherein the combination $(V)_m$ and $(W)_m$ is one of the following:

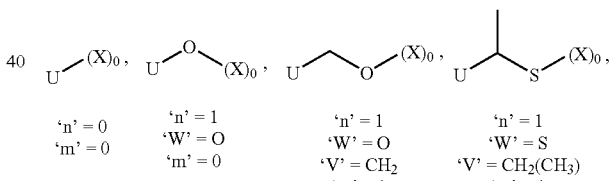

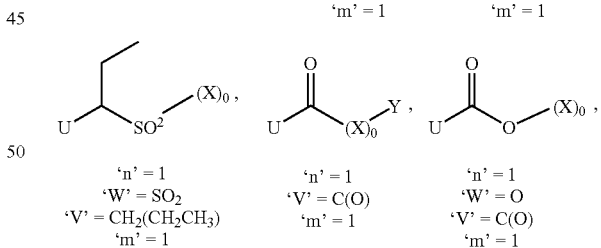

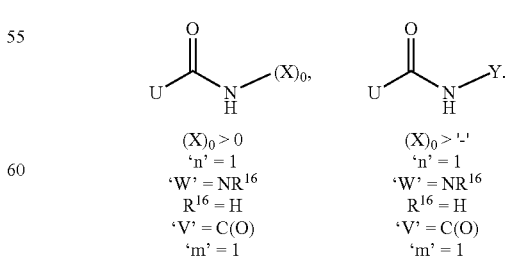

19. A compound as claimed in claim 1 wherein the combination of $(X)_o$, $(V)_m$ and $(W)_m$ is one of the following:

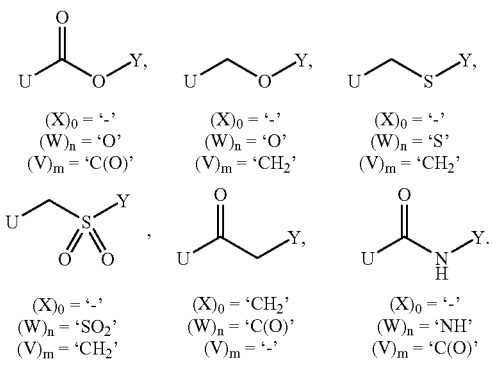

20. A compound as claimed in claim 1 wherein U is an optionally substituted 5- or 6-membered saturated or unsaturated heterocycle.

21. A compound as claimed in claim 20 wherein U is one of the following:

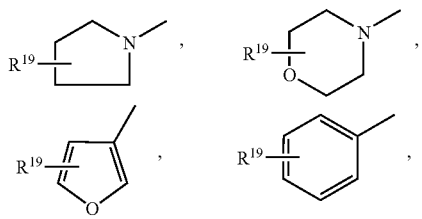

wherein $R^{19}$ is as defined in claim 1.

22. A compound as claimed in claim 1 wherein U is a bulky alkyl or aryl group at the para position of an aryl Ar.

23. A compound as claimed in any one of claim 1 wherein U is a meta or para-biaryl Ar—Ar, where Ar is as defined in claim 1.

24. A compound as claimed in claim 1, wherein U is selected from the group consisting of:

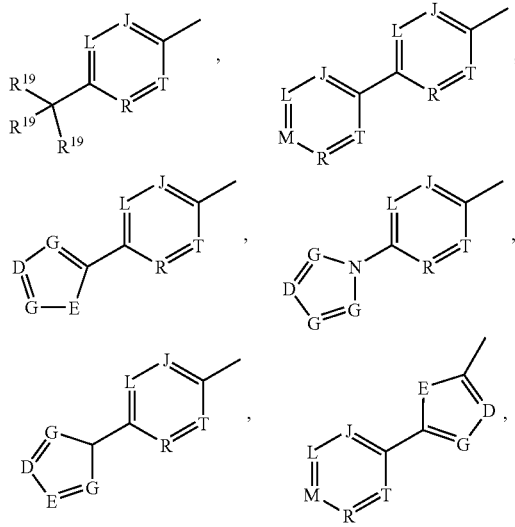

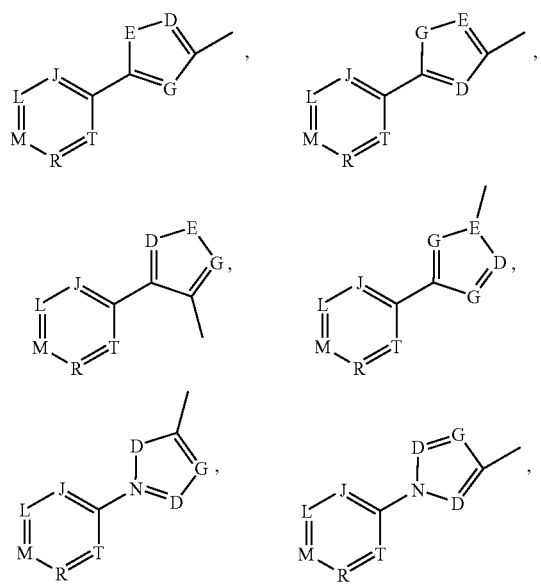

wherein $R^{19}$, D, E, G, J, L, M, R, and T are as defined in claim 1.

25. A compound as claimed in claim 1, wherein U the group consisting of

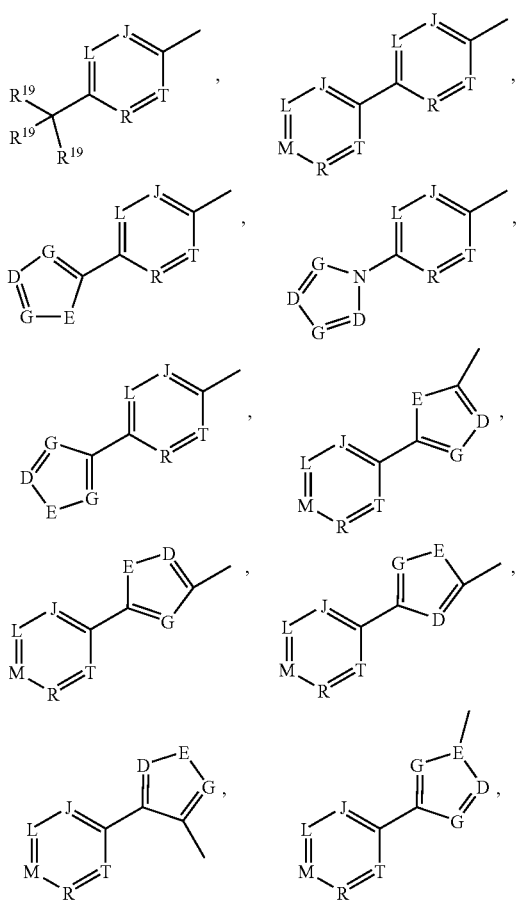

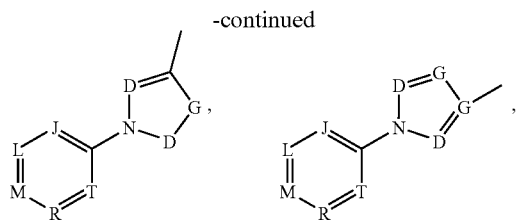

wherein $R^{19}$, D, E, G, J, L, M, R and T are as defined in claim 1.

26. A compound as claimed in claim 1, wherein U represents a group

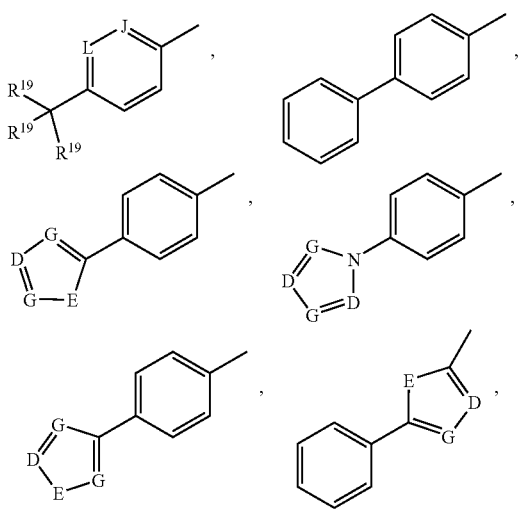

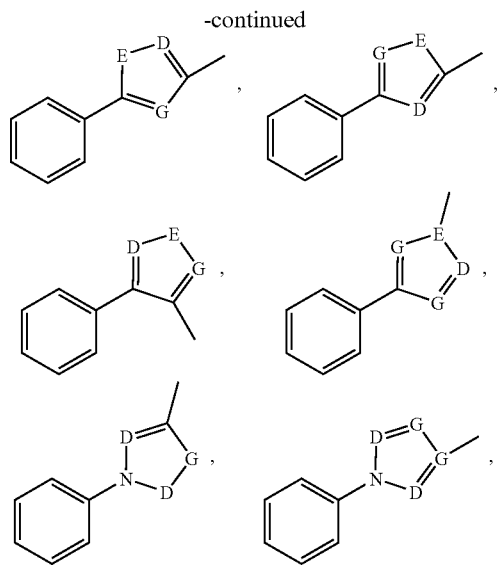

wherein $R^{19}$, D, E, G, J and L are as defined in claim 1.

27. A composition comprising a compound as claimed in claim 1, or a salt thereof, and a pharmaceutically or veterinarily acceptable carrier.

28. A method for treating Chagas' disease comprising administering an effective amount of a compound of claim 1, or a salt thereof.

29. A method for treating osteoporosis, the method comprising administering to a mammal in need thereof an effective amount of a compound of claim 1, or a salt thereof.

* * * * *